United States Patent
Luo et al.

(10) Patent No.: US 11,787,875 B2
(45) Date of Patent: Oct. 17, 2023

(54) MATERIALS AND METHODS FOR IMPROVED SINGLE CHAIN VARIABLE FRAGMENTS

(71) Applicant: Janssen Biotech, Inc., Horsham, PA (US)

(72) Inventors: Jinquan Luo, Malvern, PA (US); Lauren Boucher, Waukegan, IL (US); Michael Feldkamp, Blue Bell, PA (US); Michael Diem, Havertown, PA (US); Anthony A. Armstrong, Lawrence Township, NJ (US); Alexey Teplyakov, Middletown, MD (US); Chichi Huang, Malvern, PA (US)

(73) Assignee: Janssen Biotech, Inc., Horsham, PA (US)

( * ) Notice: Subject to any disclaimer, the term of this patent is extended or adjusted under 35 U.S.C. 154(b) by 359 days.

(21) Appl. No.: 16/994,065

(22) Filed: Aug. 14, 2020

(65) Prior Publication Data

US 2021/0047435 A1 Feb. 18, 2021

Related U.S. Application Data

(60) Provisional application No. 62/887,514, filed on Aug. 15, 2019, provisional application No. 62/887,519, filed on Aug. 15, 2019, provisional application No. 62/887,524, filed on Aug. 15, 2019, provisional application No. 62/887,527, filed on Aug. 15, 2019, provisional application No. 62/887,529, filed on Aug. 15, 2019, provisional application No. 62/946,865, filed on Dec. 11, 2019, provisional application No. 62/946,877, filed on Dec. 11, 2019, provisional application No. 62/946,882, filed on Dec. 11, 2019, provisional application No. 62/946,886, filed on Dec. 11, 2019, provisional application No. 62/946,897, filed on Dec. 11, 2019.

(51) Int. Cl.
*C07K 16/00* (2006.01)
*C07K 16/42* (2006.01)
*C07K 14/705* (2006.01)

(52) U.S. Cl.
CPC ........ *C07K 16/4283* (2013.01); *C07K 14/705* (2013.01); *C07K 16/00* (2013.01); *C07K 2317/31* (2013.01); *C07K 2317/524* (2013.01); *C07K 2317/526* (2013.01); *C07K 2317/53* (2013.01); *C07K 2317/567* (2013.01); *C07K 2317/622* (2013.01); *C07K 2317/624* (2013.01); *C07K 2317/94* (2013.01)

(58) Field of Classification Search
CPC ................ C07K 2317/622; C07K 2317/624
See application file for complete search history.

(56) References Cited

U.S. PATENT DOCUMENTS

| | | |
|---|---|---|
| 4,683,195 A | 7/1987 | Mullis et al. |
| 5,635,483 A | 6/1997 | Pettit et al. |
| 5,780,588 A | 7/1998 | Pettit et al. |
| 5,932,448 A | 8/1999 | Tso et al. |
| 6,150,584 A | 11/2000 | Kucherlapati et al. |
| 6,833,441 B2 | 12/2004 | Wang et al. |
| 9,150,663 B2 | 10/2015 | Labrijn et al. |
| 2007/0287170 A1 | 12/2007 | Davis et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2011/0123532 A1 | 5/2011 | Gurney et al. |
| 2011/0200594 A1* | 8/2011 | Urech ............... C07K 16/00 435/243 |
| 2012/0149876 A1 | 6/2012 | Von Kreudenstein et al. |
| 2012/0171115 A1* | 7/2012 | Hudson ............ A61K 49/0002 424/9.34 |
| 2012/0251541 A1* | 10/2012 | Baurin ............. C07K 16/2809 435/69.6 |
| 2012/0283415 A1* | 11/2012 | Humphreys ......... C07K 16/468 530/387.3 |
| 2013/0195849 A1 | 8/2013 | Von Kreudenstein et al. |
| 2014/0206847 A1 | 7/2014 | Endoh |
| 2014/0273092 A1 | 9/2014 | Flikweert et al. |
| 2014/0303356 A1 | 10/2014 | Gramer et al. |
| 2018/0118849 A1 | 5/2018 | Klein et al. |

FOREIGN PATENT DOCUMENTS

| | | |
|---|---|---|
| EP | 2142567 B1 | 1/2013 |
| WO | WO 1990004036 A1 | 4/1990 |
| WO | WO 1996027011 A1 | 9/1996 |
| WO | WO 1997045544 A1 | 12/1997 |
| WO | WO 1999045962 A1 | 9/1999 |
| WO | WO 2002043478 A2 | 6/2002 |
| WO | WO 2002043478 A3 | 6/2002 |
| WO | WO 2002066630 A1 | 8/2002 |
| WO | WO 2002088172 A2 | 11/2002 |
| WO | WO 2002088172 A3 | 11/2002 |

(Continued)

OTHER PUBLICATIONS

Adams et al., 2004, "Recent developments in the PHENIX software for automated crystallographic structure determination," J. Synchrotron Radiat, 11(Pt 1):53-55 (Epub 2003).
Atwell et al., 1997, "Stable heterodimers from remodeling the domain interface of a homodimer using a phage display library," J. Mol. Biol., 270(1):26-35.
Baert et al., 2003, "Influence of immunogenicity on the long-term efficacy of infliximab in Crohn's disease" N. Engl. J. Med., 348(7):601-608.
Bird et al., 1988, "Single-chain antigen-binding proteins," Science, 242(4877):423-426.
Brinkmann et al., 2017, "The making of bispecific antibodies," MAbs, 9(2):182-212.

(Continued)

*Primary Examiner* — Jessica H Roark
(74) *Attorney, Agent, or Firm* — Troutman Pepper Hamilton Sanders LLP

(57) ABSTRACT

Disclosed are materials and methods for improved single chain variable fragments.

26 Claims, 26 Drawing Sheets

Specification includes a Sequence Listing.

(56) References Cited

FOREIGN PATENT DOCUMENTS

| WO | WO 2007147901 A1 | 12/2007 |
|---|---|---|
| WO | WO 2008077546 A1 | 7/2008 |
| WO | WO 2008120101 A2 | 10/2008 |
| WO | WO 2008120101 A3 | 10/2008 |
| WO | WO 2009134776 A3 | 10/2008 |
| WO | WO 2009085462 A1 | 7/2009 |
| WO | WO 2009134776 A2 | 11/2009 |
| WO | WO 2010006454 A2 | 1/2010 |
| WO | WO 2010006454 A3 | 1/2010 |
| WO | WO 2010151792 A1 | 12/2010 |
| WO | WO 2011020783 A2 | 2/2011 |
| WO | WO 2011020783 A3 | 2/2011 |
| WO | WO 2011143545 A1 | 11/2011 |
| WO | WO 2012022811 A1 | 2/2012 |
| WO | WO 2012025530 A1 | 3/2012 |
| WO | WO 2013096291 A2 | 6/2013 |
| WO | WO 2013096291 A3 | 6/2013 |
| WO | WO 2013157954 A1 | 10/2013 |
| WO | WO 2013175678 A1 | 11/2013 |
| WO | WO 2019060695 A1 | 3/2019 |

OTHER PUBLICATIONS

Cai et al., 2011, "C-terminal lysine processing of human immunoglobulin G2 heavy chain in vivo," Biotechnol. Bioeng., 108(2):404-412.
Carnemolla et al., 1996, "Phage antibodies with pan-species recognition of the oncofoetal angiogenesis marker fibronectin ED-B domain," Int. J. Cancer, 68(3):397-405.
Chothia et al., 1987, "Canonical structures for the hypervariable regions of immunoglobulins," J. Mol. Biol., 196(4):901-917.
Da Silva Antunes et al., 2018, "TNFSF14 (LIGHT) Exhibits Inflammatory Activities in Lung Fibroblasts Complementary to IL-13 and TGF-β," Front Immunol., 9:576 (12 pages).
Emsley et al., 2010, "Features and development of Coot," Acta. Crystallogr. D. Biol. Crystallogr., 66(Pt4):486-501.
Fan et al., 2002, "Targeted therapy against human lung cancer in nude mice by high-affinity recombinant antimesothelin single-chain Fv immunotoxin," Mol. Cancer Ther., 1(8):595-600.
Ferrara et al., 2006, "The carbohydrate at FcgammaRIIIa Asn-162. An element required for high affinity binding to non-fucosylated IgG glycoforms," J. Biol. Chem., 281(8):5032-5036 (Epub 2005).
Gerhardt et al., 2009, "Structure of IL-17A in complex with a potent, fully human neutralizing antibody," J. Mol. Biol., 394(5):905-921.
Glockshuber et al., 1990, "A comparison of strategies to stabilize immunoglobulin Fv-fragments" Biochemistry, 29(6):1362-1367.
Gross et al., 1989, "Generation of effector T cells expressing chimeric T cell receptor with antibody type-specificity," Transplant Proc., 21(1 Pt 1):127-130.
Hassan et al., 2008, "Mesothelin targeted cancer immunotherapy," Eur. J. Cancer, 44(1):46-53 (Epub 2007).
Honegger et al., 2001, "Yet another numbering scheme for immunoglobulin variable domains: an automatic modeling and analysis tool," J. Mol. Biol., 309(3):657-670.
International Search Report and Written Opinion for International Patent Application No. PCT/US2020/046303 (Pub. No. WO 2021030657) dated Nov. 30, 2020 (10 pages).
Kabsch, 2010, "XDS," Acta. Crystallogr. D. Biol. Crystallogr., 66(Pt 2):125-132.
Kim et al., 2012, "Disulfide linkage engineering for improving biophysical properties of human VH domains," Protein Eng. Des. Sel., 25(10):581-589.
Knappik et al., 2000, "Fully synthetic human combinatorial antibody libraries (HuCAL) based on modular consensus frameworks and CDRs randomized with trinucleotides," J. Mol. Biol., 296(1):57-86.
Konno et al., 2012, "Fucose content of monoclonal antibodies can be controlled by culture medium osmolality for high antibody-dependent cellular cytotoxicity," Cytotechnology, 64(3):249-265 (Epub 2011).
LeFranc et al., 2003, "IMGT unique numbering for immunoglobulin and T cell receptor variable domains and Ig superfamily V-like domains," Dev. Comp. Immunol., 27(1):55-77.
Lukashev et al., 2006, "Targeting the lymphotoxin-beta receptor with agonist antibodies as a potential cancer therapy," Cancer Res., 66(19):9617-9624.
MacLennan et al., 1998, "Structure-function relationships in the Ca(2+)-binding and translocation domain of SERCA1: physiological correlates in Brody disease," Acta. Physiol. Scand. Suppl., 643:55-67.
Martin et al., 1996, "Structural families in loops of homologous proteins: automatic classification, modelling and application to antibodies" J. Mol. Biol., 263(5):800-815.
Merchant et al., 1998, "An efficient route to human bispecific IgG," Nat. Biotechnol., 16(7):677-681.
Mori et al., 2004. "Engineering Chinese hamster ovary cells to maximize effector function of produced antibodies using FUT8 siRNA," Biotechnol. Bioeng., 88(7):901-908.
Murshudov et al., 1997, "Refinement of macromolecular structures by the maximum-likelihood method," Acta. Crystallogr. D. Biol. Crystallogr., 53(Pt 3):240-255.
NCBI Accession No. NP_001263337.1, "fibronectin isoform b precursor [Mus musculus]," last modified Jul. 27, 2021 (5 pages).
NCBI Accession No. NP_001263338.1, "fibronectin isoform c precursor [Mus musculus]," last modified Jul. 27, 2021 (5 pages).
NCBI Accession No. NP_001263339.1, "fibronectin isoform d precursor [Mus musculus]," last modified Jul. 27, 2021 (5 pages).
NCBI Accession No. NP_001263340.1, "fibronectin isoform e precursor [Mus musculus]," last modified Jul. 27, 2021 (5 pages).
NCBI Accession No. NP_001263341.1, "fibronectin isoform f precursor [Mus musculus]," last modified Jul. 27, 2021 (5 pages).
NCBI Accession No. NP_001293058.2, "fibronectin isoform 8 precursor [Homo sapiens]," last modified Sep. 19, 2021 (6 pages).
NCBI Accession No. NP_001293059.2, "fibronectin isoform 9 precursor [Homo sapiens]," last modified Sep. 19, 2021 (5 pages).
NCBI Accession No. NP_001293060.2, "fibronectin isoform 10 precursor [Homo sapiens]," last modified Sep. 19, 2021 (5 pages).
NCBI Accession No. NP_001293061.2, "fibronectin isoform 11 precursor [Homo sapiens]," last modified Sep. 19, 2021 (5 pages).
NCBI Accession No. NP 002017.1, "fibronectin isoform 3 preproprotein [Homo sapiens]," last modified Mar. 29, 2020 (11 pages).
Olivier et al., 2010, "EB66 cell line, a duck embryonic stem cell-derived substrate for the industrial production of therapeutic monoclonal antibodies with enhanced ADCC activity," Mabs, 2(4):405-415.
Porter et al., 2011, "Chimeric Antigen Receptor Therapy for B-cell Malignancies," J. Cancer, 2:331-332.
Porter et al., 2011, "Chimeric antigen receptor-modified T cells in chronic lymphoid leukemia," N. Engl. J. Med., 365(8):725-733.
Read, 2001, "Pushing the boundaries of molecular replacement with maximum likelihood," Acta. Crystallogr. D. Biol. Crystallogr., 57(Pt 10):1373-1382 and addenda and errata (11 pages).
Reiter et al., 1996, "Engineering antibody Fv fragments for cancer detection and therapy: disulfide-stabilized Fv fragments," Nat. Biotechnol., 14(10):1239-1245.
Ridgway et al., 1996, "'Knobs-into-holes' engineering of antibody CH3 domains for heavy chain heterodimerization," Protein Eng., 9(7):617-621.
Rothlisberger et al., 2005, "Domain interactions in the Fab fragment: a comparative evaluation of the single-chain Fv and Fab format engineered with variable domains of different stability," J. Mol. Biol., 347(4):773-789.
Sasaki et al., 1998, "Structure-mutation analysis of the ATPase site of Dictyostelium discoideum myosin II," Adv. Biophys., 35:1-24.
Shi et al., 2010, "De novo selection of high-affinity antibodies from synthetic fab libraries displayed on phage as pIX fusion proteins," J. Mol. Biol., 397(2):385-396.

(56) References Cited

OTHER PUBLICATIONS

Shields et al., 2002, "Lack of fucose on human IgG1 N-linked oligosaccharide improves binding to human Fcgamma RIII and antibody-dependent cellular toxicity" J. Biol. Chem., 277(30):26733-26740.

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity" J. Biol. Chem., 278(5):3466-3473 (Epub 2002).

Stickler et al., 2011, "The human Glm1 allotype associates with CD4+ T-cell responsiveness to a highly conserved IgG1 constant region peptide and confers an asparaginyl endopeptidase cleavage site," Genes Immun., 12(3):213-221.

Tam et al., 2017, "Functional, Biophysical, and Structural Characterization of Human IgG1 and IgG4 Fc Variants with Ablated Immune Functionality," Antibodies (Basel), 6(3):12 (34 pages).

UniProt Accession No. P02751, "FINC_HUMAN," last modified Jun. 2, 2021 (38 pages).

UniProt Accession No. P02751.5, "FINC_HUMAN," last modified Jun. 17, 2020 (32 pages).

UniProt Accession No. P24821.3, "TENA_HUMAN," last modified Jun. 2, 2021 (14 pages).

Worn et al., 2001, "Stability engineering of antibody single-chain Fv fragments," J. Mol. Biol., 305(5):989-1010.

Wu et al., 1970, "An analysis of the sequences of the variable regions of Bence Jones proteins and myeloma light chains and their implications for antibody complementarity," J. Exp. Med., 132(2):211-250.

Zardi et al., 1987, "Transformed human cells produce a new fibronectin isoform by preferential alternative splicing of a previously unobserved exon" EMBO J., 6(8):2337-2342.

Arndt et al., 2001, "Helix-stabilized Fv (hsFv) antibody fragments: substituting the constant domains of a Fab fragment for a heterodimeric coiled-coil domain", J Mol Biol., 312(1):221-228.

Asial et al., 2013, "Engineering protein thermostability using a generic activity-independent biophysical screen inside the cell", Nat Commun., 4:2901 (8 pages).

Gil et al., 2013, "Strategies to stabilize compact folding and minimize aggregation of antibody-based fragments", Adv Biosci Biotechnol., 4(4a):73-84.

Monsellier et al., 2006, "Improving the stability of an antibody variable fragment by a combination of knowledge-based approaches: validation and mechanisms", J Mol Biol., 362(3):580-593.

Perchiacca et al., 2012, "Engineering aggregation-resistant antibodies", Annu Rev Chem Biomol Eng., 3:263-286.

Filler et al., 2015, "Advances in Antibody Design", Annu Rev Biomed Eng., 17:191-216.

Zhao et al., 2010, "Stabilization of the single-chain fragment variable by an interdomain disulfide bond and its effect on antibody affinity", Int J Mol Sci., 12(1):1-11.

Alberola-Ila et al., 1991, "Stimulation through the TCR/CD3 complex up-regulates the CD2 surface expression on human T lymphocytes," J. Immunol., 146(4):1085-1092.

Bailly et al., 2020, "Predicting Antibody Developability Profiles Through Early Stage Discovery Screening," MAbs, 12(1):e1743053 (28 pages).

Betz, 1993, "Disulfide bonds and the stability of globular proteins," Protein Sci., 2(10):1551-1558.

Dani et al., 2003, "MODIP revisited: re-evaluation and refinement of an automated procedure for modeling of disulfide bonds in proteins," Protein Eng., 16(3):187-193.

Fransson et al., 2010, "Human framework adaptation of a mouse anti-human IL-13 antibody," J. Mol. Biol., 398(2):214-231.

Gekko et al., 2003, "Effects of disulfide bonds on compactness of protein molecules revealed by volume compressibility, and expansibility changes during reduction," Biochemistry, 42(46):13746-13753.

GenBank Accession No. BC058291, "*Homo sapiens* tumor necrosis factor receptor superfamily, member 17, mRNA (cDNA clone MGC:61811 IMAGE:6736094), complete cds," Jul. 15, 2006 (2 pages).

Harris et al., 1997, "Refined structure of an intact IgG2a monoclonal antibody," Biochemishy, 36(7):1581-1597.

Kawasaki et al., 2001, "Presence of four major haplotypes in human BCMA gene: lack of association with systemic lupus erythematosus and rheumatoid arthritis," Genes Immun., 2(5):276-279.

Pessano et al., 1985, "The T3/T cell receptor complex: antigenic distinction between the two 20-kd T3 (T3-delta and T3-epsilon) subunits," EMBO J., 4(2):337-344.

Scapin et al., 2015, "Structure of full-length human anti-PD1 therapeutic IgG4 antibody pembrolizumab," Nat. Struct. Mol. Biol., 22(12):953-958.

Teplyakov et al., 2016, "Structural diversity in a human antibody germline library," MAbs, 8(6):1045-1063.

UniProt Accession No. P36941, "Tumor necrosis factor receptor superfamily member 3 (TNR3_HUMAN)," integrated Jun. 1, 1994, entry version 201, Dec. 14, 2022 (7 pages).

UniProt Accession No. Q02223, "Tumor necrosis factor receptor superfamily member 17 (TNR17_HUMAN)," integrated Jul. 1, 1993, entry version 203, Dec. 14, 2022 (6 pages).

Weatherill et al., 2012, "Towards a universal disulphide stabilised single chain Fv format: importance of interchain disulphide bond location and vL-vH orientation," Protein Eng. Des. Sel., 25(7):321-329.

Zhang et al., 1989, "Dependence of formation of small disulfide loops in two-cysteine peptides on the number and types of intervening amino acids," J. Biol. Chem., 264(31):18472-18479.

\* cited by examiner

VL:

```
                   10         20        30abc        40         50         60
GLk1VL     DIQMTQSPSSLSASVGDRVTITCRASQSIS---SYLNWYQQKPGKAPKLLIYAASSLQSGVPS
GLk2VL     EIVLTQSPGTLSLSPGERATLSCRASQSVSS---SYLAWYQQKPGQAPRLLIYGASSRATGIPD
CAT2200VL  NFMLTQPHS-VSESPGKTVTISCTRSSGSLAN-YYVQWYQQRPGSSPTIVIFANNQRPSGVPD
CAT2200bVL NFMLTQPHS-VSESPGKTVTISCTRSSGSLAN-YYVQWYQQRPGQSPTIVIFANNQRPSGVPD
                                                             1 ab  70         80         90    a  100
GLk1VL     RFSGSG--SGTDFTLTISSLQPEDFATYYCQQSYSTP-LTFGQGTKVEIK
GLk2VL     RFSGSG--SGTDFTLTISRLEPEDFAVYYCQQDYGFP-WTFGQGTKVEIK
CAT2200VL  RFSGSIDSSSNSASLTISGLKTEDEADYYCQTYDPYS-VVFGGGTKLTVL
CAT2200bVL RFSGSIDSSSNSASLTISGLKTEDEADYYCQTYDPYS-VVFGGGTKLTVL
                                                     2
```

```
              10         20         30 ab      40          50 abc      60
GLk1VH    EVQLLESGGGLVQPGGSLRLSCAASGFTFSS--YAMSWVRQAPGKGLEWVSAISG--SGGSTYYA
GLk2VH    EVQLVQSGAEVKKPGESLKISCKGSGYSFTS--YWISWVRQMPGKGLEWMGIIDP--SDSDTRYS
CAT2200aVH EVQLLESGGGLVQPGGSLRLSCAASGFGFSS--YAMSWVRQAPGKGLEWVSAISG--SGGSTYYA
                                                              2

70         80 abc      90         100abcdef          110
GLk1VH    DSVKGRFTISRDNSKNTLYLQMNSLRAEDTAVYYCAKYDGIYGEL----DFWGQGTLVTVSS
GLk2VH    PSFQGQVTISADKSISTAYLQWSSLKASDTAMYYCARGDGSTDL-----DYWGQGTLVTVSS
CAT2200aVH DSVKGRFTISRDNSKNTLYLQMNSLRAEDTAVYYCARDLIHGVT-----RNWGQGTLVTVSS
                                                                   1
```

FIG. 7 spFv-VHVL-unbound vs spFv-VLVH-bound (back)

COVA1484

COVA1485

COVA1486

COVA1487

COVA1480

COVA1481

COVA1482

COVA1483

COVA14107

COVA14108

COVA14133

COVA14136

SEQUENCE LISTING

```
<160> NUMBER OF SEQ ID NOS: 124

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Staple sequence

<400> SEQUENCE: 1

Cys Pro Pro Cys
1

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 4x G4S

<400> SEQUENCE: 2

Gly Gly Gly Gly Ser Gly Gly Gly Ser Gly Gly Gly Gly Ser Gly
1               5                   10                  15

Gly Gly Gly Ser
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 9+4+5

<400> SEQUENCE: 3
```

```
Gly Gly Gly Ser Gly Gly Ser Gly Gly Cys Pro Pro Cys Gly Gly Ser
1               5                   10                  15

Gly Gly

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 6+4+6

<400> SEQUENCE: 4

Gly Gly Gly Ser Gly Gly Cys Pro Pro Cys Gly Gly Gly Ser Gly Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 8+4+4

<400> SEQUENCE: 5

Gly Gly Ser Gly Gly Ser Gly Gly Cys Pro Pro Cys Gly Ser Gly Gly
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 9+4+4

<400> SEQUENCE: 6

Gly Gly Gly Ser Gly Gly Ser Gly Gly Cys Pro Pro Cys Gly Ser Gly
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 9+4+4v2

<400> SEQUENCE: 7

Gly Gly Gly Ser Gly Gly Gly Ser Gly Cys Pro Pro Cys Gly Gly Gly
1               5                   10                  15

Gly

<210> SEQ ID NO 8
<211> LENGTH: 254
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: GLk1 scFv VL-VH

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
            115                 120                 125

Glu Val Gln Leu Leu Glu Ser Gly Gly Gly Leu Val Gln Pro Gly Gly
130                 135                 140

Ser Leu Arg Leu Ser Cys Ala Ala Ser Gly Phe Thr Phe Ser Ser Tyr
145                 150                 155                 160

Ala Met Ser Trp Val Arg Gln Ala Pro Gly Lys Gly Leu Glu Trp Val
                165                 170                 175

Ser Ala Ile Ser Gly Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
210                 215                 220

Ala Lys Tyr Asp Gly Ile Tyr Gly Glu Leu Asp Phe Trp Gly Gln Gly
225                 230                 235                 240

Thr Leu Val Thr Val Ser Ser Gly His His His His His His
                245                 250

<210> SEQ ID NO 9
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk1 spFv VL-VH

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Cys Ala Pro Lys Leu Leu Ile
        35                  40                  45

Tyr Ala Ala Ser Ser Leu Gln Ser Gly Val Pro Ser Arg Phe Ser Gly
```

```
              50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys Arg Gly Gly Gly Ser
                100                 105                 110

Gly Gly Ser Gly Gly Cys Pro Pro Cys Gly Gly Ser Gly Gly Glu Val
                115                 120                 125

Gln Leu Leu Glu Ser Gly Gly Gly Leu Val Gln Pro Gly Gly Ser Leu
            130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
                180                 185                 190

Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Ala Lys
            210                 215                 220

Tyr Asp Gly Ile Tyr Gly Glu Leu Asp Phe Trp Gly Cys Gly Thr Leu
225                 230                 235                 240

Val Thr Val Ser Ser Gly His His His His His
                245                 250

<210> SEQ ID NO 10
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk1 scFv VH-VL

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Asp Gly Ile Tyr Gly Glu Leu Asp Phe Trp Gly Gln Gly
                100                 105                 110

Thr Leu Val Thr Val Ser Ser Ala Gly Gly Gly Gly Ser Gly Gly Gly
            115                 120                 125

Gly Ser Gly Gly Gly Gly Ser Gly Gly Gly Gly Ser Asp Ile Gln Met
            130                 135                 140

Thr Gln Ser Pro Ser Ser Leu Ser Ala Ser Val Gly Asp Arg Val Thr
```

```
145             150             155             160
Ile Thr Cys Arg Ala Ser Gln Ser Ile Ser Ser Tyr Leu Asn Trp Tyr
                165             170             175

Gln Gln Lys Pro Gly Lys Ala Pro Lys Leu Leu Ile Tyr Ala Ala Ser
            180             185             190

Ser Leu Gln Ser Gly Val Pro Ser Arg Phe Ser Gly Ser Gly Ser Gly
            195             200             205

Thr Asp Phe Thr Leu Thr Ile Ser Ser Leu Gln Pro Glu Asp Phe Ala
        210             215             220

Thr Tyr Tyr Cys Gln Gln Ser Tyr Ser Thr Pro Leu Thr Phe Gly Gln
225             230             235             240

Gly Thr Lys Val Glu Ile Lys Arg Gly His His His His His His
                245             250             255

<210> SEQ ID NO 11
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk1 spFv VH-VL

<400> SEQUENCE: 11

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Cys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Tyr Asp Gly Ile Tyr Gly Glu Leu Asp Phe Trp Gly Gln Gly
            100             105             110

Thr Leu Val Thr Val Ser Ser Gly Gly Gly Gly Ser Gly Gly Gly Gly
        115             120             125

Cys Pro Pro Cys Gly Gly Ser Gly Gly Asp Ile Gln Met Thr Gln Ser
    130             135             140

Pro Ser Ser Leu Ser Ala Ser Val Gly Asp Arg Val Thr Ile Thr Cys
145             150             155             160

Arg Ala Ser Gln Ser Ile Ser Ser Tyr Leu Asn Trp Tyr Gln Gln Lys
                165             170             175

Pro Gly Lys Ala Pro Lys Leu Leu Ile Tyr Ala Ala Ser Ser Leu Gln
            180             185             190

Ser Gly Val Pro Ser Arg Phe Ser Gly Ser Gly Ser Gly Thr Asp Phe
        195             200             205

Thr Leu Thr Ile Ser Ser Leu Gln Pro Glu Asp Phe Ala Thr Tyr Tyr
    210             215             220

Cys Gln Gln Ser Tyr Ser Thr Pro Leu Thr Phe Gly Cys Gly Thr Lys
225             230             235             240

Val Glu Ile Lys Arg Gly His His His His His His
```

<210> SEQ ID NO 12
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: GLk2 scFv VL-VH

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Ser Trp Val Arg Gln Met Pro Gly Lys Gly Leu Glu Trp Met
                165                 170                 175

Gly Ile Ile Asp Pro Ser Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg Gly Asp Gly Ser Thr Asp Leu Asp Tyr Trp Gly Gln Gly Thr
225                 230                 235                 240

Leu Val Thr Val Ser Ser Gly His His His His His His
                245                 250

<210> SEQ ID NO 13
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: GLk2 spFv VL-VH

<400> SEQUENCE: 13

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser
                20                  25                  30

Tyr Leu Ala Trp Tyr Gln Gln Lys Pro Gly Cys Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys Gly Gly Gly Ser
            100                 105                 110

Gly Gly Ser Gly Gly Cys Pro Pro Cys Gly Gly Ser Gly Gly Glu Val
        115                 120                 125

Gln Leu Val Gln Ser Gly Ala Glu Val Lys Lys Pro Gly Glu Ser Leu
    130                 135                 140

Lys Ile Ser Cys Lys Gly Ser Gly Tyr Ser Phe Thr Ser Tyr Trp Ile
145                 150                 155                 160

Ser Trp Val Arg Gln Met Pro Gly Lys Gly Leu Glu Trp Met Gly Ile
                165                 170                 175

Ile Asp Pro Ser Asp Ser Asp Thr Arg Tyr Ser Pro Ser Phe Gln Gly
            180                 185                 190

Gln Val Thr Ile Ser Ala Asp Lys Ser Ile Ser Thr Ala Tyr Leu Gln
    195                 200                 205

Trp Ser Ser Leu Lys Ala Ser Asp Thr Ala Met Tyr Tyr Cys Ala Arg
210                 215                 220

Gly Asp Gly Ser Thr Asp Leu Asp Tyr Trp Gly Cys Gly Thr Leu Val
225                 230                 235                 240

Thr Val Ser Ser Gly His His His His His His
                245                 250

<210> SEQ ID NO 14
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk2 scFv VH-VL

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110
```

Leu Val Thr Val Ser Ser Gly Gly Gly Gly Gly Ser
            115                 120                 125

Gly Gly Gly Gly Ser Gly Gly Gly Ser Glu Ile Val Leu Thr Gln
130                 135                 140

Ser Pro Gly Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln
                165                 170                 175

Gln Lys Pro Gly Gln Ala Pro Arg Leu Leu Ile Tyr Gly Ala Ser Ser
                180                 185                 190

Arg Ala Thr Gly Ile Pro Asp Arg Phe Ser Gly Ser Gly Ser Gly Thr
                195                 200                 205

Asp Phe Thr Leu Thr Ile Ser Arg Leu Glu Pro Glu Asp Phe Ala Val
210                 215                 220

Tyr Tyr Cys Gln Gln Asp Tyr Gly Phe Pro Trp Thr Phe Gly Gln Gly
225                 230                 235                 240

Thr Lys Val Glu Ile Lys Gly His His His His His His
                245                 250

<210> SEQ ID NO 15
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk2 spFv VH-VL

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ser Trp Val Arg Gln Met Pro Gly Cys Gly Leu Glu Trp Met
            35                  40                  45

Gly Ile Ile Asp Pro Ser Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser Gly Gly Gly Ser Gly Gly Cys Pro Pro Cys
            115                 120                 125

Gly Gly Gly Ser Gly Gly Glu Ile Val Leu Thr Gln Ser Pro Gly Thr
130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
                180                 185                 190

Ile Pro Asp Arg Phe Ser Gly Ser Gly Ser Gly Thr Asp Phe Thr Leu
            195                 200                 205

```
Thr Ile Ser Arg Leu Glu Pro Glu Asp Phe Ala Val Tyr Tyr Cys Gln
    210                 215                 220
Gln Asp Tyr Gly Phe Pro Trp Thr Phe Gly Cys Gly Thr Lys Val Glu
225                 230                 235                 240
Ile Lys Gly His His His His His His
                245
```

<210> SEQ ID NO 16
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200a scFv VL-VH

<400> SEQUENCE: 16

```
Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Leu Ala Asn Tyr
            20                  25                  30
Tyr Val Gln Trp Tyr Gln Arg Pro Gly Ser Ser Pro Thr Ile Val
        35                  40                  45
Ile Phe Ala Asn Asn Gln Arg Pro Ser Gly Val Pro Asp Arg Phe Ser
    50                  55                  60
Gly Ser Ile Asp Ser Ser Ser Asn Ser Ala Ser Leu Thr Ile Ser Gly
65                  70                  75                  80
Leu Lys Thr Glu Asp Glu Ala Asp Tyr Tyr Cys Gln Thr Tyr Asp Pro
                85                  90                  95
Tyr Ser Val Val Phe Gly Gly Gly Thr Lys Leu Thr Val Leu Gly Gly
            100                 105                 110
Gly Gly Ser Gly Gly Gly Gly Ser Gly Gly Gly Gly Ser Gly Gly Gly
        115                 120                 125
Gly Ser Glu Val Gln Leu Leu Glu Ser Gly Gly Gly Leu Val Gln Pro
    130                 135                 140
Gly Gly Ser Leu Arg Leu Ser Cys Ala Ala Ser Gly Phe Gly Phe Ser
145                 150                 155                 160
Ser Tyr Ala Met Ser Trp Val Arg Gln Ala Pro Gly Lys Gly Leu Glu
                165                 170                 175
Trp Val Ser Ala Ile Ser Gly Ser Gly Gly Ser Thr Tyr Tyr Ala Asp
            180                 185                 190
Ser Val Lys Gly Arg Phe Thr Ile Ser Arg Asp Asn Ser Lys Asn Thr
        195                 200                 205
Leu Tyr Leu Gln Met Asn Ser Leu Arg Ala Glu Asp Thr Ala Val Tyr
    210                 215                 220
Tyr Cys Ala Arg Asp Leu Ile His Gly Val Thr Arg Asn Trp Gly Gln
225                 230                 235                 240
Gly Thr Leu Val Thr Val Ser Ser Gly His His His His His
                245                 250                 255
```

<210> SEQ ID NO 17
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: CAT2200a spFv VL-VH

<400> SEQUENCE: 17

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Cys Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu Gly Gly
            100                 105                 110

Ser Gly Gly Ser Gly Gly Cys Pro Pro Cys Gly Ser Gly Gly Glu Val
        115                 120                 125

Gln Leu Leu Glu Ser Gly Gly Gly Leu Val Gln Pro Gly Gly Ser Leu
    130                 135                 140

Arg Leu Ser Cys Ala Ala Ser Gly Phe Gly Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Asp Leu Ile His Gly Val Thr Arg Asn Trp Gly Cys Gly Thr Leu Val
225                 230                 235                 240

Thr Val Ser Ser Gly His His His His His
                245                 250

<210> SEQ ID NO 18
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200b scFv VL-VH

<400> SEQUENCE: 18

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Gln Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

```
Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu Gly Gly
            100                 105                 110

Gly Gly Ser Gly Gly Gly Gly Ser Gly Gly Gly Ser Gly Gly Gly Gly
        115                 120                 125

Gly Ser Glu Val Gln Leu Leu Glu Ser Gly Gly Gly Leu Val Gln Pro
    130                 135                 140

Gly Gly Ser Leu Arg Leu Ser Cys Ala Ala Ser Gly Phe Gly Phe Ser
145                 150                 155                 160

Ser Tyr Ala Met Ser Trp Val Arg Gln Ala Pro Gly Lys Gly Leu Glu
                165                 170                 175

Trp Val Ser Ala Ile Ser Gly Ser Gly Gly Ser Thr Tyr Tyr Ala Asp
                180                 185                 190

Ser Val Lys Gly Arg Phe Thr Ile Ser Arg Asp Asn Ser Lys Asn Thr
                195                 200                 205

Leu Tyr Leu Gln Met Asn Ser Leu Arg Ala Glu Asp Thr Ala Val Tyr
        210                 215                 220

Tyr Cys Ala Arg Asp Leu Ile His Gly Val Thr Arg Asn Trp Gly Gln
225                 230                 235                 240

Gly Thr Leu Val Thr Val Ser Ser Gly His His His His His
                245                 250                 255

<210> SEQ ID NO 19
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200a spFv VL-VH

<400> SEQUENCE: 19

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
                20                  25                  30

Tyr Val Gln Trp Tyr Gln Gln Arg Pro Gly Cys Ser Pro Thr Ile Val
            35                  40                  45

Ile Phe Ala Asn Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu Gly Gly
            100                 105                 110

Gly Ser Gly Gly Ser Gly Gly Cys Pro Pro Cys Gly Ser Gly Gly Glu
        115                 120                 125

Val Gln Leu Leu Glu Ser Gly Gly Gly Leu Val Gln Pro Gly Gly Ser
    130                 135                 140

Leu Arg Leu Ser Cys Ala Ala Ser Gly Phe Gly Phe Ser Ser Tyr Ala
145                 150                 155                 160

Met Ser Trp Val Arg Gln Ala Pro Gly Lys Gly Leu Glu Trp Val Ser
                165                 170                 175
```

```
Ala Ile Ser Gly Ser Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
210                 215                 220

Arg Asp Leu Ile His Gly Val Thr Arg Asn Trp Gly Cys Gly Thr Leu
225                 230                 235                 240

Val Thr Val Ser Ser Gly His His His His His
                245                 250
```

<210> SEQ ID NO 20
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200a scFv VH-VL

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gly Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Gly Gly Gly Ser Asn Phe Met Leu Thr Gln
    130                 135                 140

Pro His Ser Val Ser Glu Ser Pro Gly Lys Thr Val Thr Ile Ser Cys
145                 150                 155                 160

Thr Arg Ser Ser Gly Ser Leu Ala Asn Tyr Tyr Val Gln Trp Tyr Gln
                165                 170                 175

Gln Arg Pro Gly Ser Ser Pro Thr Ile Val Ile Phe Ala Asn Asn Gln
            180                 185                 190

Arg Pro Ser Gly Val Pro Asp Arg Phe Ser Gly Ser Ile Asp Ser Ser
        195                 200                 205

Ser Asn Ser Ala Ser Leu Thr Ile Ser Gly Leu Lys Thr Glu Asp Glu
    210                 215                 220

Ala Asp Tyr Tyr Cys Gln Thr Tyr Asp Pro Tyr Ser Val Val Phe Gly
225                 230                 235                 240

Gly Gly Thr Lys Leu Thr Val Leu Gly His His His His His
                245                 250                 255
```

<210> SEQ ID NO 21

<211> LENGTH: 252
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CAT2200b spFv VH-VL

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gly Phe Ser Ser Tyr
            20                  25                  30

Ala Met Ser Trp Val Arg Gln Ala Pro Gly Cys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser Gly Gly Ser Gly Gly Ser Gly Cys
        115                 120                 125

Pro Pro Cys Gly Gly Gly Gly Asn Phe Met Leu Thr Gln Pro His Ser
    130                 135                 140

Val Ser Glu Ser Pro Gly Lys Thr Val Thr Ile Ser Cys Thr Arg Ser
145                 150                 155                 160

Ser Gly Ser Leu Ala Asn Tyr Tyr Val Gln Trp Tyr Gln Gln Arg Pro
                165                 170                 175

Gly Gln Ser Pro Thr Ile Val Ile Phe Ala Asn Asn Gln Arg Pro Ser
            180                 185                 190

Gly Val Pro Asp Arg Phe Ser Gly Ser Ile Asp Ser Ser Ser Asn Ser
        195                 200                 205

Ala Ser Leu Thr Ile Ser Gly Leu Lys Thr Glu Asp Glu Ala Asp Tyr
    210                 215                 220

Tyr Cys Gln Thr Tyr Asp Pro Tyr Ser Val Val Phe Gly Cys Gly Thr
225                 230                 235                 240

Lys Leu Thr Val Leu Gly His His His His His
                245                 250
```

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-17A mutant

<400> SEQUENCE: 22

```
Met Asn Ser Glu Asp Lys Asn Phe Pro Arg Thr Val Met Val Asn Leu
1               5                   10                  15

Asn Ile His Asn Arg Asn Thr Asn Thr Asn Pro Lys Arg Ser Ser Asp
            20                  25                  30

Tyr Tyr Asn Arg Ser Thr Ser Pro Trp Asn Leu His Arg Asn Glu Asp
```

```
            35                  40                  45
Pro Glu Arg Tyr Pro Ser Val Ile Trp Glu Ala Gln Cys Arg His Leu
    50                  55                  60

Gly Cys Ile Asn Ala Asp Gly Asn Val Asp Tyr His Met Asn Ser Val
65                  70                  75                  80

Pro Ile Gln Gln Glu Ile Leu Val Leu Arg Glu Pro Pro His Ser
                85                  90                  95

Pro Asn Ser Phe Arg Leu Glu Lys Ile Leu Val Ser Val Gly Cys Thr
            100                 105                 110

Cys Val Thr Pro Ile Val His His Val Gln
        115                 120

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 1
<220> FEATURE:
<221> NAME/KEY: MOD_RES
<222> LOCATION: (2)..(4)
<223> OTHER INFORMATION: Gly, Ser, Pro, Ala, Arg, Asn, Asp, Glu, Gln,
      His, Ile, Leu, Lys, Phe, Thr, Trp, or Tyr
<220> FEATURE:
<221> NAME/KEY: MISC_FEATURE
<222> LOCATION: (2)..(4)
<223> OTHER INFORMATION: This region may encompass 1-3 residues

<400> SEQUENCE: 23

Cys Xaa Xaa Xaa Cys
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 2
<220> FEATURE:
<221> NAME/KEY: MOD_RES
<222> LOCATION: (2)..(4)
<223> OTHER INFORMATION: Gly, Ser or Pro
<220> FEATURE:
<221> NAME/KEY: MISC_FEATURE
<222> LOCATION: (2)..(4)
<223> OTHER INFORMATION: This region may encompass 1-3 residues

<400> SEQUENCE: 24

Cys Xaa Xaa Xaa Cys
1               5

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 3
<220> FEATURE:
<221> NAME/KEY: MOD_RES
<222> LOCATION: (1)..(9)
```

```
<223> OTHER INFORMATION: Gly, Ser, Pro, Ala, Arg, Asn, Asp, Glu, Gln,
      His, Ile, Leu, Lys, Phe, Thr, Trp or Tyr
<220> FEATURE:
<221> NAME/KEY: MISC_FEATURE
<222> LOCATION: (1)..(9)
<223> OTHER INFORMATION: This region may encompass 6-9 residues
<220> FEATURE:
<221> NAME/KEY: MOD_RES
<222> LOCATION: (11)..(13)
<223> OTHER INFORMATION: Gly, Ser, Pro, Ala, Arg, Asn, Asp, Glu, Gln,
      His, Ile, Leu, Lys, Phe, Thr, Trp or Tyr
<220> FEATURE:
<221> NAME/KEY: MISC_FEATURE
<222> LOCATION: (11)..(13)
<223> OTHER INFORMATION: This region may encompass 1-3 residues
<220> FEATURE:
<221> NAME/KEY: MOD_RES
<222> LOCATION: (15)..(20)
<223> OTHER INFORMATION: Gly, Ser, Pro, Ala, Arg, Asn, Asp, Glu, Gln,
      His, Ile, Leu, Lys, Phe, Thr, Trp or Tyr
<220> FEATURE:
<221> NAME/KEY: MISC_FEATURE
<222> LOCATION: (15)..(20)
<223> OTHER INFORMATION: This region may encompass 4-6 residues

<400> SEQUENCE: 25

Xaa Xaa Xaa Xaa Xaa Xaa Xaa Xaa Xaa Cys Xaa Xaa Xaa Cys Xaa Xaa
1               5                   10                  15

Xaa Xaa Xaa Xaa
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 4
<220> FEATURE:
<221> NAME/KEY: MOD_RES
<222> LOCATION: (1)..(9)
<223> OTHER INFORMATION: Gly, Ser, Pro, Ala, Arg, Asn, Asp, Glu, Gln,
      His, Ile, Leu, Lys, Thr or Tyr
<220> FEATURE:
<221> NAME/KEY: MISC_FEATURE
<222> LOCATION: (1)..(9)
<223> OTHER INFORMATION: This region may encompass 6-9 residues
<220> FEATURE:
<221> NAME/KEY: MOD_RES
<222> LOCATION: (11)..(13)
<223> OTHER INFORMATION: Gly, Ser, Pro, Ala, Arg, Asn, Asp, Glu, Gln,
      His, Ile, Leu, Lys, Thr or Tyr
<220> FEATURE:
<221> NAME/KEY: MISC_FEATURE
<222> LOCATION: (11)..(13)
<223> OTHER INFORMATION: This region may encompass 1-3 residues
<220> FEATURE:
<221> NAME/KEY: MOD_RES
<222> LOCATION: (15)..(20)
<223> OTHER INFORMATION: Gly, Ser, Pro, Ala, Arg, Asn, Asp, Glu, Gln,
      His, Ile, Leu, Lys, Thr or Tyr
<220> FEATURE:
<221> NAME/KEY: MISC_FEATURE
<222> LOCATION: (15)..(20)
<223> OTHER INFORMATION: This region may encompass 4-6 residues

<400> SEQUENCE: 26

Xaa Xaa Xaa Xaa Xaa Xaa Xaa Xaa Xaa Cys Xaa Xaa Xaa Cys Xaa Xaa
1               5                   10                  15

Xaa Xaa Xaa Xaa
            20
```

```
<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 5
<220> FEATURE:
<221> NAME/KEY: MOD_RES
<222> LOCATION: (1)..(9)
<223> OTHER INFORMATION: Gly or Pro
<220> FEATURE:
<221> NAME/KEY: MISC_FEATURE
<222> LOCATION: (1)..(9)
<223> OTHER INFORMATION: This region may encompass 6-9 residues
<220> FEATURE:
<221> NAME/KEY: MOD_RES
<222> LOCATION: (11)..(13)
<223> OTHER INFORMATION: Gly or Pro
<220> FEATURE:
<221> NAME/KEY: MISC_FEATURE
<222> LOCATION: (11)..(13)
<223> OTHER INFORMATION: This region may encompass 1-3 residues
<220> FEATURE:
<221> NAME/KEY: MOD_RES
<222> LOCATION: (15)..(20)
<223> OTHER INFORMATION: Gly or Pro
<220> FEATURE:
<221> NAME/KEY: MISC_FEATURE
<222> LOCATION: (15)..(20)
<223> OTHER INFORMATION: This region may encompass 4-6 residues

<400> SEQUENCE: 27

Xaa Xaa Xaa Xaa Xaa Xaa Xaa Xaa Xaa Cys Xaa Xaa Xaa Cys Xaa Xaa
1               5                   10                  15

Xaa Xaa Xaa Xaa
            20

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 6

<400> SEQUENCE: 28

Cys Gly Pro Cys
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 7

<400> SEQUENCE: 29

Cys Pro Gly Cys
1

<210> SEQ ID NO 30
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 8

<400> SEQUENCE: 30

Cys Gly Gly Cys
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 9

<400> SEQUENCE: 31

Cys Ser Pro Gly
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 10

<400> SEQUENCE: 32

Cys Pro Ser Cys
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 11

<400> SEQUENCE: 33

Cys Ser Ser Cys
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 12

<400> SEQUENCE: 34

Cys Gly Ser Cys
1

<210> SEQ ID NO 35
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 13

<400> SEQUENCE: 35

Cys Ser Gly Cys
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 14

<400> SEQUENCE: 36

Cys Pro Pro Pro Cys
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 15

<400> SEQUENCE: 37

Cys Gly Pro Pro Cys
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 16

<400> SEQUENCE: 38

Cys Pro Gly Pro Cys
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 17

<400> SEQUENCE: 39

Cys Pro Pro Gly Cys
1               5

<210> SEQ ID NO 40
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 18

<400> SEQUENCE: 40

Cys Gly Gly Pro Cys
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 19

<400> SEQUENCE: 41

Cys Pro Gly Gly Cys
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 20

<400> SEQUENCE: 42

Cys Gly Gly Gly Cys
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 21

<400> SEQUENCE: 43

Cys Ser Pro Pro Cys
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 22

<400> SEQUENCE: 44

Cys Pro Ser Pro Cys
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 23

<400> SEQUENCE: 45

Cys Pro Pro Ser Cys
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 24

<400> SEQUENCE: 46

Cys Ser Ser Pro Cys
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 25

<400> SEQUENCE: 47

Cys Pro Ser Ser Cys
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 26

<400> SEQUENCE: 48

Cys Ser Ser Ser Cys
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 27

<400> SEQUENCE: 49

Cys Gly Ser Pro Cys
1               5
```

```
<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 28

<400> SEQUENCE: 50

Cys Pro Gly Ser Cys
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 29

<400> SEQUENCE: 51

Cys Ser Gly Pro Cys
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary L 30

<400> SEQUENCE: 52

Cys Pro Ser Gly Cys
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 1xG4S

<400> SEQUENCE: 53

Gly Gly Gly Gly Ser
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker 2xG4S

<400> SEQUENCE: 54

Gly Gly Gly Gly Ser Gly Gly Gly Gly Ser
1               5                   10
```

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: Linker 3x G4S

<400> SEQUENCE: 55

Gly Gly Gly Gly Ser Gly Gly Gly Gly Ser Gly Gly Gly Gly Ser
1               5                   10                  15

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: GLk1VL

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: GLk2VL

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Asp Tyr Gly Phe Pro
            85                  90                  95

Trp Thr Phe Gly Gln Gly Thr Lys Val Glu Ile Lys
            100                 105
```

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200VL

<400> SEQUENCE: 58

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Ser Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu
            100                 105                 110
```

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200bVL

<400> SEQUENCE: 59

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Leu Ala Asn Tyr
            20                  25                  30

Tyr Val Gln Trp Tyr Gln Gln Arg Pro Gly Gln Ser Pro Thr Ile Val
        35                  40                  45

Ile Phe Ala Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Pro
                85                  90                  95

Tyr Ser Val Val Phe Gly Gly Gly Thr Lys Leu Thr Val Leu
            100                 105                 110
```

<210> SEQ ID NO 60
<211> LENGTH: 119
<212> TYPE: PRT
<213> ORGANISM: Artificial Sequence -continued

```
<220> FEATURE:
<223> OTHER INFORMATION: Description of Artificial Sequence: Synthetic
      polypeptide
<220> FEATURE:
<223> OTHER INFORMATION: GLk1VH

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Ile Tyr Gly Glu Leu Asp Phe Trp Gly Gln Gly
            100                 105                 110

Thr Leu Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GLk2VH

<400> SEQUENCE: 61

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser
        115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAT2200aVH
```

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gly Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ile His Gly Val Thr Arg Asn Trp Gly Gln Gly Thr
            100                 105                 110

Leu Val Thr Val Ser Ser
            115

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary IgG1 hinge region 1

<400> SEQUENCE: 63

Glu Pro Lys Ser Cys Asp Lys Thr His Thr Cys Pro Pro Cys Pro
1               5                   10                  15

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Exemplary IgG1 hinge region 2

<400> SEQUENCE: 64

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: IgG2 hinge

<400> SEQUENCE: 65

Glu Arg Lys Cys Cys Val Glu Cys Pro Pro Cys Pro
1               5                   10

```
<210> SEQ ID NO 66
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Wild-type IgG1

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 326
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Wild-type IgG2

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 68
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Wild-type IgG4

<400> SEQUENCE: 68

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 69
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH BHA10

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser
            115
```

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL BHA10

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Lys Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys
            100                 105
```

<210> SEQ ID NO 71
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH L19

<400> SEQUENCE: 71

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

```
Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
             100                 105                 110

Thr Val Ser Ser
         115

<210> SEQ ID NO 72
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL L19

<400> SEQUENCE: 72

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Phe Leu Ala Trp Tyr Gln Gln Lys Pro Gly Gln Ala Pro Arg Leu Leu
         35                  40                  45

Ile Tyr Tyr Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Gly Arg Ile Pro
                 85                  90                  95

Pro Thr Phe Gly Gln Gly Thr Lys Val Glu Ile Lys
             100                 105

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH B21M

<400> SEQUENCE: 73

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Ala Leu Glu
         35                  40                  45

Trp Leu Ala His Ile Tyr Trp Asp Asp Lys Arg Tyr Asn Pro Ser
 50                  55                  60

Leu Lys Ser Arg Leu Thr Ile Thr Lys Asp Thr Ser Lys Asn Gln Val
```

```
                65                  70                  75                  80
Val Leu Thr Met Thr Asn Met Asp Pro Val Asp Thr Ala Thr Tyr Tyr
                    85                  90                  95

Cys Ala Arg Leu Tyr Gly Phe Thr Tyr Gly Phe Ala Tyr Trp Gly Gln
                    100                 105                 110

Gly Thr Leu Val Thr Val Ser Ser
                    115                 120
```

<210> SEQ ID NO 74
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL B21M

<400> SEQUENCE: 74

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
                20                  25                  30

Gly Ile Ser Tyr Met His Trp Tyr Gln Gln Lys Pro Gly Gln Pro Pro
            35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys
                100                 105                 110
```

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH MSLNmAb1

<400> SEQUENCE: 75

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
                100                 105                 110
```

Thr Pro Val Thr Val Ser Ser
            115

<210> SEQ ID NO 76
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL MSLNmAb1

<400> SEQUENCE: 76

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105

<210> SEQ ID NO 77
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv BHA10 (VH-VL)

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Cys Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Ser Gly Gly Ser Gly Cys Pro Pro
            115                 120                 125

Cys Gly Gly Gly Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

```
Asn Val Gly Ile Asn Val Ala Trp Tyr Gln Gln Lys Pro Gly Lys Ala
                165                 170                 175

Pro Lys Ser Leu Ile Ser Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Phe Cys Gln Gln Tyr
    210                 215                 220

Asp Thr Tyr Pro Phe Thr Phe Gly Cys Gly Thr Lys Val Glu Ile Lys
225                 230                 235                 240

<210> SEQ ID NO 78
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M N-term stapled BHA10 (VH-VL), IgG1s,
      knob, with pA mutations

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Cys Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Ser Gly Cys Pro Pro
        115                 120                 125

Cys Gly Gly Gly Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asn Val Gly Ile Asn Val Ala Trp Tyr Gln Gln Lys Pro Gly Lys Ala
                165                 170                 175

Pro Lys Ser Leu Ile Ser Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Phe Cys Gln Gln Tyr
    210                 215                 220

Asp Thr Tyr Pro Phe Thr Phe Gly Cys Gly Thr Lys Val Glu Ile Lys
225                 230                 235                 240

Gly Gly Gly Gly Ser Gly Gly Gly Ser Gly Gly Gly Ser
                245                 250                 255

Gly Gly Gly Ser Gly Gly Gly Gly Ser Gln Ile Thr Leu Lys Glu Ser
```

-continued

```
            260                 265                 270
Gly Pro Thr Leu Val Lys Pro Thr Gln Thr Leu Thr Leu Thr Cys Thr
            275                 280                 285
Phe Ser Gly Phe Ser Leu Ser Thr Ser Gly Met Gly Val Ser Trp Ile
            290                 295                 300
Arg Gln Pro Pro Gly Lys Ala Leu Glu Trp Leu Ala His Ile Tyr Trp
305                 310                 315                 320
Asp Asp Asp Lys Arg Tyr Asn Pro Ser Leu Lys Ser Arg Leu Thr Ile
                325                 330                 335
Thr Lys Asp Thr Ser Lys Asn Gln Val Val Leu Thr Met Thr Asn Met
            340                 345                 350
Asp Pro Val Asp Thr Ala Thr Tyr Tyr Cys Ala Arg Leu Tyr Gly Phe
            355                 360                 365
Thr Tyr Gly Phe Ala Tyr Trp Gly Gln Gly Thr Leu Val Thr Val Ser
            370                 375                 380
Ser Ala Ser Thr Lys Gly Pro Ser Val Phe Pro Leu Ala Pro Ser Ser
385                 390                 395                 400
Lys Ser Thr Ser Gly Gly Thr Ala Ala Leu Gly Cys Leu Val Lys Asp
                405                 410                 415
Tyr Phe Pro Glu Pro Val Thr Val Ser Trp Asn Ser Gly Ala Leu Thr
            420                 425                 430
Ser Gly Val His Thr Phe Pro Ala Val Leu Gln Ser Ser Gly Leu Tyr
            435                 440                 445
Ser Leu Ser Ser Val Val Thr Val Pro Ser Ser Ser Leu Gly Thr Gln
            450                 455                 460
Thr Tyr Ile Cys Asn Val Asn His Lys Pro Ser Asn Thr Lys Val Asp
465                 470                 475                 480
Lys Lys Val Glu Pro Lys Ser Cys Asp Lys Thr His Thr Cys Pro Pro
                485                 490                 495
Cys Pro Ala Pro Glu Ala Ala Gly Ala Ser Ser Val Phe Leu Phe Pro
            500                 505                 510
Pro Lys Pro Lys Asp Thr Leu Met Ile Ser Arg Thr Pro Glu Val Thr
            515                 520                 525
Cys Val Val Val Asp Val Ser Ala Glu Asp Pro Glu Val Lys Phe Asn
            530                 535                 540
Trp Tyr Val Asp Gly Val Glu Val His Asn Ala Lys Thr Lys Pro Arg
545                 550                 555                 560
Glu Glu Gln Tyr Asn Ser Thr Tyr Arg Val Val Ser Val Leu Thr Val
                565                 570                 575
Leu His Gln Asp Trp Leu Asn Gly Lys Glu Tyr Lys Cys Lys Val Ser
            580                 585                 590
Asn Lys Ala Leu Pro Ser Ser Ile Glu Lys Thr Ile Ser Lys Ala Lys
            595                 600                 605
Gly Gln Pro Arg Glu Pro Gln Val Tyr Thr Leu Pro Pro Cys Arg Glu
            610                 615                 620
Glu Met Thr Lys Asn Gln Val Ser Leu Trp Cys Leu Val Lys Gly Phe
625                 630                 635                 640
Tyr Pro Ser Asp Ile Ala Val Glu Trp Glu Ser Asn Gly Gln Pro Glu
                645                 650                 655
Asn Asn Tyr Lys Thr Thr Pro Pro Val Leu Asp Ser Asp Gly Ser Phe
            660                 665                 670
Phe Leu Tyr Ser Lys Leu Thr Val Asp Lys Ser Arg Trp Gln Gln Gly
            675                 680                 685
```

-continued

```
Asn Val Phe Ser Cys Ser Val Met His Glu Ala Leu His Asn Arg Phe
    690                 695                 700

Thr Gln Lys Ser Leu Ser Leu Ser Pro Gly Lys
705                 710                 715

<210> SEQ ID NO 79
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M (RSV) IgG1s knob with pA mutations

<400> SEQUENCE: 79

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 80
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M (RSV) IgG1s hole

<400> SEQUENCE: 80

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 81
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC B21M (RSV)

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

```
Glu Asp Pro Trp Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 82
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv BHA10 (VL-VH)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Cys Ala Pro Lys Ser Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Gly Gly Ser Gly Gly
            100                 105                 110

Ser Gly Gly Cys Pro Pro Cys Gly Ser Gly Gly Gln Val Gln Leu Val
        115                 120                 125

Gln Ser Gly Ala Glu Val Lys Lys Pro Gly Ser Ser Val Lys Val Ser
    130                 135                 140

Cys Lys Ala Ser Gly Tyr Thr Phe Thr Thr Tyr Tyr Leu His Trp Val
145                 150                 155                 160

Arg Gln Ala Pro Gly Gln Gly Leu Glu Trp Met Gly Trp Ile Tyr Pro
                165                 170                 175

Gly Asn Val His Ala Gln Tyr Asn Glu Lys Phe Lys Gly Arg Val Thr
            180                 185                 190

Ile Thr Ala Asp Lys Ser Thr Ser Thr Ala Tyr Met Glu Leu Ser Ser
        195                 200                 205

Leu Arg Ser Glu Asp Thr Ala Val Tyr Tyr Cys Ala Arg Ser Trp Glu
    210                 215                 220
```

-continued

```
Gly Phe Pro Tyr Trp Gly Cys Gly Thr Thr Val Thr Val Ser Ser
225                 230                 235

<210> SEQ ID NO 83
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HCB21M N-term stapled BHA10 (VL-VH), IgG1s,
      knob, with pA mutations

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Cys Ala Pro Lys Ser Leu Ile
        35                  40                  45

Ser Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Gly Gly Ser Gly Gly
            100                 105                 110

Ser Gly Gly Cys Pro Pro Cys Gly Ser Gly Gly Gln Val Gln Leu Val
        115                 120                 125

Gln Ser Gly Ala Glu Val Lys Lys Pro Gly Ser Ser Val Lys Val Ser
130                 135                 140

Cys Lys Ala Ser Gly Tyr Thr Phe Thr Thr Tyr Tyr Leu His Trp Val
145                 150                 155                 160

Arg Gln Ala Pro Gly Gln Gly Leu Glu Trp Met Gly Trp Ile Tyr Pro
                165                 170                 175

Gly Asn Val His Ala Gln Tyr Asn Glu Lys Phe Lys Gly Arg Val Thr
            180                 185                 190

Ile Thr Ala Asp Lys Ser Thr Ser Thr Ala Tyr Met Glu Leu Ser Ser
        195                 200                 205

Leu Arg Ser Glu Asp Thr Ala Val Tyr Tyr Cys Ala Arg Ser Trp Glu
210                 215                 220

Gly Phe Pro Tyr Trp Gly Cys Gly Thr Thr Val Thr Val Ser Ser Gly
225                 230                 235                 240

Gly Gly Ser Gly Gly Gly Gly Ser Gly Gly Gly Ser Gly Gly
                245                 250                 255

Gly Gly Ser Gly Gly Gly Ser Gln Ile Thr Leu Lys Glu Ser Gly
            260                 265                 270

Pro Thr Leu Val Lys Pro Thr Gln Thr Leu Thr Leu Thr Cys Thr Phe
            275                 280                 285

Ser Gly Phe Ser Leu Ser Thr Ser Gly Met Gly Val Ser Trp Ile Arg
        290                 295                 300

Gln Pro Pro Gly Lys Ala Leu Glu Trp Leu Ala His Ile Tyr Trp Asp
305                 310                 315                 320

Asp Asp Lys Arg Tyr Asn Pro Ser Leu Lys Ser Arg Leu Thr Ile Thr
```

325                 330                 335
Lys Asp Thr Ser Lys Asn Gln Val Val Leu Thr Met Thr Asn Met Asp
            340                 345                 350

Pro Val Asp Thr Ala Thr Tyr Tyr Cys Ala Arg Leu Tyr Gly Phe Thr
        355                 360                 365

Tyr Gly Phe Ala Tyr Trp Gly Gln Gly Thr Leu Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Lys Val Glu Pro Lys Ser Cys Asp Lys Thr His Thr Cys Pro Pro Cys
                485                 490                 495

Pro Ala Pro Glu Ala Ala Gly Ala Ser Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser Ala Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ser Ser Ile Glu Lys Thr Ile Ser Lys Ala Lys Gly
        595                 600                 605

Gln Pro Arg Glu Pro Gln Val Tyr Thr Leu Pro Pro Cys Arg Glu Glu
    610                 615                 620

Met Thr Lys Asn Gln Val Ser Leu Trp Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn Arg Phe Thr
    690                 695                 700

Gln Lys Ser Leu Ser Leu Ser Pro Gly Lys
705                 710

<210> SEQ ID NO 84
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M C-term stapled BHA (VH-VL), IgG1s,
      knob, with pA mutations

<400> SEQUENCE: 84

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Ala Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
        355                 360                 365

Trp Cys Leu Val Lys Gly Phe Tyr Pro Ser Asp Ile Ala Val Glu Trp

```
                    370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn Arg Phe Thr Gln Lys Ser Leu Ser Leu Ser Pro
            435                 440                 445

Gly Lys Gly Gly Gly Gly Ser Gly Gly Gly Gly Ser Gly Gly Gly Gly
450                 455                 460

Ser Gln Val Gln Leu Val Gln Ser Gly Ala Glu Val Lys Lys Pro Gly
465                 470                 475                 480

Ser Ser Val Lys Val Ser Cys Lys Ala Ser Gly Tyr Thr Phe Thr Thr
                485                 490                 495

Tyr Tyr Leu His Trp Val Arg Gln Ala Pro Gly Cys Gly Leu Glu Trp
                500                 505                 510

Met Gly Trp Ile Tyr Pro Gly Asn Val His Ala Gln Tyr Asn Glu Lys
            515                 520                 525

Phe Lys Gly Arg Val Thr Ile Thr Ala Asp Lys Ser Thr Ser Thr Ala
530                 535                 540

Tyr Met Glu Leu Ser Ser Leu Arg Ser Glu Asp Thr Ala Val Tyr Tyr
545                 550                 555                 560

Cys Ala Arg Ser Trp Glu Gly Phe Pro Tyr Trp Gly Gln Gly Thr Thr
                565                 570                 575

Val Thr Val Ser Ser Gly Gly Ser Gly Gly Ser Gly Cys Pro
                580                 585                 590

Pro Cys Gly Gly Gly Asp Ile Gln Met Thr Gln Ser Pro Ser Ser
            595                 600                 605

Leu Ser Ala Ser Val Gly Asp Arg Val Thr Ile Thr Cys Lys Ala Ser
            610                 615                 620

Gln Asn Val Gly Ile Asn Val Ala Trp Tyr Gln Gln Lys Pro Gly Lys
625                 630                 635                 640

Ala Pro Lys Ser Leu Ile Ser Ser Ala Ser Tyr Arg Tyr Ser Gly Val
                645                 650                 655

Pro Ser Arg Phe Ser Gly Ser Gly Ser Gly Thr Asp Phe Thr Leu Thr
                660                 665                 670

Ile Ser Ser Leu Gln Pro Glu Asp Phe Ala Thr Tyr Phe Cys Gln Gln
            675                 680                 685

Tyr Asp Thr Tyr Pro Phe Thr Phe Gly Cys Gly Thr Lys Val Glu Ile
            690                 695                 700

Lys
705

<210> SEQ ID NO 85
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M C-term stapled BHA (VL-VH), IgG1s,
      knob, with pA mutations

<400> SEQUENCE: 85
```

```
Gln Ile Thr Leu Lys Glu Ser Gly Pro Thr Leu Val Lys Pro Gln
  1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Ala Leu Glu
             35                  40                  45

Trp Leu Ala His Ile Tyr Trp Asp Asp Lys Arg Tyr Asn Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
             85                  90                  95

Cys Ala Arg Leu Tyr Gly Phe Thr Tyr Gly Phe Ala Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
             130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
             210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser Ala Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
             290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
             325                 330                 335

Lys Thr Ile Ser Lys Ala Lys Gly Gln Pro Arg Glu Pro Gln Val Tyr
             340                 345                 350

Thr Leu Pro Pro Cys Arg Glu Glu Met Thr Lys Asn Gln Val Ser Leu
             355                 360                 365

Trp Cys Leu Val Lys Gly Phe Tyr Pro Ser Asp Ile Ala Val Glu Trp
             370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
             405                 410                 415

Lys Ser Arg Trp Gln Gln Gly Asn Val Phe Ser Cys Ser Val Met His
```

```
                420             425             430
Glu Ala Leu His Asn Arg Phe Thr Gln Lys Ser Leu Ser Leu Ser Pro
            435                 440                 445
Gly Lys Gly Gly Gly Gly Ser Gly Gly Gly Gly Ser Gly Gly Gly Gly
        450                 455                 460
Ser Asp Ile Gln Met Thr Gln Ser Pro Ser Ser Leu Ser Ala Ser Val
465                 470                 475                 480
Gly Asp Arg Val Thr Ile Thr Cys Lys Ala Ser Gln Asn Val Gly Ile
                485                 490                 495
Asn Val Ala Trp Tyr Gln Gln Lys Pro Gly Cys Ala Pro Lys Ser Leu
            500                 505                 510
Ile Ser Ser Ala Ser Tyr Arg Tyr Ser Gly Val Pro Ser Arg Phe Ser
        515                 520                 525
Gly Ser Gly Ser Gly Thr Asp Phe Thr Leu Thr Ile Ser Ser Leu Gln
    530                 535                 540
Pro Glu Asp Phe Ala Thr Tyr Phe Cys Gln Gln Tyr Asp Thr Tyr Pro
545                 550                 555                 560
Phe Thr Phe Gly Gln Gly Thr Lys Val Glu Ile Lys Gly Gly Ser Gly
                565                 570                 575
Gly Ser Gly Gly Cys Pro Pro Cys Gly Ser Gly Gly Gln Val Gln Leu
            580                 585                 590
Val Gln Ser Gly Ala Glu Val Lys Lys Pro Gly Ser Ser Val Lys Val
        595                 600                 605
Ser Cys Lys Ala Ser Gly Tyr Thr Phe Thr Thr Tyr Tyr Leu His Trp
    610                 615                 620
Val Arg Gln Ala Pro Gly Gln Gly Leu Glu Trp Met Gly Trp Ile Tyr
625                 630                 635                 640
Pro Gly Asn Val His Ala Gln Tyr Asn Glu Lys Phe Lys Gly Arg Val
                645                 650                 655
Thr Ile Thr Ala Asp Lys Ser Thr Ser Thr Ala Tyr Met Glu Leu Ser
            660                 665                 670
Ser Leu Arg Ser Glu Asp Thr Ala Val Tyr Tyr Cys Ala Arg Ser Trp
        675                 680                 685
Glu Gly Phe Pro Tyr Trp Gly Cys Gly Thr Thr Val Thr Val Ser Ser
    690                 695                 700

<210> SEQ ID NO 86
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 N-term stapled BHA10 (VH-VL), IgG1s,
      knob, with pA mutations

<400> SEQUENCE: 86

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Thr Tyr
            20                  25                  30
Tyr Leu His Trp Val Arg Gln Ala Pro Gly Cys Gly Leu Glu Trp Met
        35                  40                  45
Gly Trp Ile Tyr Pro Gly Asn Val His Ala Gln Tyr Asn Glu Lys Phe
    50                  55                  60
```

-continued

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Gly Ser Gly Cys Pro Pro
        115                 120                 125

Cys Gly Gly Gly Gly Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asn Val Gly Ile Asn Val Ala Trp Tyr Gln Gln Lys Pro Gly Lys Ala
                165                 170                 175

Pro Lys Ser Leu Ile Ser Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Phe Cys Gln Gln Tyr
    210                 215                 220

Asp Thr Tyr Pro Phe Thr Phe Gly Cys Gly Thr Lys Val Glu Ile Lys
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Glu Val Gln Leu Leu Glu Ser
            260                 265                 270

Gly Gly Gly Leu Val Gln Pro Gly Gly Ser Leu Arg Leu Ser Cys Ala
        275                 280                 285

Ala Ser Gly Phe Thr Phe Ser Ser Phe Ser Met Ser Trp Val Arg Gln
    290                 295                 300

Ala Pro Gly Lys Gly Leu Glu Trp Val Ser Ser Ile Ser Gly Ser Ser
305                 310                 315                 320

Gly Thr Thr Tyr Tyr Ala Asp Ser Val Lys Gly Arg Phe Thr Ile Ser
                325                 330                 335

Arg Asp Asn Ser Lys Asn Thr Leu Tyr Leu Gln Met Asn Ser Leu Arg
            340                 345                 350

Ala Glu Asp Thr Ala Val Tyr Tyr Cys Ala Lys Pro Phe Pro Tyr Phe
        355                 360                 365

Asp Tyr Trp Gly Gln Gly Thr Leu Val Thr Val Ser Ser Ala Ser Thr
    370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415

Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
        435                 440                 445

Val Val Thr Val Pro Ser Ser Ser Leu Gly Thr Gln Thr Tyr Ile Cys
    450                 455                 460

Asn Val Asn His Lys Pro Ser Asn Thr Lys Val Asp Lys Lys Val Glu
465                 470                 475                 480

Pro Lys Ser Cys Asp Lys Thr His Thr Cys Pro Pro Cys Pro Ala Pro 485                 490                 495

Glu Ala Ala Gly Ala Ser Ser Val Phe Leu Phe Pro Pro Lys Pro Lys
                500                 505                 510

Asp Thr Leu Met Ile Ser Arg Thr Pro Glu Val Thr Cys Val Val Val
            515                 520                 525

Asp Val Ser Ala Glu Asp Pro Glu Val Lys Phe Asn Trp Tyr Val Asp
530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ser Ser Ile Glu Lys Thr Ile Ser Lys Ala Lys Gly Gln Pro Arg
        595                 600                 605

Glu Pro Gln Val Tyr Thr Leu Pro Pro Cys Arg Glu Glu Met Thr Lys
    610                 615                 620

Asn Gln Val Ser Leu Trp Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn Arg Phe Thr Gln Lys Ser
    690                 695                 700

Leu Ser Leu Ser Pro Gly Lys
705                 710

<210> SEQ ID NO 87
<211> LENGTH: 445
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: HC L19 IgG1s knob with pA mutations

<400> SEQUENCE: 87

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Phe Ser
            20                  25                  30

Met Ser Trp Val Arg Gln Ala Pro Gly Lys Gly Leu Glu Trp Val Ser
        35                  40                  45

Ser Ile Ser Gly Ser Ser Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Pro Phe Pro Tyr Phe Asp Tyr Trp Gly Gln Gly Thr Leu Val Thr
            100                 105                 110

Val Ser Ser Ala Ser Thr Lys Gly Pro Ser Val Phe Pro Leu Ala Pro

-continued

```
                115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
    210                 215                 220
Pro Pro Cys Pro Ala Pro Glu Ala Ala Gly Ala Ser Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Ala Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ser Ser Ile Glu Lys Thr Ile Ser Lys
                325                 330                 335
Ala Lys Gly Gln Pro Arg Glu Pro Gln Val Tyr Thr Leu Pro Pro Cys
            340                 345                 350
Arg Glu Glu Met Thr Lys Asn Gln Val Ser Leu Trp Cys Leu Val Lys
            355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
Arg Phe Thr Gln Lys Ser Leu Ser Leu Ser Pro Gly Lys
            435                 440                 445

<210> SEQ ID NO 88
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 IgG1s hole

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
```

```
             20                  25                  30
Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
            325                 330                 335

Lys Ala Lys Gly Gln Pro Arg Glu Pro Gln Val Cys Thr Leu Pro Pro
            340                 345                 350

Ser Arg Glu Glu Met Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 89
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC L19

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 90
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 N-term stapled BHA10 (VL-VH), IgG1s,
      knob, with pA mutations

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Cys Ala Pro Lys Ser Leu Ile
        35                  40                  45

-continued

```
Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
                85                  90                  95

Thr Phe Gly Gln Gly Thr Lys Val Glu Ile Lys Gly Gly Ser Gly Gly
            100                 105                 110

Ser Gly Gly Cys Pro Pro Cys Gly Ser Gly Gln Val Gln Leu Val
            115                 120                 125

Gln Ser Gly Ala Glu Val Lys Lys Pro Gly Ser Ser Val Lys Val Ser
    130                 135                 140

Cys Lys Ala Ser Gly Tyr Thr Phe Thr Thr Tyr Tyr Leu His Trp Val
145                 150                 155                 160

Arg Gln Ala Pro Gly Gln Gly Leu Glu Trp Met Gly Trp Ile Tyr Pro
                165                 170                 175

Gly Asn Val His Ala Gln Tyr Asn Glu Lys Phe Lys Gly Arg Val Thr
            180                 185                 190

Ile Thr Ala Asp Lys Ser Thr Ser Thr Ala Tyr Met Glu Leu Ser Ser
            195                 200                 205

Leu Arg Ser Glu Asp Thr Ala Val Tyr Tyr Cys Ala Arg Ser Trp Glu
    210                 215                 220

Gly Phe Pro Tyr Trp Gly Cys Gly Thr Thr Val Thr Val Ser Ser Gly
225                 230                 235                 240

Gly Gly Gly Ser Gly Gly Gly Ser Gly Gly Gly Ser Gly Gly
                245                 250                 255

Gly Gly Ser Gly Gly Gly Gly Ser Glu Val Gln Leu Leu Glu Ser Gly
            260                 265                 270

Gly Gly Leu Val Gln Pro Gly Gly Ser Leu Arg Leu Ser Cys Ala Ala
    275                 280                 285

Ser Gly Phe Thr Phe Ser Ser Phe Ser Met Ser Trp Val Arg Gln Ala
    290                 295                 300

Pro Gly Lys Gly Leu Glu Trp Val Ser Ser Ile Ser Gly Ser Ser Gly
305                 310                 315                 320

Thr Thr Tyr Tyr Ala Asp Ser Val Lys Gly Arg Phe Thr Ile Ser Arg
                325                 330                 335

Asp Asn Ser Lys Asn Thr Leu Tyr Leu Gln Met Asn Ser Leu Arg Ala
            340                 345                 350

Glu Asp Thr Ala Val Tyr Tyr Cys Ala Lys Pro Phe Pro Tyr Phe Asp
            355                 360                 365

Tyr Trp Gly Gln Gly Thr Leu Val Thr Val Ser Ser Ala Ser Thr Lys
370                 375                 380

Gly Pro Ser Val Phe Pro Leu Ala Pro Ser Ser Lys Ser Thr Ser Gly
385                 390                 395                 400

Gly Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
            420                 425                 430

Phe Pro Ala Val Leu Gln Ser Ser Gly Leu Tyr Ser Leu Ser Ser Val
            435                 440                 445

Val Thr Val Pro Ser Ser Leu Gly Thr Gln Thr Tyr Ile Cys Asn
    450                 455                 460

Val Asn His Lys Pro Ser Asn Thr Lys Val Asp Lys Lys Val Glu Pro
```

```
                465                 470                 475                 480

Lys Ser Cys Asp Lys Thr His Thr Cys Pro Pro Cys Pro Ala Pro Glu
                    485                 490                 495

Ala Ala Gly Ala Ser Ser Val Phe Leu Phe Pro Pro Lys Pro Lys Asp
                500                 505                 510

Thr Leu Met Ile Ser Arg Thr Pro Glu Val Thr Cys Val Val Val Asp
                515                 520                 525

Val Ser Ala Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
                580                 585                 590

Ser Ser Ile Glu Lys Thr Ile Ser Lys Ala Lys Gly Gln Pro Arg Glu
                595                 600                 605

Pro Gln Val Tyr Thr Leu Pro Pro Cys Arg Glu Glu Met Thr Lys Asn
    610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
                660                 665                 670

Leu Thr Val Asp Lys Ser Arg Trp Gln Gln Gly Asn Val Phe Ser Cys
                675                 680                 685

Ser Val Met His Glu Ala Leu His Asn Arg Phe Thr Gln Lys Ser Leu
                690                 695                 700

Ser Leu Ser Pro Gly Lys
705                 710

<210> SEQ ID NO 91
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 C-term stapled BHA10 (VH-VL), IgG1s,
      knob, with pA mutations

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
                35                  40                  45

Ser Ser Ile Ser Gly Ser Ser Gly Thr Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn Arg Phe Thr Gln Lys Ser Leu Ser Leu Ser Pro Gly Lys Gly Gly
        435                 440                 445

Gly Gly Ser Gly Gly Gly Ser Gly Gly Gly Ser Gln Val Gln
    450                 455                 460

Leu Val Gln Ser Gly Ala Glu Val Lys Lys Pro Gly Ser Ser Val Lys
465                 470                 475                 480

Val Ser Cys Lys Ala Ser Gly Tyr Thr Phe Thr Thr Tyr Tyr Leu His
                485                 490                 495

Trp Val Arg Gln Ala Pro Gly Cys Gly Leu Glu Trp Met Gly Trp Ile
            500                 505                 510

Tyr Pro Gly Asn Val His Ala Gln Tyr Asn Glu Lys Phe Lys Gly Arg
```

```
                515                 520                 525
Val Thr Ile Thr Ala Asp Lys Ser Thr Ser Thr Ala Tyr Met Glu Leu
        530                 535                 540

Ser Ser Leu Arg Ser Glu Asp Thr Ala Val Tyr Tyr Cys Ala Arg Ser
545                 550                 555                 560

Trp Glu Gly Phe Pro Tyr Trp Gly Gln Gly Thr Thr Val Thr Val Ser
                565                 570                 575

Ser Gly Gly Gly Ser Gly Gly Gly Ser Gly Cys Pro Pro Cys Gly Gly
            580                 585                 590

Gly Gly Asp Ile Gln Met Thr Gln Ser Pro Ser Ser Leu Ser Ala Ser
            595                 600                 605

Val Gly Asp Arg Val Thr Ile Thr Cys Lys Ala Ser Gln Asn Val Gly
        610                 615                 620

Ile Asn Val Ala Trp Tyr Gln Gln Lys Pro Gly Lys Ala Pro Lys Ser
625                 630                 635                 640

Leu Ile Ser Ser Ala Ser Tyr Arg Tyr Ser Gly Val Pro Ser Arg Phe
                645                 650                 655

Ser Gly Ser Gly Ser Gly Thr Asp Phe Thr Leu Thr Ile Ser Ser Leu
            660                 665                 670

Gln Pro Glu Asp Phe Ala Thr Tyr Phe Cys Gln Gln Tyr Asp Thr Tyr
            675                 680                 685

Pro Phe Thr Phe Gly Cys Gly Thr Lys Val Glu Ile Lys
        690                 695                 700

<210> SEQ ID NO 92
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 C-term stapled BHA10 (VL-VH), IgG1s,
      knob, with pA mutations

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Cys Arg Glu Glu Met Thr Lys Asn Gln Val Ser Leu Trp Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn Arg Phe Thr Gln Lys Ser Leu Ser Leu Ser Pro Gly Lys Gly Gly
            435                 440                 445

Gly Gly Ser Gly Gly Gly Ser Gly Gly Gly Ser Asp Ile Gln
            450                 455                 460

Met Thr Gln Ser Pro Ser Ser Leu Ser Ala Ser Val Gly Asp Arg Val
465                 470                 475                 480

Thr Ile Thr Cys Lys Ala Ser Gln Asn Val Gly Ile Asn Val Ala Trp
            485                 490                 495

Tyr Gln Gln Lys Pro Gly Cys Ala Pro Lys Ser Leu Ile Ser Ser Ala
            500                 505                 510

Ser Tyr Arg Tyr Ser Gly Val Pro Ser Arg Phe Ser Gly Ser Gly Ser
            515                 520                 525

Gly Thr Asp Phe Thr Leu Thr Ile Ser Ser Leu Gln Pro Glu Asp Phe
            530                 535                 540

Ala Thr Tyr Phe Cys Gln Gln Tyr Asp Thr Tyr Pro Phe Thr Phe Gly
545                 550                 555                 560

Gln Gly Thr Lys Val Glu Ile Lys Gly Gly Ser Gly Gly Ser Gly Gly
            565                 570                 575

Cys Pro Pro Cys Gly Ser Gly Gly Gln Val Gln Leu Val Gln Ser Gly
```

```
                580              585              590
Ala Glu Val Lys Lys Pro Gly Ser Ser Val Lys Val Ser Cys Lys Ala
                    595              600              605

Ser Gly Tyr Thr Phe Thr Thr Tyr Tyr Leu His Trp Val Arg Gln Ala
        610              615              620

Pro Gly Gln Gly Leu Glu Trp Met Gly Trp Ile Tyr Pro Gly Asn Val
625              630              635              640

His Ala Gln Tyr Asn Glu Lys Phe Lys Gly Arg Val Thr Ile Thr Ala
                645              650              655

Asp Lys Ser Thr Ser Thr Ala Tyr Met Glu Leu Ser Ser Leu Arg Ser
            660              665              670

Glu Asp Thr Ala Val Tyr Tyr Cys Ala Arg Ser Trp Glu Gly Phe Pro
        675              680              685

Tyr Trp Gly Cys Gly Thr Thr Val Thr Val Ser Ser
    690              695              700

<210> SEQ ID NO 93
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv (VL3_Y36F_S49Y_F87Y) BHA10 (VH-VL)

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Cys Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Ser Gly Gly Ser Gly Cys Pro Pro
            115                 120                 125

Cys Gly Gly Gly Asp Ile Gln Met Thr Gln Ser Pro Ser Ser Leu
        130                 135                 140

Ser Ala Ser Val Gly Asp Arg Val Thr Ile Thr Cys Lys Ala Ser Gln
145                 150                 155                 160

Asn Val Gly Ile Asn Val Ala Trp Phe Gln Gln Lys Pro Gly Lys Ala
                165                 170                 175

Pro Lys Ser Leu Ile Tyr Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Tyr
    210                 215                 220

Asp Thr Tyr Pro Phe Thr Phe Gly Cys Gly Thr Lys Val Glu Ile Lys
```

<210> SEQ ID NO 94
<211> LENGTH: 701
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: HC L19 C-term stapled (VL3_Y36F_S49Y_F87Y) BHA (VH-VL), IgG1s, knob, with pA mutations

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335
```

Lys Ala Lys Gly Gln Pro Arg Glu Pro Gln Val Tyr Thr Leu Pro Pro
              340                 345                 350

Cys Arg Glu Glu Met Thr Lys Asn Gln Val Ser Leu Trp Cys Leu Val
          355                 360                 365

Lys Gly Phe Tyr Pro Ser Asp Ile Ala Val Glu Trp Glu Ser Asn Gly
      370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
              405                 410                 415

Gln Gln Gly Asn Val Phe Ser Cys Ser Val Met His Glu Ala Leu His
          420                 425                 430

Asn Arg Phe Thr Gln Lys Ser Leu Ser Leu Ser Pro Gly Lys Gly Gly
      435                 440                 445

Gly Gly Ser Gly Gly Gly Gly Ser Gly Gly Gly Gly Ser Gln Val Gln
450                 455                 460

Leu Val Gln Ser Gly Ala Glu Val Lys Lys Pro Gly Ser Ser Val Lys
465                 470                 475                 480

Val Ser Cys Lys Ala Ser Gly Tyr Thr Phe Thr Thr Tyr Tyr Leu His
              485                 490                 495

Trp Val Arg Gln Ala Pro Gly Cys Gly Leu Glu Trp Met Gly Trp Ile
          500                 505                 510

Tyr Pro Gly Asn Val His Ala Gln Tyr Asn Glu Lys Phe Lys Gly Arg
      515                 520                 525

Val Thr Ile Thr Ala Asp Lys Ser Thr Ser Thr Ala Tyr Met Glu Leu
530                 535                 540

Ser Ser Leu Arg Ser Glu Asp Thr Ala Val Tyr Tyr Cys Ala Arg Ser
545                 550                 555                 560

Trp Glu Gly Phe Pro Tyr Trp Gly Gln Gly Thr Thr Val Thr Val Ser
              565                 570                 575

Ser Gly Gly Gly Ser Gly Gly Gly Ser Gly Cys Pro Pro Cys Gly Gly
          580                 585                 590

Gly Gly Asp Ile Gln Met Thr Gln Ser Pro Ser Ser Leu Ser Ala Ser
      595                 600                 605

Val Gly Asp Arg Val Thr Ile Thr Cys Lys Ala Ser Gln Asn Val Gly
610                 615                 620

Ile Asn Val Ala Trp Phe Gln Gln Lys Pro Gly Lys Ala Pro Lys Ser
625                 630                 635                 640

Leu Ile Tyr Ser Ala Ser Tyr Arg Tyr Ser Gly Val Pro Ser Arg Phe
              645                 650                 655

Ser Gly Ser Gly Ser Gly Thr Asp Phe Thr Leu Thr Ile Ser Ser Leu
          660                 665                 670

Gln Pro Glu Asp Phe Ala Thr Tyr Tyr Cys Gln Gln Tyr Asp Thr Tyr
      675                 680                 685

Pro Phe Thr Phe Gly Cys Gly Thr Lys Val Glu Ile Lys
      690                 695                 700

<210> SEQ ID NO 95
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv (VH_CDR1_Y33A) BHA10 (VH-VL)

<400> SEQUENCE: 95

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Ala Leu His Trp Val Arg Gln Ala Pro Gly Cys Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Gly Gly Ser Gly Cys Pro Pro
        115                 120                 125

Cys Gly Gly Gly Gly Asp Ile Gln Met Thr Gln Ser Pro Ser Ser Leu
130                 135                 140

Ser Ala Ser Val Gly Asp Arg Val Thr Ile Thr Cys Lys Ala Ser Gln
145                 150                 155                 160

Asn Val Gly Ile Asn Val Ala Trp Tyr Gln Gln Lys Pro Gly Lys Ala
                165                 170                 175

Pro Lys Ser Leu Ile Ser Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Phe Cys Gln Gln Tyr
    210                 215                 220

Asp Thr Tyr Pro Phe Thr Phe Gly Cys Gly Thr Lys Val Glu Ile Lys
225                 230                 235                 240
```

<210> SEQ ID NO 96
<211> LENGTH: 701
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: HC L19 C-term stapled (VH_CDR1_Y33A) BHA10 (VH-VL), IgG1s, knob, with pA mutations

<400> SEQUENCE: 96

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn Arg Phe Thr Gln Lys Ser Leu Ser Leu Ser Pro Gly Lys Gly Gly
        435                 440                 445

Gly Gly Ser Gly Gly Gly Ser Gly Gly Gly Ser Gln Val Gln
    450                 455                 460

Leu Val Gln Ser Gly Ala Glu Val Lys Lys Pro Gly Ser Ser Val Lys
465                 470                 475                 480

Val Ser Cys Lys Ala Ser Gly Tyr Thr Phe Thr Thr Tyr Ala Leu His
                485                 490                 495

Trp Val Arg Gln Ala Pro Gly Cys Gly Leu Glu Trp Met Gly Trp Ile
            500                 505                 510
```

Tyr Pro Gly Asn Val His Ala Gln Tyr Asn Glu Lys Phe Lys Gly Arg
            515                 520                 525

Val Thr Ile Thr Ala Asp Lys Ser Thr Ser Thr Ala Tyr Met Glu Leu
    530                 535                 540

Ser Ser Leu Arg Ser Glu Asp Thr Ala Val Tyr Tyr Cys Ala Arg Ser
545                 550                 555                 560

Trp Glu Gly Phe Pro Tyr Trp Gly Gln Gly Thr Thr Val Thr Val Ser
                565                 570                 575

Ser Gly Gly Gly Ser Gly Gly Gly Ser Gly Cys Pro Pro Cys Gly Gly
            580                 585                 590

Gly Gly Asp Ile Gln Met Thr Gln Ser Pro Ser Ser Leu Ser Ala Ser
        595                 600                 605

Val Gly Asp Arg Val Thr Ile Thr Cys Lys Ala Ser Gln Asn Val Gly
    610                 615                 620

Ile Asn Val Ala Trp Tyr Gln Gln Lys Pro Gly Lys Ala Pro Lys Ser
625                 630                 635                 640

Leu Ile Ser Ser Ala Ser Tyr Arg Tyr Ser Gly Val Pro Ser Arg Phe
                645                 650                 655

Ser Gly Ser Gly Ser Gly Thr Asp Phe Thr Leu Thr Ile Ser Ser Leu
            660                 665                 670

Gln Pro Glu Asp Phe Ala Thr Tyr Phe Cys Gln Gln Tyr Asp Thr Tyr
        675                 680                 685

Pro Phe Thr Phe Gly Cys Gly Thr Lys Val Glu Ile Lys
    690                 695                 700

<210> SEQ ID NO 97
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 C-term stapled BHA10 (VH-VL), IgG1s,
      knob, no pA mutations

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

-continued

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Gly Ser Gly Gly Gly Gly Ser Gln Val Gln
    450                 455                 460

Leu Val Gln Ser Gly Ala Glu Val Lys Lys Pro Gly Ser Ser Val Lys
465                 470                 475                 480

Val Ser Cys Lys Ala Ser Gly Tyr Thr Phe Thr Thr Tyr Tyr Leu His
                485                 490                 495

Trp Val Arg Gln Ala Pro Gly Cys Gly Leu Glu Trp Met Gly Trp Ile
            500                 505                 510

Tyr Pro Gly Asn Val His Ala Gln Tyr Asn Glu Lys Phe Lys Gly Arg
        515                 520                 525

Val Thr Ile Thr Ala Asp Lys Ser Thr Ser Thr Ala Tyr Met Glu Leu
    530                 535                 540

Ser Ser Leu Arg Ser Glu Asp Thr Ala Val Tyr Tyr Cys Ala Arg Ser
545                 550                 555                 560

Trp Glu Gly Phe Pro Tyr Trp Gly Gln Gly Thr Thr Val Thr Val Ser
                565                 570                 575

```
Ser Gly Gly Gly Ser Gly Gly Ser Gly Cys Pro Cys Gly Gly
            580                 585                 590

Gly Gly Asp Ile Gln Met Thr Gln Ser Pro Ser Ser Leu Ser Ala Ser
        595                 600                 605

Val Gly Asp Arg Val Thr Ile Thr Cys Lys Ala Ser Gln Asn Val Gly
    610                 615                 620

Ile Asn Val Ala Trp Tyr Gln Gln Lys Pro Gly Lys Ala Pro Lys Ser
625                 630                 635                 640

Leu Ile Ser Ser Ala Ser Tyr Arg Tyr Ser Gly Val Pro Ser Arg Phe
                645                 650                 655

Ser Gly Ser Gly Ser Gly Thr Asp Phe Thr Leu Thr Ile Ser Ser Leu
            660                 665                 670

Gln Pro Glu Asp Phe Ala Thr Tyr Phe Cys Gln Gln Tyr Asp Thr Tyr
        675                 680                 685

Pro Phe Thr Phe Gly Cys Gly Thr Lys Val Glu Ile Lys
    690                 695                 700

<210> SEQ ID NO 98
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC L19 IgG1s knob

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

Cys Pro Pro Cys Pro Ala Pro Glu Ala Ala Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Ala Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 99
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M C-term stapled BHA10 (VH-VL), IgG1s,
      knob, no pA mutations

<400> SEQUENCE: 99

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
                245                 250                 255

Ser Arg Thr Pro Glu Val Thr Cys Val Val Asp Val Ser Ala Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Glu Glu Met Thr Lys Asn Gln Val Ser Leu
    355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
    435                 440                 445

Gly Lys Gly Gly Gly Gly Ser Gly Gly Gly Ser Gly Gly Gly Gly
450                 455                 460

Ser Gln Val Gln Leu Val Gln Ser Gly Ala Glu Val Lys Lys Pro Gly
465                 470                 475                 480

Ser Ser Val Lys Val Ser Cys Lys Ala Ser Gly Tyr Thr Phe Thr Thr
                485                 490                 495

Tyr Tyr Leu His Trp Val Arg Gln Ala Pro Gly Cys Gly Leu Glu Trp
            500                 505                 510

Met Gly Trp Ile Tyr Pro Gly Asn Val His Ala Gln Tyr Asn Glu Lys
    515                 520                 525

Phe Lys Gly Arg Val Thr Ile Thr Ala Asp Lys Ser Thr Ser Thr Ala
530                 535                 540
```

-continued

```
Tyr Met Glu Leu Ser Ser Leu Arg Ser Glu Asp Thr Ala Val Tyr Tyr
545                 550                 555                 560

Cys Ala Arg Ser Trp Glu Gly Phe Pro Tyr Trp Gly Gln Gly Thr Thr
            565                 570                 575

Val Thr Val Ser Ser Gly Gly Gly Ser Gly Gly Gly Ser Gly Cys Pro
        580                 585                 590

Pro Cys Gly Gly Gly Asp Ile Gln Met Thr Gln Ser Pro Ser Ser
    595                 600                 605

Leu Ser Ala Ser Val Gly Asp Arg Val Thr Ile Thr Cys Lys Ala Ser
610                 615                 620

Gln Asn Val Gly Ile Asn Val Ala Trp Tyr Gln Gln Lys Pro Gly Lys
625                 630                 635                 640

Ala Pro Lys Ser Leu Ile Ser Ser Ala Ser Tyr Arg Tyr Ser Gly Val
            645                 650                 655

Pro Ser Arg Phe Ser Gly Ser Gly Ser Gly Thr Asp Phe Thr Leu Thr
            660                 665                 670

Ile Ser Ser Leu Gln Pro Glu Asp Phe Ala Thr Tyr Phe Cys Gln Gln
        675                 680                 685

Tyr Asp Thr Tyr Pro Phe Thr Phe Gly Cys Gly Thr Lys Val Glu Ile
    690                 695                 700

Lys
705

<210> SEQ ID NO 100
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC B21M (RSV) IgG1s knob

<400> SEQUENCE: 100

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175
```

-continued

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Ser Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Ala Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Cys Arg Glu Glu Met Thr Lys Asn Gln Val Ser Leu
    355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 101
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MSLNmAb1 HC C-term stapled BHA10 (VH-VL),
      IgG1s, knob, with pA mutations

<400> SEQUENCE: 101

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60
```

```
Arg Gly Lys Ala Thr Leu Thr Val Asp Lys Ser Ser Thr Ala Tyr
 65                  70                  75                  80

Met Asp Leu Leu Ser Leu Thr Ser Glu Asp Ser Ala Val Tyr Phe Cys
                 85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
            435                 440                 445

Lys Gly Gly Gly Gly Ser Gly Gly Gly Gly Ser Gly Gly Gly Gly Ser
            450                 455                 460

Gln Val Gln Leu Val Gln Ser Gly Ala Glu Val Lys Lys Pro Gly Ser
465                 470                 475                 480
```

```
Ser Val Lys Val Ser Cys Lys Ala Ser Gly Tyr Thr Phe Thr Thr Tyr
            485                 490                 495

Tyr Leu His Trp Val Arg Gln Ala Pro Gly Cys Gly Leu Glu Trp Met
        500                 505                 510

Gly Trp Ile Tyr Pro Gly Asn Val His Ala Gln Tyr Asn Glu Lys Phe
            515                 520                 525

Lys Gly Arg Val Thr Ile Thr Ala Asp Lys Ser Thr Ser Thr Ala Tyr
530                 535                 540

Met Glu Leu Ser Ser Leu Arg Ser Glu Asp Thr Ala Val Tyr Tyr Cys
545                 550                 555                 560

Ala Arg Ser Trp Glu Gly Phe Pro Tyr Trp Gly Gln Gly Thr Thr Val
            565                 570                 575

Thr Val Ser Ser Gly Gly Gly Ser Gly Gly Gly Ser Gly Cys Pro Pro
            580                 585                 590

Cys Gly Gly Gly Asp Ile Gln Met Thr Gln Ser Pro Ser Ser Leu
            595                 600                 605

Ser Ala Ser Val Gly Asp Arg Val Thr Ile Thr Cys Lys Ala Ser Gln
610                 615                 620

Asn Val Gly Ile Asn Val Ala Trp Tyr Gln Gln Lys Pro Gly Lys Ala
625                 630                 635                 640

Pro Lys Ser Leu Ile Ser Ser Ala Ser Tyr Arg Tyr Ser Gly Val Pro
            645                 650                 655

Ser Arg Phe Ser Gly Ser Gly Ser Gly Thr Asp Phe Thr Leu Thr Ile
            660                 665                 670

Ser Ser Leu Gln Pro Glu Asp Phe Ala Thr Tyr Phe Cys Gln Gln Tyr
            675                 680                 685

Asp Thr Tyr Pro Phe Thr Phe Gly Cys Gly Thr Lys Val Glu Ile Lys
690                 695                 700

<210> SEQ ID NO 102
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MSLNmAb1 HC, IgG1s, knob, with pA mutations

<400> SEQUENCE: 102

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Ser
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Ala Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445

Lys

<210> SEQ ID NO 103
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC MSLNmAb1 IgG1s hole

<400> SEQUENCE: 103

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr

-continued

```
            20                  25                  30
Thr Met Asn Trp Val Lys Gln Ser His Gly Lys Ser Leu Glu Trp Ile
        35                  40                  45
Gly Leu Ile Thr Pro Tyr Asn Gly Ala Ser Ser Tyr Asn Gln Lys Phe
    50                  55                  60
Arg Gly Lys Ala Thr Leu Thr Val Asp Lys Ser Ser Ser Thr Ala Tyr
65                  70                  75                  80
Met Asp Leu Leu Ser Leu Thr Ser Glu Asp Ser Ala Val Tyr Phe Cys
                85                  90                  95
Ala Arg Gly Gly Tyr Asp Gly Arg Gly Phe Asp Tyr Trp Gly Ser Gly
                100                 105                 110
Thr Pro Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Ala Ala Gly Ala Ser
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Ala Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ser Ser Ile Glu Lys
                325                 330                 335
Thr Ile Ser Lys Ala Lys Gly Gln Pro Arg Glu Pro Gln Val Cys Thr
                340                 345                 350
Leu Pro Pro Ser Arg Glu Glu Met Thr Lys Asn Gln Val Ser Leu Ser
            355                 360                 365
Cys Ala Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
```

Lys

<210> SEQ ID NO 104
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: LC MLSNmAb1

<400> SEQUENCE: 104

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 105
<211> LENGTH: 371
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: fibronectin domains 7B89

<400> SEQUENCE: 105

```
Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45
```

Leu Glu Glu Val Val His Ala Asp Gln Ser Ser Cys Thr Phe Asp Asn
        50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro Glu Val Pro
                85                  90                  95

Gln Leu Thr Asp Leu Ser Phe Val Asp Ile Thr Asp Ser Ser Ile Gly
            100                 105                 110

Leu Arg Trp Thr Pro Leu Asn Ser Ser Thr Ile Ile Gly Tyr Arg Ile
        115                 120                 125

Thr Val Val Ala Ala Gly Glu Gly Ile Pro Ile Phe Glu Asp Phe Val
    130                 135                 140

Asp Ser Ser Val Gly Tyr Tyr Thr Val Thr Gly Leu Glu Pro Gly Ile
145                 150                 155                 160

Asp Tyr Asp Ile Ser Val Ile Thr Leu Ile Asn Gly Gly Glu Ser Ala
                165                 170                 175

Pro Thr Thr Leu Thr Gln Gln Thr Ala Val Pro Pro Thr Asp Leu
            180                 185                 190

Arg Phe Thr Asn Ile Gly Pro Asp Thr Met Arg Val Thr Trp Ala Pro
        195                 200                 205

Pro Pro Ser Ile Asp Leu Thr Asn Phe Leu Val Arg Tyr Ser Pro Val
    210                 215                 220

Lys Asn Glu Glu Asp Val Ala Glu Leu Ser Ile Ser Pro Ser Asp Asn
225                 230                 235                 240

Ala Val Val Leu Thr Asn Leu Leu Pro Gly Thr Glu Tyr Val Val Ser
                245                 250                 255

Val Ser Ser Val Tyr Glu Gln His Glu Ser Thr Pro Leu Arg Gly Arg
            260                 265                 270

Gln Lys Thr Gly Leu Asp Ser Pro Thr Gly Ile Asp Phe Ser Asp Ile
        275                 280                 285

Thr Ala Asn Ser Phe Thr Val His Trp Ile Ala Pro Arg Ala Thr Ile
    290                 295                 300

Thr Gly Tyr Arg Ile Arg His His Pro Glu His Phe Ser Gly Arg Pro
305                 310                 315                 320

Arg Glu Asp Arg Val Pro His Ser Arg Asn Ser Ile Thr Leu Thr Asn
                325                 330                 335

Leu Thr Pro Gly Thr Glu Tyr Val Val Ser Ile Val Ala Leu Asn Gly
            340                 345                 350

Arg Glu Glu Ser Pro Leu Leu Ile Gly Gln Gln Ser Thr His His His
        355                 360                 365

His His His
    370

<210> SEQ ID NO 106
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: fibronectin domains 789

<400> SEQUENCE: 106

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
            35                  40                  45

Leu Glu Glu Val Val His Ala Asp Gln Ser Ser Cys Thr Phe Asp Asn
50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro Ala Val Pro
                85                  90                  95

Pro Pro Thr Asp Leu Arg Phe Thr Asn Ile Gly Pro Asp Thr Met Arg
            100                 105                 110

Val Thr Trp Ala Pro Pro Pro Ser Ile Asp Leu Thr Asn Phe Leu Val
            115                 120                 125

Arg Tyr Ser Pro Val Lys Asn Glu Glu Asp Val Ala Glu Leu Ser Ile
            130                 135                 140

Ser Pro Ser Asp Asn Ala Val Val Leu Thr Asn Leu Leu Pro Gly Thr
145                 150                 155                 160

Glu Tyr Val Val Ser Val Ser Ser Val Tyr Glu Gln His Glu Ser Thr
                165                 170                 175

Pro Leu Arg Gly Arg Gln Lys Thr Gly Leu Asp Ser Pro Thr Gly Ile
            180                 185                 190

Asp Phe Ser Asp Ile Thr Ala Asn Ser Phe Thr Val His Trp Ile Ala
            195                 200                 205

Pro Arg Ala Thr Ile Thr Gly Tyr Arg Ile Arg His His Pro Glu His
            210                 215                 220

Phe Ser Gly Arg Pro Arg Glu Asp Arg Val Pro His Ser Arg Asn Ser
225                 230                 235                 240

Ile Thr Leu Thr Asn Leu Thr Pro Gly Thr Glu Tyr Val Val Ser Ile
                245                 250                 255

Val Ala Leu Asn Gly Arg Glu Glu Ser Pro Leu Leu Ile Gly Gln Gln
            260                 265                 270

Ser Thr His His His His His His
            275                 280

<210> SEQ ID NO 107
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv (VL3_Y36F_S49Y_F87Y) BHA10 (VH-VL)

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Cys Gly Leu Glu Trp Met
            35                  40                  45

Gly Trp Ile Tyr Pro Gly Asn Val His Ala Gln Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Ser Gly Cys Pro Pro
        115                 120                 125

Cys Gly Gly Gly Gly Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asn Val Gly Ile Asn Val Ala Trp Phe Gln Gln Lys Pro Gly Lys Ala
                165                 170                 175

Pro Lys Ser Leu Ile Tyr Ser Ala Ser Tyr Arg Tyr Ser Gly Val Pro
            180                 185                 190

Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Tyr
    210                 215                 220

Asp Thr Tyr Pro Phe Thr Phe Gly Cys Gly Thr Lys Val Glu Ile Lys
225                 230                 235                 240

<210> SEQ ID NO 108
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: stapled scFv (VH_CDR1_Y33A) BHA10 (VH-VL)

<400> SEQUENCE: 108

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Ala Leu His Trp Val Arg Gln Ala Pro Gly Cys Gly Leu Glu Trp Met
        35                  40                  45

Gly Trp Ile Tyr Pro Gly Asn Val His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Pro Tyr Trp Gly Gln Gly Thr Thr Val
            100                 105                 110

Thr Val Ser Ser Gly Gly Gly Ser Gly Gly Ser Gly Cys Pro Pro
        115                 120                 125

Cys Gly Gly Gly Gly Asp Ile Gln Met Thr Gln Ser Pro Ser Ser Leu
    130                 135                 140

Ser Ala Ser Val Gly Asp Arg Val Thr Ile Thr Cys Lys Ala Ser Gln
145                 150                 155                 160

Asn Val Gly Ile Asn Val Ala Trp Tyr Gln Gln Lys Pro Gly Lys Ala
                165                 170                 175

Pro Lys Ser Leu Ile Ser Ser Ala Ser Tyr Arg Tyr Ser Gly Val Pro
            180                 185                 190

-continued

```
Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Phe Cys Gln Gln Tyr
    210                 215                 220

Asp Thr Tyr Pro Phe Thr Phe Gly Cys Gly Thr Lys Val Glu Ile Lys
225                 230                 235                 240

<210> SEQ ID NO 109
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH of Anti-TnCA2 Ab 2B10

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Gly Ala Phe Asp Tyr Trp Gly
            100                 105                 110

Gln Gly Thr Thr Val Thr Val Ser Ser
        115                 120

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL of Anti-TnCA2 Ab 2B10

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
```

```
                100             105

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Anti- EDA Ab F8

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 112
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Anti-EDA Ab F8

<400> SEQUENCE: 112

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 113
<211> LENGTH: 703
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: F8 HC with BHA10 stapled (VH-VL) scFv C-ter
fused, IgG1 sigma, knob mutations

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Ser Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Ala Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Ser Gly Gly Gly Ser Gln
    450                 455                 460

Val Gln Leu Val Gln Ser Gly Ala Glu Val Lys Lys Pro Gly Ser Ser
465                 470                 475                 480

Val Lys Val Ser Cys Lys Ala Ser Gly Tyr Thr Phe Thr Thr Tyr Tyr
                485                 490                 495

Leu His Trp Val Arg Gln Ala Pro Gly Cys Gly Leu Glu Trp Met Gly
            500                 505                 510

Trp Ile Tyr Pro Gly Asn Val His Ala Gln Tyr Asn Glu Lys Phe Lys
        515                 520                 525

Gly Arg Val Thr Ile Thr Ala Asp Lys Ser Thr Ser Thr Ala Tyr Met
530                 535                 540

Glu Leu Ser Ser Leu Arg Ser Glu Asp Thr Ala Val Tyr Tyr Cys Ala
545                 550                 555                 560

Arg Ser Trp Glu Gly Phe Pro Tyr Trp Gly Gln Gly Thr Thr Val Thr
                565                 570                 575

Val Ser Ser Gly Gly Gly Ser Gly Gly Gly Ser Gly Cys Pro Pro Cys
            580                 585                 590

Gly Gly Gly Gly Asp Ile Gln Met Thr Gln Ser Pro Ser Ser Leu Ser
        595                 600                 605

Ala Ser Val Gly Asp Arg Val Thr Ile Thr Cys Lys Ala Ser Gln Asn
610                 615                 620

Val Gly Ile Asn Val Ala Trp Tyr Gln Gln Lys Pro Gly Lys Ala Pro
625                 630                 635                 640

Lys Ser Leu Ile Ser Ser Ala Ser Tyr Arg Tyr Ser Gly Val Pro Ser
                645                 650                 655

Arg Phe Ser Gly Ser Gly Ser Gly Thr Asp Phe Thr Leu Thr Ile Ser
            660                 665                 670

Ser Leu Gln Pro Glu Asp Phe Ala Thr Tyr Phe Cys Gln Gln Tyr Asp
        675                 680                 685

Thr Tyr Pro Phe Thr Phe Gly Cys Gly Thr Lys Val Glu Ile Lys
690                 695                 700

<210> SEQ ID NO 114
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: F8 HC,IgG1 sigma, knob mutations

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
                20                  25                  30
```

```
Thr Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65              70                  75                      80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
             100             105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
         130                 135                 140

Cys Leu Val Lys Asp Tyr Phe Pro Glu Pro Val Thr Val Ser Trp Asn
145             150                 155                     160

Ser Gly Ala Leu Thr Ser Gly Val His Thr Phe Pro Ala Val Leu Gln
                 165                 170                 175

Ser Ser Gly Leu Tyr Ser Leu Ser Val Val Thr Val Pro Ser Ser
                 180                 185                 190

Ser Leu Gly Thr Gln Thr Tyr Ile Cys Asn Val Asn His Lys Pro Ser
             195                 200                 205

Asn Thr Lys Val Asp Lys Lys Val Glu Pro Lys Ser Cys Asp Lys Thr
         210                 215                 220

His Thr Cys Pro Pro Cys Pro Ala Pro Glu Ala Ala Gly Ala Ser Ser
225             230                 235                     240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser Ala Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
         290                 295                 300

Ser Val Leu Thr Val Leu His Gln Asp Trp Leu Asn Gly Lys Glu Tyr
305             310                 315                     320

Lys Cys Lys Val Ser Asn Lys Ala Leu Pro Ser Ser Ile Glu Lys Thr
                 325                 330                 335

Ile Ser Lys Ala Lys Gly Gln Pro Arg Glu Pro Gln Val Tyr Thr Leu
             340                 345                 350

Pro Pro Cys Arg Glu Glu Met Thr Lys Asn Gln Val Ser Leu Trp Cys
         355                 360                 365

Leu Val Lys Gly Phe Tyr Pro Ser Asp Ile Ala Val Glu Trp Glu Ser
         370                 375                 380

Asn Gly Gln Pro Glu Asn Asn Tyr Lys Thr Thr Pro Pro Val Leu Asp
385             390                 395                     400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430

Leu His Asn His Tyr Thr Gln Lys Ser Leu Ser Leu Ser Pro Gly Lys
         435                 440                 445
```

<210> SEQ ID NO 115
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: F8 HC, IgG1 sigma and hole mutations

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Ser Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Ala Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ser Ser Ile Glu Lys Thr
                325                 330                 335

Ile Ser Lys Ala Lys Gly Gln Pro Arg Glu Pro Gln Val Cys Thr Leu
            340                 345                 350

```
Pro Pro Ser Arg Glu Glu Met Thr Lys Asn Gln Val Ser Leu Ser Cys
            355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445
```

<210> SEQ ID NO 116
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: F8 LC

<400> SEQUENCE: 116

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 117
<211> LENGTH: 706
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: 2B10 HC with BHA10 stapled (VH-VL) scFv C-ter
fused, IgG1 sigma, knob mutations

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Ser Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Ala
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys Gly Gly Gly Ser Gly Gly Gly Ser Gly Gly Gly
450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Tyr Thr Phe Thr
            485                 490                 495

Thr Tyr Tyr Leu His Trp Val Arg Gln Ala Pro Gly Cys Gly Leu Glu
            500                 505                 510

Trp Met Gly Trp Ile Tyr Pro Gly Asn Val His Ala Gln Tyr Asn Glu
        515                 520                 525

Lys Phe Lys Gly Arg Val Thr Ile Thr Ala Asp Lys Ser Thr Ser Thr
530                 535                 540

Ala Tyr Met Glu Leu Ser Ser Leu Arg Ser Glu Asp Thr Ala Val Tyr
545                 550                 555                 560

Tyr Cys Ala Arg Ser Trp Glu Gly Phe Pro Tyr Trp Gly Gln Gly Thr
            565                 570                 575

Thr Val Thr Val Ser Ser Gly Gly Ser Gly Gly Gly Ser Gly Cys
            580                 585                 590

Pro Pro Cys Gly Gly Gly Gly Asp Ile Gln Met Thr Gln Ser Pro Ser
        595                 600                 605

Ser Leu Ser Ala Ser Val Gly Asp Arg Val Thr Ile Thr Cys Lys Ala
    610                 615                 620

Ser Gln Asn Val Gly Ile Asn Val Ala Trp Tyr Gln Gln Lys Pro Gly
625                 630                 635                 640

Lys Ala Pro Lys Ser Leu Ile Ser Ser Ala Ser Tyr Arg Tyr Ser Gly
            645                 650                 655

Val Pro Ser Arg Phe Ser Gly Ser Gly Ser Gly Thr Asp Phe Thr Leu
            660                 665                 670

Thr Ile Ser Ser Leu Gln Pro Glu Asp Phe Ala Thr Tyr Phe Cys Gln
        675                 680                 685

Gln Tyr Asp Thr Tyr Pro Phe Thr Phe Gly Cys Gly Thr Lys Val Glu
        690                 695                 700

Ile Lys
705

<210> SEQ ID NO 118
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2B10 HC, IgG1 sigma, knob mutations

<400> SEQUENCE: 118

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
 130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Ala Ala Gly
225                 230                 235                 240

Ala Ser Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Ala
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
            355                 360                 365

Leu Trp Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445
Pro Gly Lys
    450

<210> SEQ ID NO 119
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2B10 HC, IgG1 sigma and hole mutations

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Ser Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Ala
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 120
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2B10 LC

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 121
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Hu tenascin C domains A1-A2-A3, including
      (His)6- Tag for purification

<400> SEQUENCE: 121

Glu Gln Ala Pro Glu Leu Glu Asn Leu Thr Val Thr Glu Val Gly Trp
1               5                   10                  15

Asp Gly Leu Arg Leu Asn Trp Thr Ala Ala Asp Gln Ala Tyr Glu His
            20                  25                  30

Phe Ile Ile Gln Val Gln Glu Ala Asn Lys Val Glu Ala Ala Arg Asn
        35                  40                  45

Leu Thr Val Pro Gly Ser Leu Arg Ala Val Asp Ile Pro Gly Leu Lys
    50                  55                  60

Ala Ala Thr Pro Tyr Thr Val Ser Ile Tyr Gly Val Ile Gln Gly Tyr
65                  70                  75                  80

Arg Thr Pro Val Leu Ser Ala Glu Ala Ser Thr Gly Glu Thr Pro Asn
                85                  90                  95

Leu Gly Glu Val Val Val Ala Glu Val Gly Trp Asp Ala Leu Lys Leu
            100                 105                 110

Asn Trp Thr Ala Pro Glu Gly Ala Tyr Glu Tyr Phe Phe Ile Gln Val
        115                 120                 125

Gln Glu Ala Asp Thr Val Glu Ala Gln Asn Leu Thr Val Pro Gly Gly
    130                 135                 140

Gly Leu Arg Ser Thr Asp Leu Pro Gly Leu Lys Ala Ala Thr His Tyr
145                 150                 155                 160

Thr Ile Thr Ile Arg Gly Val Thr Gln Asp Phe Ser Thr Thr Pro Leu
                165                 170                 175

Ser Val Glu Val Leu Thr Glu Val Pro Asp Met Gly Asn Leu Thr
            180                 185                 190

Val Thr Glu Val Ser Trp Asp Ala Leu Arg Leu Asn Trp Thr Thr Pro
        195                 200                 205

Asp Gly Thr Tyr Asp Gln Phe Thr Ile Gln Val Gln Glu Ala Asp Gln
    210                 215                 220

Val Glu Glu Ala His Asn Leu Thr Val Pro Gly Ser Leu Arg Ser Met
225                 230                 235                 240

Glu Ile Pro Gly Leu Arg Ala Gly Thr Pro Tyr Thr Val Thr Leu His
                245                 250                 255

Gly Glu Val Arg Gly His Ser Thr Arg Pro Leu Ala Val Glu Val Val
            260                 265                 270

Thr His His His His His His
    275

<210> SEQ ID NO 122
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Hu tenascin C domains A1-A3, including (His)6-
     Tag for purification

<400> SEQUENCE: 122

Glu Gln Ala Pro Glu Leu Glu Asn Leu Thr Val Thr Glu Val Gly Trp
1               5                   10                  15

Asp Gly Leu Arg Leu Asn Trp Thr Ala Ala Asp Gln Ala Tyr Glu His
            20                  25                  30

Phe Ile Ile Gln Val Gln Glu Ala Asn Lys Val Glu Ala Ala Arg Asn
        35                  40                  45

Leu Thr Val Pro Gly Ser Leu Arg Ala Val Asp Ile Pro Gly Leu Lys
50                  55                  60

Ala Ala Thr Pro Tyr Thr Val Ser Ile Tyr Gly Val Ile Gln Gly Tyr
65                  70                  75                  80

Arg Thr Pro Val Leu Ser Ala Glu Glu Val Pro Asp Met Gly Asn
            85                  90                  95

Leu Thr Val Thr Glu Val Ser Trp Asp Ala Leu Arg Leu Asn Trp Thr
            100                 105                 110

Thr Pro Asp Gly Thr Tyr Asp Gln Phe Thr Ile Gln Val Gln Glu Ala
        115                 120                 125

Asp Gln Val Glu Glu Ala His Asn Leu Thr Val Pro Gly Ser Leu Arg
130                 135                 140

Ser Met Glu Ile Pro Gly Leu Arg Ala Gly Thr Pro Tyr Thr Val Thr
145                 150                 155                 160

Leu His Gly Glu Val Arg Gly His Ser Thr Arg Pro Leu Ala Val Glu
            165                 170                 175

Val Val Thr His His His His His His
            180                 185

<210> SEQ ID NO 123
<211> LENGTH: 278
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Hu fibronectin domains 11-A-12, including (His)
     6- Tag for purification

<400> SEQUENCE: 123

Glu Ile Asp Lys Pro Ser Gln Met Gln Val Thr Asp Val Gln Asp Asn
1               5                   10                  15

Ser Ile Ser Val Lys Trp Leu Pro Ser Ser Pro Val Thr Gly Tyr
            20                  25                  30

Arg Val Thr Thr Thr Pro Lys Asn Gly Pro Gly Pro Thr Lys Thr Lys
        35                  40                  45

Thr Ala Gly Pro Asp Gln Thr Glu Met Thr Ile Glu Gly Leu Gln Pro
50                  55                  60

Thr Val Glu Tyr Val Val Ser Val Tyr Ala Gln Asn Pro Ser Gly Glu
65                  70                  75                  80

Ser Gln Pro Leu Val Gln Thr Ala Val Thr Asn Ile Asp Arg Pro Lys
            85                  90                  95

```
Gly Leu Ala Phe Thr Asp Val Asp Val Asp Ser Ile Lys Ile Ala Trp
            100                 105                 110

Glu Ser Pro Gln Gly Gln Val Ser Arg Tyr Arg Val Thr Tyr Ser Ser
        115                 120                 125

Pro Glu Asp Gly Ile His Glu Leu Phe Pro Ala Pro Asp Gly Glu Glu
    130                 135                 140

Asp Thr Ala Glu Leu Gln Gly Leu Arg Pro Gly Ser Glu Tyr Thr Val
145                 150                 155                 160

Ser Val Val Ala Leu His Asp Asp Met Glu Ser Gln Pro Leu Ile Gly
                165                 170                 175

Thr Gln Ser Thr Ala Ile Pro Ala Pro Thr Asp Leu Lys Phe Thr Gln
            180                 185                 190

Val Thr Pro Thr Ser Leu Ser Ala Gln Trp Thr Pro Pro Asn Val Gln
        195                 200                 205

Leu Thr Gly Tyr Arg Val Arg Val Thr Pro Lys Glu Lys Thr Gly Pro
    210                 215                 220

Met Lys Glu Ile Asn Leu Ala Pro Asp Ser Ser Ser Val Val Val Ser
225                 230                 235                 240

Gly Leu Met Val Ala Thr Lys Tyr Glu Val Ser Val Tyr Ala Leu Lys
                245                 250                 255

Asp Thr Leu Thr Ser Arg Pro Ala Gln Gly Val Val Thr Thr Leu Glu
            260                 265                 270

His His His His His His
        275

<210> SEQ ID NO 124
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Hu fibronectin domains 11-12, including
      (His)6- Tag for purification

<400> SEQUENCE: 124

Glu Ile Asp Lys Pro Ser Gln Met Gln Val Thr Asp Val Gln Asp Asn
1               5                   10                  15

Ser Ile Ser Val Lys Trp Leu Pro Ser Ser Pro Val Thr Gly Tyr
            20                  25                  30

Arg Val Thr Thr Thr Pro Lys Asn Gly Pro Gly Pro Thr Lys Thr Lys
        35                  40                  45

Thr Ala Gly Pro Asp Gln Thr Glu Met Thr Ile Glu Gly Leu Gln Pro
50                  55                  60

Thr Val Glu Tyr Val Val Ser Val Tyr Ala Gln Asn Pro Ser Gly Glu
65                  70                  75                  80

Ser Gln Pro Leu Val Gln Thr Ala Val Thr Thr Ile Pro Ala Pro Thr
                85                  90                  95

Asp Leu Lys Phe Thr Gln Val Thr Pro Thr Ser Leu Ser Ala Gln Trp
            100                 105                 110

Thr Pro Pro Asn Val Gln Leu Thr Gly Tyr Arg Val Arg Val Thr Pro
        115                 120                 125

Lys Glu Lys Thr Gly Pro Met Lys Glu Ile Asn Leu Ala Pro Asp Ser
    130                 135                 140

Ser Ser Val Val Val Ser Gly Leu Met Val Ala Thr Lys Tyr Glu Val
145                 150                 155                 160
```

```
Ser Val Tyr Ala Leu Lys Asp Thr Leu Thr Ser Arg Pro Ala Gln Gly
            165                 170                 175

Val Val Thr Thr Leu Glu His His His His His His
            180                 185
```

MATERIALS AND METHODS FOR IMPROVED SINGLE CHAIN VARIABLE FRAGMENTS

CROSS-REFERENCE TO RELATED APPLICATIONS

This application claims the benefit of U.S. Provisional Patent Application No. 62/946,897, filed Dec. 11, 2019, U.S. Provisional Patent Application No. 62/946,886, filed Dec. 11, 2019, U.S. Provisional Patent Application No. 62/946,882, filed Dec. 11, 2019, U.S. Provisional Patent Application No. 62/946,877, filed Dec. 11, 2019, U.S. Provisional Patent Application No. 62/946,865, filed Dec. 11, 2019, U.S. Provisional Patent Application No. 62/887,529, filed Aug. 15, 2019, U.S. Provisional Patent Application No. 62/887,527, filed Aug. 15, 2019, U.S. Provisional Patent Application No. 62/887,524, filed Aug. 15, 2019, U.S. Provisional Patent Application No. 62/887,519, filed Aug. 15, 2019, and U.S. Provisional Patent Application No. 62/887,514, filed Aug. 15, 2019, each of which is incorporated by reference herein in its entirety.

SEQUENCE LISTING

This application incorporates by reference a Sequence Listing submitted with this application as a text format, entitled "14620-227-999_SL.txt," created on Aug. 5, 2020 having a size of 258,724 bytes.

1. TECHNICAL FIELD

Disclosed are materials and methods for improved single chain variable fragments.

2. BACKGROUND

Antigen binding single chain variable fragments (scFv) are modules that can be utilized broadly as therapeutics, imaging agents, diagnostic agents or as portions of heterologous molecules such as multispecific molecules. One of the challenges of scFvs is the low stability and tendencies to aggregate (reviewed in Worn and Pluckthun (2001) *J Mol Biol* 305: 989-1010; Rothlisberger et al., (2005) *J Mol Biol* 347: 773-789; Gross et al., (1989) *Transplant Proc* 21(1 Pt 1): 127-130, Porter et al., (2011) *J Cancer* 2: 331-332; Porter et al., (2011) *N Engl J Med* 365: 725-733). Therefore there is a need for improved scFv designs that may be optionally incorporated into multispecific molecules and heterologous molecules.

3. SUMMARY

In one aspect, the disclosure provides an isolated single chain variable fragment (scFv) comprising a heavy chain variable region (VH), a linker (L) and a light chain variable region (VL), wherein the scFv comprises
    a first disulfide bond between a structurally conserved surface exposed VH cysteine (Cys) and a first L Cys;
    a second disulfide bond between a structurally conserved surface exposed VL Cys and a second L Cys; or
    the first disulfide bond between the structurally conserved surface exposed VH Cys and the first L Cys and the second disulfide bond between the structurally conserved surface exposed VL Cys and the second L Cys.
The disclosure also provides an isolated scFv comprising a VH, a L and a VL, wherein
    the VH comprises a VH Cys at a structurally conserved surface exposed VH framework residue position and the L comprises a first L Cys;
    the VL comprises a VL Cys at a structurally conserved surface exposed VL framework residue position and the L comprises a second L Cys; or
    the VH comprises the VH Cys at a structurally conserved surface exposed VH framework residue position, the VL comprises the VL Cys at a structurally conserved surface exposed VL framework residue position and the L comprises the first L Cys and the second L Cys, wherein
    the VH Cys and the first L Cys are capable of forming a disulfide bond and the VL Cys and the second L Cys are capable of forming a disulfide bond.
The disclosure also provides an scFv comprising a VH, a L and a VL, wherein
    the VH comprises Cys at H105;
    the VL comprises Cys at L42;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H105;
    the VL comprises Cys at L45;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H105;
    the VL comprises Cys at L39;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H5;
    the VL comprises Cys at L42;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H5;
    the VL comprises Cys at L45;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H5;
    the VL comprises Cys at L39;
    the L comprises an amino acid sequence of SEQ ID NOs: 2, 3, 4, 5, 6 or 7; and
    the scFv is in the VL-L-VH orientation.
The disclosure also provides a scFv comprising a VH, a L and a VL, wherein
    the VH comprises Cys at H3;
    the VL comprises Cys at L42;
    the L comprises an amino acid sequence of SEQ ID NOs: 2, 3, 4, 5, 6 or 7; and
    the scFv is in the VL-L-VH orientation.

The disclosure also provides a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

The disclosure also provides a pharmaceutical composition comprising the spFv of the disclosure and a pharmaceutically acceptable carrier.

The disclosure also provides a polynucleotide encoding the spFv of the disclosure.

The disclosure also provides a vector comprising the polynucleotide of the disclosure.

The disclosure also provides a host cell comprising the vector of the disclosure.

The disclosure also provides a method of producing the spFv of the disclosure, comprising culturing the host cell of the disclosure in conditions that the spFv is produced, and purifying the spFv.

The disclosure also provides an anti-idiotypic antibody that binds to the spFv of the disclosure.

The disclosure also provides a kit comprising the spFv of the disclosure.

In another aspect, the disclosure provides a multispecific molecule comprising a single chain variable fragment (scFv) comprising a heavy chain variable region (VH), a linker (L) and a light chain variable region (VL), wherein the scFv comprises
a first disulfide bond between a structurally conserved surface exposed VH cysteine (Cys) and a first L Cys;
a second disulfide bond between a structurally conserved surface exposed VL Cys and a second L Cys; or
the first disulfide bond between the structurally conserved surface exposed VH Cys and the first L Cys and the second disulfide bond between the structurally conserved surface exposed VL Cys and the second L Cys.

The disclosure also provides a multispecific molecule comprising a scFv comprising a VH, a L and a VL, wherein
the VH comprises a VH Cys at a structurally conserved surface exposed VH framework residue position and the L comprises a first L Cys;

the VL comprises a VL Cys at a structurally conserved surface exposed VL framework residue position and the L comprises a second L Cys; or the VH comprises the VH Cys at a structurally conserved surface exposed VH framework residue position, the VL comprises the VL Cys at a structurally conserved surface exposed VL framework residue position and the L comprises the first L Cys and the second L Cys, wherein the VH Cys and the first L Cys are capable of forming a disulfide bond and the VL Cys and the second L Cys are capable of forming a disulfide bond.

The disclosure also provides a multispecific molecule comprising a scFv comprising a VH, a L and a VL, wherein
the VH comprises Cys at H105;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H105;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H105;
the VL comprises Cys at L39;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L100;

the L comprises an amino acid sequence of SEQ ID NOs: 2, 3, 4, 5, 6 or 7; and the scFv is in the VH-L-VL orientation.

The disclosure also provides a multispecific molecule comprising a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

The disclosure also provides a pharmaceutical composition comprising the multispecific molecule provided herein and a pharmaceutically acceptable carrier.

In yet another aspect, the disclosure provides a heterologous molecule comprising a single chain variable fragment (scFv) comprising a heavy chain variable region (VH), a linker (L) and a light chain variable region (VL), wherein the scFv comprises
a first disulfide bond between a structurally conserved surface exposed VH cysteine (Cys) and a first L Cys;
a second disulfide bond between a structurally conserved surface exposed VL Cys and a second L Cys; or
the first disulfide bond between the structurally conserved surface exposed VH Cys and the first L Cys and the second disulfide bond between the structurally conserved surface exposed VL Cys and the second L Cys.

The disclosure also provides a heterologous molecule comprising a scFv comprising a VH, a L and a VL, wherein
the VH comprises a VH Cys at a structurally conserved surface exposed VH framework residue position and the L comprises a first L Cys;
the VL comprises a VL Cys at a structurally conserved surface exposed VL framework residue position and the L comprises a second L Cys; or
the VH comprises the VH Cys at a structurally conserved surface exposed VH framework residue position, the VL comprises the VL Cys at a structurally conserved surface exposed VL framework residue position and the L comprises the first L Cys and the second L Cys, wherein
the VH Cys and the first L Cys are capable of forming a disulfide bond and the VL Cys and the second L Cys are capable of forming a disulfide bond.

The disclosure also provides a heterologous molecule comprising a scFv comprising a VH, a L and a VL, wherein
the VH comprises Cys at H105;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H105;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H105;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

The disclosure also provides a pharmaceutical composition comprising the heterologous molecule of the disclosure and a pharmaceutically acceptable carrier.

In yet another aspect, the disclosure provides a process for preparing a stabilized scFv, comprising:
providing a heavy chain variable region (VH) and a light chain variable region (VL) that form an antigen binding domain;
providing a linker (L) that comprises or is engineered to comprise a first L Cys;
engineering the VH to comprise a VH Cys at a structurally conserved surface exposed VH framework residue position; and
forming a disulfide bond between the VH Cys and the first L Cys to prepare the stabilized scFv.

The disclosure also provides a process for preparing a stabilized scFv, comprising: providing a VH and a VL that form an antigen binding domain;
providing a L that comprises or is engineered to comprise a second L Cys;
engineering the VL to comprise a VL Cys at a structurally conserved surface exposed VL framework residue position; and
forming a disulfide bond between the VL Cys and the second L Cys to prepare the stabilized scFv.

The disclosure also provides a process for preparing a stabilized scFv, comprising: providing a VH and a VL that form an antigen binding domain;
providing a L that comprises or is engineered to comprise a first L Cys and a second L Cys;
engineering the VH to comprise a VH Cys at a structurally conserved surface exposed VH framework residue position;
engineering the VL to comprise a VL Cys at a structurally conserved surface exposed VL framework residue position; and
forming a disulfide bond between the VH Cys and the first L Cys and a disulfide bond between the VL Cys and the second L Cys to prepare the stabilized scFv.

The disclosure also provides a process for preparing a stabilized scFv, comprising providing a polynucleotide encoding a VH, a L and a VL, wherein
the VH comprises Cys at H105 and the VL comprises Cys at L42;
the VH comprises Cys at H43 and the VL comprises Cys at a L100;
the VH comprises Cys at H3 and the VL comprises Cys at L3;
the VH comprises Cys at H3 and the VL comprises Cys at L5;
the VH comprises Cys at H3 and the VL comprises Cys at L39;
the VH comprises Cys at H3 and the VL comprises Cys at L42;
the VH comprises Cys at H3 and the VL comprises Cys at L45;
the VH comprises Cys at H3 and the VL comprises Cys at L100;
the VH comprises Cys at H3 and the VL comprises Cys at L102;
the VH comprises Cys at H5 and the VL comprises Cys at L3;
the VH comprises Cys at H5 and the VL comprises Cys at L5;

the VH comprises Cys at H5 and the VL comprises Cys at L39;
the VH comprises Cys at H5 and the VL comprises Cys at L42;
the VH comprises Cys at H5 and the VL comprises Cys at L45;
the VH comprises Cys at H5 and the VL comprises Cys at L100;
the VH comprises Cys at H5 and the VL comprises Cys at L102;
the VH comprises Cys at H40 and the VL comprises Cys at L3;
the VH comprises Cys at H40 and the VL comprises Cys at L5;
the VH comprises Cys at H40 and the VL comprises Cys at L39;
the VH comprises Cys at H40 and the VL comprises Cys at L42;
the VH comprises Cys at H40 and the VL comprises Cys at L45;
the VH comprises Cys at H40 and the VL comprises Cys at L100;
the VH comprises Cys at H40 and the VL comprises Cys at L102;
the VH comprises Cys at H43 and the VL comprises Cys at L3;
the VH comprises Cys at H43 and the VL comprises Cys at L5;
the VH comprises Cys at H43 and the VL comprises Cys at L39;
the VH comprises Cys at H43 and the VL comprises Cys at L42;
the VH comprises Cys at H43 and the VL comprises Cys at L45;
the VH comprises Cys at H43 and the VL comprises Cys at L102;
the VH comprises Cys at H46 and the VL comprises Cys at L3;
the VH comprises Cys at H46 and the VL comprises Cys at L5;
the VH comprises Cys at H46 and the VL comprises Cys at L39;
the VH comprises Cys at H46 and the VL comprises Cys at L42;
the VH comprises Cys at H46 and the VL comprises Cys at L45;
the VH comprises Cys at H46 and the VL comprises Cys at L100;
the VH comprises Cys at H46 and the VL comprises Cys at L102;
the VH comprises Cys at H105 and the VL comprises Cys at L3;
the VH comprises Cys at H105 and the VL comprises Cys at L5;
the VH comprises Cys at H105 and the VL comprises Cys at L39;
the VH comprises Cys at H105 and the VL comprises Cys at L45;
the VH comprises Cys at H105 and the VL comprises Cys at L100; or
the VH comprises Cys at H105 and the VL comprises Cys at L102, wherein residue numbering is according to Chothia.
the L comprises an amino acid sequence of SEQ ID NOs: 2, 3, 4, 5, 6 or 7; and expressing the polynucleotide in a host cell to produce the stabilized scFv.

In yet another aspect, the disclosure provides an isolated single chain variable fragment (scFv) comprising a heavy chain variable region (VH), a means for linking (L) and a light chain variable region (VL), wherein the scFv comprises:
a first disulfide bond between a structurally conserved surface exposed VH cysteine (Cys) and a first L Cys;
a second disulfide bond between a structurally conserved surface exposed VL Cys and a second L Cys; or
the first disulfide bond between the structurally conserved surface exposed VH Cys and the first L Cys and the second disulfide bond between the structurally conserved surface exposed VL Cys and the second L Cys.

The disclosure also provides an isolated single chain variable fragment (scFv) comprising a means for antigen binding, a linker (L) and a light chain variable region (VL), wherein the scFv comprises
a first disulfide bond between a structurally conserved surface exposed antigen binding means cysteine (Cys) and a first L Cys;
a second disulfide bond between a structurally conserved surface exposed VL Cys and a second L Cys; or
the first disulfide bond between the structurally conserved surface exposed antigen binding means Cys and the first L Cys and the second disulfide bond between the structurally conserved surface exposed VL Cys and the second L Cys.

The disclosure also provides an isolated single chain variable fragment (scFv) comprising a heavy chain variable region (VH), a linker (L) and a means for antigen binding, wherein the scFv comprises
a first disulfide bond between a structurally conserved surface exposed VH cysteine (Cys) and a first L Cys;
a second disulfide bond between a structurally conserved surface exposed antigen binding means Cys and a second L Cys; or
the first disulfide bond between the structurally conserved surface exposed VH Cys and the first L Cys and the second disulfide bond between the structurally conserved surface exposed antigen binding means Cys and the second L Cys.

The disclosure also provides a multispecific molecule comprising a single chain variable fragment (scFv) comprising a heavy chain variable region (VH), a a means for linking (L) and a light chain variable region (VL), wherein the scFv comprises
a first disulfide bond between a structurally conserved surface exposed VH cysteine (Cys) and a first L Cys;
a second disulfide bond between a structurally conserved surface exposed VL Cys and a second L Cys; or
the first disulfide bond between the structurally conserved surface exposed VH Cys and the first L Cys and the second disulfide bond between the structurally conserved surface exposed VL Cys and the second L Cys.

The disclosure also provides a multispecific molecule comprising a single chain variable fragment (scFv) comprising a means for antigen binding, a linker (L) and a light chain variable region (VL), wherein the scFv comprises
a first disulfide bond between a structurally conserved surface exposed antigen binding means cysteine (Cys) and a first L Cys;
a second disulfide bond between a structurally conserved surface exposed VL Cys and a second L Cys; or
the first disulfide bond between the structurally conserved surface exposed antigen binding means Cys and the first L Cys and the second disulfide bond between the structurally conserved surface exposed VL Cys and the second L Cys.

The disclosure also provides a multispecific molecule comprising a single chain variable fragment (scFv) comprising a heavy chain variable region (VH), a linker (L) and a means for antigen binding (VL), wherein the scFv comprises
- a first disulfide bond between a structurally conserved surface exposed VH cysteine (Cys) and a first L Cys;
- a second disulfide bond between a structurally conserved surface exposed antigen binding means Cys and a second L Cys; or
- the first disulfide bond between the structurally conserved surface exposed VH Cys and the first L Cys and the second disulfide bond between the structurally conserved surface exposed antigen binding means Cys and the second L Cys.

The disclosure also provides a heterologous molecule comprising a single chain variable fragment (scFv) comprising a heavy chain variable region (VH), a means for linking (L) and a light chain variable region (VL), wherein the scFv comprises
- a first disulfide bond between a structurally conserved surface exposed VH cysteine (Cys) and a first L Cys;
- a second disulfide bond between a structurally conserved surface exposed VL Cys and a second L Cys; or
- the first disulfide bond between the structurally conserved surface exposed VH Cys and the first L Cys and the second disulfide bond between the structurally conserved surface exposed VL Cys and the second L Cys.

The disclosure also provides a heterologous molecule comprising a single chain variable fragment (scFv) comprising a means for antigen binding, a linker (L) and a light chain variable region (VL), wherein the scFv comprises
- a first disulfide bond between a structurally conserved surface exposed antigen binding means cysteine (Cys) and a first L Cys;
- a second disulfide bond between a structurally conserved surface exposed VL Cys and a second L Cys; or
- the first disulfide bond between the structurally conserved surface exposed antigen binding means Cys and the first L Cys and the second disulfide bond between the structurally conserved surface exposed VL Cys and the second L Cys.

The disclosure also provides a heterologous molecule comprising a single chain variable fragment (scFv) comprising a heavy chain variable region (VH), a linker (L) and a means for antigen binding, wherein the scFv comprises
- a first disulfide bond between a structurally conserved surface exposed VH cysteine (Cys) and a first L Cys;
- a second disulfide bond between a structurally conserved surface exposed antigen binding means Cys and a second L Cys; or
- the first disulfide bond between the structurally conserved surface exposed VH Cys and the first L Cys and the second disulfide bond between the structurally conserved surface exposed antigen binding means Cys and the second L Cys.

The disclosure also provides a means for encoding the scFv provided herein.

The disclosure also provides an means for replicating the vector provided herein.

The disclosure also provides a composition comprising a means for stabilizing a scFv.

The disclosure also provides a composition comprising a means for increasing thermostability of a scFv.

The disclosure also provides a multispecific molecule comprising a means for stabilizing a scFv.

The disclosure also provides a multispecific molecule comprising a means for increasing thermostability of a scFv.

The disclosure also provides a heterologous molecule comprising a means for stabilizing a scFv.

The disclosure also provides a heterologous molecule comprising a means for increasing thermostability of a scFv.

4. BRIEF DESCRIPTION OF THE DRAWINGS

FIG. 1 shows an exemplary design of the stabilized scFv (spFv). The VL and the VH are connected by a flexible linker shown as a dashed line in the Figure containing a staple sequence CPPC (SEQ ID NO: 1) "SS" indicates disulfide bonds between the staple sequence in the linker and anchor points.

FIG. 2 shows a graphical illustration of anchor point selection for spFv in the VL-linker-VH orientation. Fv of the germline human antibody (pdb id 5119, GLk1) was used for graphics and illustrative distance measurements. Distances shown in dashed lines are between Cβ atoms of the residues in A. Structurally conserved framework positions with desired distances were chosen as anchor points for mutation into Cys. Anchor points for VL-linker-VH orientation were Chothia position 42 for VL (K42 in the Figure) and position 105 for VH (Q105 in the Figure). The C-terminal VL residue (K107) and the N-terminal VH residue (Q1) are also shown.

FIG. 3 shows a graphical illustration of anchor point selection for spFv in the VH-linker-VL orientation. Fv of the germline human antibody (pdb id 5119, GLk1) was used for graphics and illustrative distance measurements. Distances shown in dashed lines are between Cβ atoms of the residues in A. Structurally conserved framework positions with desired distances were chosen as anchor points for mutation into Cys. Anchor points for VH-linker-VL orientation were Chothia position 43 for VH (K43 in the Figure) and position 100 for VL (Q100 in the Figure). The C-terminal VH residue (S114) and the N-terminal VL residue (D1) are also shown.

Figure 1:
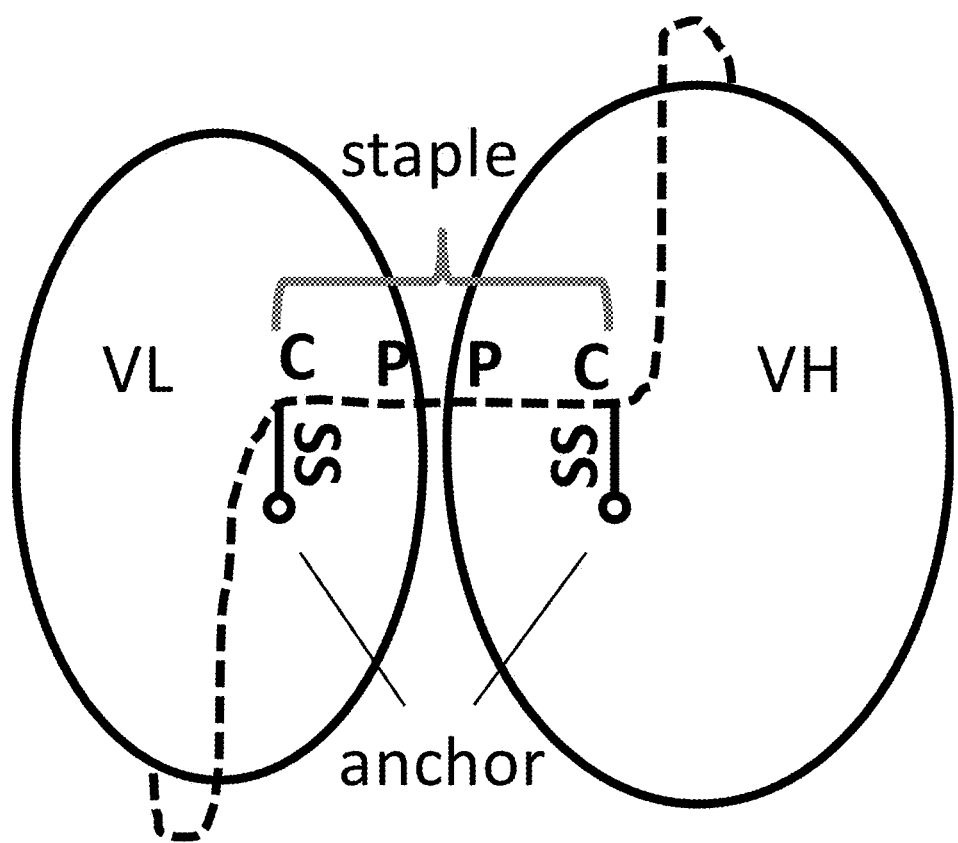

FIG. 6 shows the chosen VL anchor points highlighted in grey and numbered as 1 and 2 below the amino acid alignments. The VL sequences are numbered according to the Chothia numbering scheme. The VL anchor point 1 (Chothia position 42) was used in spFv in the VL-linker-VH orientation and the VL anchor point 2 (Chothia position 100) was used in spFv in the VH-linker-VL orientation. GLk1VL: SEQ ID NO: 56, GLk2VL: SEQ ID NO: 57, CAT2200VL: SEQ ID NO: 58; CAT2200bVL: SEQ ID NO: 59.

FIG. 7 shows the chosen VH anchor points highlighted in grey and numbered as 1 and 2 below the amino acid alignments. The VH sequences are numbered according to the Chothia numbering scheme. The VH anchor point 1 (Chothia position 105) was used in spFv in the VL-linker-VH orientation and the VH anchor point 2 (Chothia position 43) was used in spFv in the VH-linker-VL orientation. GLk1VH: SEQ ID NO: 60; GLk2VH: SEQ ID NO: 61, CAT2200aVH: SEQ ID NO: 62.

Figure 8:
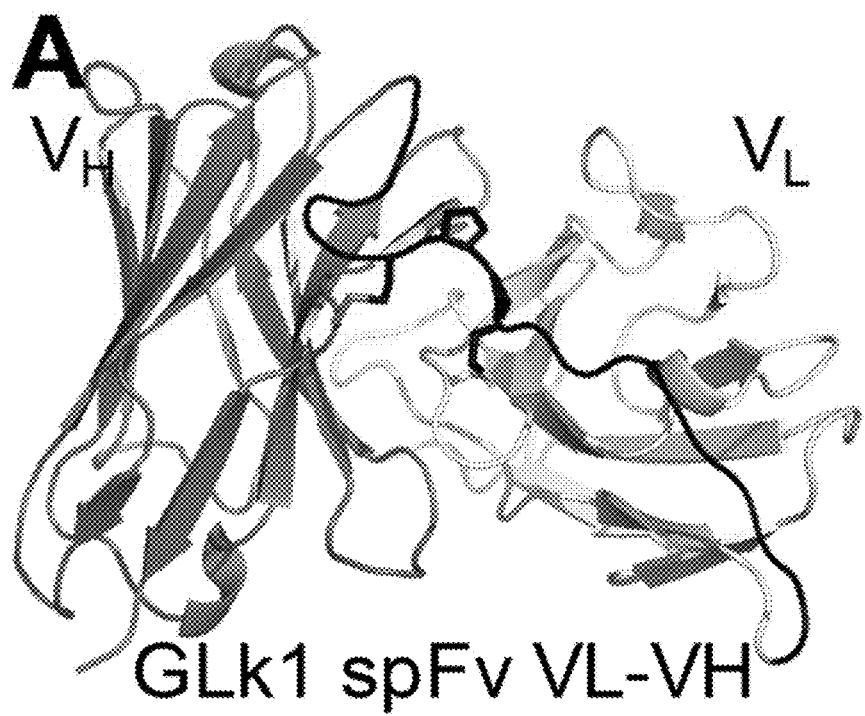

FIG. 8 shows the structure of GLk1 spFv VL-VH. The formation of the staple between the VH and VL anchor points and the linker is evident from the structure.

Figure 9:
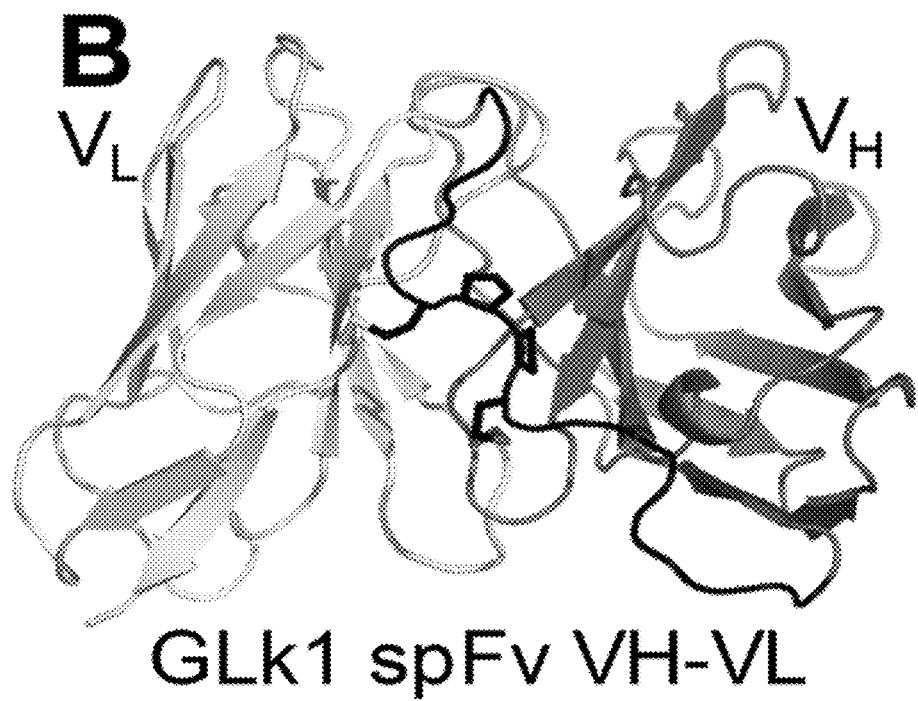

FIG. 9 shows the structure of GLk1 spFv VH-VL. The formation of the staple between the VH and VL anchor points and the linker is evident from the structure.

Figure 10:
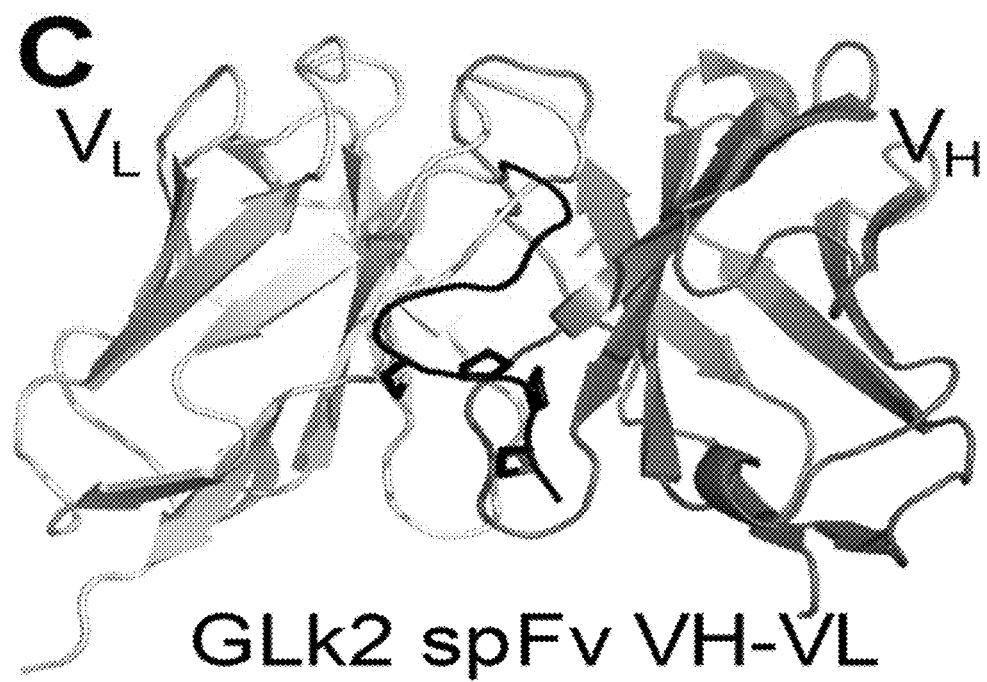

FIG. 10 shows the structure of GLk2 spFv VH-VL. The formation of the staple between the VH and VL anchor points and the linker is evident from the structure.

Figure 11:
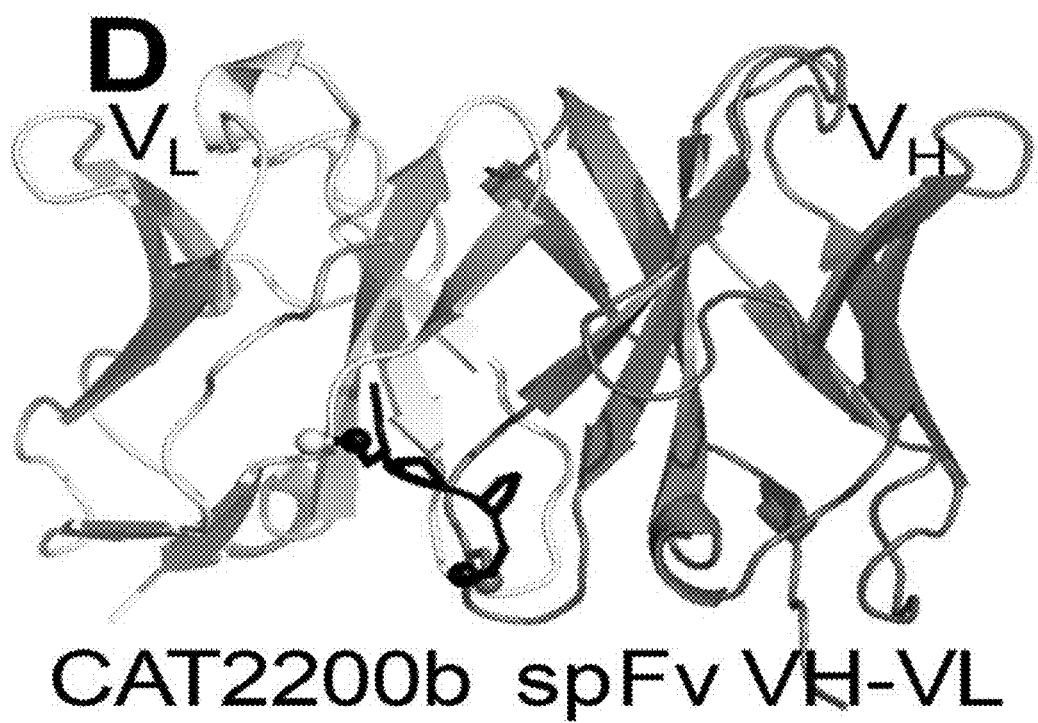

FIG. 11 shows the structure of CAT2200b spFv VH-VL. The formation of the staple between the VH and VL anchor points and the linker is evident from the structure.

Figure 12:
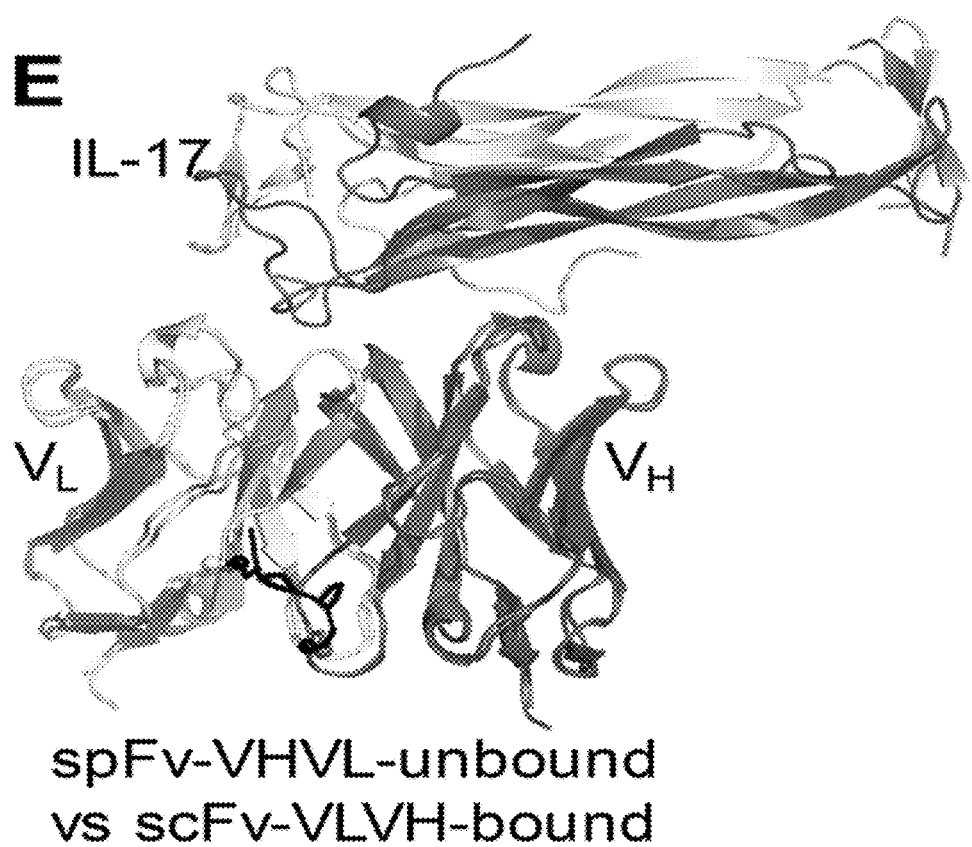

FIG. 12 shows the comparison of the unbound CAT2200b spFv VH-VL (top) compared to CAT2200a scFv VL-VH bound to IL-17A (bottom).

Figure 13:
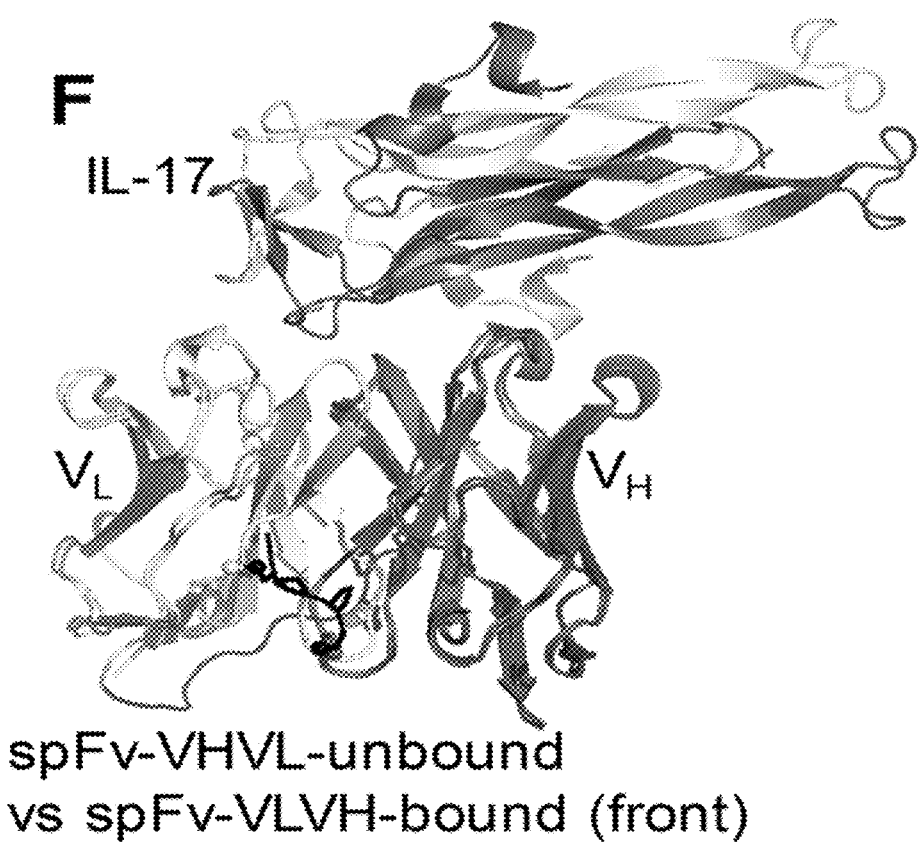

FIG. 13 shows the comparison of the front views of the structures of unbound CAT2200b spFv VH-VL (top) compared to CAT2200a spFv VL-VH bound to IL-17A (bottom).

Figure 14:
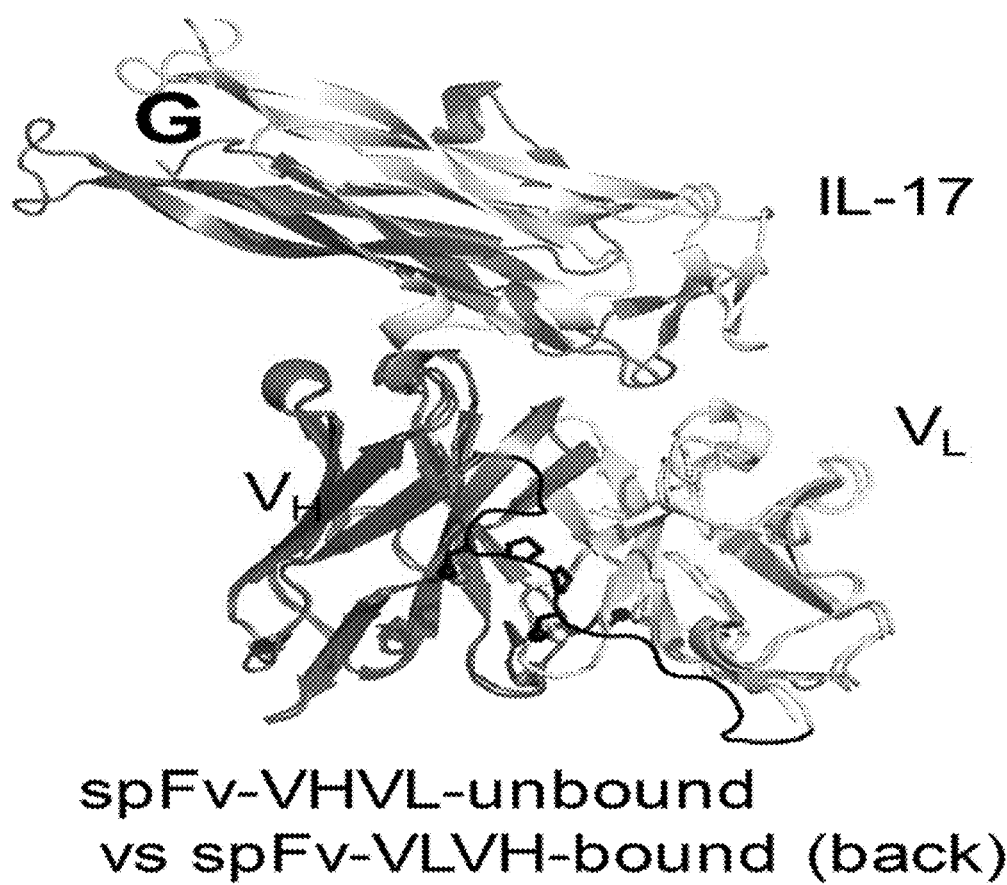

FIG. 14 shows the comparison of the back views of the structures of unbound CAT2200b spFv VH-VL (top) compared to CAT2200a spFv VL-VH bound to IL-17A (bottom).

FIGS. 15A-15M show schematic representations of antibodies fused to stapled scFv.

Figure 15A:
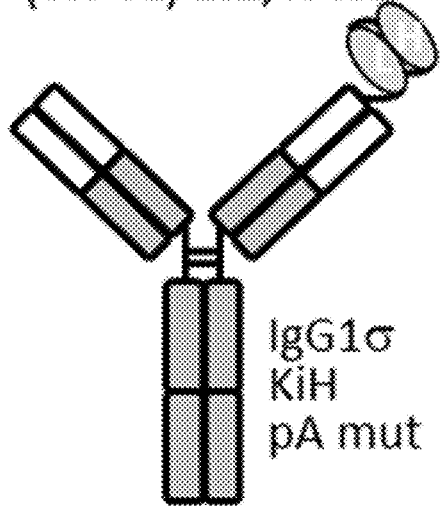
Figure 15B:
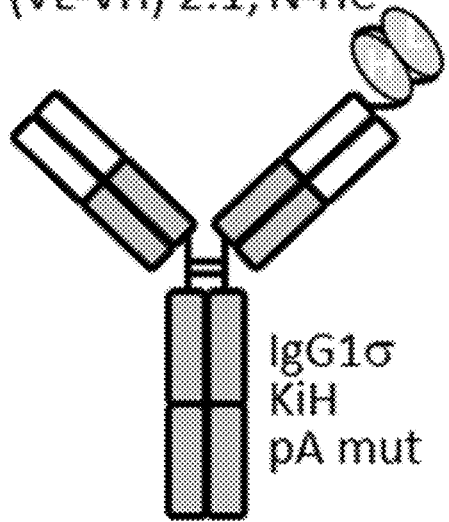
Figure 15C:
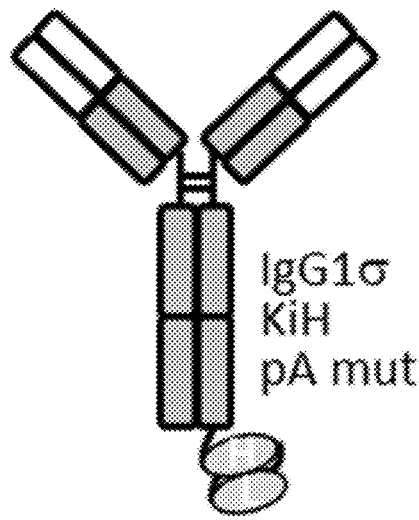
Figure 15D:
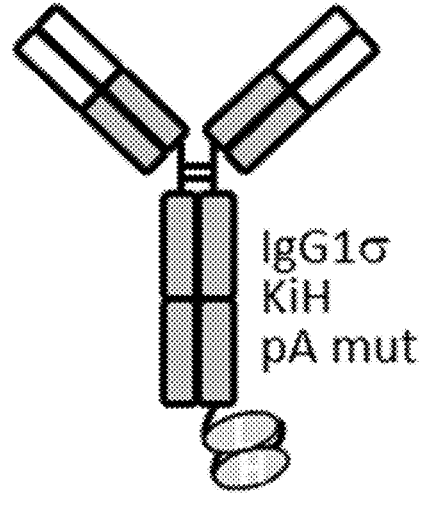
Figure 15E:
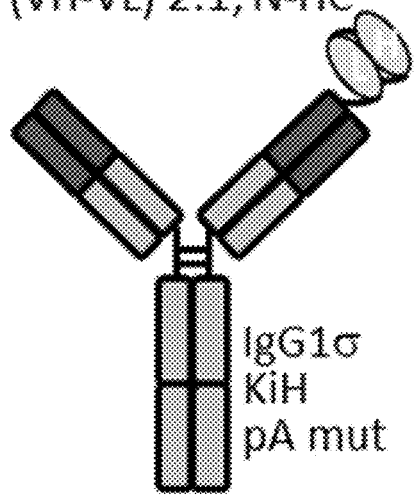
Figure 15F:
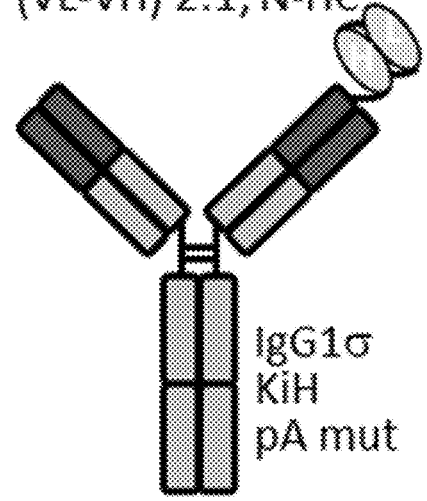
Figure 15G:
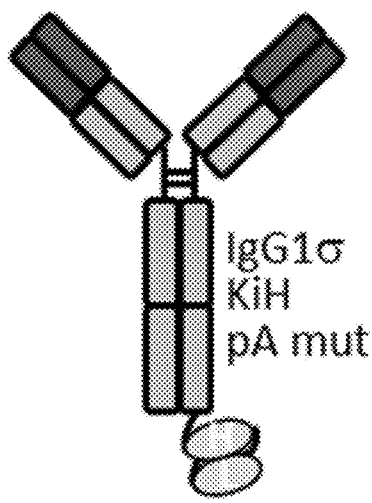
Figure 15H:
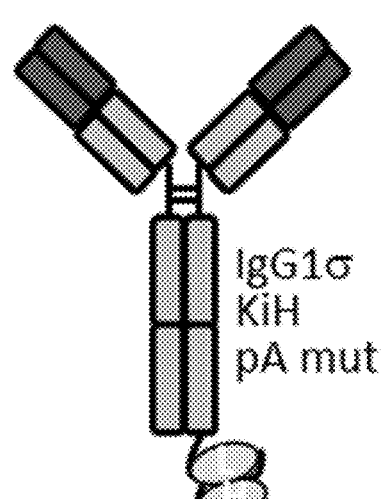
Figure 15I:
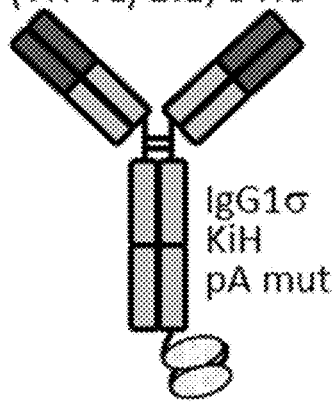
Figure 15J:
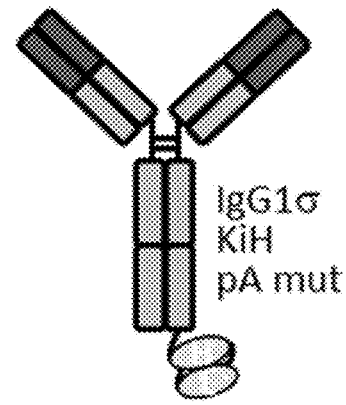
Figure 15K:
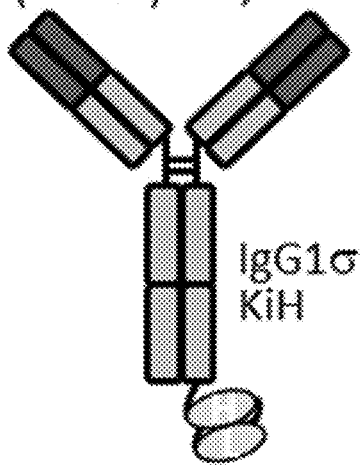
Figure 15L:
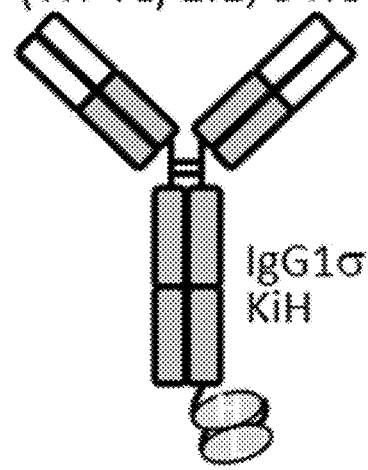
Figure 15M:
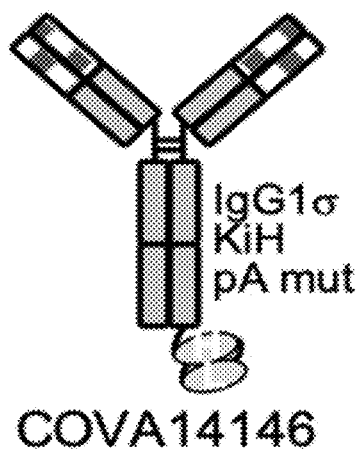

FIGS. 15A-15D show 2:1 heterodimers, isotype control antibody fused to stapled scFv derived from LTBRmAb1. FIGS. 15E-15H show 2:1 heterodimers, EDBmAb1 fused to stapled scFv derived from LTBRmAb1. FIGS. 15I-15J show 2:1 heterodimers, EDBmAb1 fused to stapled scFv derived from lower affinity variants of LTBRmAb1. FIGS. 15K-15L show 2:1 heterodimers, EDBmAb1 or B21M fused to stapled scFv derived from LTBRmAb1, without protein A mutations in the Fc region. FIG. 15M shows a 2:1 heterodimer, MSLNmAb1 fused to stapled scFv derived from LTBRmAb1.

Figure 16A:
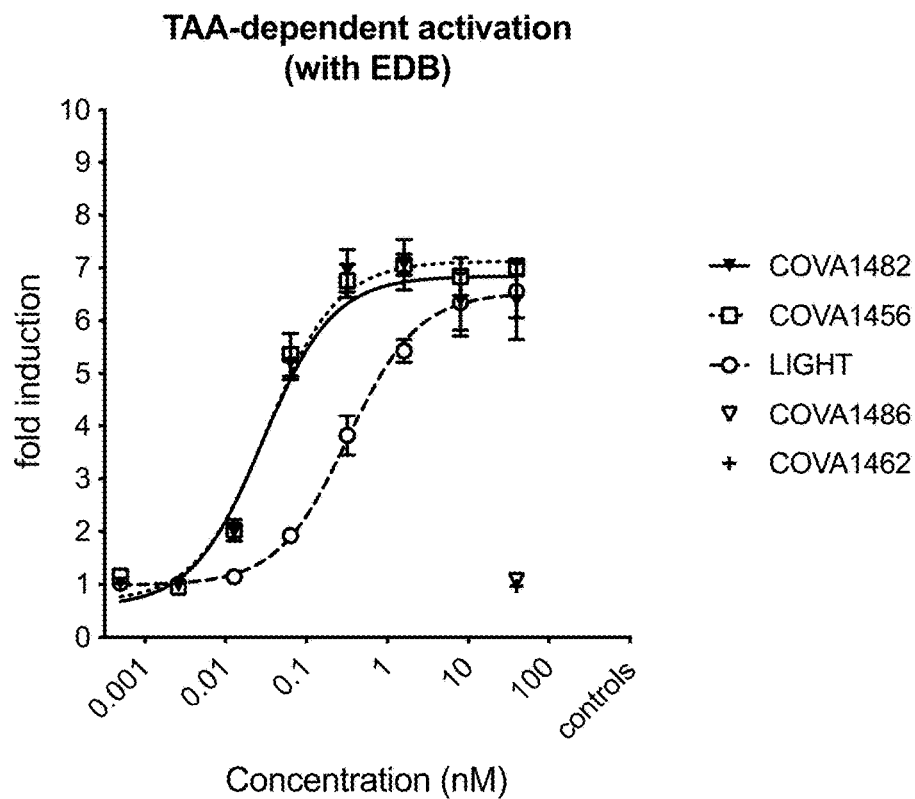
Figure 16B:
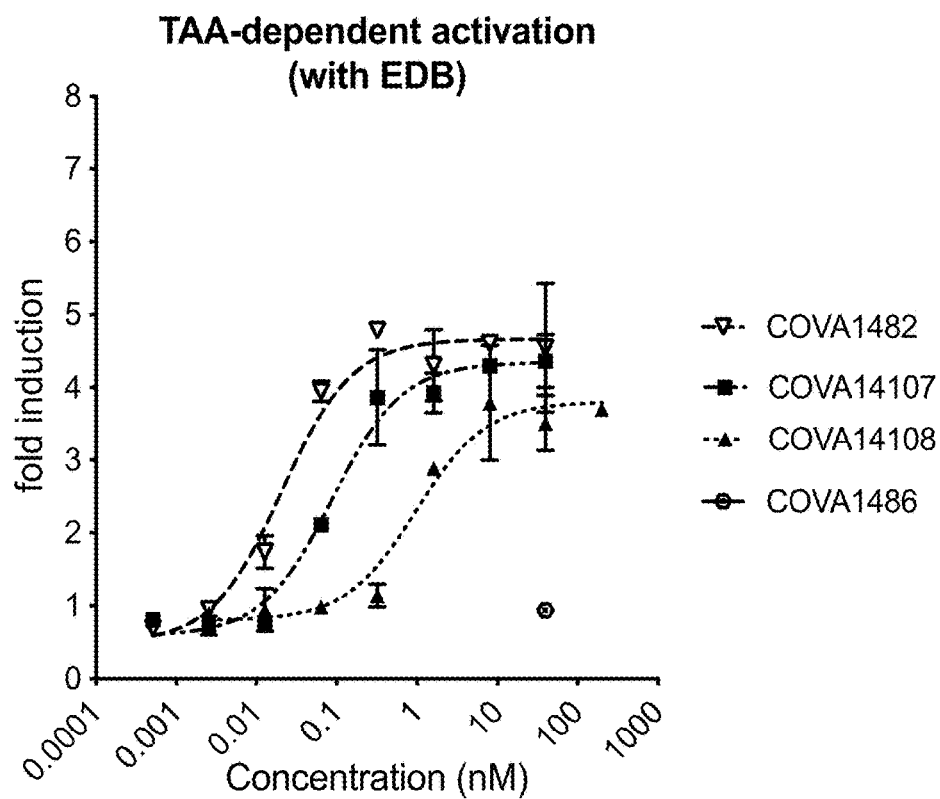
Figure 16C:
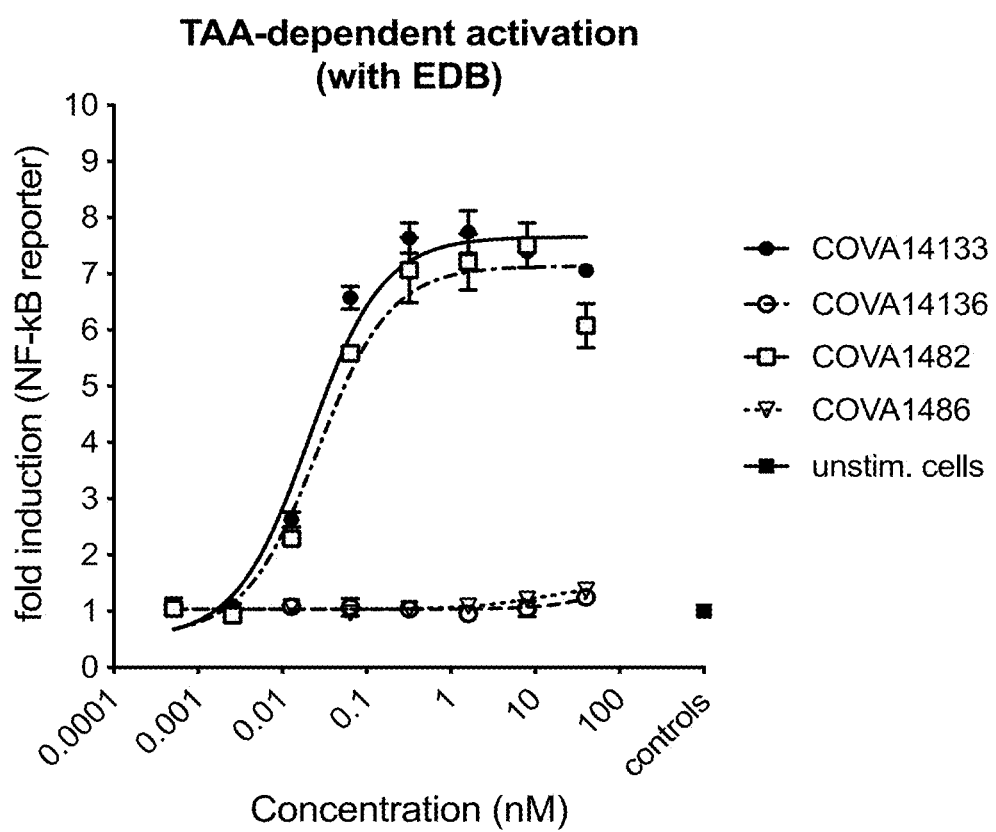

FIGS. 16A-16C show graphs demonstrating the results of A549 NF-κB reporter assays using 2:1 bispecific antibodies. FIG. 16A: Comparison of TAA-dependent LTBR activation by COVA1456 with COVA1482, their respective control molecules COVA1462 and COVA1486, and recombinant human LIGHT; FIG. 16B: Comparison of TAA-dependent LTBR activation by COVA1482 and bispecifics containing lower affinity variants of LTBRmAb1 COVA14107 and COVA14108, and COVA1486; FIG. 16C: Comparison of TAA-dependent LTBR activation by COVA1482 and COVA14133 (construct without protein A mutations), and their respective control molecules COVA1486 and COVA14136.

Figure 17:
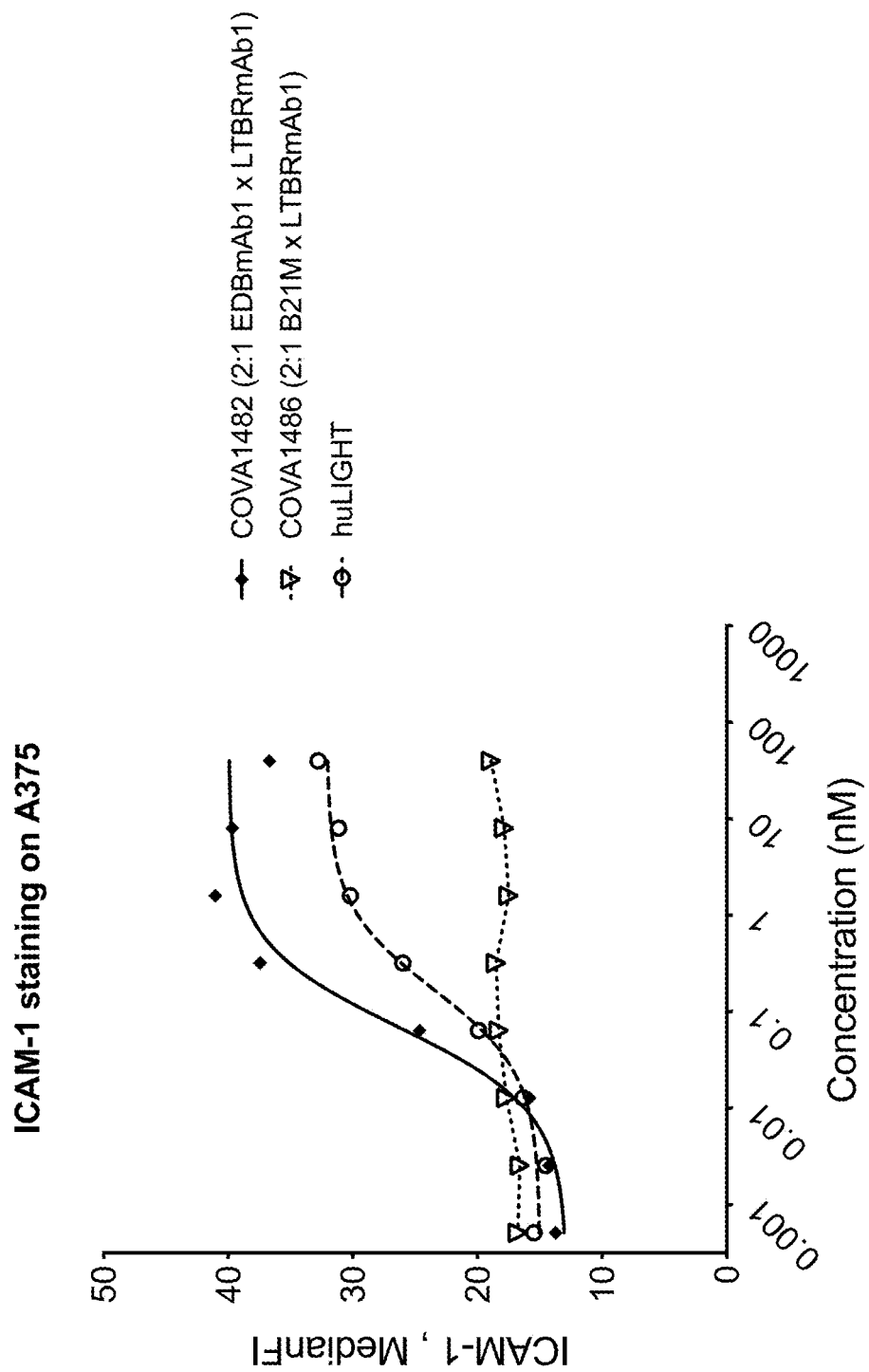

FIG. 17 shows the results of flow cytometry staining of ICAM-1 on A375 cells after co-culture experiment. COVA1482 and its control molecule COVA1486 are compared to recombinant human LIGHT.

Figure 18A:
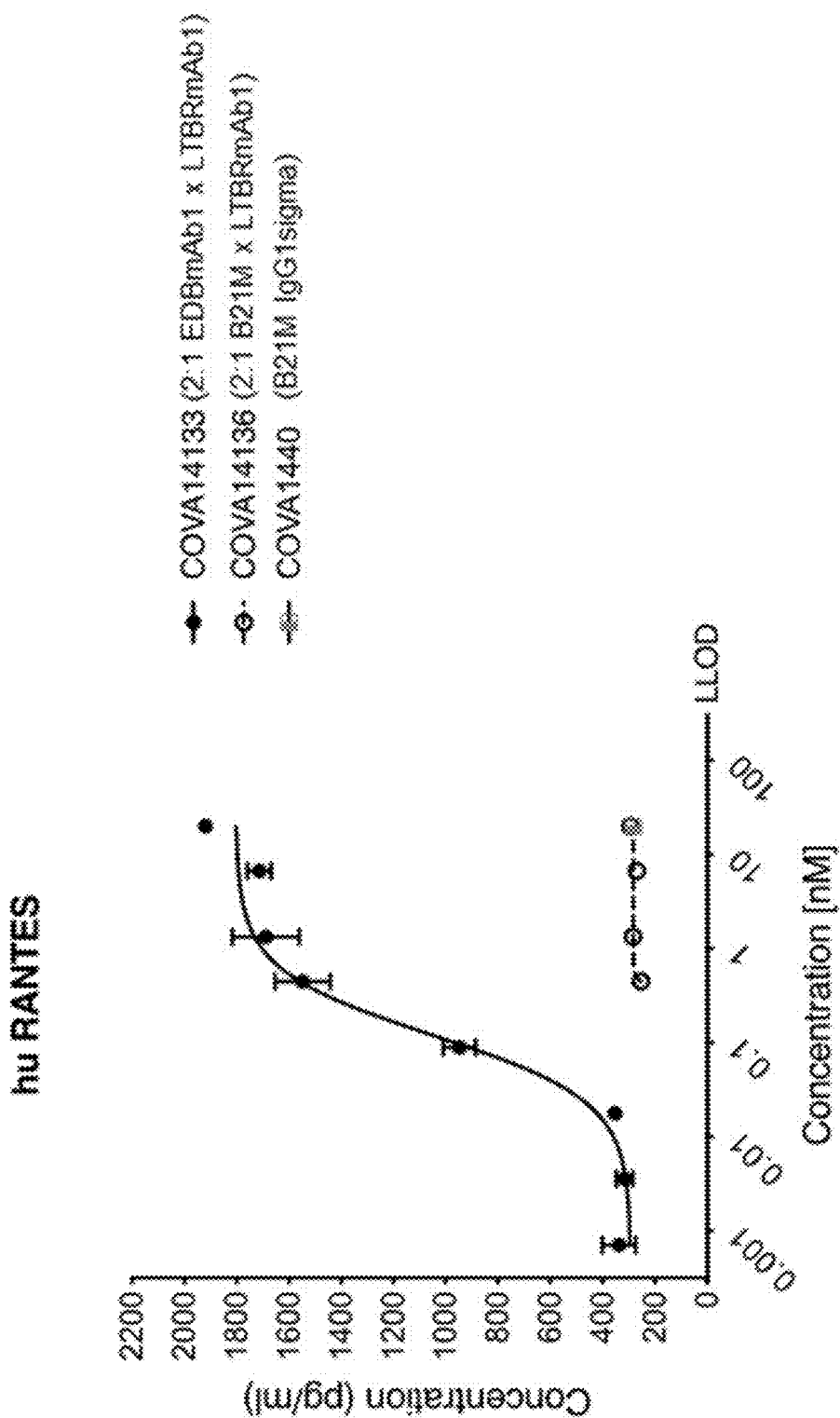
Figure 18B:
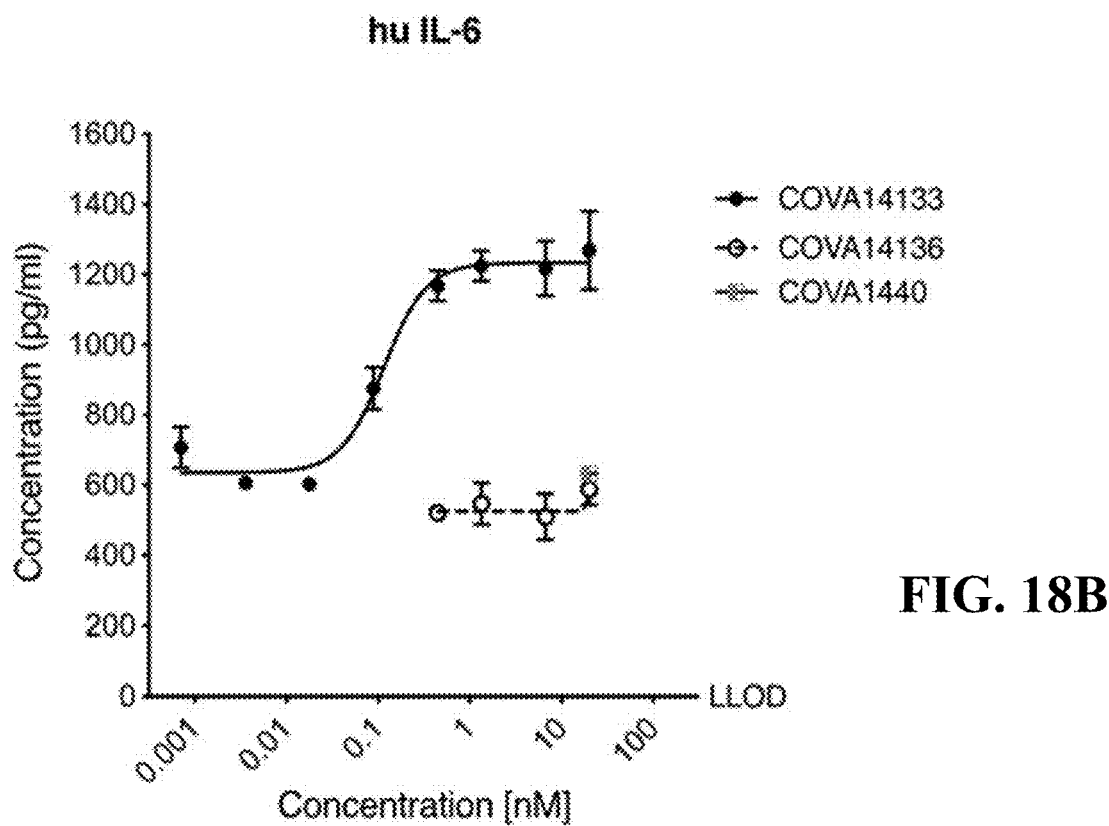
Figure 18C:
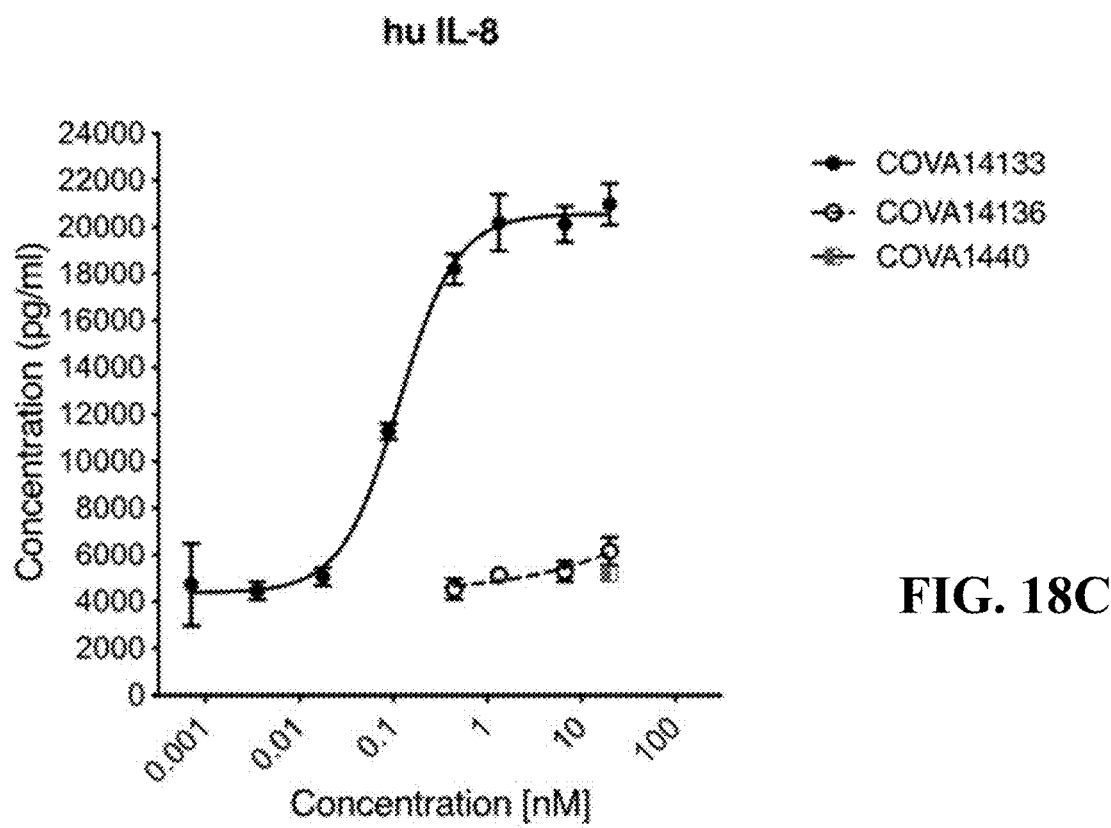
Figure 18D:
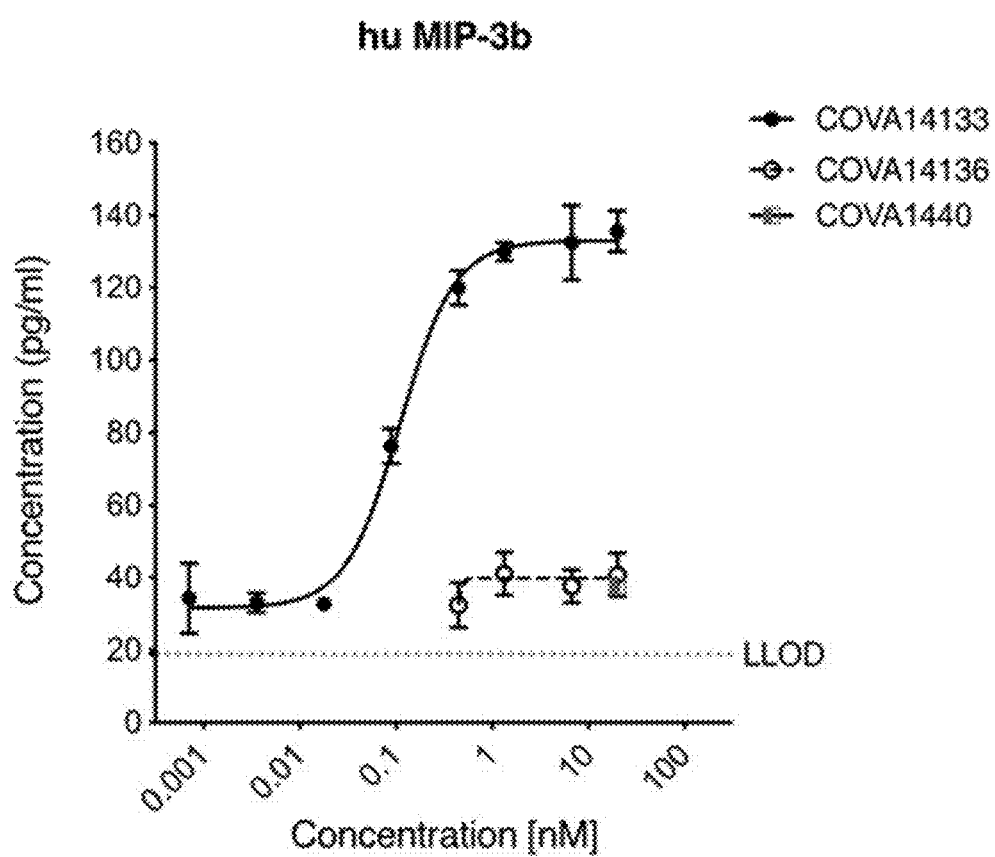

FIGS. 18A-18D show graphs demonstrating measurements of cytokines in supernatants of co-cultures treated with anti-EDB/anti-LTBR bispecific antibodies COVA14133 compared to COVA14136 and COVA1440. Assays are performed using the MSD platform. FIG. 18A: Concentrations of human RANTES; FIG. 18B: Concentrations of human IL-6; FIG. 18C: Concentrations of human IL-8; FIG. 18D: Concentrations of human MIP-3b.

Figure 19A:
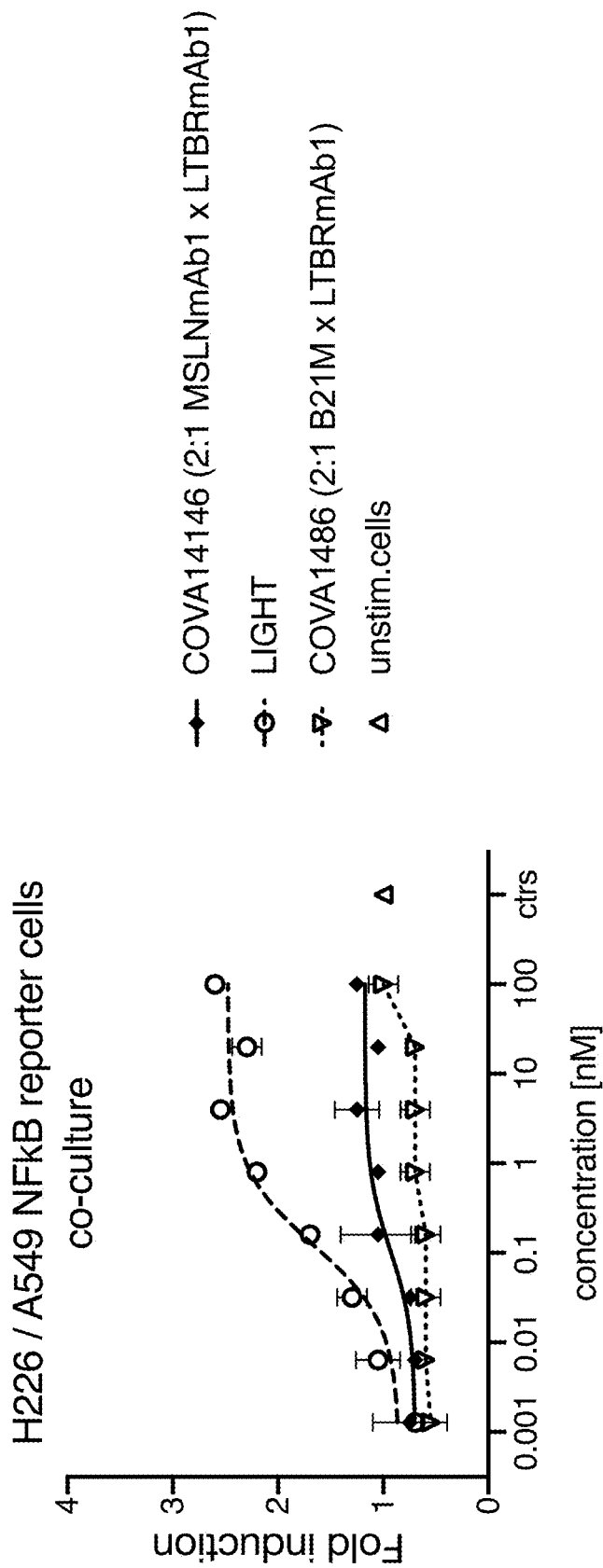
Figure 19B:
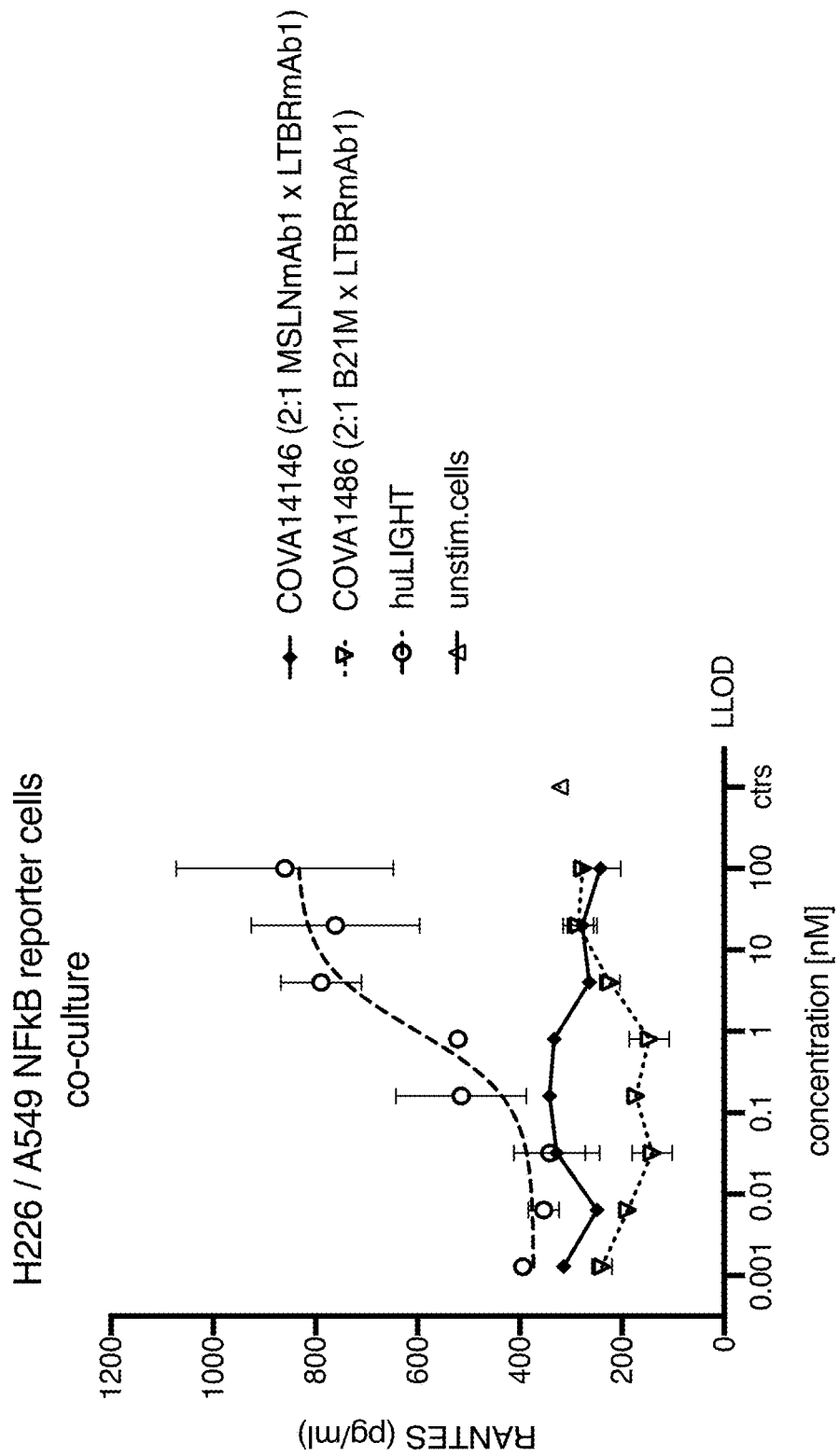

FIGS. 19A-19B show LTBR activation by a MSLN/LTBR bispecific in A549 NF-κB reporter/CHOK1MSLN or A549 NF-κB reporter/H226 co-culture cell assays. FIG. 19A: Activation of LTBR in A549 NF-κB reporter/H226 co-culture assay. COVA14146 (2:1 MSLNmAb1×LTBRmAb1) compared to LIGHT and to the isotype control 2:1 constructs COVA1486; FIG. 19B: Concentration of secreted RANTES upon activation of LTBR in A549 NF-κB reporter/H226 co-culture assay. COVA14146 (2:1 MSLNmAb1×LTBRmAb1) compared to LIGHT and to the isotype control 2:1 constructs COVA1486.

5. DETAILED DESCRIPTION

The disclosed methods may be understood more readily by reference to the following detailed description taken in connection with the accompanying Figures, which form a part of this disclosure. It is to be understood that the disclosed methods are not limited to the specific methods described and/or shown herein, and that the terminology used herein is for the purpose of describing particular embodiments by way of example only and is not intended to be limiting.

All patents, published patent applications and publications cited herein are incorporated by reference as if set forth fully herein.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Antibody-dependent cellular cytotoxicity," "antibody-dependent cell-mediated cytotoxicity" or "ADCC" refers to the mechanism of inducing cell death that depends upon the interaction of antibody-coated target cells with effector cells possessing lytic activity, such as natural killer cells (NK), monocytes, macrophages and neutrophils via Fc gamma receptors (FcγR) expressed on effector cells.

"Antibody-dependent cellular phagocytosis" or "ADCP" refers to the mechanism of elimination of antibody-coated target cells by internalization by phagocytic cells, such as macrophages or dendritic cells.

"Antigen" refers to any molecule (e.g., protein, peptide, polysaccharide, glycoprotein, glycolipid, nucleic acid, portions thereof, or combinations thereof) that is capable of mediating an immune response. Exemplary immune responses include antibody production and activation of immune cells, such as T cells, B cells or NK cells.

"Antigen binding fragment" or "antigen binding domain" refers to a portion of a protein that binds the antigen. Antigen binding fragments may be synthetic, enzymatically obtainable or genetically engineered polypeptides and include portions of an immunoglobulin that bind an antigen, such as a VH, a VL, the VH and the VL, Fab, Fab', F(ab')$_2$, Fd and Fv fragments, domain antibodies (dAb) consisting of one VH domain or one VL domain, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen binding fragments. Antigen binding fragments (such as the VH and the VL) may be linked together via a synthetic linker to form various types of single antibody designs in which the VH/VL domains may pair intramolecularly, or intermolecularly in those cases when the VH and the VL domains are expressed by separate single chains, to form a monovalent antigen binding domain, such as single chain Fv (scFv) or diabody. Antigen binding fragments may also be conjugated to other antibodies, proteins, antigen binding fragments or alternative scaffolds which may be monospecific or multispecific to engineer bispecific and multispecific proteins.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific, etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g., IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Bispecific" refers to a molecule (such as an antibody) that specifically binds two distinct antigens or two distinct epitopes within the same antigen. The bispecific molecule may have cross-reactivity to other related antigens, for example to the same antigen from other species (homologs), such as human or monkey, for example Macaca cynomolgus (cynomolgus, cyno) or Pan troglodytes, or may bind an epitope that is shared between two or more distinct antigens.

"Chimeric antigen receptor" or "CAR" refers to engineered T cell receptors which graft a ligand or antigen specificity onto T cells (for example naïve T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"Complement-dependent cytotoxicity" or "CDC", refers to the mechanism of inducing cell death in which the Fc effector domain of a target-bound protein binds and activates complement component C1q which in turn activates the complement cascade leading to target cell death. Activation of complement may also result in deposition of complement components on the target cell surface that facilitate CDC by binding complement receptors (e.g., CR3) on leukocytes.

"Complementarity determining regions" (CDR) are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al., (1970) J Exp Med 132: 211-250; Kabat et al., Sequences of Proteins of Immunological Interest, 5th Ed. Public Health Service, National Institutes of Health, Bethesda, Md., 1991), Chothia (Chothia et al., (1987) J Mol Biol 196: 901-17), IMGT (Lefranc et al., (2003) Dev Comp Immunol 27: 55-77) and AbM (Martin and Thornton (1996) J Bmol Biol 263: 800-815). The correspondence between the various delineations and variable region numbering is described (see e.g., Lefranc et al. (2003) Dev Comp Immunol 27: 55-77; Honegger and Pluckthun, J Mol Biol (2001) 309:657-670; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

"Decrease," "lower" or "reduce," refers generally to the ability of a test molecule to mediate a reduced response (i.e., downstream effect) when compared to the response mediated by a control or a vehicle. Exemplary responses include binding of a protein to its antigen or receptor, enhanced binding to FcγR or enhanced Fc effector functions such as enhanced ADCC, CDC and/or ADCP. Decrease may be a statistically significant difference in the measured response between the test molecule and the control (or the vehicle), or a decrease in the measured response, such as a decrease of about 1.1, 1.2, 1.5, 2, 3, 4, 5, 6, 7, 8, 9, 10, 15, 20 or 30 fold or more, such as 500, 600, 700, 800, 900 or 1000 fold or more.

"Enhance," "promote" or "increase," refers generally to the ability of the test molecule to mediate a greater response (i.e., downstream effect) when compared to the response mediated by a control or a vehicle. Exemplary responses are binding of a protein to its antigen or receptor, enhanced binding to FcγR or enhanced Fc effector functions such as enhanced ADCC, CDC and/or ADCP. Enhance may be a statistically significant difference in the measured response between the test molecule and control (or vehicle), or an increase in the measured response, such as an increase of about 1.1, 1.2, 1.5, 2, 3, 4, 5, 6, 7, 8, 9, 10, 15, 20 or 30 fold or more, such as 500, 600, 700, 800, 900 or 1000 fold or more.

"Expression vector" refers to a vector that can be utilized in a biological system or in a reconstituted biological system to direct the translation of a polypeptide encoded by a polynucleotide sequence present in the expression vector.

"Heterologous" refers to a polypeptide or a polynucleotide that comprises two or more polypeptides or two or more polynucleotides which are not found in the same relationship to each other in nature.

"Heterologous polynucleotide" refers to a polynucleotide that comprises two or more polynucleotides which are not found in the same relationship to each other in nature.

"Heterologous polypeptide" refers to a polypeptide that comprises two or more polypeptides which are not found in the same relationship to each other in nature.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) *J Mol Biol* 296:57-86, or a synthetic HCDR3 incorporated into human immunoglobulin gene libraries displayed on phage, for example as described in Shi et al., (2010) *J Mol Biol* 397:385-396, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as scFv of the disclosure or heterologous proteins comprising the scFv of the disclosure) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Modulate" refers to either enhanced or decreased ability of a test molecule to mediate an enhanced or a reduced response (i.e., downstream effect) when compared to the response mediated by a control or a vehicle.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Multispecific" refers to a molecule that binds two or more distinct antigens or two or more distinct epitopes within the same antigen. Multispecific molecule may have cross-reactivity to other related antigens, for example to the same antigen from other species (homologs), such as human or monkey, for example *Macaca fascicularis* (*cynomolgus*, cyno) or Pan troglodytes, or may bind an epitope that is shared between two or more distinct antigens.

"Polynucleotide" refers to a molecule comprising a chain of nucleotides covalently linked by a sugar-phosphate backbone or other equivalent covalent chemistry. cDNA is a typical example of a polynucleotide.

"Protein" or "polypeptide" are used interchangeably herein are refers to a molecule that comprises one or more polypeptides each comprised of at least two amino acid residues linked by a peptide bond. Protein may be a monomer, or may be a protein complex of two or more subunits, the subunits being identical or distinct. Small polypeptides of less than 50 amino acids may be referred to as "peptides". Protein may be a heterologous fusion protein, a glycoprotein, or a protein modified by post-translational modifications such as phosphorylation, acetylation, myristoylation, palmitoylation, glycosylation, oxidation, formylation, amidation, citrullination, polyglutamylation, ADP-ribosylation, pegylation or biotinylation.

"Recombinant" refers to polynucleotides, polypeptides, vectors, viruses and other macromolecules that are prepared, expressed, created or isolated by recombinant means.

"Single chain Fv" or "scFv" refers to a single chain protein comprising a VH, a VL and a linker between the VH and the VL. The scFv may have the VL and VH variable regions in either orientation, e.g., with respect to the N- to C-terminal order of the VH and the VL. The scFv may thus be in the orientation VL-linker-VH or VH-linker-VL. scFv may be engineered to comprise disulfide bonds between the VH, the VL and the linker.

"Specifically binds," "specific binding," "specifically binding" or "binds" refers to a protein such as a scFv binding to an antigen or an epitope within the antigen with greater affinity than for other antigens. Typically, the protein, such as the scFv binds to the antigen or the epitope within the antigen with an equilibrium dissociation constant ($K_D$) of about $1\times10^{-6}$ M or less, about $1\times10^{-7}$ M or less, about $5\times10^{-8}$M or less, about $1\times10^{-8}$ M or less, about $1\times10^{-9}$ M or less, about $1\times10^{-10}$ M or less, about $1\times10^{-11}$ M or less, or about $1\times10^{-12}$M or less, typically with the $K_D$ that is at least one hundred fold less than its $K_D$ for binding to a non-specific antigen (e.g., BSA, casein).

"Stapled single chain Fv" or "spFv" refers to a scFv that comprises one or more disulfide bonds between the VH and the linker or the VL and the linker. Typically the spFv may comprise one disulfide bond between the VH and the linker, one disulfide bond between the VL and the linker, or two disulfide bonds between the VH and the linker and the VL and the linker. scFv molecules which comprise disulfide bonds between the VH and the VL are excluded from the term "spFv".

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual.

"Treat," "treating" or "treatment" of a disease or disorder refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Trispecific" refers to a molecule (such as an antibody) that specifically binds three distinct antigens or three distinct epitopes within the same antigen. The trispecific molecule may have cross-reactivity to other related antigens, for example to the same antigen from other species (homologs), such as human or monkey, for example *Macaca cynomolgus* (*cynomolgus*, cyno) or Pan troglodytes, or may bind an epitope that is shared between three or more distinct antigens.

"Variant," "mutant" or "altered" refers to a polypeptide or a polynucleotide that differs from a reference polypeptide or a reference polynucleotide by one or more modifications, for example one or more substitutions, insertions or deletions.

The numbering of amino acid residues of the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated.

Mutations in the Ig constant regions are referred to as follows: L351Y_F405A_Y407V refers to L351Y, F405A and Y407V mutations in one immunoglobulin constant region. L351Y_F405A_Y407V/T394W refers to L351Y, F405A and Y407V mutations in the first Ig constant region and T394W mutation in the second Ig constant region present in the molecule.

The numbering of the variable regions is according to Chothia unless otherwise explicitly stated.

"VH Cysteine" or "VH Cys" refers to a Cys residue that resides in the VH framework.

"VL Cysteine" or "VL Cys" refers to a Cys residue that resides in the VL framework.

"Stabilized" refers to a The scFvs retaining comparable binding to hK2 when compared to a non-heated scFv sample are referred to as being thermostable.

"Improved stability" refers to the spFv of the disclosure having an elevated melting point (Tm) when compared to a parent scFv that is devoid of disulfide bonds and Cys residues introduced into the spFv. The elevated Tm may be an elevation of 2° C. or more, such as 3° C., 4° C., 5° C., 6° C., 7° C., 8° C., 9° C., 10° C., 11° C., 12° C., 13° C., 14° C. or 15° C.

"Anchor point" refers to a scFv VH or a VL framework Cys residue that can be mutagenized to Cys without adverse effect to the overall scFv structure and is capable of forming a disulfide bond with a Cys residing in the scFv linker.

"Staple" refers to the scFv linker that contains one or two Cys residues which are capable of forming a disulfide bond with the anchor point Cys.

"Surface exposed" refers to an amino acid residue that is at least partially exposed to a surface of a protein and accessible to solvent, such as accessible to deuteriation. Algorithms are well-known in the art for predicting surface accessibility of residues based on primary sequence or a protein. Alternatively, surface exposed residues may be identified from a crystal structure of the protein.

"LTBR" refers to a polypeptide that is a cell surface receptor for lymphotoxin involved in apoptosis and cytokine release, which is a member of the tumor necrosis factor receptor superfamily. LTBR can also be referred to as "tumor necrosis factor receptor superfamily member 3 (TN-FRSF3)." LTBR is expressed on the surface of many cell types, including cells of epithelial and myeloid lineages. LTBR can specifically bind the lymphotoxin membrane form (a complex of lymphotoxin-alpha and lymphotoxin-beta). Activation of LTBR can trigger apoptosis via TRAF3 and TRAF5 and can lead to the release of interleukin 8. Unless noted, preferably the LTBR is a human LTBR. A human LTBR amino acid sequence is provided by UniProt number P36941.

"EDB" or "extra domain B" refers to a domain of fibronectin that can be included in fibronectin molecules based on the splicing pattern of the fibronectin pre-mRNA. Extra domain B is a complete fibronectin (FN) type III repeat that comprises 91 amino acid residues. Generally, EDB is undetectable in normal adult tissues, but exhibits greater expression in fetal and tumor tissues in the extracellular matrix, and accumulates around neovasculature during angiogenic processes, thus making EDB a potential marker and target of angiogenesis. Unless noted, preferably EDB is a human EDB. A human EDB containing fibronectin isoform amino acid sequence is provided by UniProt number P02751.

"Fibronectin" refers to a polypeptide that is a high molecular weight glycoprotein of the extracellular matrix. Fibronectin can bind to membrane-spanning receptor proteins, referred to as integrins. Fibronectin can also bind other extracellular matrix proteins, such as collagen, fibrin, and heparan sulfate proteoglycans. Fibronectin can exist as a protein dimer, consisting of two nearly identical monomers linked by a pair of disulfide bonds. Fibronectin is produced from a single gene, but alternative splicing of the fibronectin pre-mRNA molecule leads to the creation of several isoforms of fibronectin, one of which is EDB fibronectin. Fibronectin can play a role in cell adhesion, growth, migration, and differentiation, and it can be important for processes such as wound healing and embryonic development. A human fibronectin amino acid sequence is provided by UniProt number P02751, which contains extra domain B, and NCBI Accession Numbers NP_001263337 (isoform B), NP_001263338 (isoform c), NP_001263339 (isoform d), NP_001263340 (isoform e), and NP_001263341 (isoform f), NP_001293058 (isoform 8), NP_001293059 (isoform 9), NP_001293060 (isoform 10), NP_001293061 (isoform 11), and NP_002017 (isoform 3).

5.1 Compositions of Matter

The disclosure provides stabilized scFv molecules (herein referred to as spFv (stapled Fv), heterologous and multispecific molecules comprising the spFv, polynucleotides encoding them, vectors, host cells and methods of making and using them. The disclosure is based, at least in part, on the identification of suitable residue positions in the VH and/or the VL (herein referred to as VH anchor point or VL anchor point) and in the flexible linker (herein referred to as staple) which may be engineered to cysteine residues resulting in formation of disulfide bonds between the linker and the variable domains in the scFv. The "stapling" strategy described herein is widely applicable to all VH/VL domains and pre-existing scFv molecules providing structural identity to scFv with improved stability. The spFv described herein may be conjugated into any heterologous protein, bispecific or multispecific format, including chimeric antigen receptors (CAR), T cell redirection molecules, bi- and multispecific molecules and may be used as therapeutic, diagnostic and detection molecules.

spFv of the Disclosure

The disclosure provides an isolated single chain variable fragment (scFv) comprising a heavy chain variable region (VH), a linker (L) and a light chain variable region (VL), wherein the scFv comprises
 a first disulfide bond between a structurally conserved surface exposed VH cysteine (Cys) and a first L Cys;
 a second disulfide bond between a structurally conserved surface exposed VL Cys and a second L Cys; or
 the first disulfide bond between the structurally conserved surface exposed VH Cys and the first L Cys and the second disulfide bond between the structurally conserved surface exposed VL Cys and the second L Cys.

The disclosure also provides an isolated scFv comprising a VH, a L and a VL, wherein
 the VH comprises a VH Cys at a structurally conserved surface exposed VH framework residue position and the L comprises a first L Cys;
 the VL comprises a VL Cys at a structurally conserved surface exposed VL framework residue position and the L comprises a second L Cys; or
 the VH comprises the VH Cys at a structurally conserved surface exposed VH framework residue position, the VL comprises the VL Cys at a structurally conserved surface exposed VL framework residue position and the L comprises the first L Cys and the second L Cys, wherein
 the VH Cys and the first L Cys are capable of forming a disulfide bond and the VL Cys and the second L Cys are capable of forming a disulfide bond. The disulfide bond typically forms during expression of the scFv of the disclosure.

While the specific examples disclose spFv with two disulfide bonds, it is readily envisioned that spFv with one disulfide bond, formed between the linker Cys and either the VH Cys or the VL Cys can be made and utilized, generating "half-anchored" molecules. The anchor positions are the same in spFv having one or two disulfide bonds. The linker Cys position may vary in the half-anchored molecule as long as it satisfies distance and geometry requirements for disulfide bond formation with the anchor point. It is expected that the half-anchored spFv will restrain VL/VH relative movement similar to the VL/VH pair stabilized with two disulfide bonds, and thus will also be stabilizing.

The spFv of the disclosure exhibited increased thermal stability when compared to the parent scFv devoid of the disulfide bonds. In general, the Tm of the spFv was about 10° C. higher when compared to the parent scFv devoid of the disulfide bonds regardless of the Tm of the parent scFv. Stability in general may be thermal stability or mechanical stability.

Thermostability may be evaluated using differential thermal calorimetry (DSC), in which DSC scans are performed using heated protein samples (such as samples heated to 60° C.) followed by analyses of the resulting thermal melting profiles using 2-state or non-2-state transitions. For non-2-state transitions, two transitions (Tm1 and Tm2) are recorded which correspond to the melting Tm of the VL and the VH domains, respectively.

In some embodiments, the distance between the VH Cys and the VL Cys is from about 7 Å to about 9 Å. In some embodiments, the distance between the VH Cys and the VL Cys is about 7 Å. In some embodiments, the distance between the VH Cys and the VL Cys is about 8 Å. In some embodiments, the distance between the VH Cys and the VL Cys is about 9 Å.

In some embodiments, the VH Cys is at H3, H5, H40, H43, H46 or H105, wherein residue numbering is according to Chothia.
 In some embodiments, the VH Cys is at H3.
 In some embodiments, the VH Cys is at H5.
 In some embodiments, the VH Cys is at H40.
 In some embodiments, the VH Cys is at H43.
 In some embodiments, the VH Cys is at H46.
 In some embodiments, the VH Cys is at H105
 In some embodiments, the VL Cys is at L3, L5, L39, L42, L45, L100 or L102, wherein residue numbering is according to Chothia.
 In some embodiments, the VL Cys is at L3.
 In some embodiments, the VL Cys is at L5.
 In some embodiments, the VL Cys is at L39.
 In some embodiments, the VL Cys is at L42.
 In some embodiments, the VL Cys is at L45.
 In some embodiments, the VL Cys is at L100.
 In some embodiments, the VL Cys is at L102.
 In some embodiments, the VH Cys is at H105 and the VL Cys is at L42.
 In some embodiments, the VH Cys is at H43 and the VL Cys is at a L100.
 In some embodiments, the VH Cys is at H3 and the VL Cys is at L3.

In some embodiments, the VH Cys is at H3 and the VL Cys is at L5.

In some embodiments, the VH Cys is at H3 and the VL Cys is at L39.

In some embodiments, the VH Cys is at H3 and the VL Cys is at L42.

In some embodiments, the VH Cys is at H3 and the VL Cys is at L45.

In some embodiments, the VH Cys is at H3 and the VL Cys is at L100.

In some embodiments, the VH Cys is at H3 and the VL Cys is at L102.

In some embodiments, the VH Cys is at H5 and the VL Cys is at L3.

In some embodiments, the VH Cys is at H5 and the VL Cys is at L5.

In some embodiments, the VH Cys is at H5 and the VL Cys is at L39.

In some embodiments, the VH Cys is at H5 and the VL Cys is at L42.

In some embodiments, the VH Cys is at H5 and the VL Cys is at L45.

In some embodiments, the VH Cys is at H5 and the VL Cys is at L100.

In some embodiments, the VH Cys is at H5 and the VL Cys is at L102.

In some embodiments, the VH Cys is at H40 and the VL Cys is at L3.

In some embodiments, the VH Cys is at H40 and the VL Cys is at L5.

In some embodiments, the VH Cys is at H40 and the VL Cys is at L39.

In some embodiments, the VH Cys is at H40 and the VL Cys is at L42.

In some embodiments, the VH Cys is at H40 and the VL Cys is at L45.

In some embodiments, the VH Cys is at H40 and the VL Cys is at L100.

In some embodiments, the VH Cys is at H40 and the VL Cys is at L102.

In some embodiments, the VH Cys is at H43 and the VL Cys is at L3.

In some embodiments, the VH Cys is at H43 and the VL Cys is at L5.

In some embodiments, the VH Cys is at H43 and the VL Cys is at L39.

In some embodiments, the VH Cys is at H43 and the VL Cys is at L42.

In some embodiments, the VH Cys is at H43 and the VL Cys is at L45.

In some embodiments, the VH Cys is at H43 and the VL Cys is at L102.

In some embodiments, the VH Cys is at H46 and the VL Cys is at L3.

In some embodiments, the VH Cys is at H46 and the VL Cys is at L5.

In some embodiments, the VH Cys is at H46 and the VL Cys is at L39.

In some embodiments, the VH Cys is at H46 and the VL Cys is at L42.

In some embodiments, the VH Cys is at H46 and the VL Cys is at L45.

In some embodiments, the VH Cys is at H46 and the VL Cys is at L100.

In some embodiments, the VH Cys is at H46 and the VL Cys is at L102.

In some embodiments, the VH Cys is at H105 and the VL Cys is at L3.

In some embodiments, the VH Cys is at H105 and the VL Cys is at L5.

In some embodiments, the VH Cys is at H105 and the VL Cys is at L39.

In some embodiments, the VH Cys is at H105 and the VL Cys is at L45.

In some embodiments, the VH Cys is at H105 and the VL Cys is at L100.

In some embodiments, the VH Cys is at H105 and the VL Cys is at L102.

The residue numbering of the VH and the VL regions are according to Chothia.

Chothia numbering is well known. Other numbering systems, such as Kabat or IMGT numbering, or sequential numbering may be used to number the VH and the VL residue positions. Table 1 shows the correspondence between Chothia, Kabat and sequential numbering for an exemplary VH, GLk1 VH (SEQ ID NO: 60). Table 2 shows the correspondence between Chothia, Kabat and sequential numbering for an exemplary VL, GLk1 VL (SEQ ID NO: 56).

TABLE 1

| Chothia numbering | Kabat numbering | Sequential numbering | Amino acid residue at position |
|---|---|---|---|
| H1 | H1 | 1 | E |
| H2 | H2 | 2 | V |
| H3 | H3 | 3 | Q |
| H4 | H4 | 4 | L |
| H5 | H5 | 5 | L |
| H6 | H6 | 6 | E |
| H7 | H7 | 7 | S |
| H8 | H8 | 8 | G |
| H9 | H9 | 9 | G |
| H10 | H10 | 10 | G |
| H11 | H11 | 11 | L |
| H12 | H12 | 12 | V |
| H13 | H13 | 13 | Q |
| H14 | H14 | 14 | P |
| H15 | H15 | 15 | G |
| H16 | H16 | 16 | G |
| H17 | H17 | 17 | S |
| H18 | H18 | 18 | L |
| H19 | H19 | 19 | R |
| H20 | H20 | 20 | L |
| H21 | H21 | 21 | S |
| H22 | H22 | 22 | C |
| H23 | H23 | 23 | A |
| H24 | H24 | 24 | A |
| H25 | H25 | 25 | S |
| H26 | H26 | 26 | G |
| H27 | H27 | 27 | F |
| H28 | H28 | 28 | T |
| H29 | H29 | 29 | F |
| H30 | H30 | 30 | S |
| H31 | H31 | 31 | S |
| H32 | H32 | 32 | Y |
| H33 | H33 | 33 | A |
| H34 | H34 | 34 | M |
| H35 | H35 | 35 | S |
| H36 | H36 | 36 | W |
| H37 | H37 | 37 | V |
| H38 | H38 | 38 | R |
| H39 | H39 | 39 | Q |
| H40 | H40 | 40 | A |
| H41 | H41 | 41 | P |
| H42 | H42 | 42 | G |
| H43 | H43 | 43 | K |
| H44 | H44 | 44 | G |
| H45 | H45 | 45 | L |
| H46 | H46 | 46 | E |

TABLE 1-continued

| Chothia numbering | Kabat numbering | Sequential numbering | Amino acid residue at position |
|---|---|---|---|
| H47 | H47 | 47 | W |
| H48 | H48 | 48 | V |
| H49 | H49 | 49 | S |
| H50 | H50 | 50 | A |
| H51 | H51 | 51 | I |
| H52 | H52 | 52 | S |
| H52A | H52A | 53 | G |
| H53 | H53 | 54 | S |
| H54 | H54 | 55 | G |
| H55 | H55 | 56 | G |
| H56 | H56 | 57 | S |
| H57 | H57 | 58 | T |
| H58 | H58 | 59 | Y |
| H59 | H59 | 60 | Y |
| H60 | H60 | 61 | A |
| H61 | H61 | 62 | D |
| H62 | H62 | 63 | S |
| H63 | H63 | 64 | V |
| H64 | H64 | 65 | K |
| H65 | H65 | 66 | G |
| H66 | H66 | 67 | R |
| H67 | H67 | 68 | F |
| H68 | H68 | 69 | T |
| H69 | H69 | 70 | I |
| H70 | H70 | 71 | S |
| H71 | H71 | 72 | R |
| H72 | H72 | 73 | D |
| H73 | H73 | 74 | N |
| H74 | H74 | 75 | S |
| H75 | H75 | 76 | K |
| H76 | H76 | 77 | N |
| H77 | H77 | 78 | T |
| H78 | H78 | 79 | L |
| H79 | H79 | 80 | Y |
| H80 | H80 | 81 | L |
| H81 | H81 | 82 | Q |
| H82 | H82 | 83 | M |
| H82A | H82A | 84 | N |
| H82B | H82B | 85 | S |
| H82C | H82C | 86 | L |
| H83 | H83 | 87 | R |
| H84 | H84 | 88 | A |
| H85 | H85 | 89 | E |
| H86 | H86 | 90 | D |
| H87 | H87 | 91 | T |
| H88 | H88 | 92 | A |
| H89 | H89 | 93 | V |
| H90 | H90 | 94 | Y |
| H91 | H91 | 95 | Y |
| H92 | H92 | 96 | C |
| H93 | H93 | 97 | A |
| H94 | H94 | 98 | K |
| H95 | H95 | 99 | Y |
| H96 | H96 | 100 | D |
| H97 | H97 | 101 | G |
| H98 | H98 | 102 | I |
| H99 | H99 | 103 | Y |
| H100 | H100 | 104 | G |
| H100A | H100A | 105 | E |
| H100B | H100B | 106 | L |
| H101 | H101 | 107 | D |
| H102 | H102 | 108 | F |
| H103 | H103 | 109 | W |
| H104 | H104 | 110 | G |
| H105 | H105 | 111 | Q |
| H106 | H106 | 112 | G |
| H107 | H107 | 113 | T |
| H108 | H108 | 114 | L |
| H109 | H109 | 115 | V |
| H110 | H110 | 116 | T |
| H111 | H111 | 117 | V |
| H112 | H112 | 118 | S |
| H113 | H113 | 119 | S |

TABLE 2

| Chothia numbering | Kabat numbering | Sequential numbering | Amino acid residue at position |
|---|---|---|---|
| L1 | L1 | 1 | D |
| L2 | L2 | 2 | I |
| L3 | L3 | 3 | Q |
| L4 | L4 | 4 | M |
| L5 | L5 | 5 | T |
| L6 | L6 | 6 | Q |
| L7 | L7 | 7 | S |
| L8 | L8 | 8 | P |
| L9 | L9 | 9 | S |
| L10 | L10 | 10 | S |
| L11 | L11 | 11 | L |
| L12 | L12 | 12 | S |
| L13 | L13 | 13 | A |
| L14 | L14 | 14 | S |
| L15 | L15 | 15 | V |
| L16 | L16 | 16 | G |
| L17 | L17 | 17 | D |
| L18 | L18 | 18 | R |
| L19 | L19 | 19 | V |
| L20 | L20 | 20 | T |
| L21 | L21 | 21 | I |
| L22 | L22 | 22 | T |
| L23 | L23 | 23 | C |
| L24 | L24 | 24 | R |
| L25 | L25 | 25 | A |
| L26 | L26 | 26 | S |
| L27 | L27 | 27 | Q |
| L28 | L28 | 28 | S |
| L29 | L29 | 29 | I |
| L30 | L30 | 30 | S |
| L31 | L31 | 31 | S |
| L32 | L32 | 32 | Y |
| L33 | L33 | 33 | L |
| L34 | L34 | 34 | N |
| L35 | L35 | 35 | W |
| L36 | L36 | 36 | Y |
| L37 | L37 | 37 | Q |
| L38 | L38 | 38 | Q |
| L39 | L39 | 39 | K |
| L40 | L40 | 40 | P |
| L41 | L41 | 41 | G |
| L42 | L42 | 42 | K |
| L43 | L43 | 43 | A |
| L44 | L44 | 44 | P |
| L45 | L45 | 45 | K |
| L46 | L46 | 46 | L |
| L47 | L47 | 47 | L |
| L48 | L48 | 48 | I |
| L49 | L49 | 49 | Y |
| L50 | L50 | 50 | A |
| L51 | L51 | 51 | A |
| L52 | L52 | 52 | S |
| L53 | L53 | 53 | S |
| L54 | L54 | 54 | L |
| L55 | L55 | 55 | Q |
| L56 | L56 | 56 | S |
| L57 | L57 | 57 | G |
| L58 | L58 | 58 | V |
| L59 | L59 | 59 | P |
| L60 | L60 | 60 | S |
| L61 | L61 | 61 | R |
| L62 | L62 | 62 | F |
| L63 | L63 | 63 | S |
| L64 | L64 | 64 | G |
| L65 | L65 | 65 | S |
| L66 | L66 | 66 | G |
| L67 | L67 | 67 | S |
| L68 | L68 | 68 | G |
| L69 | L69 | 69 | T |
| L70 | L70 | 70 | D |
| L71 | L71 | 71 | F |
| L72 | L72 | 72 | T |
| L73 | L73 | 73 | L |
| L74 | L74 | 74 | T |
| L75 | L75 | 75 | I |
| L76 | L76 | 76 | S |

TABLE 2-continued

| Chothia numbering | Kabat numbering | Sequential numbering | Amino acid residue at position |
|---|---|---|---|
| L77 | L77 | 77 | S |
| L78 | L78 | 78 | L |
| L79 | L79 | 79 | Q |
| L80 | L80 | 80 | P |
| L81 | L81 | 81 | E |
| L82 | L82 | 82 | D |
| L83 | L83 | 83 | F |
| L84 | L84 | 84 | A |
| L85 | L85 | 85 | T |
| L86 | L86 | 86 | Y |
| L87 | L87 | 87 | Y |
| L88 | L88 | 88 | C |
| L89 | L89 | 89 | Q |
| L90 | L90 | 90 | Q |
| L91 | L91 | 91 | S |
| L92 | L92 | 92 | Y |
| L93 | L93 | 93 | S |
| L94 | L94 | 94 | T |
| L95 | L95 | 95 | P |
| L96 | L96 | 96 | L |
| L97 | L97 | 97 | T |
| L98 | L98 | 98 | F |
| L99 | L99 | 99 | G |
| L100 | L100 | 100 | Q |
| L101 | L101 | 101 | G |
| L102 | L102 | 102 | T |
| L103 | L103 | 103 | K |
| L104 | L104 | 104 | V |
| L105 | L105 | 105 | E |
| L106 | L106 | 106 | I |
| L107 | L107 | 107 | K |
| L108 | L108 | 108 | R |

In some embodiments, the L comprises a contiguous amino acid sequence derived from an immunoglobulin (Ig) hinge region.

In some embodiments, the Ig hinge region is derived from a human or a non-human Ig hinge region. Exemplary non-human Ig hinge regions are those from mouse, rat, dog, chicken and non-human primates, such as monkeys.

In some embodiments, the Ig hinge region is derived from the human Ig hinge region.

In some embodiments, the human Ig hinge region is an IgG1, IgG2, IgG3, IgG4, IgM, IgA or IgE isotype.

The Ig hinge region is in general defined as including residue 216 and terminating at residue 230 of human IgG, wherein residue numbering is according to the EU Index. In some instances, a lower hinge region from about residue 231 to about residue 237 may also be included into the hinge. An IgG1 hinge region therefore may comprise the amino acid sequence EPKSCDKTHTCPPCP (SEQ ID NO: 63), or when the lower hinge is included, the amino acid sequence EPKSCDKTHTCPPCPAPELLGG (SEQ ID NO: 64). The hinge regions of other Ig isotypes are well known and their amino acid sequences may be obtained for example at ImMunoGeneTics web site. For example, IgG2 hinge comprises the amino acid sequence ERKCCVECPPCP (SEQ ID NO: 65).

The L comprises the contiguous amino acid sequence which is "derived from" the Ig hinge region in those instances when the L comprises at least a portion of the Ig hinge region amino acid sequence or at least a portion of an engineered Ig hinge region. Engineered Ig hinge region comprises one or more mutations when compared to the wild-type Ig hinge. Exemplary mutations that may be introduced are substitutions of Cys residues to reduce the number of Cys in the L to one or two, substitution of Pro residues, or any conservative modifications, such as conservative substitutions.

"Conservative modifications" refer to amino acid modifications that do not significantly affect or alter the binding characteristics of the antibody containing the amino acid modifications. Conservative modifications include amino acid substitutions, additions and deletions. Conservative amino acid substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand* Suppl 643:55-67; Sasaki et al., (1988) *Adv Biophys* 35:1-24). Amino acid substitutions to may be made by known methods for example by PCR mutagenesis (U.S. Pat. No. 4,683,195). The resulting variant hinges may be incorporated into the spFv constructs of the disclosure and tested for their characteristics such as stability and binding to an antigen using known assays and assays described herein.

In some embodiments, the L comprises an amino acid sequence C(X)$_y$C (SEQ ID NO: 23), wherein X is glycine (Gly), serine (Ser), proline (Pro), alanine (Ala), arginine (Arg), asparagine (Asn), aspartic acid (Asp), glutamic acid (Glu), glutamine (Gln), histidine (His), isoleucine (Ile), leucine (Leu), lysine (Lys), phenylalanine (Phe), threonine (Thr), tryptophan (Trp) or tyrosine (Tyr), and y is an integer from 1 to 3. Pro may be included into the linker to provide rigidity. Gly may be included into the linker to allow maximum flexibility. Any other amino acid may also be used in the L except for Cys and Met.

In some embodiments, the L comprises the amino acid sequence C(X)$_y$C (SEQ ID NO: 24), wherein X is Gly, Ser or Pro, and y is an integer from 1 to 3.

In some embodiments, the L comprises the amino acid sequence CPC, CGC, CSC, CPPC (SEQ ID NO: 1), CGPC (SEQ ID NO: 28), CPGC (SEQ ID NO: 29), CGGC (SEQ ID NO: 30), CSPG (SEQ ID NO: 31), CPSC (SEQ ID NO: 32), CSSC (SEQ ID NO: 33), CGSC (SEQ ID NO: 34), CSGC (SEQ ID NO: 35), CPPPC (SEQ ID NO: 36), CGPPC (SEQ ID NO: 37), CPGPC (SEQ ID NO: 38), CPPGC (SEQ ID NO: 39), CGGPC (SEQ ID NO: 40), CPGGC (SEQ ID NO: 41), CGGGC (SEQ ID NO: 42), CSPPC (SEQ ID NO: 43), CPSPC (SEQ ID NO: 44), CPPSC (SEQ ID NO: 45), CSSPC (SEQ ID NO: 46), CPSSC (SEQ ID NO: 47), CSSSC (SEQ ID NO: 48), CGSPC (SEQ ID NO: 49), CPGSC (SEQ ID NO: 50), CSGPC (SEQ ID NO: 51) or CPSGC (SEQ ID NO: 52).

In some embodiments, the L comprises the amino acid sequence CPC.

In some embodiments, the L comprises the amino acid sequence CGC.

In some embodiments, the L comprises the amino acid sequence CSC.

In some embodiments, the L comprises the amino acid sequence CPPC (SEQ ID NO: 1).

In some embodiments, the L comprises the amino acid sequence CGPC (SEQ ID NO: 28).

In some embodiments, the L comprises the amino acid sequence CPGC (SEQ ID NO: 29).

In some embodiments, the L comprises the amino acid sequence CGGC (SEQ ID NO: 30).

In some embodiments, the L comprises the amino acid sequence CSPG (SEQ ID NO: 31).

In some embodiments, the L comprises the amino acid sequence CPSC (SEQ ID NO: 32).

In some embodiments, the L comprises the amino acid sequence CSSC (SEQ ID NO: 33).

In some embodiments, the L comprises the amino acid sequence CGSC (SEQ ID NO: 34).

In some embodiments, the L comprises the amino acid sequence CSGC (SEQ ID NO: 35).

In some embodiments, the L comprises the amino acid sequence CPPPC (SEQ ID NO: 36).

In some embodiments, the L comprises the amino acid sequence CGPPC (SEQ ID NO: 37).

In some embodiments, the L comprises the amino acid sequence CPGPC (SEQ ID NO: 38).

In some embodiments, the L comprises the amino acid sequence CPPGC (SEQ ID NO: 39).

In some embodiments, the L comprises the amino acid sequence CGGPC (SEQ ID NO: 40).

In some embodiments, the L comprises the amino acid sequence CPGGC (SEQ ID NO: 41).

In some embodiments, the L comprises the amino acid sequence CGGGC (SEQ ID NO: 42).

In some embodiments, the L comprises the amino acid sequence CSPPC (SEQ ID NO: 43).

In some embodiments, the L comprises the amino acid sequence CPSPC (SEQ ID NO: 44).

In some embodiments, the L comprises the amino acid sequence CPPSC (SEQ ID NO: 45).

In some embodiments, the L comprises the amino acid sequence CSSPC (SEQ ID NO: 46).

In some embodiments, the L comprises the amino acid sequence CPSSC (SEQ ID NO: 47).

In some embodiments, the L comprises the amino acid sequence CSSSC (SEQ ID NO: 48).

In some embodiments, the L comprises the amino acid sequence CGSPC (SEQ ID NO: 49).

In some embodiments, the L comprises the amino acid sequence CPGSC (SEQ ID NO: 50).

In some embodiments, the L comprises the amino acid sequence CSGPC (SEQ ID NO: 51).

In some embodiments, the L comprises the amino acid sequence CPSGC (SEQ ID NO: 52).

In some embodiments, the L comprises from about 14 to about 19 amino acids.

In some embodiments, the L comprises about 14 amino acids.

In some embodiments, the L comprises about 15 amino acids.

In some embodiments, the L comprises about 16 amino acids.

In some embodiments, the L comprises about 17 amino acids.

In some embodiments, the L comprises about 18 amino acids.

In some embodiments, the L comprises about 19 amino acids.

In some embodiments, the L comprises the amino acid sequence $(X)_m C(X)_y C(X)_n$ (SEQ ID NO: 25), wherein X is Gly, Ser, Pro, Ala, Arg, Asn, Asp, Glu, Gln, His, Ile, leu, Lys, Phe Thr, Trp or Tyr, m is an integer from 6 to 9, y is an integer from 1 to 3 and n is an integer from 4 to 6.

In some embodiments, the L comprises the amino acid sequence $(X)_m C(X)_y C(X)_n$ (SEQ ID NO: 26), wherein X is Gly, Ser, Pro, Ala, Arg, Asn, Asp, Glu, Gln, His, Ile, Leu, Lys, Thr or Tyr, m is an integer from 6 to 9, y is an integer from 1 to 3 and n is an integer from 4 to 6.

In some embodiments, the L comprises the amino acid sequence $(X)_m C(X)_y C(X)_n$ (SEQ ID NO: 27); wherein X is Gly or Pro, m is an integer from 6 to 9, y is an integer from 1 to 3 and n is an integer from 4 to 6.

In some embodiments, the L comprises the amino acid sequence of SEQ ID NOs: 2, 3, 4, 5, 6 or 7.

In some embodiments, the L comprises the amino acid sequence of SEQ ID NO: 2.

In some embodiments, the L comprises the amino acid sequence of SEQ ID NO: 3.

In some embodiments, the L comprises the amino acid sequence of SEQ ID NO: 4.

In some embodiments, the L comprises the amino acid sequence of SEQ ID NO: 5.

In some embodiments, the L comprises the amino acid sequence of SEQ ID NO: 6.

In some embodiments, the L comprises the amino acid sequence of SEQ ID NO: 7.

In some embodiments, the spFv of the disclosure is in the VL-L-VH orientation.

In some embodiments, the spFv of the disclosure is in the VH-L-VL orientation.

The disclosure also provides a scFv comprising a VH, a L and a VL, wherein
 the VH comprises Cys at H105;
 the VL comprises Cys at L42;
 the L comprises an amino acid sequence of SEQ ID NOs: 2, 3, 4, 5, 6 or 7; and
 the scFv is in the VL-L-VH orientation.

The disclosure also provides a scFv comprising a VH, a L and a VL, wherein
 the VH comprises Cys at H105;
 the VL comprises Cys at L45;
 the L comprises an amino acid sequence of SEQ ID NOs: 2, 3, 4, 5, 6 or 7; and
 the scFv is in the VL-L-VH orientation.

The disclosure also provides a scFv comprising a VH, a L and a VL, wherein
 the VH comprises Cys at H105;
 the VL comprises Cys at L39;
 the L comprises an amino acid sequence of SEQ ID NOs: 2, 3, 4, 5, 6 or 7; and
 the scFv is in the VL-L-VH orientation.

The disclosure also provides a scFv comprising a VH, a L and a VL, wherein
 the VH comprises Cys at H5;
 the VL comprises Cys at L42;
 the L comprises an amino acid sequence of SEQ ID NOs: 2, 3, 4, 5, 6 or 7; and
 the scFv is in the VL-L-VH orientation.

The disclosure also provides a scFv comprising a VH, a L and a VL, wherein
 the VH comprises Cys at H5;
 the VL comprises Cys at L45;
 the L comprises an amino acid sequence of SEQ ID NOs: 2, 3, 4, 5, 6 or 7; and
 the scFv is in the VL-L-VH orientation.

The disclosure also provides a scFv comprising a VH, a L and a VL, wherein
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

In some embodiments, the L comprises the amino acid sequence of SEQ ID NO: 3.

In some embodiments, the L comprises the amino acid sequence of SEQ ID NO: 4.

In some embodiments, the L comprises the amino acid sequence of SEQ ID NO: 5.

In some embodiments, the L comprises the amino acid sequence of SEQ ID NO: 6.

In some embodiments, the L comprises the amino acid sequence of SEQ ID NO: 7.

Heterologous Molecules Comprising the spFv of the Disclosure

The spFv of the disclosure may be conjugated to a second molecule similarly to non-stabilized scFv devoid of disulfide bonds as known in the art. Exemplary second molecules are disclosed herein and include half-life extending moieties, imaging agents, therapeutic agents, antibodies comprising various antibody formats and fragments thereof, antigen binding domains, Fc regions, immunoglobulin heavy/light chains or fragments thereof, multispecific molecules and chimeric antigen receptors (CAR).

The disclosure also provides a heterologous molecule comprising a single chain variable fragment (scFv) comprising a heavy chain variable region (VH), a linker (L) and a light chain variable region (VL), wherein the scFv comprises
  a first disulfide bond between a structurally conserved surface exposed VH cysteine (Cys) and a first L Cys;
  a second disulfide bond between a structurally conserved surface exposed VL Cys and a second L Cys; or
  the first disulfide bond between the structurally conserved surface exposed VH Cys and the first L Cys and the second disulfide bond between the structurally conserved surface exposed VL Cys and the second L Cys.

The disclosure also provides a heterologous molecule comprising a scFv comprising a VH, a L and a VL, wherein
  the VH comprises a VH Cys at a structurally conserved surface exposed VH framework residue position and the L comprises a first L Cys;
  the VL comprises a VL Cys at a structurally conserved surface exposed VL framework residue position and the L comprises a second L Cys; or
  the VH comprises the VH Cys at a structurally conserved surface exposed VH framework residue position, the VL comprises the VL Cys at a structurally conserved surface exposed VL framework residue position and the L comprises the first L Cys and the second L Cys, wherein
  the VH Cys and the first L Cys are capable of forming a disulfide bond and the VL Cys and the second L Cys are capable of forming a disulfide bond.

In some embodiments, the distance between the VH Cys and the VL Cys is from about 7 Å to about 9 Å.

In some embodiments, the VH Cys is at H3, H5, H40, H43, H46 or H105, wherein residue numbering is according to Chothia.

In some embodiments, the VL Cys is at L3, L5, L39, L42, L45, L100 or L102, wherein residue numbering is according to Chothia.

In some embodiments, the VH Cys is at H105 and the VL Cys is at L42.

In some embodiments, the VH Cys is at H43 and the VL Cys is at a L100.

In some embodiments, the VH Cys is at H3 and the VL Cys is at L3.

In some embodiments, the VH Cys is at H3 and the VL Cys is at L5.

In some embodiments, the VH Cys is at H3 and the VL Cys is at L39.

In some embodiments, the VH Cys is at H3 and the VL Cys is at L42.

In some embodiments, the VH Cys is at H3 and the VL Cys is at L45.

In some embodiments, the VH Cys is at H3 and the VL Cys is at L100.

In some embodiments, the VH Cys is at H3 and the VL Cys is at L102.

In some embodiments, the VH Cys is at H5 and the VL Cys is at L3.

In some embodiments, the VH Cys is at H5 and the VL Cys is at L5.

In some embodiments, the VH Cys is at H5 and the VL Cys is at L39.

In some embodiments, the VH Cys is at H5 and the VL Cys is at L42.

In some embodiments, the VH Cys is at H5 and the VL Cys is at L45.

In some embodiments, the VH Cys is at H5 and the VL Cys is at L100.

In some embodiments, the VH Cys is at H5 and the VL Cys is at L102.

In some embodiments, the VH Cys is at H40 and the VL Cys is at L3.

In some embodiments, the VH Cys is at H40 and the VL Cys is at L5.

In some embodiments, the VH Cys is at H40 and the VL Cys is at L39.

In some embodiments, the VH Cys is at H40 and the VL Cys is at L42.

In some embodiments, the VH Cys is at H40 and the VL Cys is at L45.

In some embodiments, the VH Cys is at H40 and the VL Cys is at L100.

In some embodiments, the VH Cys is at H40 and the VL Cys is at L102.

In some embodiments, the VH Cys is at H43 and the VL Cys is at L3.

In some embodiments, the VH Cys is at H43 and the VL Cys is at L5.

In some embodiments, the VH Cys is at H43 and the VL Cys is at L39.

In some embodiments, the VH Cys is at H43 and the VL Cys is at L42.

In some embodiments, the VH Cys is at H43 and the VL Cys is at L45.

In some embodiments, the VH Cys is at H43 and the VL Cys is at L100.

In some embodiments, the VH Cys is at H43 and the VL Cys is at L102.

In some embodiments, the VH Cys is at H46 and the VL Cys is at L3.

In some embodiments, the VH Cys is at H46 and the VL Cys is at L5.

In some embodiments, the VH Cys is at H46 and the VL Cys is at L39.

In some embodiments, the VH Cys is at H46 and the VL Cys is at L42.

In some embodiments, the VH Cys is at H46 and the VL Cys is at L45.

In some embodiments, the VH Cys is at H46 and the VL Cys is at L100.

In some embodiments, the VH Cys is at H46 and the VL Cys is at L102.

In some embodiments, the VH Cys is at H105 and the VL Cys is at L3.

In some embodiments, the VH Cys is at H105 and the VL Cys is at L5.

In some embodiments, the VH Cys is at H105 and the VL Cys is at L39.

In some embodiments, the VH Cys is at H105 and the VL Cys is at L42.

In some embodiments, the VH Cys is at H105 and the VL Cys is at L45.

In some embodiments, the VH Cys is at H105 and the VL Cys is at L100.

In some embodiments, the VH Cys is at H105 and the VL Cys is at L102.

The residue numbering of the VH and the VL regions are according to Chothia.

In some embodiments, the L comprises a contiguous amino acid sequence derived from an immunoglobulin (Ig) hinge region.

In some embodiments, the Ig hinge region is derived from a human or a non-human Ig hinge region. Exemplary non-human Ig hinge regions are those from mouse, rat, dog, chicken and non-human primates, such as monkeys.

In some embodiments, the Ig hinge region is derived from the human Ig hinge region.

In some embodiments, the human Ig hinge region is an IgG1, IgG2, IgG3, IgG4, IgM, IgA or IgE isotype.

In some embodiments, the L comprises an amino acid sequence $C(X)_yC$ (SEQ ID NO: 23), wherein X is Gly, Ser, Pro, Ala, Arg, Asn, Asp, Glu, Gln, His, Ile, Leu, Lys, Phe, Thr, Trp or Tyr, and y is an integer from 1 to 3. Pro may be included into the linker to provide rigidity. Gly may be included into the linker to allow maximum flexibility. Any other amino acid may also be used in the L except for Cys and Met.

In some embodiments, the L comprises the amino acid sequence $C(X)_yC$ (SEQ ID NO: 24), wherein X is Gly, Ser or Pro, and y is an integer from 1 to 3.

In some embodiments, the L comprises the amino acid sequence CPC, CGC, CSC, CPPC (SEQ ID NO: 1), CGPC (SEQ ID NO: 28), CPGC (SEQ ID NO: 29), CGGC (SEQ ID NO: 30), CSPG (SEQ ID NO: 31), CPSC (SEQ ID NO: 32), CSSC (SEQ ID NO: 33), CGSC (SEQ ID NO: 34), CSGC (SEQ ID NO: 35), CPPPC (SEQ ID NO: 36), CGPPC (SEQ ID NO: 37), CPGPC (SEQ ID NO: 38), CPPGC (SEQ ID NO: 39), CGGPC (SEQ ID NO: 40), CPGGC (SEQ ID NO: 41), CGGGC (SEQ ID NO: 42), CSPPC (SEQ ID NO: 43), CPSPC (SEQ ID NO: 44), CPPSC (SEQ ID NO: 45), CSSPC (SEQ ID NO: 46), CPSSC (SEQ ID NO: 47), CSSSC (SEQ ID NO: 48), CGSPC (SEQ ID NO: 49), CPGSC (SEQ ID NO: 50), CSGPC (SEQ ID NO: 51) or CPSGC (SEQ ID NO: 52).

In some embodiments, the L comprises from about 14 to about 19 amino acids.

In some embodiments, the L comprises about 14 amino acids.

In some embodiments, the L comprises about 15 amino acids.

In some embodiments, the L comprises about 16 amino acids.

In some embodiments, the L comprises about 17 amino acids.

In some embodiments, the L comprises about 18 amino acids.

In some embodiments, the L comprises about 19 amino acids.

In some embodiments, the L comprises the amino acid sequence $(X)_mC(X)_yC(X)_n$ (SEQ ID NO: 25); wherein X is Gly, Ser, Pro, Ala, Arg, Asn, Asp, Glu, Gln, His, Ile, leu, Lys, Phe Thr, Trp or Tyr, m is an integer from 6 to 9, y is an integer from 1 to 3 and n is an integer from 4 to 6.

In some embodiments, the L comprises the amino acid sequence $(X)_mC(X)_yC(X)_n$ (SEQ ID NO: 26); wherein X is Gly, Ser or Pro, Ala, Arg, Asn, Asp, Glu, Gln, His, Ile, Leu, Lys, Thr or Tyr, m is an integer from 6 to 9, y is an integer from 1 to 3 and n is an integer from 4 to 6.

In some embodiments, the L comprises the amino acid sequence $(X)_mC(X)_yC(X)_n$ (SEQ ID NO: 27); wherein X is Gly or Pro, m is an integer from 6 to 9, y is an integer from 1 to 3 and n is an integer from 4 to 6.

In some embodiments, the L comprises the amino acid sequence of SEQ ID NOs: 2, 3, 4, 5, 6 or 7.

In some embodiments, the spFv of the disclosure is in the VL-L-VH orientation.

In some embodiments, the spFv of the disclosure is in the VH-L-VL orientation.

The disclosure also provides a heterologous molecule comprising a scFv comprising a VH, a L and a VL, wherein the VH comprises Cys at H105;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H105;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H105;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a heterologous molecule comprising a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and the scFv is in the VH-L-VL orientation.

The disclosure also provides a heterologous molecule comprising a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a heterologous molecule comprising a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

In some embodiments, the L comprises the amino acid sequence of SEQ ID NO: 3.

In some embodiments, the L comprises the amino acid sequence of SEQ ID NO: 4.

In some embodiments, the L comprises the amino acid sequence of SEQ ID NO: 5.

In some embodiments, the L comprises the amino acid sequence of SEQ ID NO: 6.

In some embodiments, the L comprises the amino acid sequence of SEQ ID NO: 7.

In some embodiments, the scFv of the disclosure is conjugated to a second protein, a polynucleotide, a therapeutic agent, a cytotoxic agent or a detectable label.

In some embodiments, the second protein is a half-life extending moiety.

In some embodiments, the second protein is an antibody or a fragment thereof.

In some embodiments, the second protein is an antigen binding fragment.

In some embodiments, the second protein is a therapeutic molecule.

Heterologous Molecules Comprising the spFv of the Disclosure and Half-Life Extending Moiety In some embodiments, the spFv of the disclosure is conjugated to a half-life extending moiety.

Exemplary half-life extending moieties are an immunoglobulin (Ig), a fragment of the Ig, an Ig constant region, a fragment of the Ig constant region, a Fc region, transferrin, albumin, albumin variants, an albumin binding domain or polyethylene glycol. Amino acid sequences of the human Ig are well known, and include IgG1, IgG2, IgG3, IgG4, IgM, IgA and IgE.

In some embodiments, the spFv of the disclosure is conjugated to the Ig or the fragment of the Ig.

In some embodiments, the spFv of the disclosure is conjugated to the Fc region.

In some embodiments, the spFv of the disclosure is conjugated to transferrin.

In some embodiments, the spFv of the disclosure is conjugated to albumin.

In some embodiments, the spFv of the disclosure is conjugated to albumin binding protein.

In some embodiments, the spFv of the disclosure is conjugated to polyethylene glycol (PEG). Exemplary PEG molecules are PEG5000 or PEG20,000.

In some embodiments, the spFv of the disclosure is conjugated to a fatty acid or a fatty acid ester. Exemplary fatty acids and fatty acid esters are laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties.

The half-life extending moiety may be a direct fusion with the spFv of the disclosure and may be generated by standard cloning and expression techniques. Alternatively, well-known chemical coupling methods may be used to attach the moieties to recombinantly produced spFvs of the disclosure.
Heterologous Molecules Comprising the spFv of the Disclosure and a Cytotoxic Agent or a Detectable Label The disclosure also provides a heterologous molecule comprising the spFv of the disclosure, wherein the spFv of the disclosure is conjugated to a second protein, a polynucleotide, a therapeutic agent, a cytotoxic agent or a detectable label.

The heterologous molecule comprising the spFv of the disclosure may be used to direct therapeutics, mediate killing, visualize, identify or purify cells that express the antigen the spFv binds to, in vitro or in vivo.

In some embodiments, the detectable label is also a cytotoxic agent.

Detectable label includes compositions that, when conjugated to the spFv of the disclosure, renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}$H, $^{11}$C, $^{13}$C, $^{15}$N, $^{18}$F, $^{19}$F, $^{55}$Co, $^{57}$Co, $^{60}$Co, $^{61}$Cu, $^{62}$Cu, $^{64}$Cu, $^{67}$Cu, $^{68}$Ga, $^{72}$As, $^{75}$Br, $^{86}$Y, $^{89}$Zr, $^{90}$Sr, $^{94m}$Tc, $^{99m}$Tc, $^{115}$In, $^{123}$I, $^{124}$I, $^{125}$I, $^{131}$I, $^{211}$At, $^{212}$Bi, $^{213}$Bi, $^{223}$Ra, $^{226}$Ra, $^{225}$Ac and $^{227}$Ac.

Exemplary metal atoms are metals with an atomic number greater than 20, such as calcium, scandium, titanium, vanadium, chromium, manganese, iron, cobalt, nickel, copper, zinc, gallium, germanium, arsenic, selenium, bromine, krypton, rubidium, strontium, yttrium, zirconium, niobium, molybdenum, technetium, ruthenium, rhodium, palladium, silver, cadmium, indium, tin, antimony, tellurium, iodine, xenon, cesium, barium, lanthanum, hafnium, tantalum, tungsten, rhenium, osmium, iridium, platinum, gold, mercury, thallium, lead, bismuth, francium, radium, actinium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$.

The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The heterologous molecule comprising the scFv of the disclosure conjugated to a detectable label may be used as an imaging agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y, and $^{186}$Re.

In some embodiments, the cytotoxic agent is dolastatins or dolastatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division and have anticancer and antifungal activity. The dolastatin or auristatin drug moiety may be attached to the antibody of the invention through the N (amino) terminus or the C (carboxyl) terminus of the peptidic drug moiety (see e.g., WO02/088172), or via any cysteine engineered into a protein Conjugation to a detectable label may be done using known methods.

In some embodiments, the detectable label is complexed with a chelating agent.

In some embodiments, the detectable label is conjugated to the spFv of the disclosure via a linker.

The detectable label or the cytotoxic moiety may be linked directly, or indirectly, to the spFv of the disclosure using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Heterologous Molecules Comprising the spFv of the Disclosure and Immunoglobulin (Ig) Constant Region or Fragments Thereof The spFv of the disclosure may be conjugated to an Ig constant region or a fragment of the Ig constant region to impart antibody-like properties, including Fc effector functions C1q binding, complement dependent cytotoxicity (CDC), Fc receptor binding, antibody-dependent cell-mediated cytotoxicity (ADCC), phagocytosis or down regulation of cell surface receptors (e.g., B cell receptor; BCR). The Ig constant region or the fragment of the Ig constant region functions also as a half-life extending moiety as described herein. The spFv of the disclosure may also be engineered into full length antibodies using standard methods. The full length antibodies comprising the spFv of the disclosure may further be engineered as described herein.

Immunoglobulin heavy chain constant region is comprised of subdomains CH1, hinge, CH2 and CH3. The CH1 domain spans residues 118-215, the CH2 domain residues 231-340 and the CH3 domain residues 341-447 on the heavy chain, residue numbering according to the EU Index. In some instances residue 341 is referred as a CH2 domain residue. Hinge is generally defined as including residue 216 and terminating at 230 of human IgG1 but may also include a lower hinge region from about residue 231 to about residue 237 as described herein. Ig Fc region comprises at least the CH2 and the CH3 domains of the Ig constant region, and therefore comprises at least a region from about 231 to 447 of Ig heavy chain constant region.

The invention also provides a spFv of the disclosure conjugated to an immunoglobulin (Ig) constant region or a fragment of the Ig constant region.

In some embodiments, the Ig constant region is a heavy chain constant region

In some embodiments, the Ig constant region is a light chain constant region.

In some embodiments, the fragment of the Ig constant region comprises a Fc region.

In some embodiments, the fragment of the Ig constant region comprises a CH2 domain.

In some embodiments, the fragment of the Ig constant region comprises a CH3 domain.

In some embodiments, the fragment of the Ig constant region comprises the CH2 domain and the CH3 domain.

In some embodiments, the fragment of the Ig constant region comprises at least portion of a hinge, the CH2 domain and the CH3 domain. Portion of the hinge refers to one or more amino acid residues of the Ig hinge.

In some embodiments, the fragment of the Ig constant region comprises the hinge, the CH2 domain and the CH3 domain.

In some embodiments, the spFv of the disclosure is conjugated to the N-terminus of the Ig constant region or the fragment of the Ig constant region.

In some embodiments, the spFv of the disclosure is conjugated to the C-terminus of the Ig constant region or the fragment of the Ig constant region.

The spFv of the disclosure conjugated to Ig constant region or the fragment of the Ig constant region may be assessed for their functionality using several known assays. Binding to target antigen may be assessed using methods described herein. Altered properties imparted by the Ig constant domain or the fragment of the Ig constant region such as Fc region may be assayed in Fc receptor binding assays using soluble forms of the receptors, such as FcγRI, FcγRII, FcγRIII or FcRn, or using cell-based assays measuring for example ADCC, CDC or ADCP.

ADCC may be assessed using an in vitro assay using cells that express the antigen to which the spFv of the disclosure binds to as target cells and NK cells as effector cells. Cytolysis may be detected by the release of label (e.g., radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

ADCP may be evaluated by using monocyte-derived macrophages as effector cells and any cell that express the antigen to which the spFv of the disclosure binds to as target cells which are engineered to express GFP or other labeled molecule. In an exemplary assay, effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the $CD11^+CD14^+$ macrophages using standard methods.

CDC of cells may be measured for example by plating Daudi cells at $1\times10^5$ cells/well (50 μL/well) in RPMI-B (RPMI supplemented with 1% BSA), adding 50 μL of test protein to the wells at final concentration between 0-100 μg/mL, incubating the reaction for 15 min at room temperature, adding 11 μL of pooled human serum to the wells, and incubation the reaction for 45 min at 37° C. Percentage (%) lysed cells may be detected as % propidium iodide stained cells in FACS assay using standard methods.

Heterologous Molecules Comprising the spFv of the Disclosure and a Chimeric Antigen Receptor (CAR) or a Fragment Thereof The spFv of the disclosure may be conjugated to a chimeric antigen receptor (CAR) or to a fragment of the CAR. The CAR comprising the spFv of the disclosure may hence be monospecific or multispecific, comprising, as its extracellular domain, one or more scFv molecules of the disclosure.

Chimeric antigen receptors (CARs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on target cells, an immune cell that expresses the CAR can target and kill the target cell.

CAR typically comprises an extracellular domain that binds the antigen ad an optional linker, a transmembrane domain, and a cytosolic domain comprising a costimulatory domain and/or a signaling domain.

The extracellular domain of CAR may contain any polypeptide that binds the desired antigen, such as the scFv of the disclosure. CARs may also be engineered to bind two or more desired antigens that may be arranged in tandem and separated by linker sequences. For example, one or more scFvs of the disclosure, domain antibodies, llama VHH antibodies or other VH only antibody fragments may be organized in tandem via a linker to generate bispecific or multispecific CARs.

The transmembrane domain of CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1 BB (CD137), 4-1 BBL, GITR, CD40, BAFFR, HVEM (LIGHTR), SLAMF7, NKp80 (KLRFI), CD160, CD1 9, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI 1a, LFA-1, ITGAM, CDI 1b, ITGAX, CDI 1c, ITGB1, CD29, ITGB2, CD1 8, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMF1), CD152 (CTLA4), CD223 (LAG3), CD270 (HVEM), CD278 (ICOS), DAP10, LAT, NKD2C SLP76, TRIM, and ZAP70.

The intracellular signaling domain of CAR may be derived from the signaling domains of for example CD3ζ, CD3ε, CD22, CD79a, CD66d or CD39. "Intracellular signaling domain" refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker within CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Exemplary cleavable linkers include 2A.

An exemplary CAR comprises the scFv of the disclosure, CD8 transmembrane domain and CD3ζ signaling domain. Another exemplary CAR comprise the scFv of the disclosure, CD8 or CD28 transmembrane domain, CD28, 41BB or OX40 costimulatory domain and CD3ζ signaling domain.

CARs are generated by standard molecular biology techniques.

The spFv of the disclosure may be conjugated directly to the second molecule or via a linker. Exemplary linkers include portions of immunoglobulin hinge area, CL or CH1 derived from any immunoglobulin heavy or light chain isotype, Gly rich linkers, Gly and Ser containing linkers, Gly and Ala containing linkers, Ala and Ser containing linkers and Pro containing linkers. Exemplary amino acids that may be included into the linker are Gly, Ser Pro, Thr, Glu, Lys, Arg, Ile, Leu and His. Alternatively, a variety of non-proteinaceous polymers, including polyethylene glycol (PEG), polypropylene glycol, polyoxyalkylenes, or copolymers of polyethylene glycol and polypropylene glycol, may find use as linkers. Exemplary linkers are described for example in Int. Pat. Publ. No. WO2019/060695.

In some embodiments, the heterologous molecule is monospecific.

In some embodiments, the heterologous molecule is multispecific.

In some embodiments, the heterologous molecule is bispecific.

In some embodiments, the heterologous molecule is trispecific.

In some embodiments, the heterologous molecule is tetraspecific.

Multispecific Molecules Comprising the spFv of the Disclosure

The disclosure also provides a multispecific molecule comprising a single chain variable fragment (scFv) comprising a heavy chain variable region (VH), a linker (L) and a light chain variable region (VL), wherein the scFv comprises
  a first disulfide bond between a structurally conserved surface exposed VH cysteine (Cys) and a first L Cys;
  a second disulfide bond between a structurally conserved surface exposed VL Cys and a second L Cys; or
  the first disulfide bond between the structurally conserved surface exposed VH Cys and the first L Cys and the second disulfide bond between the structurally conserved surface exposed VL Cys and the second L Cys.

The disclosure also provides a multispecific molecule comprising a scFv comprising a VH, a L and a VL, wherein
  the VH comprises a VH Cys at a structurally conserved surface exposed VH framework residue position and the L comprises a first L Cys;
  the VL comprises a VL Cys at a structurally conserved surface exposed VL framework residue position and the L comprises a second L Cys; or the VH comprises the VH Cys at a structurally conserved surface exposed VH framework residue position, the VL comprises the VL Cys at a structurally conserved surface exposed VL framework residue position and the L comprises the first L Cys and the second L Cys, wherein the VH Cys and the first L Cys are capable of forming a disulfide bond and the VL Cys and the second L Cys are capable of forming a disulfide bond.

In some embodiments, the distance between the VH Cys and the VL Cys is from about 7 Å to about 9 Å.

In some embodiments, the VH Cys is at H3, H5, H40, H43, H46 or H105, wherein residue numbering is according to Chothia.

In some embodiments, the VL Cys is at L3, L5, L39, L42, L45, L100 or L102, wherein residue numbering is according to Chothia.

In some embodiments,
the VH Cys is at H105 and the VL Cys is at L42;
the VH Cys is at H43 and the VL Cys is at a L100;
the VH Cys is at H3 and the VL Cys is at L3;
the VH Cys is at H3 and the VL Cys is at L5;
the VH Cys is at H3 and the VL Cys is at L39;
the VH Cys is at H3 and the VL Cys is at L42;
the VH Cys is at H3 and the VL Cys is at L45;
the VH Cys is at H3 and the VL Cys is at L100;
the VH Cys is at H3 and the VL Cys is at L102;
the VH Cys is at H5 and the VL Cys is at L3;
the VH Cys is at H5 and the VL Cys is at L5;
the VH Cys is at H5 and the VL Cys is at L39;
the VH Cys is at H5 and the VL Cys is at L42;
the VH Cys is at H5 and the VL Cys is at L45;
the VH Cys is at H5 and the VL Cys is at L100;
the VH Cys is at H5 and the VL Cys is at L102;
the VH Cys is at H40 and the VL Cys is at L3;
the VH Cys is at H40 and the VL Cys is at L5;
the VH Cys is at H40 and the VL Cys is at L39;
the VH Cys is at H40 and the VL Cys is at L42;
the VH Cys is at H40 and the VL Cys is at L45;
the VH Cys is at H40 and the VL Cys is at L100;
the VH Cys is at H40 and the VL Cys is at L102;
the VH Cys is at H43 and the VL Cys is at L3;
the VH Cys is at H43 and the VL Cys is at L5;
the VH Cys is at H43 and the VL Cys is at L39;
the VH Cys is at H43 and the VL Cys is at L42;
the VH Cys is at H43 and the VL Cys is at L45;
the VH Cys is at H43 and the VL Cys is at L102;
the VH Cys is at H46 and the VL Cys is at L3;
the VH Cys is at H46 and the VL Cys is at L5;
the VH Cys is at H46 and the VL Cys is at L39;
the VH Cys is at H46 and the VL Cys is at L42;
the VH Cys is at H46 and the VL Cys is at L45;
the VH Cys is at H46 and the VL Cys is at L100;
the VH Cys is at H46 and the VL Cys is at L102;
the VH Cys is at H105 and the VL Cys is at L3;
the VH Cys is at H105 and the VL Cys is at L5;
the VH Cys is at H105 and the VL Cys is at L39;
the VH Cys is at H105 and the VL Cys is at L45;
the VH Cys is at H105 and the VL Cys is at L100; or
the VH Cys is at H105 and the VL Cys is at L102;
herein residue numbering is according to Chothia.

In some embodiments, the L comprises a contiguous amino acid sequence derived from an immunoglobulin (Ig) hinge region.

In some embodiments, the Ig hinge region is derived from a human or a non-human Ig hinge region.

In some embodiments, the Ig hinge region is derived from the human Ig hinge region.

In some embodiments, the human Ig hinge region is an IgG1, IgG2, IgG3 or IgG4 isotype.

In some embodiments, the L comprises an amino acid sequence $C(X)_yC$ (SEQ ID NO: 23), wherein X is Gly, Ser, Pro, Ala, Arg, Asn, Asp, Glu, Gln, His, Ile, Leu, Lys, Phe, Thr, Trp or Tyr, and y is an integer from 1 to 3.

In some embodiments, the L comprises the amino acid sequence $C(X)_yC$ (SEQ ID NO: 24), wherein X is Gly, Ser or Pro, and y is an integer from 1 to 3.

In some embodiments, the L comprises the amino acid sequence CPC, CGC, CSC, CPPC (SEQ ID NO: 1), CGPC (SEQ ID NO: 28), CPGC (SEQ ID NO: 29), CGGC (SEQ ID NO: 30), CSPG (SEQ ID NO: 31), CPSC (SEQ ID NO: 32), CSSC (SEQ ID NO: 33), CGSC (SEQ ID NO: 34), CSGC (SEQ ID NO: 35), CPPPC (SEQ ID NO: 36), CGPPC (SEQ ID NO: 37), CPGPC (SEQ ID NO: 38), CPPGC (SEQ ID NO: 39), CGGPC (SEQ ID NO: 40), CPGGC (SEQ ID NO: 41), CGGGC (SEQ ID NO: 42), CSPPC (SEQ ID NO: 43), CPSPC (SEQ ID NO: 44), CPPSC (SEQ ID NO: 45), CSSPC (SEQ ID NO: 46), CPSSC (SEQ ID NO: 47), CSSSC (SEQ ID NO: 48), CGSPC (SEQ ID NO: 49), CPGSC (SEQ ID NO: 50), CSGPC (SEQ ID NO: 51) or CPSGC (SEQ ID NO: 52).

In some embodiments, the L comprises from about 14 to about 19 amino acids, such as about 14, about 15, about 16, about 17, about 18 or about 19 amino acids.

In some embodiments, the L comprises the amino acid sequence $(X)_mC(X)_yC(X)_n$ (SEQ ID NO: 25); wherein X is Gly, Ser, Pro, Ala, Arg, Asn, Asp, Glu, Gln, His, Ile, leu, Lys, Phe Thr, Trp or Tyr, m is an integer from 6 to 9, y is an integer from 1 to 3 and n is an integer from 4 to 6.

In some embodiments, the L comprises the amino acid sequence $(X)_mC(X)_yC(X)_n$ (SEQ ID NO: 26); wherein X is Gly, Ser, Pro, Ala, Arg, Asn, Asp, Glu, Gln, His, Ile, Leu, Lys, Thr or Tyr, m is an integer from 6 to 9, y is an integer from 1 to 3 and n is an integer from 4 to 6.

In some embodiments, the L comprises the amino acid sequence $(X)_mC(X)_yC(X)_n$ (SEQ ID NO: 27); wherein X is Gly or Pro, m is an integer from 6 to 9, y is an integer from 1 to 3 and n is an integer from 4 to 6.

In some embodiments, the L comprises the amino acid sequence of SEQ ID NOs: 2, 3, 4, 5, 6 or 7.

In some embodiments, the spFv of the disclosure is in the VL-L-VH orientation.

In some embodiments, the spFv of the disclosure is in the VH-L-VL orientation.

The disclosure also provides a multispecific molecule comprising a scFv comprising a VH, a L and a VL, wherein
the VH comprises Cys at H105;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H105;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H105;
the VL comprises Cys at L39;

the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

The disclosure also provides a multispecific molecule comprising a scFv comprising a VH, a L and a VL, wherein
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

The disclosure also provides a multispecific molecule comprising a scFv comprising a VH, a L and a VL, wherein
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

In some embodiments, the L comprises the amino acid sequence of SEQ ID NO: 3.

In some embodiments, the L comprises the amino acid sequence of SEQ ID NO: 6.

In some embodiments, the L comprises the amino acid sequence of SEQ ID NO: 7.

In some embodiments, the multispecific molecule comprises an antibody or an antibody fragment.

In some embodiments, the multispecific protein comprises an Ig constant region or a fragment of the Ig constant region.

In some embodiments, the Ig constant region comprises a Fc region.

In some embodiments, the Ig constant region comprises a CH2 domain.

In some embodiments, the fragment of the Ig constant region comprises a CH3 domain.

In some embodiments, the fragment of the Ig constant region comprises the CH2 domain and the CH3 domain.

In some embodiments, the fragment of the Ig constant region comprises at least a portion of a hinge, the CH2 domain and the CH3 domain.

In some embodiments, the fragment of the Ig constant region comprises the hinge, the CH2 domain and the CH3 domain.

In some embodiments, the spFv of the disclosure is conjugated to the N-terminus of the Ig constant region or to the N-terminus of the fragment of the Ig constant region.

In some embodiments, the spFv of the disclosure is conjugated to the C-terminus of the Ig constant region or to the C-terminus of the fragment of the Ig constant region.

In some embodiments, the Ig constant region or the fragment of the Ig constant region is an IgG1, an IgG2, and IgG3 or an IgG4 isotype.

In some embodiments, the Ig constant region or the fragment of the Ig constant region comprises at least one mutation that results in reduced binding of the multispecific molecule to FcγR.

In some embodiments, the at least one mutation that results in reduced binding of the multispecific molecule to FcγR is selected from the group consisting of F234A/L235A, L234A/L235A, L234A/L235A/D265S, V234A/G237A/P238S/H268A/V309L/A330S/P331S, F234A/L235A, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S and S228P/F234A/L235A/G236-deleted/G237A/P238S, wherein residue numbering is according to the EU index.

In some embodiments, the Ig constant region or the fragment of the Ig constant region comprises at least one mutation that results in enhanced binding of the multispecific molecule to FcγR.

In some embodiments, the at least one mutation that results in enhanced binding of the multispecific molecule to FcγR is selected from the group consisting of S239D/I332E, S298A/E333A/K334A, F243L/R292P/Y300L, F243L/R292P/Y300L/P396L, F243L/R292P/Y300L/V305I/P396L and G236A/S239D/I332E, wherein residue numbering is according to the EU index.

In some embodiments, FcγR is FcγRI, FcγRIIA, FcγRIIB or FcγRIII.

In some embodiments, the Ig constant region or fragment of the Ig constant region comprises at least one mutation that modulates a half-life of the multispecific molecule.

In some embodiments, the at least one mutation that modulates the half-life of the multispecific molecule is selected from the group consisting of H435A, P257I/N434H, D376V/N434H, M252Y/S254T/T256E/H433K/N434F, T308P/N434A and H435R, wherein residue numbering is according to the EU index.

In some embodiments, the Ig constant region or fragment of the Ig constant region comprises at least one mutation in the CH3 domain.

In some embodiments, the at least one mutation in the CH3 domain is selected from the group consisting of T350V, L351Y, F405A, Y407V, T366Y, T366W, F405W, T394W, T394S, Y407T, Y407A, T366S/L368A/Y407V, L351Y/F405A/Y407V, T366I/K392M/T394W, F405A/Y407V, T366L/K392M/T394W, L351Y/Y407A, T366A/K409F, L351Y/Y407A, T366V/K409F, T366A/K409F, T350V/L351Y/F405A/Y407V and T350V/T366L/K392L/T394W, wherein residue numbering is according to the EU index.

In some embodiments, the multispecific molecule is bispecific.

In some embodiments, the multispecific molecule is trispecific.

In some embodiments, the multispecific molecule is tetraspecific.

5.2 Generation of Multispecific Proteins that Comprise the spFv of the Disclosure The spFv of the disclosure may be engineered into multispecific molecules of any known format using known recombinant technologies, expression and purification protocols.

The spFv of the disclosure may be engineered into full length multispecific antibodies having one or more mutations in the CH3 domain which promoter stability of the two half molecules. These multispecific antibodies may be generated in vitro using Fab arm exchange or by co-expression of the various chains. For in vitro Fab arm exchange, two monospecific bivalent antibodies are engineered to have the one or more substitutions in the CH3 domain, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

CH3 mutations that may be used include technologies such as Knob-in-Hole mutations (Genentech), electrostatically-matched mutations (Chugai, Amgen, NovoNordisk, Oncomed), the Strand Exchange Engineered Domain body (SEEDbody) (EMD Serono), Duobody® mutations (Genmab), and other asymmetric mutations (e.g., Zymeworks).

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y/Y407A/T366A_K409F, L351Y_Y407A/T366V_K409F, K392D/D399K, K392D/E356K, K253E_D282K_K322D/D239K_E240K_K292D, K392D_K409D/D356K_D399K as described in WO2007/147901, WO 2011/143545, WO2013/157954, WO2013/096291 and US2018/0118849.

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Additional bispecific or multispecific structures into which the spFv of the disclosure may be incorporated include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

The scFv of the disclosure may also be engineered into multispecific protein which comprises three polypeptide chains. In such designs, at least one antigen binding domain is in the form of a scFv of the disclosure. Exemplary designs include (in which "1" indicates the first antigen binding domain, "2" indicates the second antigen binding domain and "3" indicates the third antigen binding domain:

Design 1: Chain A) scFv1-CH2-CH3; Chain B) VL2-CL; Chain C) VH2-CH1-hinge-CH2-CH3

Design 2: Chain A) scFv1-hinge-CH2-CH3; Chain B) VL2-CL; Chain C) VH2-CH1-hinge-CH2-CH3

Design 3: Chain A) scFv1-CH1-hinge-CH2-CH3; Chain B) VL2-CL; Chain C) VH2-CH1-hinge-CH2-CH3

Design 4: Chain A) CH2-CH3-scFv1; Chain B) VL2-CL; Chain C) VH2-CH1-hinge-CH2-CH3

CH3 engineering may be incorporated to the Designs 1-4, such as mutations L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

5.3 Isotypes, Allotypes and Fc Engineering

The Ig constant region or the fragment of the Ig constant region, such as the Fc region present in the multispecific molecules or in the heterologous molecules of the disclosure may be of any allotype or isotype.

In some embodiments, the Ig constant region or the fragment of the Ig constant region is an IgG1 isotype.

In some embodiments, the Ig constant region or the fragment of the Ig constant region is an IgG2 isotype.

In some embodiments, the Ig constant region or the fragment of the Ig constant region is an IgG3 isotype.

In some embodiments, the Ig constant region or the fragment of the Ig constant region is an IgG4 isotype.

The Ig constant region or the fragment of the Ig constant region may be of any allotype. It is expected that allotype has no influence on properties of the Ig constant region, such as binding or Fc-mediated effector functions. Immunogenicity of therapeutic proteins comprising Ig constant regions of fragments thereof is associated with increased risk of infusion reactions and decreased duration of therapeutic response (Baert et al., (2003) N Engl J Med 348:602-608). The extent to which therapeutic proteins comprising Ig constant regions of fragments thereof induce an immune response in the host may be determined in part by the allotype of the Ig constant region (Stickler et al., (2011) Genes and Immunity 12:213-221). Ig constant region allotype is related to amino acid sequence variations at specific locations in the constant region sequences of the antibody. Table 3 shows select IgG1, IgG2 and IgG4 allotypes.

TABLE 3

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n) | T | M | | | | | | |
| G2m(n−) | P | V | | | | | | |

TABLE 3-continued

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n)/(n−) | T | V | | | | | | |
| nG4m(a) | | | L | R | | | | |
| G1m(17) | | | | | K | E | M | A |
| G1m(17, 1) | | | | | K | D | L | A |

C-terminal lysine (CTL) may be removed from the Ig constant region by endogenous circulating carboxypeptidases in the blood stream (Cai et al., (2011) *Biotechnol Bioeng* 108:404-412). During manufacturing, CTL removal may be controlled to less than the maximum level by control of concentration of extracellular $Zn^{2+}$, EDTA or EDTA-$Fe^{3+}$ as described in U.S. Patent Publ. No. US2014/0273092. CTL content of proteins may be measured using known methods.

In some embodiments, the spFv of the disclosure conjugated to the Ig constant region has a C-terminal lysine content from about 10% to about 90%. In some embodiments, the C-terminal lysine content is from about 20% to about 80%. In some embodiments, the C-terminal lysine content is from about 40% to about 70%. In some embodiments, the C-terminal lysine content is from about 55% to about 70%. In some embodiments, the C-terminal lysine content is about 60%.

Fc region mutations may be made to the multispecific molecules or the heterologous molecules of the disclosure comprising the Ig constant region or the fragment of the Ig constant region to modulate their effector functions such as ADCC, ADCP and/or ADCP and/or pharmacokinetic properties. This may be achieved by introducing mutation(s) into the Fc that modulate binding of the mutated Fc to activating FcγRs (FcγRI, FcγRIIa, FcγRIII), inhibitory FcγRIIb and/or to FcRn.

In some embodiments, the multispecific molecule or the heterologous molecule of the disclosure comprises at least one mutation in the Ig constant region or in the fragment of the Ig constant region.

In some embodiments, the at least one mutation is in the Fc region.

In some embodiments, the multispecific molecule or the heterologous molecule of the disclosure comprises at least one, two, three, four, five, six, seven, eight, nine, ten, eleven, twelve, thirteen, fourteen or fifteen mutations in the Fc region.

In some embodiments, the multispecific molecule or the heterologous molecule of the disclosure comprises at least one mutation in the Fc region that modulates binding of the antibody to FcRn.

Fc positions that may be mutated to modulate half-life (e.g., binding to FcRn) include positions 250, 252, 253, 254, 256, 257, 307, 376, 380, 428, 434 and 435. Exemplary mutations that may be made singularly or in combination are mutations T250Q, M252Y, I253A, S254T, T256E, P257I, T307A, D376V, E380A, M428L, H433K, N434S, N434A, N434H, N434F, H435A and H435R. Exemplary singular or combination mutations that may be made to increase the half-life are mutations M428L/N434S, M252Y/S254T/T256E, T250Q/M428L, N434A and T307A/E380A/N434A. Exemplary singular or combination mutations that may be made to reduce the half-life are mutations H435A, P257I/ N434H, D376V/N434H, M252Y/S254T/T256E/H433K/ N434F, T308P/N434A and H435R.

In some embodiments, the multispecific molecule or the heterologous molecule of the disclosure comprises M252Y/ S254T/T256E mutation in the Fc region.

In some embodiments, the multispecific molecule or the heterologous molecule of the disclosure comprises at least one mutation in the Fc region that reduces binding of the protein to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the multispecific molecule or the heterologous molecule of the disclosure to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, D265S, S267E, H268A, H268Q, Q268A, N297A, A327Q, P329A, D270A, Q295A, V309L, A327S, L328F, A330S and P331S in IgG1, IgG2, IgG3 or IgG4. Exemplary combination mutations that result in the multispecific molecule or the heterologous molecule of the disclosure with reduced ADCC are mutations L234A/ L235A on IgG1, L234A/L235A/D265S on IgG1, V234A/ G237A/P238S/H268A/V309L/A330S/P331S on IgG2, F234A/L235A on IgG4, S228P/F234A/L235A on IgG4, N297A on all Ig isotypes, V234A/G237A on IgG2, K214T/ E233P/L234V/L235A/G236-deleted/A327G/P331A/ D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

Exemplary mutation that results in the multispecific molecule or the heterologous molecule of the disclosure with reduced CDC is a K322A mutation.

Well-known S228P mutation may be made in IgG4 to enhance IgG4 stability.

In some embodiments, the multispecific molecule or the heterologous molecule of the disclosure comprises at least one mutation in the Fc region selected from the group consisting of K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S.

In some embodiments, the multispecific molecule or the heterologous molecule of the disclosure comprises L234A/ L235A/D265S mutation in the Fc region.

In some embodiments, the multispecific molecule or the heterologous molecule of the disclosure comprises L234A/ L235A mutation in the Fc region.

In some embodiments, the multispecific molecule or the heterologous molecule of the disclosure comprises at least one mutation in the Fc region that enhances binding of the multispecific molecule or the heterologous molecule of the disclosure to FcγR and/or enhances Fc effector functions such as C1q binding, complement dependent cytotoxicity (CDC), antibody-dependent cell-mediated cytotoxicity (ADCC) and/or phagocytosis (ADCP).

Fc positions that may be mutated to increase binding of the multispecific molecule or the heterologous molecule of the disclosure to the activating FcγR and/or enhance Fc effector functions include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are G236A, S239D, F243L, T256A, K290A, R292P, S298A, Y300L, V305L, K326A, A330K, I332E, E333A, K334A, A339T and P396L. Exemplary combination mutations that result in proteins with increased ADCC or ADCP are a S239D/I332E, S298A/E333A/K334A, F243L/R292P/Y300L, F243L/R292P/Y300L/P396L, F243L/R292P/Y300L/V305I/P396L and G236A/S239D/I332E.

Fc positions that may be mutated to enhance CDC include positions 267, 268, 324, 326, 333, 345 and 430. Exemplary mutations that may be made singularly or in combination are S267E, F1268F, S324T, K326A, K326W, E333A, E345K, E345Q, E345R, E345Y, E430S, E430F and E430T. Exemplary combination mutations that result in the multispecific molecule or the heterologous molecule of the disclosure with increased CDC are K326A/E333A, K326W/E333A, H268F/S324T, S267E/H268F, S267E/S324T and S267E/H268F/S324T.

The specific mutations described herein are mutations when compared to the IgG1, IgG2 and IgG4 wild-type amino acid sequences of SEQ ID NOs: 66, 67 and 68, respectively.

```
wild-type IgG1
                                     SEQ ID NO: 66
ASTKGPSVFPLAPSSKSTSGGTAALGCLVKDYFPEPVTVSWN

SGALTSGVHTFPAVLQSSGLYSLSSVVTVPSSSLGTQTYICN

VNHKPSNTKVDKKVEPKSCDKTHTCPPCPAPELLGGPSVFLF

PPKPKDTLMISRTPEVTCVVVDVSHEDPEVKFNWYVDGVEVH

NAKTKPREEQYNSTYRVVSVLTVLHQDWLNGKEYKCKVSNKA

LPAPIEKTISKAKGQPREPQVYTLPPSRDELTKNQVSLTCLV

KGFYPSDIAVEWESNGQPENNYKTTPPVLDSDGSFFLYSKLT

VDKSRWQQGNVFSCSVMHEALHNHYTQKSLSLSPGK, wild-type IgG2
                                     SEQ ID NO: 67
ASTKGPSVFPLAPCSRSTSESTAALGCLVKDYFPEPVTVSWN

SGALTSGVHTFPAVLQSSGLYSLSSVVTVPSSNFGTQTYTCN

VDHKPSNTKVDKTVERKCCVECPPCPAPPVAGPSVFLFPPKP

KDTLMISRTPEVTCVVVDVSHEDPEVQFNWYVDGVEVHNAKT

KPREEQFNSTFRVVSVLTVVHQDWLNGKEYKCKVSNKGLPAP

IEKTISKTKGQPREPQVYTLPPSREEMTKNQVSLTCLVKGFY

PSDISVEWESNGQPENNYKTTPPMLDSDGSFFLYSKLTVDKS

RWQQGNVFSCSVMHEALHNHYTQKSLSLSPGK;

wild-type IgG4
                                     SEQ ID NO: 68
ASTKGPSVFPLAPCSRSTSESTAALGCLVKDYFPEPVTVSWN

SGALTSGVHTFPAVLQSSGLYSLSSVVTVPSSSLGTKTYTCN

VDHKPSNTKVDKRVESKYGPPCPSCPAPEFLGGPSVFLFPPK

PKDTLMISRTPEVTCVVVDVSQEDPEVQFNWYVDGVEVHNAK

TKPREEQFNSTYRVVSVLTVLHQDWLNGKEYKCKVSNKGLPS

SIEKTISKAKGQPREPQVYTLPPSQEEMTKNQVSLTCLVKGF

YPSDIAVEWESNGQPENNYKTTPPVLDSDGSFFLYSRLTVDK

SRWQEGNVFSCSVMHEALHNHYTQKSLSLSLGK;
```

Binding of the multispecific molecule or the heterologous molecule of the disclosure to FcγR or FcRn may be assessed on cells engineered to express each receptor using flow cytometry. In an exemplary binding assay, 2×10$^5$ cells per well are seeded in 96-well plate and blocked in BSA Stain Buffer (BD Biosciences, San Jose, USA) for 30 min at 4° C. Cells are incubated with a test multispecific molecule or a test heterologous molecule of the disclosure on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

5.4 Glycoengineering

The ability of the multispecific molecule or the heterologous molecule of the disclosure conjugated to the Ig constant region or to the fragment of the Ig constant region to mediate ADCC can be enhanced by engineering the Ig constant region or the fragment of the Ig constant region oligosaccharide component. Human IgG1 or IgG3 are N-glycosylated at Asn297 with the majority of the glycans in the well-known biantennary G0, G0F, G1, G1F, G2 or G2F forms. Ig constant region containing proteins may be produced by non-engineered CHO cells typically have a glycan fucose content of about at least 85%. The removal of the core fucose from the biantennary complex-type oligosaccharides attached to the Ig constant region or to the fragment of the Ig constant region enhances ADCC of the multispecific molecule or the heterologous molecule of the disclosure via improved FcγRIIIa binding without altering antigen binding or CDC activity. Such multispecific molecules or heterologous molecules can be achieved using different methods reported to lead to the successful expression of relatively high defucosylated immunoglobulins bearing the biantennary complex-type of Fc oligosaccharides such as control of culture osmolality (Konno et al., (2012) *Cytotechnology* 64:249-265), application of a variant CHO line Lec13 as the host cell line (Shields et al., (2002) *J Biol Chem* 277:26733-26740), application of a variant CHO line EB66 as the host cell line (Olivier et al., (2010) MAbs; 2: 405-415), application of a rat hybridoma cell line YB2/0 as the host cell line (Shinkawa et al., (2003) *J Biol Chem* 278:3466-3473), introduction of small interfering RNA specifically against the a 1,6-fucosyltrasferase (FUT8) gene (Mori et al., (2004) *Biotechnol Bioeng* 88:901-908), or coexpression of β-1,4-N-acetylglucosaminyltransferase III and Golgi α-mannosidase II or a potent alpha-mannosidase I inhibitor, kifunensine (Ferrara et al., (2006) *J Biol Chem* 281:5032-5036).

In some embodiments, the multispecific molecule or the heterologous molecule of the disclosure comprising the Ig constant region or to the fragment of the Ig constant region has a biantennary glycan structure with fucose content of about between 1% to about 15%, for example about 15%, 14%, 13%, 12%, 11% 10%, 9%, 8%, 7%, 6%, 5%, 4%, 3%, 2% or 1%. In some embodiments, the multispecific molecule or the heterologous molecule of the disclosure comprising the Ig constant region or to the fragment of the Ig constant region has a glycan structure with fucose content of about 50%, 40%, 45%, 40%, 35%, 30%, 25%, or 20%.

"Fucose content" refers to the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g., complex, hybrid and oligo- and high-mannose structures) as described in Int Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); 5) Separation of the mAb oligosaccharides from the mAb protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" refers to the multispecific molecule or the heterologous molecule of the disclosure comprising the Ig constant region or to the fragment of the Ig constant region with fucose content of about between 1%-15%.

"Normal fucose" or "normal fucose content" refers to the multispecific molecule or the heterologous molecule of the disclosure comprising the Ig constant region or to the fragment of the Ig constant region with fucose content of about over 50%, typically about over 80% or over 85%.

5.5 Anti-Idiotypic Antibodies

Anti-idiotypic antibodies are antibodies that specifically bind to the spFv of the disclosure.

The invention also provides an anti-idiotypic antibody that specifically binds to the spFv of the disclosure.

In some embodiments, the anti-idiotypic antibody binds to the disulfide bond in the spFv of the disclosure.

In some embodiments, the anti-idiotypic antibody binds to the antigen binding domain of the spFv of the disclosure.

5.6 Polynucleotides, Vectors, Host Cells

The disclosure also provides an isolated polynucleotide encoding the spFv of the disclosure.

The disclosure also provides a vector comprising the polynucleotide of the disclosure.

In some embodiments, the vector is an expression vector. Expression vectors may be plasmid vectors, viral vectors, vectors for baculovirus expression, vectors for prokaryotic expression, vectors for eukaryotic expression, transposon based vectors or any other vector suitable for introduction of the polynucleotide of the disclosure into a given cell or organism.

The polynucleotide encoding the spFv of the disclosure may be operably linked to control sequences in the expression vector that facilitate the expression of the spFv. Such regulatory elements may include a transcriptional promoter, sequences encoding suitable mRNA ribosomal binding sites, and sequences that control the termination of transcription and translation. Expression vectors may also include one or more nontranscribed elements such as an origin of replication, other 5' or 3' flanking nontranscribed sequences, 5' or 3' nontranslated sequences (such as necessary ribosome binding sites), splice donor and acceptor sites, or selection markers. The polynucleotide may be a cDNA. The promoter driving spFv expression may be strong, weak, tissue-specific, inducible or developmental-specific promoter. Exemplary promoters that may be used are hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. Inducible promoters such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes and ADAR1. Vectors of the disclosure may also contain one or more Internal Ribosome Entry Site(s) (IRES). Inclusion of an IRES sequence into fusion vectors may be beneficial for enhancing expression of some proteins. Vectors of the disclosure may be circular or linear. They may be prepared to contain a replication system functional in a prokaryotic or eukaryotic host cell. Replication systems can be derived, e.g., from ColE1, SV40, 2μ plasmid, λ, bovine papilloma virus, and the like. The expression vectors can be designed for either transient expression, for stable expression, or for both. The expression vectors can be made for constitutive expression or for inducible expression.

Exemplary vectors that may be used are Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia), pEE6.4 (Lonza) and pEE12.4 (Lonza). Additional vectors include the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Exemplary plant expression vectors include pBI01, pBI01.2, pBI121, pBI101.3, and pBIN19 (Clontech). Exemplary animal expression vectors include pEUK-C1, pMAM, and pMAMneo (Clontech). The expression vector may be a viral vector, e.g., a retroviral vector, e.g., a gamma retroviral vector.

The disclosure also provides a host cell comprising the vector of the disclosure.

"Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells. *Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

The disclosure also provides a method of producing the spFv of the disclosure, comprising culturing the host cell of the disclosure in conditions that the spFv is produced, and recovering the spFv produced by the host cell. Methods of making scFvs and purifying them are known. Once synthesized (either chemically or recombinantly), the spFv of the disclosure may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). The scFv of the disclosure may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the subject protein The polynucleotides encoding the scFv of the disclosure may be incorporated into vectors using standard molecular biology methods. Host cell transformation, culture, antibody expression and purification are done using well known methods.

5.7 Pharmaceutical Compositions and Administration

The disclosure also provides a pharmaceutical composition comprising the spFv, the heterologous molecule comprising the spFv or the multispecific molecule comprising the spFv of the disclosure and a pharmaceutically acceptable carrier. For therapeutic use, the spFv, the heterologous molecule comprising the spFv or the multispecific molecule comprising the spFv of the disclosure may be prepared as pharmaceutical compositions containing an effective amount of the spFv, the heterologous molecule comprising the spFv or the multispecific molecule comprising the spFv of the disclosure as an active ingredient in a pharmaceutically acceptable carrier. "Carrier" refers to a diluent, adjuvant, excipient, or vehicle with which the spFv, the heterologous molecule comprising the spFv or the multispecific molecule comprising the spFv of the disclosure is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the spFv, the heterologous molecule comprising the spFv or the multispecific molecule comprising the spFv of the disclosure in such pharmaceutical formulation may vary, from less than about 0.5%, usually to at least about 1% to as much as 15 or 20% by weight and may be selected primarily based on required dose, fluid volumes, viscosities, etc., according to the mode of administration selected. Suitable vehicles and formulations, inclusive of other human proteins, e.g., human serum albumin, are described, for example, in e.g., Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration of the spFv, the heterologous molecule comprising the spFv or the multispecific molecule comprising the spFv of the disclosure may be any suitable route such as parenteral administration, e.g., intradermal, intramuscular, intraperitoneal, intravenous or subcutaneous, transmucosal (oral, intranasal, intravaginal, rectal) or other means appreciated by the skilled artisan, as well known in the art.

5.8 Process for Preparing the spFv of the Disclosure

The disclosure also provides a process for preparing a stabilized scFv, comprising: providing a heavy chain variable region (VH) and a light chain variable region (VL) that form an antigen binding site;

providing a linker (L) that comprises or is engineered to comprise a first L Cys;

engineering the VH to comprise a VH Cys at a structurally conserved surface exposed VH framework residue position; and forming a disulfide bond between the VH Cys and the first L Cys to prepare the stabilized scFv.

The disclosure also provides a process for preparing stabilized scFv, comprising: providing a VH and a VL that form an antigen binding site;

providing a L that comprises or is engineered to comprise a second L Cys;

engineering the VL to comprise a VL Cys at a structurally conserved surface exposed VL framework residue position; and forming a disulfide bond between the VL Cys and the second L Cys to prepare the stabilized scFv.

The disclosure also provides a process for preparing a stabilized scFv, comprising: providing a heavy chain variable region (VH) and a light chain variable region (VL) that form an antigen binding site;

providing a linker (L) that comprises or is engineered to comprise a first L Cys and a second L Cys;

engineering the VH to comprise a VH Cys at a structurally conserved surface exposed VH framework residue position;

engineering the VL to comprise a VL Cys at a structurally conserved surface exposed VL framework residue position; and forming a disulfide bond between the VH Cys and the first L Cys and a disulfide bond between the VL Cys and the second L Cys to prepare the stabilized scFv.

The disulfide bond is typically formed during expression of the scFv.

Any known VH/VL pair of scFv that forms an antigen binding domain may be engineered into the stabilized scFvs of the disclosure. Alternatively, antigen binding VH/VL pairs of interest may be identified de novo using known methods and the resulting VH/VL pairs may be engineered into spFv format.

For example, the hybridoma method of Kohler and Milstein may be used to identify VH/VL pairs that bind an antigen of interest and the resulting VH/VL pairs may be engineered as spFvs. Alternatively, transgenic animals, such as mice, rat or chicken carrying human immunoglobulin (Ig) loci in their genome may be used to generate antigen binding fragments, and are described in for example U.S. Pat. No. 6,150,584, Int. Patent Publ. No. WO1999/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www_trianni_com) and Ablexis (http://_www_ablexis_com) may be engaged to provide human antibodies directed against a selected antigen using technologies as described above. Phage display may also be used to generate antigen binding fragments which can be engineered as spFvs.

In some embodiments, the spFv of the disclosure is humanized. In some embodiments, the spFv of the disclosure is human. In some embodiments, the spFv of the disclosure is noon-human.

In some embodiments, the distance between the VH Cys and the VL Cys is from about 7 Å to about 9 Å in the stabilized scFv.

In some embodiments, the VH Cys is at H3, H5, H40, H43, H46 or H105, wherein residue numbering is according to Chothia.

In some embodiments, the VL Cys is at L3, L5, L39, L42, L45, L100 or L102, wherein residue numbering is according to Chothia.

In some embodiments,
the VH Cys is at H105 and the VL Cys is at L42;
the VH Cys is at H43 and the VL Cys is at a L100;
the VH Cys is at H3 and the VL Cys is at L3;
the VH Cys is at H3 and the VL Cys is at L5;
the VH Cys is at H3 and the VL Cys is at L39;
the VH Cys is at H3 and the VL Cys is at L42;
the VH Cys is at H3 and the VL Cys is at L45;
the VH Cys is at H3 and the VL Cys is at L100;
the VH Cys is at H3 and the VL Cys is at L102;
the VH Cys is at H5 and the VL Cys is at L3;
the VH Cys is at H5 and the VL Cys is at L5;
the VH Cys is at H5 and the VL Cys is at L39;
the VH Cys is at H5 and the VL Cys is at L42;
the VH Cys is at H5 and the VL Cys is at L45;
the VH Cys is at H5 and the VL Cys is at L100;
the VH Cys is at H5 and the VL Cys is at L102;
the VH Cys is at H40 and the VL Cys is at L3;
the VH Cys is at H40 and the VL Cys is at L5;
the VH Cys is at H40 and the VL Cys is at L39;
the VH Cys is at H40 and the VL Cys is at L42;
the VH Cys is at H40 and the VL Cys is at L45;
the VH Cys is at H40 and the VL Cys is at L100;
the VH Cys is at H40 and the VL Cys is at L102;
the VH Cys is at H43 and the VL Cys is at L3;
the VH Cys is at H43 and the VL Cys is at L5;
the VH Cys is at H43 and the VL Cys is at L39;
the VH Cys is at H43 and the VL Cys is at L42;
the VH Cys is at H43 and the VL Cys is at L45;
the VH Cys is at H43 and the VL Cys is at L102;
the VH Cys is at H46 and the VL Cys is at L3;
the VH Cys is at H46 and the VL Cys is at L5;
the VH Cys is at H46 and the VL Cys is at L39;
the VH Cys is at H46 and the VL Cys is at L42;
the VH Cys is at H46 and the VL Cys is at L45;
the VH Cys is at H46 and the VL Cys is at L100;
the VH Cys is at H46 and the VL Cys is at L102;
the VH Cys is at H105 and the VL Cys is at L3;
the VH Cys is at H105 and the VL Cys is at L5;
the VH Cys is at H105 and the VL Cys is at L39;
the VH Cys is at H105 and the VL Cys is at L45;
the VH Cys is at H105 and the VL Cys is at L100; or
the VH Cys is at H105 and the VL Cys is at L102, wherein residue numbering is according to Chothia.

In some embodiments, the L comprises a contiguous amino acid sequence derived from an immunoglobulin (Ig) hinge region.

In some embodiments, the Ig hinge region is derived from a human or a non-human Ig hinge region.

In some embodiments, the Ig hinge region is derived from the human Ig hinge region.

In some embodiments, the human Ig hinge region is an IgG1, IgG2, IgG3 or IgG4 isotype.

In some embodiments, the L comprises an amino acid sequence $C(X)_yC$ (SEQ ID NO: 23), wherein X is Gly, Ser, Pro, Ala, Arg Asn, Asp, Glu, Gln, His, Ile, Leu, Lys, Phe, Thr, Trp or Tyr, and y is an integer from 1 to 3

In some embodiments, the L comprises an amino acid sequence $C(X)_yC$ (SEQ ID NO: 24), wherein X is Gly, Ser or Pro, and y is an integer from 1 to 3.

In some embodiments, the L comprises the amino acid sequence CPC, CGC, CSC, CPPC (SEQ ID NO: 1), CGPC (SEQ ID NO: 28), CPGC (SEQ ID NO: 29), CGGC (SEQ ID NO: 30), CSPG (SEQ ID NO: 31), CPSC (SEQ ID NO: 32), CSSC (SEQ ID NO: 33), CGSC (SEQ ID NO: 34), CSGC (SEQ ID NO: 35), CPPPC (SEQ ID NO: 36), CGPPC (SEQ ID NO: 37), CPGPC (SEQ ID NO: 38), CPPGC (SEQ ID NO: 39), CGGPC (SEQ ID NO: 40), CPGGC (SEQ ID NO: 41), CGGGC (SEQ ID NO: 42), CSPPC (SEQ ID NO: 43), CPSPC (SEQ ID NO: 44), CPPSC (SEQ ID NO: 45), CSSPC (SEQ ID NO: 46), CPSSC (SEQ ID NO: 47), CSSSC (SEQ ID NO: 48), CGSPC (SEQ ID NO: 49), CPGSC (SEQ ID NO: 50), CSGPC (SEQ ID NO: 51) or CPSGC (SEQ ID NO: 52).

In some embodiments, the L comprises from about 14 to about 19 amino acids, such as such as about 14, about 15, about 16, about 17, about 18 or about 19 amino acids.

In some embodiments, the L comprises the amino acid sequence $(X)_m C(X)_y C(X)_n$ (SEQ ID NO: 25); wherein X is Gly, Ser, Pro, Ala, Arg, Asn, Asp, Glu, Gln, His, Ile, leu, Lys, Phe Thr, Trp or Tyr, m is an integer from 6 to 9, y is an integer from 1 to 3 and n is an integer from 4 to 6.

In some embodiments, the L comprises the amino acid sequence $(X)_m C(X)_y C(X)_n$ (SEQ ID NO: 26); wherein X is Gly, Ser, Pro, Ala, Arg, Asn, Asp, Glu, Gln, His, Ile, Leu, Lys, Thr or Tyr, m is an integer from 6 to 9, y is an integer from 1 to 3 and n is an integer from 4 to 6.

In some embodiments, the L comprises the amino acid sequence $(X)_m C(X)_y C(X)_n$ (SEQ ID NO: 27); wherein X is Gly or Pro, m is an integer from 6 to 9, y is an integer from 1 to 3 and n is an integer from 4 to 6.

In some embodiments, the L comprises the amino acid sequence of SEQ ID NOs: 2, 3, 4, 5, 6, or 7.

In some embodiments, the stabilized spFv of the disclosure is in the VL-L-VH orientation.

In some embodiments, the stabilized spFv of the disclosure is in the VH-L-VL orientation.

In some embodiments,
the VH comprises Cys at H105;
the VL comprises Cys at L42;
the L comprises an amino acid sequence of SEQ ID NOs: 2, 3, 4, 5, 6 or 7; and
the scFv is in the VL-L-VH orientation.

In some embodiments,
the VH comprises Cys at H105;
the VL comprises Cys at L45;
the L comprises an amino acid sequence of SEQ ID NOs: 2, 3, 4, 5, 6 or 7; and
the scFv is in the VL-L-VH orientation.

In some embodiments,
the VH comprises Cys at H105;
the VL comprises Cys at L39;
the L comprises an amino acid sequence of SEQ ID NOs: 2, 3, 4, 5, 6 or 7; and
the scFv is in the VL-L-VH orientation.

In some embodiments,
the VH comprises Cys at H5;
the VL comprises Cys at L42;
the L comprises an amino acid sequence of SEQ ID NOs: 2, 3, 4, 5, 6 or 7; and
the scFv is in the VL-L-VH orientation.

In some embodiments,
the VH comprises Cys at H5;
the VL comprises Cys at L45;
the L comprises an amino acid sequence of SEQ ID NOs: 2, 3, 4, 5, 6 or 7; and
the scFv is in the VL-L-VH orientation.

In some embodiments,
the VH comprises Cys at H5;
the VL comprises Cys at L39;
the L comprises an amino acid sequence of SEQ ID NOs: 2, 3, 4, 5, 6 or 7; and
the scFv is in the VL-L-VH orientation.

In some embodiments,
the VH comprises Cys at H3;
the VL comprises Cys at L42;
the L comprises an amino acid sequence of SEQ ID NOs: 2, 3, 4, 5, 6 or 7; and
the scFv is in the VL-L-VH orientation.

In some embodiments,
the VH comprises Cys at H3;
the VL comprises Cys at L45;
the L comprises an amino acid sequence of SEQ ID NOs: 2, 3, 4, 5, 6 or 7; and
the scFv is in the VL-L-VH orientation.

In some embodiments,
the VH comprises Cys at H3;
the VL comprises Cys at L39;
the L comprises an amino acid sequence of SEQ ID NOs: 2, 3, 4, 5, 6 or 7; and
the scFv is in the VL-L-VH orientation.

In some embodiments,
the VH comprises Cys at H43;
the VL comprises Cys at L100;
the L comprises an amino acid sequence of SEQ ID NOs: 2, 3, 4, 5, 6 or 7; and
the scFv is in the VH-L-VL orientation.

In some embodiments,
the VH comprises Cys at H43;
the VL comprises Cys at L102;
the L comprises an amino acid sequence of SEQ ID NOs: 2, 3, 4, 5, 6 or 7; and
the scFv is in the VH-L-VL orientation.

In some embodiments,
the VH comprises Cys at H43;
the VL comprises Cys at L5;
the L comprises an amino acid sequence of SEQ ID NOs: 2, 3, 4, 5, 6 or 7; and
the scFv is in the VH-L-VL orientation.

In some embodiments,
the VH comprises Cys at H43;
the VL comprises Cys at L3;
the L comprises an amino acid sequence of SEQ ID NOs: 2, 3, 4, 5, 6 or 7; and
the scFv is in the VH-L-VL orientation.

In some embodiments,
the VH comprises Cys at H40;
the VL comprises Cys at L100;
the L comprises an amino acid sequence of SEQ ID NOs: 2, 3, 4, 5, 6 or 7; and
the scFv is in the VH-L-VL orientation.

In some embodiments,
the VH comprises Cys at H40;
the VL comprises Cys at L102;
the L comprises an amino acid sequence of SEQ ID NOs: 2, 3, 4, 5, 6 or 7; and
the scFv is in the VH-L-VL orientation.

In some embodiments,
the VH comprises Cys at H40;
the VL comprises Cys at L5;
the L comprises an amino acid sequence of SEQ ID NOs: 2, 3, 4, 5, 6 or 7; and
the scFv is in the VH-L-VL orientation.

In some embodiments,
the VH comprises Cys at H40;
the VL comprises Cys at L3;
the L comprises an amino acid sequence of SEQ ID NOs: 2, 3, 4, 5, 6 or 7; and
the scFv is in the VH-L-VL orientation.

In some embodiments,
the VH comprises Cys at H46;
the VL comprises Cys at L100;
the L comprises an amino acid sequence of SEQ ID NOs: 2, 3, 4, 5, 6 or 7; and
the scFv is in the VH-L-VL orientation.

In some embodiments,
the VH comprises Cys at H46;
the VL comprises Cys at L102;
the L comprises an amino acid sequence of SEQ ID NOs: 2, 3, 4, 5, 6 or 7; and
the scFv is in the VH-L-VL orientation.

In some embodiments,
the VH comprises Cys at H46;
the VL comprises Cys at L5;
the L comprises an amino acid sequence of SEQ ID NOs: 2, 3, 4, 5, 6 or 7; and
the scFv is in the VH-L-VL orientation.

In some embodiments,
the VH comprises Cys at H46;
the VL comprises Cys at L3;
the L comprises an amino acid sequence of SEQ ID NOs: 2, 3, 4, 5, 6 or 7; and
the scFv is in the VH-L-VL orientation.

In some embodiments, the L comprises the amino acid sequence of SEQ ID NO: 3.

In some embodiments, the L comprises the amino acid sequence of SEQ ID NO: 6.

In some embodiments, the L comprises the amino acid sequence of SEQ ID NO: 7.

In some embodiments, the stabilized spFv of the disclosure binds an antigen with comparable affinity when compared to a parent scFv that is devoid of the disulfide bonds.

The disclosure also provides a process for preparing a stabilized scFv, comprising providing a polynucleotide encoding a VH, a L and a VL, wherein
the VH comprises Cys at H105 and the VL comprises Cys at L42;
the VH comprises Cys at H43 and the VL comprises Cys at a L100;
the VH comprises Cys at H3 and the VL comprises Cys at L3;
the VH comprises Cys at H3 and the VL comprises Cys at L5;
the VH comprises Cys at H3 and the VL comprises Cys at L39;
the VH comprises Cys at H3 and the VL comprises Cys at L42;
the VH comprises Cys at H3 and the VL comprises Cys at L45;
the VH comprises Cys at H3 and the VL comprises Cys at L100;
the VH comprises Cys at H3 and the VL comprises Cys at L102;
the VH comprises Cys at H5 and the VL comprises Cys at L3;
the VH comprises Cys at H5 and the VL comprises Cys at L5;
the VH comprises Cys at H5 and the VL comprises Cys at L39;
the VH comprises Cys at H5 and the VL comprises Cys at L42;
the VH comprises Cys at H5 and the VL comprises Cys at L45;
the VH comprises Cys at H5 and the VL comprises Cys at L100;
the VH comprises Cys at H5 and the VL comprises Cys at L102;
the VH comprises Cys at H40 and the VL comprises Cys at L3;
the VH comprises Cys at H40 and the VL comprises Cys at L5;
the VH comprises Cys at H40 and the VL comprises Cys at L39;
the VH comprises Cys at H40 and the VL comprises Cys at L42;
the VH comprises Cys at H40 and the VL comprises Cys at L45;
the VH comprises Cys at H40 and the VL comprises Cys at L100;
the VH comprises Cys at H40 and the VL comprises Cys at L102;
the VH comprises Cys at H43 and the VL comprises Cys at L3;
the VH comprises Cys at H43 and the VL comprises Cys at L5;
the VH comprises Cys at H43 and the VL comprises Cys at L39;
the VH comprises Cys at H43 and the VL comprises Cys at L42;
the VH comprises Cys at H43 and the VL comprises Cys at L45;
the VH comprises Cys at H43 and the VL comprises Cys at L102;
the VH comprises Cys at H46 and the VL comprises Cys at L3;
the VH comprises Cys at H46 and the VL comprises Cys at L5;
the VH comprises Cys at H46 and the VL comprises Cys at L39;
the VH comprises Cys at H46 and the VL comprises Cys at L42;
the VH comprises Cys at H46 and the VL comprises Cys at L45;
the VH comprises Cys at H46 and the VL comprises Cys at L100;
the VH comprises Cys at H46 and the VL comprises Cys at L102;
the VH comprises Cys at H105 and the VL comprises Cys at L3;
the VH comprises Cys at H105 and the VL comprises Cys at L5;
the VH comprises Cys at H105 and the VL comprises Cys at L39;
the VH comprises Cys at H105 and the VL comprises Cys at L45;
the VH comprises Cys at H105 and the VL comprises Cys at L100; or
the VH comprises Cys at H105 and the VL comprises Cys at L102, wherein residue numbering is according to Chothia;
the L comprises an amino acid sequence of SEQ ID NOs: 2, 3, 4, 5, 6 or 7; and
expressing the polynucleotide in a host cell to produce the stabilized scFv.

In some embodiments, the host cell is a prokaryotic cell.

In some embodiments, the host cell is an eukaryotic cell.

The following examples are provided to further describe some of the embodiments disclosed herein. The examples are intended to illustrate, not to limit, the disclosed embodiments.

6. EXAMPLES

6.1 Example 1: Design of Stabilized scFvs

A monoclonal antibody (mAb) recognizes its target antigen through the two variable domains VL and VH. A single chain Fv (scFv) was first designed by Bird et al. (1988)

Science 242:423-426 (1988) as a genetic fusion of VL and VH with a flexible linker in either VL-linker-VH or VH-linker-VL orientations. The flexible linker is typically three or four repeats of glycine-serine linker such as (GGGGS)n; n=1-4 (SEQ ID NO: 2, SEQ ID NO: 53, SEQ ID NO: 54, SEQ ID NO: 55). A scFv recapitulates the antigen binding specificity and largely the affinity of its parental mAb. These scFv molecules have found wide applications as detection/diagnostics reagents or as building blocks for making more elaborate molecules such as bi-, multi-specific therapeutics (Brinkmann and Kontermann (2017) MAbs 9: 182-212) or in CAR-T therapeutics (Gross et al., (1989), *Transplant Proc* 21(1 Pt 1): 127-130; Porter et al., (2011) *J Cancer* 2: 331-332; Porter et al., (2011) *N Engl J Med* 365: 725-733).

One of the challenges of scFv molecules is the low stability and tendencies to aggregate (reviewed in Worn and Pluckthun (2001) *J Mol Biol* 305: 989-1010; Rothlisberger et al., (2005) *J Mol Biol* 347: 773-789). A number of strategies have been attempted to improve their properties (Arnd et al., (2001) *J Mol Biol* 312: 221-228; Monsellier et al., (2006) *J Mol Biol* 362: 580-593; Zhao et al., (2010) *Int J Mol Sci* 12: 1-11; Perchiacca and Tessier (2012) *Annu Rev Chem Biomol Eng* 3: 263-286; Asial et al., (2013) *Nat Commmun* 4: 2901; Gil and Schrum (2013) *Adv Biosci Biteccchnol* 4: 73-84; Tiller and Tessier (2015) *Annu rev Biomed Eng* 17: 191-216) These strategies include introducing disulfide bonds between VL/VH domains, improving VL/VH domain stability and/or interface interactions using different experimental methods, using additional dimerization motifs and others. A key difficulty is that most of these strategies are often specific to the VH/VL pair and cannot be readily transferred to other VH/VL pairs. Sometimes, engineering may have negative impact on the VL/VH structure and the scFv property. Recently, Zhang et al. introduced a disulfide between position 44 of VH and position 100 of VL of a an anti-aflatoxin Bi scFv (H4) and successfully achieved significant stabilization of the scFv while preserving its binding affinity (Zhao et al., (2010) *Int J Mol Sci* 12: 1-11). However, because of the distance and angle restraints between the chosen two positions, the inter-VL/VH disulfide, if applied to other VL/VH pairs, may restrict/distort the relative orientation between the two domains, which is often required for binding.

The interface between the heavy and light chains of the Fab fragment comprises VH/VL and CH1/CL interactions. The two independent sets of interactions provide synergistic stabilization effects. In addition, the V/C junction also contributes some stabilization effects. In comparison, in a scFv the VH/VL interface is maintained by the VH/VL interactions only. The linker, being designed to be flexible and non-restrictive except in cases where the length is designed to be so short to promote inter-scFv interactions for dimer and oligomer formation, only loosely couples the two together. It is known that the length and nature of the linker, when long enough, contributes little to the stability of the scFv.

6.1.1 "Stapling" Design

The purpose of the work was to design and generate stabilized scFvs by restraining but not negatively impacting the relative movements between the VH and the VL forming the scFv. This was accomplished by stabilizing the scFv by engineering disulfide bonds between the VH and the linker and between the VL and the linker. The restraints (i.e., disulfide bonds), when properly positioned, would then play the role of the synergistic effects afforded by the CH1/CL and V/C interactions discussed above. To this end, two structurally conserved surface exposed framework positions (anchor points) were identified, one each on VH and VL, which were non-overlapping with the typical predicted antigen binding site, and mutated into cysteine (Cys) residues. Two positions were subsequently chosen in the flexible linker for Cys positions. When the distances and locations between the linker Cys residues were designed in a manner that facilitated formation of disulfide bonds between the linker Cys and each anchor point, the VH and the VL would be tethered more tightly together when compared to tethering in the absence of the disulfide bonds. This scheme is depicted in FIG. 1 with an exemplary linker containing CPPC sequence (SEQ ID NO: 1). The concept of forming disulfide bonds between the flexible linker and anchor points is herein referred to as "stapling". The resulting "stapled" scFv molecules are herein referred as spFv ("stapled Fv").

6.1.2 Choice of the Anchor Points, Design of Staple Sequences and Linkers

For the stapling scheme to be widely applicable, it is important that the anchor points be structurally conserved, exposed on surface of both VL and VH and whose mutation to Cys residue will not impact folding of VL and VH or binding to antigens. The distances and geometry of the anchor points and the N and C termini of the VL and VH domains are also important considerations for proper disulfide formation.

Figure 2:
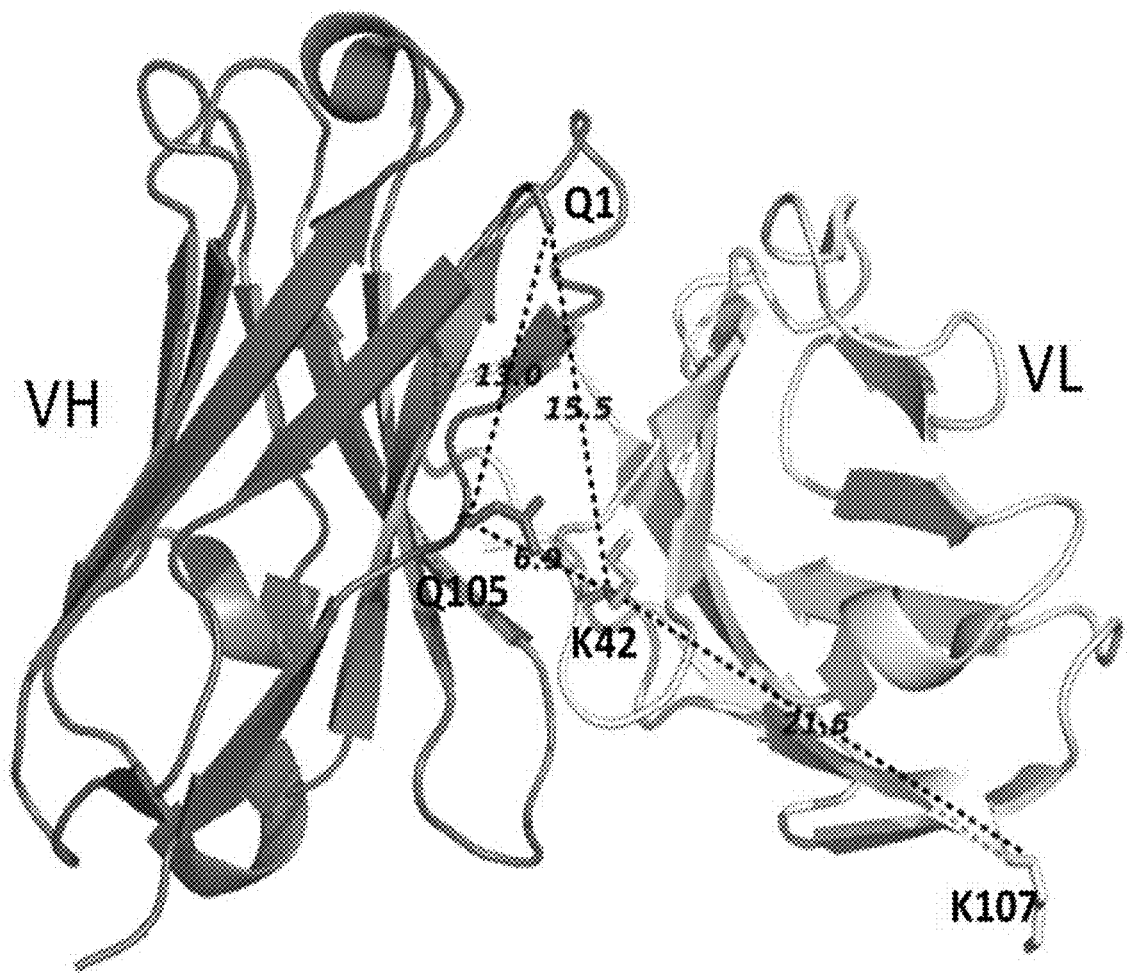
Figure 3:
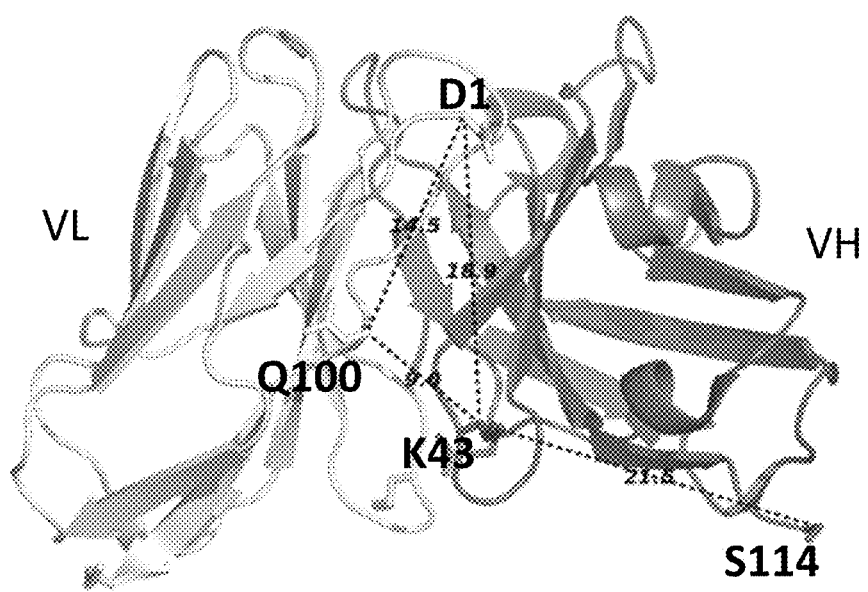

The anchor points were chosen separately for spFv in the VL-linker-VH and VH-linker-VL orientation. For the VL-linker-VH orientation, Chothia position 42 in the VL and Chothia position 105 in the VH were chosen as anchor points. A graphical illustration of the chosen anchor points for the spFv in the VL-linker-VH orientation is shown in FIG. 2 within the Fv of a human germline antibody (pdb ID 5119, GLk1 hereafter). In GLk1, VL Chothia position 42 is lysine (K) and VH Chothia position 105 glutamine (Q). For the VH-linker-VL orientation, Chothia position 100 in the VL and Chothia position 43 in the VH were chosen as anchor points. FIG. 3 shows the graphical illustration of the chosen anchor points for the spFv in the VH-linker-VL orientation within the Fv of a human germline antibody (pdb ID 5119, GLk1). In GLk1, VL Chothia position 100 is glutamine (Q) and VH Chothia position 43 is lysine (K). The chosen anchor points were structurally conserved, and the geometry was very similar in antibodies containing either kappa or lambda light chains. The distances between the pairs of the anchor points ranged from approximately 7 Å (for the VL-linker-VH orientation) to approximately 9 Å (for the VH-linker-VL orientation).

Figure 4:
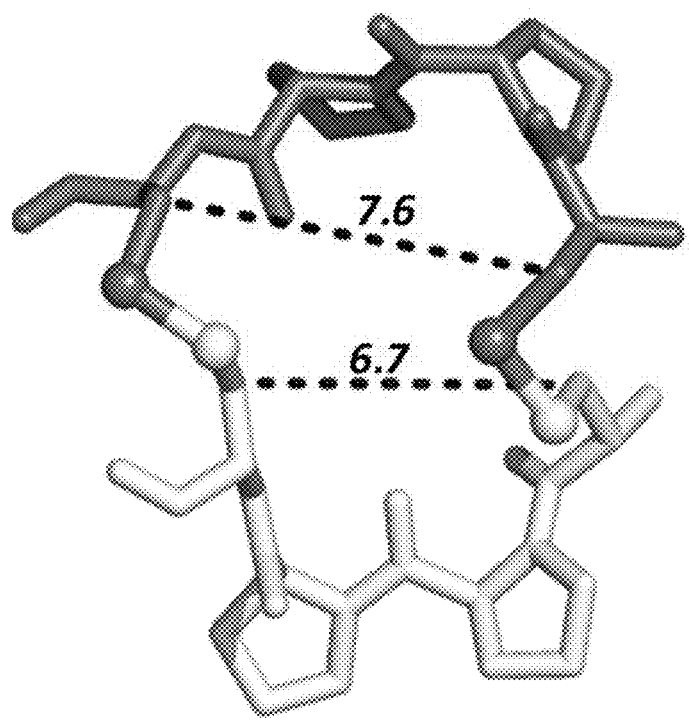
FIG. 4 shows a graphical illustration of Cβ(Cys1)-Cβ(Cys2) distance between the two Cys residues in the mouse two heavy chain IgG2a (pdb id 1igt) hinge CPPC (SEQ ID NO: 1). The distances are shown in Angstrom in the Figure.
Figure 5:
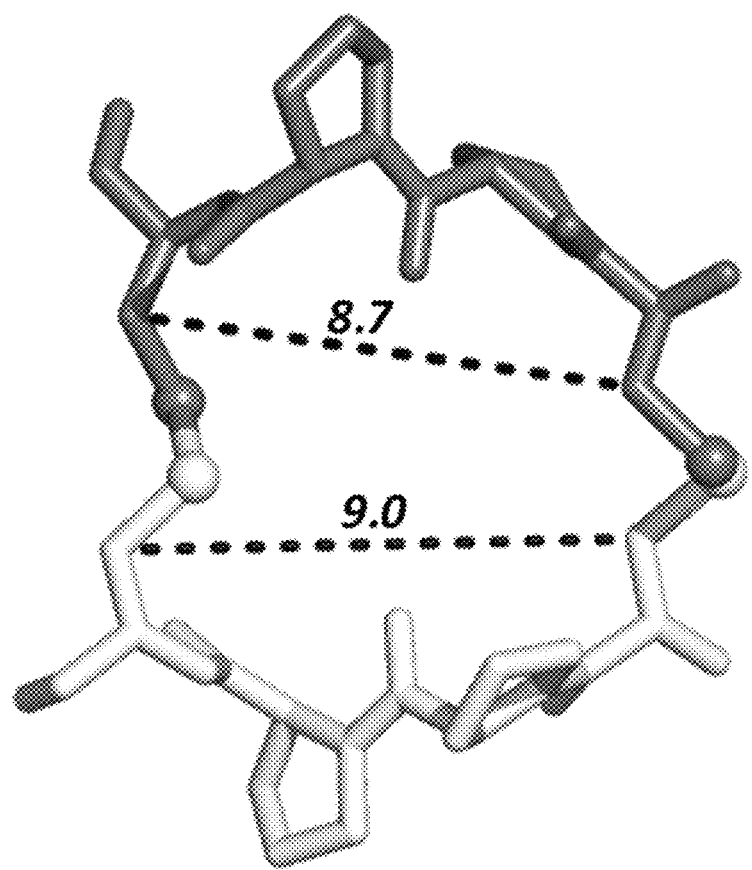
FIG. 5 shows a graphical illustration of Cβ(Cys1)-Cβ(Cys2) distance between the two Cys residues in the two heavy chains of human IgG (pdb id 5dk3) hinge CPPC (SEQ ID NO: 1). The distances are shown in Angstrom in the Figure.

The staple sequences embedded within the linker connecting the VH and the VL were designed to be of similar length with the distances between the anchor points in the spFv. As an initial example of the staple sequence, CPPC (SEQ ID NO: 1) was chosen as a possible staple sequence, partly because this sequence occurs natively in human IgG1 hinge as well as in some rodent IgGs. The structures of the hinges of human and mouse IgG molecules demonstrated that the Cβ(cys1)-Cβ(cys2) distances in a mouse IgG hinge (FIG. 4) and a human IgG (FIG. 5) ranged from about 7 Å to 9 Å. As this range was very similar to the distances between the two anchor points in both VL-linker-VH and VH-linker-VL orientations, the CPPC (SEQ ID NO: 1) staple sequence had the potential to provide correct geometry for stapling, i.e., forming proper disulfide bonds efficiently and correctly to the anchor points. In general, the staple sequences were designed to have two Cys residues. For proper stapling, the N-terminal Cys of the staple sequence formed disulfide bond with the spFv N-terminal domain anchor point and the C-terminal Cys of the staple sequence formed a disulfide bond with the spFv C-terminal domain anchor point.

The linker connecting the VH and the VL was thus designed to comprises the staple sequence and connecting sequences both N-terminal and C-terminal to the staple sequence to extend the linker to provide sufficient linker length to allow intrachain folding of the VH and the VL and to facilitate proper positioning of the staple sequence.

In the VL-linker-VH design, the distances between the VL anchor point (K42), VH anchor point (Q105), C-terminus of the VL (K107) and the N-terminus of the VH (Q1) are shown in FIG. 2. In the VH-linker-VL design, the distances between the VL anchor point (Q100), the VH anchor point (K43), the C-terminus of the VH (S114) and the N-terminus of the VL (D1) are shown in FIG. 3. Modeling suggested that these distances can be spanned by linker lengths of about 14-19 residues, in which the staple sequence of 4 residues is flanked by a N-terminal linker extension of about 6-9 residues and a C-terminal linker extension of about 4-6 residues. The designed linker length could thus be expressed as n+4+m, in which n=6-9 residues and m=4-6 residues, and 4 indicates the length of the CPPC (SEQ ID NO: 1) staple sequence. The n and m residues could be glycine or serine, or other amino acid residues. These linker lengths are expected to be long and flexible enough to allow stapling but too short to allow scrambling.

6.2 Example 2: Generation and Characterization of spFvs

In order to assess the stapling designs, three human antibodies were chosen to generate scFv and corresponding spFvs: two antibodies with kappa light chains (GLk1 and GLk2) from the synthetic phage antibody libraries (Shi et al., (2010) *J Mol Biol* 397:385-396) and a lambda-containing antibody (CAT2200) obtained from a publication (Gerhardt et al. (2009) *J Mol Biol* 394:905-921). For CAT2200, a T28G mutation was introduced in the parental VH to generate a variant (CAT2200a) to reduce some of its interactions with its target, IL-17. In addition, a S42Q mutation (Chothia) was engineered into the parental CAT2200 VL and paired with the T28G VH to generate CAT2200b. The amino acid sequences of the VL and the VH domains of GLk1, GLk2, CAT2200a and CAT2200b are shown in FIG. 6 and FIG. 7, respectively. The VH domain amino acid sequence is identical between BAT2200a and CAT2200b. GLk1VH is closest to human IGHV2-23*01 GLk2VH to human IGHV5-51, CAT2200VH to human IGHV2-23*01. GLk1VL is closest human IGKV1-39*01, GLk2VL to human IGKV3-20*01, and CAT2200VL to human IGLV6-57*01.

All scFv and spFv molecules were generated and expressed in both VL-linker-VH and VH-linker-VL orientations. For the scFv constructs, a standard (GGGGS)$_4$ (SEQ ID NO; 2) linker was used. For the spFv, different linker lengths within the n and m ranges above were used. For GLk1 spFv, 9-4-5 linkers were used for both orientations. For GLk2 spFv, the 9-4-5 and 6-4-6 linker lengths were used for the VL-VH and VH-VL orientations, respectively. For CAT2200a spFv, VL-VH molecules were made with the 8-4-4 and 9-4-4 linkers, respectively, and CAT2200b spFv VH-VL was made with the 9-4-4 linker. Table 4 shows the generated molecules and their linker sequences. Table 5 shows the amino acid sequences or the generated molecules.

TABLE 4

| Molecule name (SEQ ID NO:) | Linker type | Linker amino acid sequence | Linker SEQ ID NO: |
|---|---|---|---|
| GLk1 scFv VL-VH (8) | 4x G4S | GGGGSGGGGS GGGGSGGGGS | 2 |
| GLk1 spFv VL-VH (9) | 9 + 4 + 5 | GGGSGGSGGC PPCGGSGG | 3 |
| GLk1 scFv VH-VL (10) | 4x G4S | GGGGSGGGGS GGGGSGGGGS | 2 |
| GLk1 spFv VH-VL (11) | 9 + 4 + 5 | GGGSGGSGGC PPCGGSGG | 3 |
| GLk2 scFv VL-VH (12) | 4x G4S | GGGGSGGGGS GGGGSGGGGS | 2 |
| GLk2 spFv VL-VH (13) | 9 + 4 + 5 | GGGSGGSGGC PPCGGSGG | 3 |
| GLk2 scFv VH-VL (14) | 4x G4S | GGGGSGGGGS GGGGSGGGGS | 2 |
| GLk2 spFv VH-VL (15) | 6 + 4 + 6 | GGGSGGCPPC GGGSGG | 4 |
| CAT2200a scFv VL-VH (16) | 4x G4S | GGGGSGGGGS GGGGSGGGGS | 2 |
| CAT2200a spFv VL-VH (17) | 8 + 4 + 4 | GGSGGSGGCP PCGSGG | 5 |
| CAT2200b scFv VL-VH (18) | 4x G4S | GGGGSGGGGS GGGGSGGGGS | 2 |
| CAT2200a spFv VL-VH (19) | 9 + 4 + 4 | GGGSGGSGGC PPCGSGG | 6 |
| CAT2200a scFv VH-VL (20) | 4x G4S | GGGGSGGGGS GGGGSGGGGS | 2 |
| CAT2200b spFv VH-VL (21) | 9 + 4 + 4v2 | GGGSGGGSGC PPCGGGG | 7 |

TABLE 5

| Molecule name | Protein sequence | SEQ ID NO: |
|---|---|---|
| GLk1 scFv VL-VH | DIQMTQSPSSLSASVGDRVTITCRASQSISSYLNWYQQKPGK APKLLIYAASSLQSGVPSRFSGSGSGTDFTLTISSLQPEDFAT YYCQQSYSTPLTFGQGTKVEIKRGGGGSGGGGSGGGGSGG GGSEVQLLESGGGLVQPGGSLRLSCAASGFTFSSYAMSWVR QAPGKGLEWVSAISGSGGSTYYADSVKGRFTISRDNSKNTL YLQMNSLRAEDTAVYYCAKYDGIYGELDFWGQGTLVTVSS GHHHHHH | 8 |

TABLE 5-continued

| Molecule name | Protein sequence | SEQ ID NO: |
|---|---|---|
| GLk1 spFv VL-VH | DIQMTQSPSSLSASVGDRVTITCRASQSISSYLNWYQQKPGC APKLLIYAASSLQSGVPSRFSGSGSGTDFTLTISSLQPEDFAT YYCQQSYSTPLTFGQGTKVEIKRGGGSGGSGGCPPCGGSGG EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKYDGIYGELDFWGCGTLVTVSSGHH HHHH | 9 |
| GLk1 scFv VH-VL | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKYDGIYGELDFWGQGTLVTVSSAGG GGSGGGGSGGGGSGGGGSDIQMTQSPSSLSASVGDRVTITC RASQSISSYLNWYQQKPGKAPKLLIYAASSLQSGVPSRFSGS GSGTDFTLTISSLQPEDFATYYCQQSYSTPLTFGQGTKVEIKR GHHHHHH | 10 |
| GLk1 spFv VH-VL | EVQLLESGGGLVQPGGSLRLSCAASGFTFSSYAMSWVRQAP GCGLEWVSAISGSGGSTYYADSVKGRFTISRDNSKNTLYLQ MNSLRAEDTAVYYCAKYDGIYGELDFWGQGTLVTVSSGGG SGGSGGCPPCGGSGGDIQMTQSPSSLSASVGDRVTITCRASQ SISSYLNWYQQKPGKAPKLLIYAASSLQSGVPSRFSGSGSGT DFTLTISSLQPEDFATYYCQQSYSTPLTFGCGTKVEIKRGHH HHHH | 11 |
| GLk2 scFv VL-VH | EIVLTQSPGTLSLSPGERATLSCRASQSVSSSYLAWYQQKPG QAPRLLIYGASSRATGIPDRFSGSGSGTDFTLTISRLEPEDFA VYYCQQDYGFPWTFGQGTKVEIKGGGGSGGGGSGGGGSG GGGSEVQLVQSGAEVKKPGESLKISCKGSGYSFTSYWISWV RQMPGKGLEWMGIIDPSDSDTRYSPSFQGQVTISADKSISTA YLQWSSLKASDTAMYYCARGDGSTDLDYWGQGTLVTVSS GHHHHHH | 12 |
| GLk2 spFv VL-VH | EIVLTQSPGTLSLSPGERATLSCRASQSVSSSYLAWYQQKPG CAPRLLIYGASSRATGIPDRFSGSGSGTDFTLTISRLEPEDFAV YYCQQDYGFPWTFGQGTKVEIKGGGSGGGSGGCPPCGGSGG EVQLVQSGAEVKKPGESLKISCKGSGYSFTSYWISWVRQMP GKGLEWMGIIDPSDSDTRYSPSFQGQVTISADKSISTAYLQW SSLKASDTAMYYCARGDGSTDLDYWGCGTLVTVSSGHHH HHH | 13 |
| GLk2 scFv VH-VL | EVQLVQSGAEVKKPGESLKISCKGSGYSFTSYWISWVRQMP GKGLEWMGIIDPSDSDTRYSPSFQGQVTISADKSISTAYLQW SSLKASDTAMYYCARGDGSTDLDYWGQGTLVTVSSGGGGS GGGGSGGGGSGGGGSEIVLTQSPGTLSLSPGERATLSCRASQ SVSSSYLAWYQQKPGQAPRLLIYGASSRATGIPDRFSGSGSG TDFTLTISRLEPEDFAVYYCQQDYGFPWTFGQGTKVEIKGH HHHHH | 14 |
| GLk2 spFv VH-VL | EVQLVQSGAEVKKPGESLKISCKGSGYSFTSYWISWVRQMP GCGLEWMGIIDPSDSDTRYSPSFQGQVTISADKSISTAYLQW SSLKASDTAMYYCARGDGSTDLDYWGQGTLVTVSSGGGSG GCPPCGGSGGEIVLTQSPGTLSLSPGERATLSCRASQSVSSS YLAWYQQKPGQAPRLLIYGASSRATGIPDRFSGSGSGTDFTL TISRLEPEDFAVYYCQQDYGFPWTFGCGTKVEIKGHHHHHH | 15 |
| CAT2200a scFv VL-VH | NFMLTQPHSVSESPGKTVTISCTRSSGSLANYYVQWYQQRP GSSPTIVIFANNQRPSGVPDRFSGSIDSSSNSASLTISGLKTED EADYYCQTYDPYSVVFGGGTKLTVLGGGGSGGGGSGGGGS GGGGSEVQLLESGGGLVQPGGSLRLSCAASGFGFSSYAMS WVRQAPGKGLEWVSAISGSGGSTYYADSVKGRFTISRDNSK NTLYLQMNSLRAEDTAVYYCARDLIHGVTRNWGQGTLVT VSSGHHHHHH | 16 |
| CAT2200a spFv VL-VH | NFMLTQPHSVSESPGKTVTISCTRSSGSLANYYVQWYQQRP GCSPTIVIFANNQRPSGVPDRFSGSIDSSSNSASLTISGLKTED EADYYCQTYDPYSVVFGGGTKLTVLGGSGGGSGGCPCGSG GEVQLLESGGGLVQPGGSLRLSCAASGFGFSSYAMSWVRQ APGKGLEWVSAISGSGGSTYYADSVKGRFTISRDNSKNTLY LQMNSLRAEDTAVYYCARDLIHGVTRNWGCGTLVTVSSGH HHHH | 17 |

TABLE 5-continued

| Molecule name | Protein sequence | SEQ ID NO: |
|---|---|---|
| CAT2200b scFv VL-VH | NFMLTQPHSVSESPGKTVTISCTRSSGSLANYYVQWYQQRP GQSPTIVIFANNQRPSGVPDRFSGSIDSSSNSASLTISGLKTED EADYYCQTYDPYSVVFGGGTKLTVLGGGGSGGGGSGGGGS GGGGSEVQLLESGGGLVQPGGSLRLSCAASGFGFSSYAMS WVRQAPGKGLEWVSAISGSGGSTYYADSVKGRFTISRDNSK NTLYLQMNSLRAEDTAVYYCARDLIHGVTRNWGQGTLVT VSSGHHHHHH | 18 |
| CAT2200a spFv VL-VH | NFMLTQPHSVSESPGKTVTISCTRSSGSLANYYVQWYQQRP GCSPTIVIFANNQRPSGVPDRFSGSIDSSSNSASLTISGLKTED EADYYCQTYDPYSVVFGGGTKLTVLGGGSGGSGGCPPCGS GGEVQLLESGGGLVQPGGSLRLSCAASGFGFSSYAMSWVR QAPGKGLEWVSAISGSGGSTYYADSVKGRFTISRDNSKNTL YLQMNSLRAEDTAVYYCARDLIHGVTRNWGCGTLVTVSSG HHHHHH | 19 |
| CAT2200a scFv VH-VL | EVQLLESGGGLVQPGGSLRLSCAASGFGFSSYAMSWVRQAP GKGLEWVSAISGSGGSTYYADSVKGRFTISRDNSKNTLYLQ MNSLRAEDTAVYYCARDLIHGVTRNWGQGTLVTVSSGGG GSGGGGSGGGGSGGGGSNFMLTQPHSVSESPGKTVTISCTR SSGSLANYYVQWYQQRPGSSPTIVIFANNQRPSGVPDRFSGS IDSSSNSASLTISGLKTEDEADYYCQTYDPYSVVFGGGTKLT VLGHHHHHH | 20 |
| CAT2200b spFv VH-VL | EVQLLESGGGLVQPGGSLRLSCAASGFGFSSYAMSWVRQAP GCGLEWVSAISGSGGSTYYADSVKGRFTISRDNSKNTLYLQ MNSLRAEDTAVYYCARDLIHGVTRNWGQGTLVTVSSGGGS GGGSGCPPCGGGGNFMLTQPHSVSESPGKTVTISCTRSSGSL ANYYVQWYQQRPGQSPTIVIFANNQRPSGVPDRFSGSIDSSS NSASLTISGLKTEDEADYYCQTYDPYSVVFGCGTKLTVLGH HHHHH | 21 |

All scFv and spFv molecules except CAT2200a scFv VL-VH were cloned into a CMV promoter driven mammalian expression vector. These constructs were transfected into Expi293 cells using manufacturer protocols and cells were cultured for 5 days. Each Protein was purified from the clarified supernatant on 1 ml His-TRAP HP columns (GE Healthcare) via an AKTAXPRESS system (GE Healthcare). The column was prepared with a gradient of 0-100% Elution Buffer (Wash Buffer: 50 mM Tris, pH 7.5, 500 mM NaCl, 20 mM Imidazole; Elution Buffer: 50 mM Tris, pH 7.5, 500 mM NaCl, 500 mM Imidazole) to remove loosely bound nickel and then re-equilibration in DPBS. The cleared supernatant was first adjusted to 50 mM Tris, pH 7.5 and 20 mM imidazole and then loaded over 1 mL HisTRAP HP column at 4° C. 0.8 mL/min. The column was then washed with PBS until stable baseline was obtained. Then the column was further washed with 20 CV of Wash Buffer, eluted with Elution buffer into a single injection loop and desalted in 1×DPBS over 26/10 HiPrep Desalting Column and fractions collected. Fractions containing the purified protein were then pooled and concentrated. The Glk2 scFv and spFv proteins were dialyzed into DPBS for thermal stability measurements (DSC and NanoDSF) and 25 mM Tris, pH 7.5 and 100 mM NaCl for other studies. The other scFv and spFv proteins were dialyzed in 25 mM IVIES, pH 6.0 and 100 mM NaCl.

CAT2200a scFv VL-VH was purchased from a vendor. Concentration was 0.77 mg/mL in DPBS, pH 7.2. A mutant of IL-17 (12-132 with K70Q A132Q C106S mutations, IL-17 hereafter for simplicity (SEQ ID NO: 22) was purchased from Accelagen (CA). The protein was refolded from E. coli inclusion body following their proprietary refolding protocol and provided at 1.50 mg/mL in 20 mM NaCl, 20 mM IVIES, pH 6.0.

(IL-17A mutant)
SEQ ID NO: 22
MNSEDKNFPRTVMVNLNIHNRNTNTNPKRSSDYYNRSTSPWNLHRNEDPER

YPSVIWEAQCRHLGCINADGNVDYHMNSVPIQQEILVLRREPPHSPNSFRL

EKILVSVGCTCVTPIVHHVQ 6.2.1 Thermal Stability of the Generated scFv and spFv Molecules The thermal stability of the scFv and spFv molecules was investigated by differential thermal calorimetry (DSC). The scFv and spFv proteins were dialyzed overnight against 1×DPBS (Gibco) for GLk1 and CAT2200a/CAT2200b or MES (25 mM IVIES, pH 6.0, 100 mM NaCl) for GLk2. Dialysis buffer was then 0.22 micron filtered and used as the reference solution and for buffer-buffer blanks in the DSC experiment. Proteins were diluted to ~0.5 mg/mL in the filtered buffer and 400 µL of each protein or buffer sample was loaded into a 96-deepwell plate (MicroLiter Analytical Supplies, 07-2100) and kept at 4° C. in the autosampler drawer over the course of the experiment. A MicroCal Capillary DSC with Autosampler (Malvern) was used to perform the DSC experiments. DSC scans were performed from 25-95° C. at a 60° C./h scan rate with no sample rescans. No feedback was selected and the filtering period was set at 15 s. After each sample, cells were cleaned with a 10% Contrad-70 solution and a buffer-buffer blank was run. Data analysis was performed using Origin 7.0 with the MicroCal VP-Capillary DSC Automated Analysis add-on (Malvern). The baseline range and type were manually chosen and then subtracted. The previous buffer blank was subtracted from the sample curve followed by concentration-dependent normalization. The thermal melting profiles were analyzed using both 2-state and non-2-state transitions. Two-state fits (one transition) agreed poorly with the experimental curves. Thus, with two transitions (Tm1 and Tm2) were calculated by manually performing non-2-state fits. The Tm data are reported in Table 6. The DSC profiles of all scFv and spFv proteins exhibited a skewness that could only be fitted with non-2-state transitions. Thus, for each scFv or spFv, two transitions (Tm1 and Tm2) were reported (Table 6). Most likely, these two transitions correspond to the melting Tm of the VL and VH domains, respectively. In general, upon comparison, the differences between scFv and spFv for either Tm1 or Tm2, there is a roughly 10° C. increase by stapling, regardless of the Tm of the starting scFv. There is only one exception, i.e., the case of GLk2 scFv and spFv (VH-VL orientation) difference, at ~7° C. This is likely due to the shorter 6+4+6 linker which may have caused slight strain in the stapling geometry. The fact that ΔTm1 (VL) and ΔTm2 (VH) were nearly identical suggests that stapling lead to stabilization of the domains themselves in addition to strengthening the VL/VH interactions. Alternatively, stronger VH/VL interactions transmits the stabilization effects into stabilization of the VL/VH domains. In summary, stapling as described in this work significantly increases the stability of scFv.

TABLE 6

| Molecule name (SEQ ID NO:) | Linker type | DSC Stability | | | | | | |
|---|---|---|---|---|---|---|---|---|
| | | Tm1 (° C.) | SD(Tm1) (° C.) | Tm2 (° C.) | SD(Tm2) (° C.) | ΔTm1 (° C.) | ΔTm2 (° C.) | Δ(Tm − Tm2) |
| GLk1 scFv VL-VH (8) | 4x G4S | 68.9 | 0.2 | 72.1 | 0.0 | 9.7 | 9.0 | 3.3 |
| GLk1 spFv VL-VH (9) | 9 + 4 + 5 | 78.5 | 0.2 | 81.1 | 0.0 | | | 2.6 |
| GLk1 scFv VH-VL (10) | 4x G4S | 67.7 | 0.3 | 70.9 | 0.0 | 10.0 | 9.2 | 3.3 |
| GLk1 spFv VH-VL (11) | 9 + 4 + 5 | 77.7 | 0.2 | 80.1 | 0.1 | | | 2.4 |
| GLk2 scFv VL-VH (12) | 4x G4S | 56.6 | 0.2 | 58.6 | 0.1 | 10.9 | 10.5 | 2.0 |
| GLk2 spFv VL-VH (13) | 9 + 4 + 5 | 67.6 | 0.3 | 69.2 | 0.1 | | | 1.6 |
| GLk2 scFv VH-VL (14) | 4x G4S | 56.4 | 0.1 | 58.3 | 0.1 | 7.3 | 7.1 | 1.9 |
| GLk2 spFv VH-VL (15) | 6 + 4 + 6 | 63.7 | 0.3 | 65.4 | 0.1 | | | 1.7 |
| CAT2200a scFv VL-VH (16) | 4x G4S | | | | | | | |
| CAT2200a spFv VL-VH (17) | 8 + 4 + 4 | | | | | | | |
| CAT2200b scFv VL-VH (18) | 4x G4S | 54.7 | 0.3 | 57.6 | 0.0 | 12.0 | 11.7 | 2.9 |
| CAT2200a spFv VL-VH (19) | 9 + 4 + 4 | 66.7 | 0.3 | 69.3 | 0.0 | | | 2.6 |
| CAT2200a scFv VH-VL (20) | 4x G4S | 52.6 | 0.3 | 56.4 | 0.0 | 12.9 | 11.4 | 3.8 |
| CAT2200b spFv VH-VL (21) | 9 + 4 + 4 | 65.5 | 0.3 | 67.9 | 0.0 | | | 2.4 |

ΔTm1 (° C.): Difference in Tm1 (spFv) and Tm1 (scFv)
ΔTm2 (° C.): Difference in Tm2 (spFv) and Tm2 (scFv)
Δ(Tm1 − Tm2): Difference of Tm2 and Tm1 of an scFv or spFv CAT2200 spFvs were tested for their binding to IL-17. The binding was comparable when compared to the CAT2200 scFvs.

6.3 Example 3: Verification of Correct Stapling by Crystallization of Generated scFv and spFv Molecules Proteins were concentrated in their respective buffers: GLk1 spFv VL-VH to 8.67 mg/ml in 25 mM MES, pH 6.0, 100 mM NaCl; GLk1 spFv VH-VL to 5 mg/ml in 25 mM MES, pH 6.0, 100 mM NaCl; GLk2 spFv VH-VL to 8.66 mg/ml in 25 mM Tris, pH7.5, 100 mM NaCl; cat2200b spFv VH-VL to 25 mM MES, pH 6.0, 100 mM NaCl. Crystallization was set up for each protein in sitting drop format in Corning 3550 crystal trays using a Mosquito robot. Each well contains 100 nl of protein and 100 nl of reservoir solution and incubated against 70 µl of reservoir at 20° C. The reservoir solutions are IH1 and IH2 custom conditions as well as PEG Ion Screen HT (Hampton Research). Some initial conditions were refined by varying reservoir components in optimization attempts. Diffraction quality crystals were obtained for some of scFv and spFv proteins. Table 7 shows the summary of the conditions used. Crystals were soaked for a few seconds in the mother liquor supplemented with 20% glycerol and flash frozen in liquid N2. X-ray data were collected at IMCA-CAT Beamline 17ID at Argonne National Lab.

TABLE 7

| Molecule name | Protein | crystallization Condition | Disulfides? | Resolution (Å) |
|---|---|---|---|---|
| GLk1 spFv VL-VH | 8.67 mg/mL, 25 mM MES, pH 6.0, 100 mM NaCl | 0.1M Na Acet 4.5 pH, 18% w/v PEG 3350, 1M LiCl | yes | 1.65 |

TABLE 7-continued

| Molecule name | Protein | crystallization Condition | Disulfides? | Resolution (Å) |
|---|---|---|---|---|
| Glk1 spFv VH-VL | 5 mg/mL, 25 mM MES, pH 6.0, 100 mM NaCl | 0.1M MES 6.5 pH, 5% v/v PEG 400, 0.75M (NH4)2SO4 | yes | 2.10 |
| GLk2 spFv VH-VL | 8.66 mg/mL, 25 mM Tris, pH 7.5, 100 mM NaCl | 0.1M Na Acet 4.5 pH, 0.75M (NH4)2SO4 | yes | 1.50 |
| CAT2200b spFv VH-VL | 4.91 mg/mL, 25 mM MES, pH 6.0 100 mM NaCl | 0.1M Na Acet 4.5 pH, 1.5M (NH4)2SO4 | yes | 2.40 |
| CAT2200a scFv VL-VH/IL-17 complex | 2.69 mg/mL, 20 mM HEPES, pH 7.5, 50 mM NaCl | 0.1M Tris, pH 8.5, 18% PEG3K, 0.2M LiSO4 | non-stapled | 2.30 |
| CAT2200a spFv VL-VH/IL-17 complex | 6.0 mg/ml, 20 mM HEPES, pH 7.5, 50 mM NaCl | 15.5% PEG 3350, 0.4M NaH2PO4 | yes | 2.00 |

6.3.1 Crystallization of CAT2200a scFv VL-VH and CAT2200a spFv VL-VII in Complex with IL-17

The IL-17/CAT2200a scFv VL-VH complex was generated by mixing 333 μL of IL17 (SEQ ID NO: 22) (1.5 mg/ml) with 1.74 ml of Cat2200a scFv (0.69 mg/mL) and incubating for 3 hours at 4° C. The mixture was concentrated with 10 kDa cutoff Amicon Ultra concentrator to about 400 μL and loaded onto a Superdex75 column equilibrated in 250 mM NaCl, 20 mM HEPES, pH 7.5. The fractions corresponding to the complex were pooled and concentrated to a volume of 150 μL. The sample was diluted and concentrated 4 times: addition of 350 μL 50 mM NaCl, 20 mM HEPES, pH 7.5 and concentration to just under 150 μL. The volume was brought to ~105 μL and concentration determined to be 2.69 mg/mL. Crystallization was set up in a sitting drop format using a Mosquito crystallization robot with 150 nL protein+150 nL reservoir in Corning3550 plates against 80 μL reservoir, which is a set of buffer and precipitant conditions pre-formulated in-house. The plates were incubated at 20° C. One of conditions (Na Acetate, pH 4.5, 25% PEG 3K, 0.2M Am Acetate) produced very small crystals. These were harvested and turned into crystallization seeds using Hampton Seed Bead in 100 μL 27% PEG 3350, 200 mM ammonium acetate, 100 mM sodium acetate, pH 4.5 in a Hampton Seed Bead tube.

Diffraction quality crystals were obtained by the same procedure except with the addition of the seeds above: 150 nL protein+100 nL reservoir+50 μL seeds. Crystals grew from 0.1 M Tris 8.5, 18% PEG3K, 0.2M LiSO4 and were transferred to a synthetic mother liquor (0.1 M Tris, pH 8.5, 10% PEG 3350, 0.2 M LiSO4 and 20% glycerol) and flash frozen in liquid nitrogen. X-ray diffraction data were collected at IMCA-CAT ID17 at Argonne National Laboratory.

The IL-17/CAT2200a spFv VL-VH complex were generated by mixing 167 μl of IL-17 (250 μg) with 154 μl MSCW274 (467 μg in 250 mM NaCl, 20 mM IVIES, pH 6.5) and incubating at 4° C. overnight. The mixture was concentrated in a 10 kDa MWCO Amicon Ultra 0.5 mL concentrator to ~100 μL, then repeatedly diluted and concentrated 5 times: concentrate to ~150 μL and added 350 μL 50 mM NaCl, 20 mM HEPES, pH 7.5. The final volume was 100 μL and the concentration of the complex was determined to be 6.0 mg/ml. Crystallization was set up similarly as for scFv/IL-17 complex in sitting drops using the Mosquito robot. The sitting drop are composed of 150 nL protein+120 nL reservoir+30 nL seeds (scFv/IL-17 above). The reservoir solution were a set of conditions varying PEG 3350 concentration and salts. The crystallization plates were incubated at 20° C. Small crystals were obtained from 15.5% PEG 3350, 0.4 M NaH2PO4. Crystals were transferred into 16% PEG 3350, 0.2 M NaH2PO4, 20% Glycerol, and flash frozen LN2. X-ray diffraction data were collected at IMCA-CAT ID17 at Argonne National Laboratory.

All X-ray diffraction data were processed with XDS (Kabsch et al. (2010) *Acta Crystallogr D Biol Crystallogr* 66(Pt. 2):125-132; Monsellier and Bedouelle (2006) *J Mol Biol* 362:580-593) and CCP4 (Collaborative Computational Project, N. (1994) *Acta Crystallogr D Biol Crystallogr* 53:240-255). All crystal structures were solved by molecular replacement (MR) using Phaser (Read (2001) *Acta Crystallogr D Biol Crystallogr* 57(Pt 10):1373-1382) with homology models generated in MOE (Montreal, Canada) except for scFv CAT2200a scFv VL-VH/IL-17 complex, for which the structure of pdb id 2vxs (Gerhardt et al. (2009) *J Mol Biol* 394:905-921) was used as search models. The structural models were refined in PHENIX (Adams et al. (2004) *J Synchrotron Radiat* 11(Pt 1):53-55) and manually adjusted in Coot (Emsley et al. (2010) *Acta Crystallogr D Biol Crystallogr* 66(Pt 4):486-501). Molecular graphics figures were generated in PyMol (www_schrodinger_com).

6.3.2 The Structures

The structures of the unbound scFv and spFv molecules are shown in FIG. 8, FIG. 9, FIG. 10 and FIG. 11. FIG. 8 shows the structure of GLk1 spFv VL-VH. FIG. 9 shows the structure of GLk1 spFv VH-VL. FIG. 10 shows the structure of GLk2 spFv VH-VL. FIG. 11 shows the structure of CAT2200b spFv VH-VL. The structures were consistent with the typical Fv structures with both VL and VH domains packing against each other. In general, most of the linker residues were ordered and resolved in the electron density maps. The disulfide bonds between the staple and the anchor points were generally well ordered in both VL-VH orientations. In addition to the unbound scFv and spFv structures, we also attempted to reveal any structural impact on antigen binding. CAT2200 scFv and spFv variant molecules were crystallized in complex with its cognate target, IL-17. For the scFv and spFv of CAT2200 variants crystallized, the structures were nearly identical with and without a bound target (FIG. 12, FIG. 13, FIG. 14). FIG. 12 shows the comparison of the unbound CAT2200b spFv VH-VL compared with CAT2200a scFv VL-VH bound to IL-17. FIG. 13 shows the comparison of the front views of the structures of unbound CAT2200b spFv VH-VL compared with CAT2200a spFv VL-VH bound to IL-17. FIG. 14 shows the comparison of the back views of the structures of unbound CAT2200b spFv VH-VL compared with CAT2200a spFv VL-VH bound to IL-17. The structures were also identical regardless of orientation or presence or absence of the staple. The rmsd for all matching Ca atoms between pairs of structures were very small: 0.41 Å between unbound spFv- VH-VL and antigen-bound scFv-VL-VH (FIG. 12), 0.46 Å between unbound spFv-VH-VL and spFv-VL-VH (FIG. 13 and FIG. 14, respectively), and 0.37 Å between bound scFv and bound spFv. The structural evidence shows that the stapling works as designed. Also, stapling does not impact the domain structures of VL and VH or relative VL/VH packing.

6.4 Example 4: Design of Additional Anchor Points

The approach described in Example 1 was used to identify any additional anchor points for stapling. The following anchor points were identified:

For VL-linker-VH orientation: VL Chothia position 42, 45 and 39 and VH Chothia positions 105, 5 and 3. In FIG. 6, the VL residues on GLk1VL are K42, K45, K39 and the VH residues on GLk1 are Q105, L5 and Q3. The staple forms between any of the positions indicated.

For VH-linker-VL orientation: VH Chothia positions 43, 40 and 46, VL Chothia positions 102, 5 and 3, the staple forms between any of the positions.

The spFvs having the anchor points described in this Example are cloned, expressed and tested for the formation of the staple and their thermostability using assays described herein and in Example 2.

6.5 Example 5: Half-Stapling

Constructs are generated and expressed containing one staple, either between the VH and the linker or between the VL and the linker. The generated constructs are expressed, purified and analyzed using methods described herein.

6.6 Example 6: Multispecific Constructs Comprising spFvs

Exemplary multispecific binding molecules incorporating the spFv structures provided herein were constructed and tested in this example. Specifically, bispecific antibodies and control molecules, derived from the target binding sequences shown in Table 8, were transiently expressed in CHO suspension cultures in serum-free/animal component-free media, and purified by protein A affinity chromatography, followed by preparative size exclusion chromatography (SEC) on a SUPERDEX 200 10/300 GL column (GE Healthcare) using a ÄKTA PURE instrument (GE Healthcare). Heavy chains contained knob-into-hole (KiH) mutations to promote heterodimerization (Ridgway et al., *Protein Eng.* 9(7):617-21 (1996); Atwell et al., *J. Mol. Biol.* 270(1): 26-35 (1997); Merchant et al., *Nat. Biotechnol.* 16(7):677-81 (1998)). Antibodies contained the IgG1sigma Fc comprising a set of seven Fc mutations—L234A, L235A, G237A, P238S, H268A, A330S, and P331S—when compared to the wild type IgG1 to reduce Fc receptor interactions (Tam et al., *Antibodies* (2017)).

Bispecific antibodies were generated with IgG1sigma mutations and with KiH mutations.

TABLE 8

Target binding sequences used for the constructs of Example 6.

| Antibody/Ligand designation | Target/receptor | VH or Chain 1 | VL or Chain 2 |
|---|---|---|---|
| LTBRmAb1 (BHA10) | human LTBR | WO2004002431/ SEQ ID NO: 69 | WO2004002431/ SEQ ID NO: 70 |
| EDBmAb1* (L19) | human extra-domain B (EDB) of fibronectin | WO9745544/ SEQ ID NO: 71 | WO9745544/ SEQ ID NO: 72 |
| B21M | RSV | Vafa O et al. (2014) Methods 65(1)/ SEQ ID NO: 73 | Vafa O et al. (2014) Methods 65(1)/ SEQ ID NO: 74 |
| MSLNmAb1 | human mesothelin | EP2322560/ SEQ ID NO: 75 | EP2322560/ SEQ ID NO: 76 |

*EDBmAb1(WO9745544) used here is an anti-ED-B antibody that has been tested in the clinic, other antibodies binding to ED-B or to adjacent domains have been described previously (Carnemolla et al. *Int. J. Cancer* 68: 397-405 (1996))

The sequences in Table 8 are as follows:

(VH BHA10)
SEQ ID NO: 69
QVQLVQSGAEVKKPGSSVKVSCKASGYTFTTYYLHWVRQAPGQGLEWMGWI
YPGNVHAQYNEKFKGRVTITADKSTSTAYMELSSLRSEDTAVYYCARSWEG
FPYWGQGTTVTVSS (VL BHA10)
SEQ ID NO: 70
DIQMTQSPSSLSASVGDRVTITCKASQNVGINVAWYQQKPGKAPKSLISSA
SYRYSGVPSRFSGSGSGTDFTLTISSLQPEDFATYFCQQYDTYPFTFGQGT
KVEIK (VH L19)
SEQ ID NO: 71
EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPY
FDYWGQGTLVTVSS (VL L19)
SEQ ID NO: 72
EIVLTQSPGTLSLSPGERATLSCRASQSVSSSFLAWYQQKPGQAPRLLIYY
ASSRATGIPDRFSGSGSGTDFTLTISRLEPEDFAVYYCQQTGRIPPTFGQG
TKVEIK (VH B21M)
SEQ ID NO: 73
QITLKESGPTLVKPTQTLTLTCTFSGFSLSTSGMGVSWIRQPPGKALEWLA
HIYWDDDKRYNPSLKSRLTITKDTSKNQVVLTMTNMDPVDTATYYCARLYG
FTYGFAYWGQGTLVTVSS (VL B21M)
SEQ ID NO: 74
DIVMTQSPDSLAVSLGERATINCRASQSVDYNGISYMHWYQQKPGQPPKLL
IYAASNPESGVPDRFSGSGSGTDFTLTISSLQAEDVAVYYCQQIIEDPWTF
GQGTKVEIK (VH MSLNmAb1)
SEQ ID NO: 75
QVQLQQSGPELEKPGASVKISCKASGYSFTGYTMNWVKQSHGKSLEWIGLI
TPYNGASSYNQKFRGKATLTVDKSSSTAYMDLLSLTSEDSAVYFCARGGYD
GRGFDYWGSGTPVTVSS (VL MSLNmAb1)
SEQ ID NO: 76
DIELTQSPAIMSASPGEKVTMTCSASSSVSYMHWYQQKSGTSPKRWIYDTS

KLASGVPGRFSGSGSGNSYSLTISSVEAEDDATYYCQQWSKHPLTFGSGTK

VEIK

Protein concentration was determined by absorbance measurement at 280 nm (OD280) and purification yield determined. Analytical SEC was performed using a Bio SEC-5 column (Agilent, 5 μm particle size, 300A) on a Thermo VANQUISH HPLC system. 10 μl purified protein was loaded on the column and elution was recorded by OD280.

Table 9 shows an overview of structural properties of the bispecific antibodies and control molecules described in this example. The molecules in boldface are exemplary molecules according to the invention, while the others are controls for different aspects. Table 10 shows structural properties of another comparative bispecific antibody, targeting LTBR and mesothelin (a tumor associated antigen not present in the extracellular matrix), as discussed in Example 9.

TABLE 9

Overview of the structural properties of the EDB/LTBR bispecific antibodies and control molecules

| | | | Binding sites | | | Fc-domain | scFv features | | | |
|---|---|---|---|---|---|---|---|---|---|---|
| | Name | Format | LTBRmAb1 | EDBmAb1 | B21M (isotype control mAb) | Protein A mut.* | Stapled linker | Disulfide stabilized | Orientation | Comments |
| Asymmetric antibodies; 2:1 format | COVA1480 | 2:1 | 1 (scFv) | 2 (mAb) | — | yes | yes | — | VH-VL | scFv fused to N-term of EDBmAb1 HC |
| | COVA1481 | 2:1 | 1 (scFv) | 2 (mAb) | — | yes | yes | — | VL-VH | scFv fused to N-term of EDBmAb1 HC |
| | COVA1482 | 2:1 | 1 (scFv) | 2 (mAb) | — | yes | yes | — | VH-VL | scFv fused to C-term of EDBmAb1 HC |
| | COVA1483 | 2:1 | 1 (scFv) | 2 (mAb) | — | yes | yes | — | VL-VH | scFv fused to C-term of EDBmAb1 HC |
| | COVA1484 | 2:1 | 1 (scFv) | — | 2 (mAb) | yes | yes | — | VH-VL | LTBR/null control to COVA1480 |
| | COVA1485 | 2:1 | 1 (scFv) | — | 2 (mAb) | yes | yes | — | VL-VH | LTBR/null control to COVA1481 |
| | COVA1486 | 2:1 | 1 (scFv) | — | 2 (mAb) | yes | yes | — | VH-VL | LTBR/null control to COVA1482 and to COVA14146 |
| | COVA1487 | 2:1 | 1 (scFv) | — | 2 (mAb) | yes | yes | — | VL-VH | LTBR/null control to COVA1483 |
| | COVA14107 | 2:1 | 1 (scFv) | 2 (mAb) | — | yes | yes | No | VH-VL | scFv (C-Term fusion to EDBmAb1 HC) contains mutations for reduced affinity to LTBR (VL3: Y36F_S49Y_F87) |
| | COVA14108 | 2:1 | 1 (scFv) | 2 (mAb) | — | yes | yes | No | VH-VL | scFv (C-Term fusion to EDBmAb1 HC) ontains mutations for reduced affinity to LTBR (VH_CDR1_Y33A) |
| | COVA14133 | 2:1 | 1 (scFv) | 2 (mAb) | — | no | yes | No | VH-VL | scFv fused to C-term of EDBmAb1 HC |
| | COVA14136 | 2:1 | 1 (scFv) | — | 2 (mAb) | no | yes | No | VH-VL | LTBR/null control to COVA14133 |

*mutations in the Fc portion to abrogate binding to protein A and facilitate purification of heterodimers, described in WO2010151792.

TABLE 10

Overview of the structural properties of the MSLN/LTBR bispecific antibody

| Name | Format | Binding sites | | Fc-domain Protein A mut. | scFv features | | orientation | Comments |
|---|---|---|---|---|---|---|---|---|
| | | LTBRmAb1 | MSLNmAb1 | | Stapled linker | Disulfide stabilized | | |
| COVA14146 | 2:1 | 1 (scFv) | 2 (mAb) | yes | yes | no | VH-VL | HC C-terminal fusion of scFv derived from LTBRmAb1 to MSLNmAb1. Isotype control molecule for this construct is COVA1486 |

The asymmetric antibodies, with 2:1 stoichiometry (all IgG1sigma, all with KiH mutations), listed above were generated as follows:

i. COVA1484 was generated by co-expression of the anti-RSV B21M antibody heavy chain carrying a N-terminal stapled scFv BHA10 (VH-VL orientation SEQ ID NO: 77) fusion (SEQ ID NO: 78, comprising SEQ ID NO: 79) with the heavy chain (HC; SEQ ID NO: 80) and light chain (LC; SEQ ID NO: 81) of the anti-RSV B21M antibody (FIG. 15A).

[stapled scFv BHA10 (VH-VL)]
SEQ ID NO: 77
QVQLVQSGAEVKKPGSSVKVSCKASGYTFTTYYLHWVRQAPGCGLEWMGWI
YPGNVHAQYNEKFKGRVTITADKSTSTAYMELSSLRSEDTAVYYCARSWEG
FPYWGQGTTVTVSSGGGSGGGSGCPPCGGGGDIQMTQSPSSLSASVGDRVT
ITCKASQNVGINVAWYQQKPGKAPKSLISSASYRYSGVPSRFSGSGSGTDF
TLTISSLQPEDFATYFCQQYDTYPFTFGCGTKVEIK (HC B21M N-term stapled BHA10 (VH-VL), IgG1s, knob, with pA mutations)
SEQ ID NO: 78
QVQLVQSGAEVKKPGSSVKVSCKASGYTFTTYYLHWVRQAPGCGLEWMGWI
YPGNVHAQYNEKFKGRVTITADKSTSTAYMELSSLRSEDTAVYYCARSWEG
FPYWGQGTTVTVSSGGGSGGGSGCPPCGGGGDIQMTQSPSSLSASVGDRVT
ITCKASQNVGINVAWYQQKPGKAPKSLISSASYRYSGVPSRFSGSGSGTDF
TLTISSLQPEDFATYFCQQYDTYPFTFGCGTKVEIKGGGGSGGGGSGGGGS
GGGGSGGGGSQITLKESGPTLVKPTQTLTLTCTFSGFSLSTSGMGVSWIRQ
PPGKALEWLAHIYWDDDKRYNPSLKSRLTITKDTSKNQVVLTMTNMDPVDT
ATYYCARLYGFTYGFAYWGQGTLVTVSSASTKGPSVFPLAPSSKSTSGGTA
ALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGASSVFL
FPPKPKDTLMISRTPEVTCVVVDVSAEDPEVKFNWYVDGVEVHNAKTKPRE
EQYNSTYRVVSVLTVLHQDWLNGKEYKCKVSNKALPSSIEKTISKAKGQPR
EPQVYTLPPCREEMTKNQVSLWCLVKGFYPSDIAVEWESNGQPENNYKTTP
PVLDSDGSFFLYSKLTVDKSRWQQGNVFSCSVMHEALHNRFTQKSLSLSPG
K (HC B21M (RSV) IgG1s knob with pA mutations)
SEQ ID NO: 79
QITLKESGPTLVKPTQTLTLTCTFSGFSLSTSGMGVSWIRQPPGKALEWLA
HIYWDDDKRYNPSLKSRLTITKDTSKNQVVLTMTNMDPVDTATYYCARLYG
FTYGFAYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTLM
ISRTPEVTCVVVDVSAEDPEVKFNWYVDGVEVHNAKTKPREEQYNSTYRVV
SVLTVLHQDWLNGKEYKCKVSNKALPSSIEKTISKAKGQPREPQVYTLPPC
REEMTKNQVSLWCLVKGFYPSDIAVEWESNGQPENNYKTTPPVLDSDGSFF
LYSKLTVDKSRWQQGNVFSCSVMHEALHNRFTQKSLSLSPGK (HC B21M (RSV) IgG1s hole)
SEQ ID NO: 80
QITLKESGPTLVKPTQTLTLTCTFSGFSLSTSGMGVSWIRQPPGKALEWLA
HIYWDDDKRYNPSLKSRLTITKDTSKNQVVLTMTNMDPVDTATYYCARLYG
FTYGFAYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTLM
ISRTPEVTCVVVDVSAEDPEVKFNWYVDGVEVHNAKTKPREEQYNSTYRVV
SVLTVLHQDWLNGKEYKCKVSNKALPSSIEKTISKAKGQPREPQVCTLPPS
REEMTKNQVSLSCAVKGFYPSDIAVEWESNGQPENNYKTTPPVLDSDGSFF
LVSKLTVDKSRWQQGNVFSCSVMHEALHNHYTQKSLSLSPGK

[LC B21M (RSV)]
SEQ ID NO: 81
DIVMTQSPDSLAVSLGERATINCRASQSVDYNGISYMHWYQQKPGQPPKLL
IYAASNPESGVPDRFSGSGSGTDFTLTISSLQAEDVAVYYCQQIIEDPWTF
GQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQG
LSSPVTKSFNRGEC ii. COVA1485 was generated by co-expression of the anti-RSV B21M antibody heavy chain carrying a N-terminal stapled scFv BHA10 (VL-VH orientation SEQ ID NO: 82) fusion (SEQ ID NO: 83, comprising SEQ ID NO: 79) with the heavy chain (HC; SEQ ID NO: 80) and light chain (LC; SEQ ID NO: 81) of the anti-RSV B21M antibody (FIG. 15B).

[stapled scFv BHA10 (VL-VH)]
SEQ ID NO: 82
DIQMTQSPSSLSASVGDRVTITCKASQNVGINVAWYQQKPGCAPKSLISSA
SYRYSGVPSRFSGSGSGTDFTLTISSLQPEDFATYFCQQYDTYPFTFGQGT
KVEIKGGSGGSGGCPPCGSGGQVQLVQSGAEVKKPGSSVKVSCKASGYTFT
TYYLHWVRQAPGQGLEWMGWIYPGNVHAQYNEKFKGRVTITADKSTSTAYM
ELSSLRSEDTAVYYCARSWEGFPYWGCGTTVTVSS (HCB21M N-term stapled BHA10 (VL-VH), IgG1s, knob, with pA mutations)
SEQ ID NO: 83
DIQMTQSPSSLSASVGDRVTITCKASQNVGINVAWYQQKPGCAPKSLISSA
SYRYSGVPSRFSGSGSGTDFTLTISSLQPEDFATYFCQQYDTYPFTFGQGT
KVEIKGGSGGSGGCPPCGSGGQVQLVQSGAEVKKPGSSVKVSCKASGYTFT
TYYLHWVRQAPGQGLEWMGWIYPGNVHAQYNEKFKGRVTITADKSTSTAYM
ELSSLRSEDTAVYYCARSWEGFPYWGCGTTVTVSSGGGGSGGGGSGGGGSG
GGGSGGGGSQITLKESGPTLVKPTQTLTLTCTFSGFSLSTSGMGVSWIRQP
PGKALEWLAHIYWDDDKRYNPSLKSRLTITKDTSKNQVVLTMTNMDPVDTA
TYYCARLYGFTYGFAYWGQGTLVTVSSASTKGPSVFPLAPSSKSTSGGTAA
LGCLVKDYFPEPVTVSWNSGALTSGVHTFPAVLQSSGLYSLSSVVTVPSSS
LGTQTYICNVNHKPSNTKVDKKVEPKSCDKTHTCPPCPAPEAAGASSVFLF
PPKPKDTLMISRTPEVTCVVVDVSAEDPEVKFNWYVDGVEVHNAKTKPREE
QYNSTYRVVSVLTVLHQDWLNGKEYKCKVSNKALPSSIEKTISKAKGQPRE
PQVYTLPPCREEMTKNQVSLWCLVKGFYPSDIAVEWESNGQPENNYKTTPP
VLDSDGSFFLYSKLTVDKSRWQQGNVFSCSVMHEALHNRFTQKSLSLSPGK (HC B21M (RSV) IgG1s knob with pA mutations)
SEQ ID NO: 79
QITLKESGPTLVKPTQTLTLTCTFSGESLSTSGMGVSWIRQPPGKALEWLA
HIYWDDDKRYNPSLKSRLTITKDTSKNQVVLTMTNMDPVDTATYYCARLYG
FTYGFAYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTLM
ISRTPEVTCVVVDVSAEDPEVKFNWYVDGVEVHNAKTKPREEQYNSTYRVV
SVLTVLHQDWLNGKEYKCKVSNKALPSSIEKTISKAKGQPREPQVYTLPPC
REEMTKNQVSLWCLVKGFYPSDIAVEWESNGQPENNYKTTPPVLDSDGSFF
LYSKLTVDKSRWQQGNVFSCSVMHEALHNRFTQKSLSLSPGK (HC B21M (RSV) IgG1s hole)
SEQ ID NO: 80
QITLKESGPTLVKPTQTLTLTCTFSGFSLSTSGMGVSWIRQPPGKALEWLA
HIYWDDDKRYNPSLKSRLTITKDTSKNQVVLTMTNMDPVDTATYYCARLYG
FTYGFAYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTLM
ISRTPEVTCVVVDVSAEDPEVKFNWYVDGVEVHNAKTKPREEQYNSTYRVV
SVLTVLHQDWLNGKEYKCKVSNKALPSSIEKTISKAKGQPREPQVCTLPPS
REEMTKNQVSLSCAVKGFYPSDIAVEWESNGQPENNYKTTPPVLDSDGSFF
LVSKLTVDKSRWQQGNVFSCSVMHEALHNHYTQKSLSLSPGK

[LC B21M (RSV)]
SEQ ID NO: 81
DIVMTQSPDSLAVSLGERATINCRASQSVDYNGISYMHWYQQKPGQPPKLL
IYAASNPESGVPDRFSGSGSGTDFTLTISSLQAEDVAVYYCQQIIEDPWTF
GQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQG
LSSPVTKSFNRGEC iii. COVA1486 was generated by co-expression of the anti-RSV B21M antibody heavy chain carrying a C-terminal stapled scFv BHA10 (VH-VL orientation SEQ ID NO: 77) fusion (SEQ ID NO: 84, comprising SEQ ID NO: 79) with the heavy chain (HC; SEQ ID NO: 80) and light chain (LC; SEQ ID NO: 81) of the anti-RSV B21M antibody (FIG. 15C).

[stapled scFv BHA10 (VH-VL)]

SEQ ID NO: 77

QVQLVQSGAEVKKPGSSVKVSCKASGYTFTTYYLHWVRQAPGCGLEWMGWI

YPGNVHAQYNEKFKGRVTITADKSTSTAYMELSSLRSEDTAVYYCARSWEG

FPYWGQGTTVTVSSGGGGSGGGSGCPPCGGGGDIQMTQSPSSLSASVGDRVT

ITCKASQNVGINVAWYQQKPGKAPKSLISSASYRYSGVPSRFSGSGSGTDF

TLTISSLQPEDFATYFCQQYDTYPFTFGCGTKVEIK (HC B21M C-term stapled BHA (VH-VL), IgG1s, knob, with pA mutations)

SEQ ID NO: 84

QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVYTLPPC

REEMTKNQVSLWCLVKGFYPSDIAVEWESNGQPENNYKTTPPVLDSDGSFF

LYSKLTVDKSRWQQGNVFSCSVMHEALHNRFTQKSLSLSPGKGGGGSGGGG

SGGGGSQVQLVQSGAEVKKPGSSVKVSCKASGYTFTTYYLHWVRQAPGCGL

EWMGWIYPGNVHAQYNEKFKGRVTITADKSTSTAYMELSSLRSEDTAVYYC

ARSWEGFPYWGQGTTVTVSSGGGGSGGGSGCPPCGGGGDIQMTQSPSSLSAS

VGDRVTITCKASQNVGINVAWYQQKPGKAPKSLISSASYRYSGVPSRFSGS

GSGTDFTLTISSLQPEDFATYFCQQYDTYPFTFGCGTKVEIK (HC B21M (RSV) IgG1s knob with pA mutations)

SEQ ID NO: 79

QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

```
VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVYTLPPC

REEMTKNQVSLWCLVKGFYPSDIAVEWESNGQPENNYKTTPPVLDSDGSFF

LYSKLTVDKSRWQQGNVFSCSVMHEALHNRFTQKSLSLSPGK (HC B21M (RSV) IgG1s hole)
                                        SEQ ID NO: 80
QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVCTLPPS

REEMTKNQVSLSCAVKGFYPSDIAVEWESNGQPENNYKTTPPVLDSDGSFF

LVSKLTVDKSRWQQGNVFSCSVMHEALHNHYTQKSLSLSPGK

[LC B21M (RSV)]
                                        SEQ ID NO: 81
DIVMTQSPDSLAVSLGERATINCRASQSVDYNGISYMHWYQQKPGQPPKLL

IYAASNPESGVPDRFSGSGSGTDFTLTISSLQAEDVAVYYCQQIIEDPWTF

GQGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC
``` iv. COVA1487 was generated by co-expression of the anti-RSV B21M antibody heavy chain carrying a C-terminal stapled scFv BHA10 (VL-VH orientation SEQ ID NO: 82) fusion (SEQ ID NO: 85, comprising SEQ ID NO: 79) with the heavy chain (HC; SEQ ID NO: 80) and light chain (LC; SEQ ID NO: 81) of the anti-RSV B21M antibody (FIG. 15D).

```
[stapled scFv BHA10 (VL-VH)]
                                        SEQ ID NO: 82
DIQMTQSPSSLSASVGDRVTITCKASQNVGINVAWYQQKPGCAPKSLISSA

SYRYSGVPSRFSGSGSGTDFTLTISSLQPEDFATYFCQQYDTYPFTFGQGT

KVEIKGGSGGSGGCPPCGSGGQVQLVQSGAEVKKPGSSVKVSCKASGYTFT

TYYLHWVRQAPGQGLEWMGWIYPGNVHAQYNEKFKGRVTITADKSTSTAYM

ELSSLRSEDTAVYYCARSWEGFPYWGCGTTVTVSS (HC B21M C-term stapled BHA (VL-VH), IgG1s, knob,
with pA mutations)
                                        SEQ ID NO: 85
QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVYTLPPC

REEMTKNQVSLWCLVKGFYPSDIAVEWESNGQPENNYKTTPPVLDSDGSFF

LYSKLTVDKSRWQQGNVFSCSVMHEALHNRFTQKSLSLSPGKGGGGSGGGG

SGGGGSDIQMTQSPSSLSASVGDRVTITCKASQNVGINVAWYQQKPGCAPK

SLISSASYRYSGVPSRFSGSGSGTDFTLTISSLQPEDFATYFCQQYDTYPF

TFGQGTKVEIKGGSGGSGGCPPCGSGGQVQLVQSGAEVKKPGSSVKVSCKA

SGYTFTTYYLHWVRQAPGQGLEWMGWIYPGNVHAQYNEKFKGRVTITADKS

TSTAYMELSSLRSEDTAVYYCARSWEGFPYWGCGTTVTVSS (HC B21M (RSV) IgG1s knob with pA mutations)
                                        SEQ ID NO: 79
QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVYTLPPC

REEMTKNQVSLWCLVKGFYPSDIAVEWESNGQPENNYKTTPPVLDSDGSFF

LYSKLTVDKSRWQQGNVFSCSVMHEALHNRFTQKSLSLSPGK (HC B21M (RSV) IgG1s hole)
                                        SEQ ID NO: 80
QITLKESGPTLVKPTQTLTLTCTFSGFSLSTSGMGVSWIRQPPGKALEWLA

HIYWDDDKRYNPSLKSRLTITKDTSKNQVVLTMTNMDPVDTATYYCARLYG

FTYGFAYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRVV

SVLTVLHQDWLNGKEYKCKVSNKALPSSIEKTISKAKGQPREPQVCTLPPS

REEMTKNQVSLSCAVKGFYPSDIAVEWESNGQPENNYKTTPPVLDSDGSFF

LVSKLTVDKSRWQQGNVFSCSVMHEALHNHYTQKSLSLSPGK

[LC B21M (RSV)]
                                        SEQ ID NO: 81
DIVMTQSPDSLAVSLGERATINCRASQSVDYNGISYMHWYQQKPGQPPKLL

IYAASNPESGVPDRFSGSGSGTDFTLTISSLQAEDVAVYYCQQIIEDPWTF

GQGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSENRGEC
``` v. COVA1480 was generated by co-expression of an anti-EDB antibody EDBmAb1 heavy chain carrying a N-terminal stapled scFv BHA10 (VH-VL orientation SEQ ID NO: 77) fusion (SEQ ID NO: 86, comprising SEQ ID NO: 87) with the heavy chain (HC; SEQ ID NO: 88) and light chain (LC; SEQ ID NO: 89) of an anti-EDB antibody EDBmAb1 (FIG. 15E).

[stapled scFv BHA10 (VH-VL)]
SEQ ID NO: 77
QVQLVQSGAEVKKPGSSVKVSCKASGYTFTTYYLHWVRQAPGCGLEWMGWI
YPGNVHAQYNEKFKGRVTITADKSTSTAYMELSSLRSEDTAVYYCARSWEG
FPYWGQGTTVTVSSGGGSGGGSGCPPCGGGGDIQMTQSPSSLSASVGDRVT
ITCKASQNVGINVAWYQQKPGKAPKSLISSASYRYSGVPSRFSGSGSGTDF
TLTISSLQPEDFATYFCQQYDTYPFTFGCGTKVEIK (HC L19 N-term stapled BHA10 (VH-VL), IgG1s, knob, with pA mutations)
SEQ ID NO: 86
QVQLVQSGAEVKKPGSSVKVSCKASGYTFTTYYLHWVRQAPGCGLEWMGWI
YPGNVHAQYNEKFKGRVTITADKSTSTAYMELSSLRSEDTAVYYCARSWEG
FPYWGQGTTVTVSSGGGSGGGSGCPPCGGGGDIQMTQSPSSLSASVGDRVT
ITCKASQNVGINVAWYQQKPGKAPKSLISSASYRYSGVPSRFSGSGSGTDF
TLTISSLQPEDFATYFCQQYDTYPFTFGCGTKVEIKGGGGSGGGGSGGGGS
GGGGSGGGGSEVQLLESGGGLVQPGGSLRLSCAASGFTFSSFSMSWVRQAP
GKGLEWVSSISGSSGTTYYADSVKGRFTISRDNSKNTLYLQMNSLRAEDTA
VYYCAKPFPYFDYWGQGTLVTVSSASTKGPSVFPLAPSSKSTSGGTAALGC
LVKDYFPEPVTVSWNSGALTSGVHTFPAVLQSSGLYSLSSVVTVPSSSLGT
QTYICNVNHKPSNTKVDKKVEPKSCDKTHTCPPCPAPEAAGASSVFLFPPK
PKDTLMISRTPEVTCVVVDVSAEDPEVKFNWYVDGVEVHNAKTKPREEQYN
STYRVVSVLTVLHQDWLNGKEYKCKVSNKALPSSIEKTISKAKGQPREPQV
YTLPPCREEMTKNQVSLWCLVKGFYPSDIAVEWESNGQPENNYKTTPPVLD
SDGSFFLYSKLTVDKSRWQQGNVFSCSVMHEALHNRFTQKSLSLSPGK (HC L19 IgG1s knob with pA mutations)
SEQ ID NO: 87
VQLLESGGGLVQPGGSLRLSCAASGFTFSSFSMSWVRQAPGKGLEWVSSIS
GSSGTTYYADSVKGRFTISRDNSKNTLYLQMNSLRAEDTAVYYCAKPFPYF
DYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPEAAGASSVFLFPPKPKDTLMISRTP
EVTCVVVDVSAEDPEVKFNWYVDGVEVHNAKTKPREEQYNSTYRVVSVLTV
LHQDWLNGKEYKCKVSNKALPSSIEKTISKAKGQPREPQVYTLPPCREEMT
KNQVSLWCLVKGFYPSDIAVEWESNGQPENNYKTTPPVLDSDGSFFLYSKL
TVDKSRWQQGNVFSCSVMHEALHNRFTQKSLSLSPGK (HC L19 IgG1s hole)
SEQ ID NO: 88
EVQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFPY
FDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHK
PSNTKVDKKVEPKSCDKTHTCPPCPAPEAAGASSVFLFPPKPKDTLMISRT
PEVTCVVVDVSAEDPEVKFNWYVDGVEVHNAKTKPREEQYNSTYRVVSVLT
VLHQDWLNGKEYKCKVSNKALPSSIEKTISKAKGQPREPQVCTLPPSREEM
TKNQVSLSCAVKGFYPSDIAVEWESNGQPENNYKTTPPVLDSDGSFFLVSK
LTVDKSRWQQGNVFSCSVMHEALHNHYTQKSLSLSPGK (LC L19)
SEQ ID NO: 89
EIVLTQSPGTLSLSPGERATLSCRASQSVSSSFLAWYQQKPGQAPRLLIYY
ASSRATGIPDRFSGSGSGTDFTLTISRLEPEDFAVYYCQQTGRIPPTFGQG
TKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSS
PVTKSFNRGEC vi. COVA1481 was generated by co-expression of an anti-EDB antibody EDBmAb1 heavy chain carrying a N-terminal stapled scFv BHA10 (VL-VH orientation SEQ ID NO: 82) fusion (SEQ ID NO: 90, comprising SEQ ID NO: 87) with the heavy chain (HC; SEQ ID NO: 88) and light chain (LC; SEQ ID NO: 89) of an anti-EDB antibody EDBmAb1 (FIG. 15F).

[stapled scFv BHA10 (VL-VH)]
SEQ ID NO: 82
DIQMTQSPSSLSASVGDRVTITCKASQNVGINVAWYQQKPGCAPKSLISSA
SYRYSGVPSRFSGSGSGTDFTLTISSLQPEDFATYFCQQYDTYPFTFGQGT
KVEIKGGSGGSGGCPPCGSGGQVQLVQSGAEVKKPGSSVKVSCKASGYTFT
TYYLHWVRQAPGQGLEWMGWIYPGNVHAQYNEKFKGRVTITADKSTSTAYM
ELSSLRSEDTAVYYCARSWEGFPYWGCGTTVTVSS (HC L19 N-term stapled BHA10 (VL-VH), IgG1s, knob, with pA mutations)
SEQ ID NO: 90
DIQMTQSPSSLSASVGDRVTITCKASQNVGINVAWYQQKPGCAPKSLISSA
SYRYSGVPSRFSGSGSGTDFTLTISSLQPEDFATYFCQQYDTYPFTFGQGT
KVEIKGGSGGSGGCPPCGSGGQVQLVQSGAEVKKPGSSVKVSCKASGYTFT
TYYLHWVRQAPGQGLEWMGWIYPGNVHAQYNEKFKGRVTITADKSTSTAYM
ELSSLRSEDTAVYYCARSWEGFPYWGCGTTVTVSSGGGGSGGGGSGGGGSG
GGGSGGGGSEVQLLESGGGLVQPGGSLRLSCAASGFTFSSFSMSWVRQAPG
KGLEWVSSISGSSGTTYYADSVKGRFTISRDNSKNTLYLQMNSLRAEDTAV
YYCAKPFPYFDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSCDKTHTCPPCPAPEAAGASSVFLFPPKP
KDTLMISRTPEVTCVVVDVSAEDPEVKFNWYVDGVEVHNAKTKPREEQYNS
TYRVVSVLTVLHQDWLNGKEYKCKVSNKALPSSIEKTISKAKGQPREPQVY
TLPPCREEMTKNQVSLWCLVKGFYPSDIAVEWESNGQPENNYKTTPPVLDS
DGSFFLYSKLTVDKSRWQQGNVFSCSVMHEALHNRFTQKSLSLSPGK (HC L19 IgG1s knob with pA mutations)
SEQ ID NO: 87
VQLLESGGGLVQPGGSLRLSCAASGFTFSSFSMSWVRQAPGKGLEWVSSIS
GSSGTTYYADSVKGRFTISRDNSKNTLYLQMNSLRAEDTAVYYCAKPFPYF
DYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPEAAGASSVFLFPPKPKDTLMISRTP
EVTCVVVDVSAEDPEVKFNWYVDGVEVHNAKTKPREEQYNSTYRVVSVLTV

LHQDWLNGKEYKCKVSNKALPSSIEKTISKAKGQPREPQVYTLPPCREEMT

KNQVSLWCLVKGFYPSDIAVEWESNGQPENNYKTTPPVLDSDGSFFLYSKL

TVDKSRWQQGNVFSCSVMHEALHNRFTQKSLSLSPGK (HC L19 IgG1s hole)
SEQ ID NO: 88
EVQLLESGGGLVQPGGSLRLSCAASGFTFSSFSMSWVRQAPGKGLEWVSSI

SGSSGTTYYADSVKGRFTISRDNSKNTLYLQMNSLRAEDTAVYYCAKPFPY

FDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGASSVFLFPPKPKDTLMISRT

PEVTCVVVDVSAEDPEVKFNWYVDGVEVHNAKTKPREEQYNSTYRVVSVLT

VLHQDWLNGKEYKCKVSNKALPSSIEKTISKAKGQPREPQVCTLPPSREEM

TKNQVSLSCAVKGFYPSDIAVEWESNGQPENNYKTTPPVLDSDGSFFLVSK

LTVDKSRWQQGNVFSCSVMHEALHNYTQKSLSLSPGK (LC L19)
SEQ ID NO: 89
EIVLTQSPGTLSLSPGERATLSCRASQSVSSSFLAWYQQKPGQAPRLLIYY

ASSRATGIPDRFSGSGSGTDFTLTISRLEPEDFAVYYCQQTGRIPPTFGQG

TKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSS

PVTKSFNRGEC vii. COVA1482 was generated by co-expression of an anti-EDB antibody EDBmAb1 heavy chain carrying a C-terminal stapled scFv BHA10 (VH-VL orientation SEQ ID NO: 77) fusion (SEQ ID NO: 91, comprising SEQ ID NO: 87) with the heavy chain (HC; SEQ ID NO: 88) and light chain (LC; SEQ ID NO: 89) of an anti-EDB antibody EDBmAb1 (FIG. 15G).

[stapled scFv BHA10 (VH-VL)]
SEQ ID NO: 77
QVQLVQSGAEVKKPGSSVKVSCKASGYTFTTYYLHWVRQAPGCGLEWMGWI

YPGNVHAQYNEKFKGRVTITADKSTSTAYMELSSLRSEDTAVYYCARSWEG

FPYWGQGTTVTVSSGGGSGGGSGCPPCGGGGDIQMTQSPSSLSASVGDRVT

ITCKASQNVGINVAWYQQKPGKAPKSLISSASYRYSGVPSRFSGSGSGTDF

TLTISSLQPEDFATYFCQQYDTYPFTFGCGTKVEIK (HC L19 C-term stapled BHA10 (VH-VL), IgG1s, knob,
with pA mutations)
SEQ ID NO: 91
EVQLLESGGGLVQPGGSLRLSCAASGFTFSSFSMSWVRQAPGKGLEWVSSI

SGSSGTTYYADSVKGRFTISRDNSKNTLYLQMNSLRAEDTAVYYCAKPFPY

FDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGASSVFLFPPKPKDTLMISRT

PEVTCVVVDVSAEDPEVKFNWYVDGVEVHNAKTKPREEQYNSTYRVVSVLT

VLHQDWLNGKEYKCKVSNKALPSSIEKTISKAKGQPREPQVYTLPPCREEM

TKNQVSLWCLVKGFYPSDIAVEWESNGQPENNYKTTPPVLDSDGSFFLYSK

LTVDKSRWQQGNVFSCSVMHEALHNRFTQKSLSLSPGKGGGGSGGGGSGGG

GSQVQLVQSGAEVKKPGSSVKVSCKASGYTFTTYYLHWVRQAPGCGLEWMG

WIYPGNVHAQYNEKFKGRVTITADKSTSTAYMELSSLRSEDTAVYYCARSW

EGFPYWGQGTTVTVSSGGGSGGGSGCPPCGGGGDIQMTQSPSSLSASVGDR

VTITCKASQNVGINVAWYQQKPGKAPKSLISSASYRYSGVPSRFSGSGSGT

DFTLTISSLQPEDFATYFCQQYDTYPFTFGCGTKVEIK (HC L19 IgG1s knob with pA mutations)
SEQ ID NO: 87
VQLLESGGGLVQPGGSLRLSCAASGFTFSSFSMSWVRQAPGKGLEWVSSIS

GSSGTTYYADSVKGRFTISRDNSKNTLYLQMNSLRAEDTAVYYCAKPFPYF

DYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKP

VSNTKDKKVEPKSCDKTHTCPPCPAPEAAGASSVFLFPPKPKDTLMISRTP

EVTCVVVDVSAEDPEVKFNWYVDGVEVHNAKTKPREEQYNSTYRVVSVLTV

LHQDWLNGKEYKCKVSNKALPSSIEKTISKAKGQPREPQVYTLPPCREEMT

KNQVSLWCLVKGFYPSDIAVEWESNGQPENNYKTTPPVLDSDGSFFLYSKL

TVDKSRWQQGNVFSCSVMHEALHNRFTQKSLSLSPGK (HC L19 IgG1s hole)
SEQ ID NO: 88
EVQLLESGGGLVQPGGSLRLSCAASGFTFSSFSMSWVRQAPGKGLEWVSSI

SGSSGTTYYADSVKGRFTISRDNSKNTLYLQMNSLRAEDTAVYYCAKPFPY

FDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGASSVFLFPPKPKDTLMISRT

PEVTCVVVDVSAEDPEVKFNWYVDGVEVHNAKTKPREEQYNSTYRVVSVLT

VLHQDWLNGKEYKCKVSNKALPSSIEKTISKAKGQPREPQVCTLPPSREEM

TKNQVSLSCAVKGFYPSDIAVEWESNGQPENNYKTTPPVLDSDGSFFLVSK

LTVDKSRWQQGNVFSCSVMHEALHNYTQKSLSLSPGK (LC L19)
SEQ ID NO: 89
EIVLTQSPGTLSLSPGERATLSCRASQSVSSSFLAWYQQKPGQAPRLLIYY

ASSRATGIPDRFSGSGSGTDFTLTISRLEPEDFAVYYCQQTGRIPPTFGQG

TKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSS

PVTKSFNRGEC viii. COVA1483 was generated by co-expression of an anti-EDB antibody EDBmAb1 heavy chain carrying a C-terminal stapled scFv BHA10 (VL-VH orientation SEQ ID NO: 82) fusion (SEQ ID NO: 92, comprising SEQ ID NO: 87) with the heavy chain (HC; SEQ ID NO: 88) and light chain (LC; SEQ ID NO: 89) of an anti-EDB antibody EDBmAb1 (FIG. 15H).

[stapled scFv BHA10 (VL-VH)]
SEQ ID NO: 82
DIQMTQSPSSLSASVGDRVTITCKASQNVGINVAWYQQKPGCAPKSLISS

ASYRYSGVPSRFSGSGSGTDFTLTISSLQPEDFATYFCQQYDTYPFTFGQ

```
GTKVEIKGGSGGSGGCPPCGSGGQVQLVQSGAEVKKPGSSVKVSCKASGY
TFTTYYLHWVRQAPGQGLEWMGWIYPGNVHAQYNEKFKGRVTITADKSTS
TAYMELSSLRSEDTAVYYCARSWEGFPYWGCGTTVTVSS (HC L19 C-term stapled BHA10 (VL-VH), IgG1s, knob,
with pA mutations)
                                    SEQ ID NO: 92
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVYTL
PPCREEMTKNQVSLWCLVKGFYPSDIAVEWESNGQPENNYKTTPPVLDSD
GSFFLYSKLTVDKSRWQQGNVFSCSVMHEALHNRFTQKSLSLSPGKGGGG
SGGGGSGGGGSDIQMTQSPSSLSASVGDRVTITCKASQNVGINVAWYQQK
PGCAPKSLISSASYRYSGVPSRFSGSGSGTDFTLTISSLQPEDFATYFCQ
QYDTYPFTFGQGTKVEIKGGSGGSGGCPPCGSGGQVQLVQSGAEVKKPGS
SVKVSCKASGYTFTTYYLHWVRQAPGQGLEWMGWIYPGNVHAQYNEKFKG
RVTITADKSTSTAYMELSSLRSEDTAVYYCARSWEGFPYWGCGTTVTVSS (HC L19 IgG1s knob with pA mutations)
                                    SEQ ID NO: 87
VQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFP
YFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPEAAGASSVFLFPPKPKDTLM
ISRTPEVTCVVVDVSAEDPEVKFNWYVDGVEVHNAKTKPREEQYNSTYRV
VSVLTVLHQDWLNGKEYKCKVSNKALPSSIEKTISKAKGQPREPQVYTLP
PCREEMTKNQVSLWCLVKGFYPSDIAVEWESNGQPENNYKTTPPVLDSDG
SFFLYSKLTVDKSRWQQGNVFSCSVMHEALHNRFTQKSLSLSPGK (HC L19 IgG1s hole)
                                    SEQ ID NO: 88
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVCTL
PPSREEMTKNQVSLSCAVKGFYPSDIAVEWESNGQPENNYKTTPPVLDSD
GSFFLVSKLTVDKSRWQQGNVFSCSVMHEALHNHYTQKSLSLSPGK (LC L19)
                                    SEQ ID NO: 89
EIVLTQSPGTLSLSPGERATLSCRASQSVSSSFLAWYQQKPGQAPRLLIY
YASSRATGIPDRFSGSGSGTDFTLTISRLEPEDFAVYYCQQTGRIPPTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
``` ix. COVA14107 was generated by co-expression of an anti-EDB antibody EDBmAb1 heavy chain carrying a C-terminal stapled scFv BHA10 (VH-VL orientation, VL3 Y36F_S49Y_F87Y SEQ ID NO: 93) fusion (SEQ ID NO: 94, comprising SEQ ID NO: 87) with the heavy chain (HC; SEQ ID NO: 88) and light chain (LC; SEQ ID NO: 89) of an anti-EDB antibody EDBmAb1 (FIG. 15I).

```
[stapled scFv (VL3_Y36F_S49Y_F87Y) BHA10 (VH-VL)]
                                    SEQ ID NO: 93
QVQLVQSGAEVKKPGSSVKVSCKASGYTFTTYYLHWVRQAPGCGLEWMGW
IYPGNVHAQYNEKFKGRVTITADKSTSTAYMELSSLRSEDTAVYYCARSW
EGFPYWGQGTTVTVSSGGGSGGGSGCPPCGGGGDIQMTQSPSSLSASVGD
RVTITCKASQNVGINVAWFQQKPGKAPKSLIYSASYRYSGVPSRFSGSGS
GTDFTLTISSLQPEDFATYYCQQYDTYPFTFGCGTKVEIK (HC L19 C-term stapled (VL3_Y36F_S49Y_F87Y) BHA
(VH-VL), IgG1s, knob, with pA mutations)
                                    SEQ ID NO: 94
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVYTL
PPCREEMTKNQVSLWCLVKGFYPSDIAVEWESNGQPENNYKTTPPVLDSD
GSFFLYSKLTVDKSRWQQGNVFSCSVMHEALHNRFTQKSLSLSPGKGGGG
SGGGGSGGGSQVQLVQSGAEVKKPGSSVKVSCKASGYTFTTYYLHWVRQ
APGCGLEWMGWIYPGNVHAQYNEKFKGRVTITADKSTSTAYMELSSLRSE
DTAVYYCARSWEGFPYWGQGTTVTVSSGGGSGGGSGCPPCGGGGDIQMTQ
SPSSLSASVGDRVTITCKASQNVGINVAWFQQKPGKAPKSLIYSASYRYS
GVPSRFSGSGSGTDFTLTISSLQPEDFATYYCQQYDTYPFTFGCGTKVEI
K (HC L19 IgG1s knob with pA mutations)
                                    SEQ ID NO: 87
VQLLESGGGLVQPGGSLRLSCAASGFTFSSFSMSWVRQAPGKGLEWVSSI
SGSSGTTYYADSVKGRFTISRDNSKNTLYLQMNSLRAEDTAVYYCAKPFP
YFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPEAAGASSVFLFPPKPKDTLM
```

ISRTPEVTCVVVDVSAEDPEVKFNWYVDGVEVHNAKTKPREEQYNSTYRV

VSVLTVLHQDWLNGKEYKCKVSNKALPSSIEKTISKAKGQPREPQVYTLP

PCREEMTKNQVSLWCLVKGFYPSDIAVEWESNGQPENNYKTTPPVLDSDG

SFFLYSKLTVDKSRWQQGNVFSCSVMHEALHNRFTQKSLSLSPGK (HC L19 IgG1s hole)
SEQ ID NO: 88

EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTL

MISRTPEVTCVVVDVSAEDPEVKFNWYVDGVEVHNAKTKPREEQYNSTYR

VVSVLTVLHQDWLNGKEYKCKVSNKALPSSIEKTISKAKGQPREPQVCTL

PPSREEMTKNQVSLSCAVKGFYPSDIAVEWESNGQPENNYKTTPPVLDSD

GSFFLVSKLTVDKSRWQQGNVFSCSVMHEALHNHYTQKSLSLSPGK (LC L19)
SEQ ID NO: 89

EIVLTQSPGTLSLSPGERATLSCRASQSVSSSFLAWYQQKPGQAPRLLIY

YASSRATGIPDRFSGSGSGTDFTLTISRLEPEDFAVYYCQQTGRIPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC x. COVA14108 was generated by co-expression of an anti-EDB antibody EDBmAb1 heavy chain carrying a C-terminal stapled scFv BHA10 (VH-VL orientation, VH_CDR1_Y33A SEQ ID NO: 95) fusion (SEQ ID NO: 96, comprising SEQ ID NO: 87) with the heavy chain (HC; SEQ ID NO: 88) and light chain (LC; SEQ ID NO: 89) of an anti-EDB antibody EDBmAb1 (FIG. 15J).

[stapled scFv (VH_CDR1_Y33A) BHA10 (VH-VL)]
SEQ ID NO: 95

QVQLVQSGAEVKKPGSSVKVSCKASGYTFTTYALHWVRQAPGCGLEWMGW

IYPGNVHAQYNEKFKGRVTITADKSTSTAYMELSSLRSEDTAVYYCARSW

EGFPYWGQGTTVTVSSGGGSGGGGSGCPPCGGGGDIQMTQSPSSLSASVGD

RVTITCKASQNVGINVAWYQQKPGKAPKSLISSASYRYSGVPSRFSGSGS

GTDFTLTISSLQPEDFATYFCQQYDTYPFTFGCGTKVEIK (HC L19 C-term stapled (VH_CDR1_Y33A) BHA10
(VH-VL), IgG1s, knob, with pA mutations)
SEQ ID NO: 96

EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTL

MISRTPEVTCVVVDVSAEDPEVKFNWYVDGVEVHNAKTKPREEQYNSTYR

VVSVLTVLHQDWLNGKEYKCKVSNKALPSSIEKTISKAKGQPREPQVYTL

PPCREEMTKNQVSLWCLVKGFYPSDIAVEWESNGQPENNYKTTPPVLDSD

GSFFLYSKLTVDKSRWQQGNVFSCSVMHEALHNRFTQKSLSLSPGKGGGG

SGGGGSGGGGSQVQLVQSGAEVKKPGSSVKVSCKASGYTFTTYALHWVRQ

APGCGLEWMGWIYPGNVHAQYNEKFKGRVTITADKSTSTAYMELSSLRSE

DTAVYYCARSWEGFPYWGQGTTVTVSSGGGSGGGGSGCPPCGGGGDIQMTQ

SPSSLSASVGDRVTITCKASQNVGINVAWYQQKPGKAPKSLISSASYRYS

GVPSRFSGSGSGTDFTLTISSLQPEDFATYFCQQYDTYPFTFGCGTKVEI

K (HC L19 IgG1s knob with pA mutations)
SEQ ID NO: 87

VQLLESGGGLVQPGGSLRLSCAASGFTFSSFSMSWVRQAPGKGLEWVSSI

SGSSGTTYYADSVKGRFTISRDNSKNTLYLQMNSLRAEDTAVYYCAKPFP

YFDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPEAAGASSVFLFPPKPKDTLM

ISRTPEVTCVVVDVSAEDPEVKFNWYVDGVEVHNAKTKPREEQYNSTYRV

VSVLTVLHQDWLNGKEYKCKVSNKALPSSIEKTISKAKGQPREPQVYTLP

PCREEMTKNQVSLWCLVKGFYPSDIAVEWESNGQPENNYKTTPPVLDSDG

SFFLYSKLTVDKSRWQQGNVFSCSVMHEALHNRFTQKSLSLSPGK (HC L19 IgG1s hole)
SEQ ID NO: 88

EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPEAAGASSVFLFPPKPKDTL

MISRTPEVTCVVVDVSAEDPEVKFNWYVDGVEVHNAKTKPREEQYNSTYR

VVSVLTVLHQDWLNGKEYKCKVSNKALPSSIEKTISKAKGQPREPQVCTL

PPSREEMTKNQVSLSCAVKGFYPSDIAVEWESNGQPENNYKTTPPVLDSD

GSFFLVSKLTVDKSRWQQGNVFSCSVMHEALHNHYTQKSLSLSPGK (LC L19)
SEQ ID NO: 89

EIVLTQSPGTLSLSPGERATLSCRASQSVSSSFLAWYQQKPGQAPRLLIY

YASSRATGIPDRFSGSGSGTDFTLTISRLEPEDFAVYYCQQTGRIPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC xi. COVA14133 was generated by co-expression of an anti-EDB antibody EDBmAb1 heavy chain carrying a C-terminal stapled scFv BHA10 (VH-VL orientation SEQ ID NO: 77) fusion (SEQ ID NO: 97, comprising SEQ ID NO: 98) with the heavy chain (HC; SEQ ID NO: 88) and light chain (LC; SEQ ID NO: 89) of an anti-EDB antibody EDBmAb1 (FIG. 15K).

[stapled scFv BHA10 (VH-VL)]
SEQ ID NO: 77
QVQLVQSGAEVKKPGSSVKVSCKASGYTFTTYYLHWVRQAPGCGLEWMGW
IYPGNVHAQYNEKFKGRVTITADKSTSTAYMELSSLRSEDTAVYYCARSW
EGFPYWGQGTTVTVSSGGGSGGGSGCPPCGGGGDIQMTQSPSSLSASVGD
RVTITCKASQNVGINVAWYQQKPGKAPKSLISSASYRYSGVPSRFSGSGS
GTDFTLTISSLQPEDFATYFCQQYDTYPFTFGCGTKVEIK (HC L19 C-term stapled BHA10 (VH-VL), IgG1s, knob, no pA mutations)
SEQ ID NO: 97
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVYTL
PPCREEMTKNQVSLWCLVKGFYPSDIAVEWESNGQPENNYKTTPPVLDSD
GSFFLYSKLTVDKSRWQQGNVFSCSVMHEALHNHYTQKSLSLSPGKGGGG
SGGGGSGGGGSQVQLVQSGAEVKKPGSSVKVSCKASGYTFTTYYLHWVRQ
APGCGLEWMGWIYPGNVHAQYNEKFKGRVTITADKSTSTAYMELSSLRSE
DTAVYYCARSWEGFPYWGQGTTVTVSSGGGSGGGSGCPPCGGGGDIQMTQ
SPSSLSASVGDRVTITCKASQNVGINVAWYQQKPGKAPKSLISSASYRYS
GVPSRFSGSGSGTDFTLTISSLQPEDFATYFCQQYDTYPFTFGCGTKVEI
K (HC L19 IgG1s knob)
SEQ ID NO: 98
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVYTL
PPCREEMTKNQVSLWCLVKGFYPSDIAVEWESNGQPENNYKTTPPVLDSD
GSFFLYSKLTVDKSRWQQGNVFSCSVMHEALHNHYTQKSLSLSPGK (HC L19 IgG1s hole)
SEQ ID NO: 88
EVQLLESGGGLVQPGGSLRLSCAASGFTFSSFSMSWVRQAPGKGLEWVSS
ISGSSGTTYYADSVKGRFTISRDNSKNTLYLQMNSLRAEDTAVYYCAKPF
PYFDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPEAAGASSVFLFPPKPKDTL
MISRTPEVTCVVVDVSAEDPEVKFNWYVDGVEVHNAKTKPREEQYNSTYR
VVSVLTVLHQDWLNGKEYKCKVSNKALPSSIEKTISKAKGQPREPQVCTL
PPSREEMTKNQVSLSCAVKGFYPSDIAVEWESNGQPENNYKTTPPVLDSD
GSFFLVSKLTVDKSRWQQGNVFSCSVMHEALHNHYTQKSLSLSPGK (LC L19)
SEQ ID NO: 89
EIVLTQSPGTLSLSPGERATLSCRASQSVSSSFLAWYQQKPGQAPRLLIY
YASSRATGIPDRFSGSGSGTDFTLTISRLEPEDFAVYYCQQTGRIPPTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC xii. COVA14136 was generated by co-expression of the anti-RSV B21M antibody heavy chain carrying a C-terminal stapled scFv BHA10 (VH-VL orientation SEQ ID NO: 77) fusion (SEQ ID NO: 99, comprising SEQ ID NO: 100) with the heavy chain (HC; SEQ ID NO: 80) and light chain (LC; SEQ ID NO: 81) of an anti-EDB antibody EDBmAb1 (FIG. 15L).

[stapled scFv BHA10 (VH-VL)]
SEQ ID NO: 77
QVQLVQSGAEVKKPGSSVKVSCKASGYTFTTYYLHWVRQAPGCGLEWMGW
IYPGNVHAQYNEKFKGRVTITADKSTSTAYMELSSLRSEDTAVYYCARSW
EGFPYWGQGTTVTVSSGGGSGGGSGCPPCGGGGDIQMTQSPSSLSASVGD
RVTITCKASQNVGINVAWYQQKPGKAPKSLISSASYRYSGVPSRFSGSGS
GTDFTLTISSLQPEDFATYFCQQYDTYPFTFGCGTKVEIK (HC B21M C-term stapled BHA10 (VH-VL), IgG1s, knob, no pA mutations)
SEQ ID NO: 99
QITLKESGPTLVKPTQTLTLTCTFSGFSLSTSGMGVSWIRQPPGKALEWL
AHIYWDDDKRYNPSLKSRLTITKDTSKNQVVLTMTNMDPVDTATYYCARL
YGFTYGFAYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPEAAGASSVFLFPPKP
KDTLMISRTPEVTCVVVDVSAEDPEVKFNWYVDGVEVHNAKTKPREEQYN
STYRVVSVLTVLHQDWLNGKEYKCKVSNKALPSSIEKTISKAKGQPREPQ
VYTLPPCREEMTKNQVSLWCLVKGFYPSDIAVEWESNGQPENNYKTTPPV
LDSDGSFFLYSKLTVDKSRWQQGNVFSCSVMHEALHNHYTQKSLSLSPGK
GGGGSGGGGSGGGGSQVQLVQSGAEVKKPGSSVKVSCKASGYTFTTYYLH
WVRQAPGCGLEWMGWIYPGNVHAQYNEKFKGRVTITADKSTSTAYMELSS
LRSEDTAVYYCARSWEGFPYWGQGTTVTVSSGGGSGGGSGCPPCGGGGDI
QMTQSPSSLSASVGDRVTITCKASQNVGINVAWYQQKPGKAPKSLISSAS
YRYSGVPSRFSGSGSGTDFTLTISSLQPEDFATYFCQQYDTYPFTFGCGT
KVEIK (HC B21M (RSV) IgG1s knob)
SEQ ID NO: 100
QITLKESGPTLVKPTQTLTLTCTFSGFSLSTSGMGVSWIRQPPGKALEWL
AHIYWDDDKRYNPSLKSRLTITKDTSKNQVVLTMTNMDPVDTATYYCARL
YGFTYGFAYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT

YICNVNHKPSNTKVDKKVEPKSCDKTHTCPPCPAPEAAGASSVFLFPPKP

KDTLMISRTPEVTCVVVDVSAEDPEVKFNWYVDGVEVHNAKTKPREEQYN

STYRVVSVLTVLHQDWLNGKEYKCKVSNKALPSSIEKTISKAKGQPREPQ

VYTLPPCREEMTKNQVSLWCLVKGFYPSDIAVEWESNGQPENNYKTTPPV

LDSDGSFFLYSKLTVDKSRWQQGNVFSCSVMHEALHNHYTQKSLSLSPGK (HC B21M (RSV) IgG1s hole)

SEQ ID NO: 80

QITLKESGPTLVKPTQTLTLTCTFSGFSLSTSGMGVSWIRQPPGKALEWL

AHIYWDDDKRYNPSLKSRLTITKDTSKNQVVLTMTNMDPVDTATYYCARL

YGFTYGFAYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPEAAGASSVFLFPPKP

KDTLMISRTPEVTCVVVDVSAEDPEVKFNWYVDGVEVHNAKTKPREEQYN

STYRVVSVLTVLHQDWLNGKEYKCKVSNKALPSSIEKTISKAKGQPREPQ

VCTLPPSREEMTKNQVSLSCAVKGFYPSDIAVEWESNGQPENNYKTTPPV

LDSDGSFFLVSKLTVDKSRWQQGNVFSCSVMHEALHNHYTQKSLSLSPGK

[LC B21M (RSV)]

SEQ ID NO: 81

DIVMTQSPDSLAVSLGERATINCRASQSVDYNGISYMEIWYQQKPGQPPK

LLIYAASNPESGVPDRFSGSGSGTDFTLTISSLQAEDVAVYYCQQIIEDP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC xiii. COVA14146 was generated by co-expression of an anti-mesothelin antibody MSLNmAb1 heavy chain carrying a C-terminal stapled scFv BHA10 (VH-VL orientation SEQ ID NO: 77) fusion (SEQ ID NO: 101, comprising SEQ ID NO: 102) with the heavy chain (HC; SEQ ID NO: 103) and light chain (LC; SEQ ID NO: 104) of an anti-mesothelin antibody MSLNmAb1 (FIG. 15M).

[stapled scFv BHA10 (VH-VL)]

SEQ ID NO: 77

QVQLVQSGAEVKKPGSSVKVSCKASGYTFTTYYLHWVRQAPGCGLEWMGW

IYPGNVHAQYNEKFKGRVTITADKSTSTAYMELSSLRSEDTAVYYCARSW

EGFPYWGQGTTVTVSSGGGSGGGSGCPPCGGGGDIQMTQSPSSLSASVGD

RVTITCKASQNVGINVAWYQQKPGKAPKSLISSASYRYSGVPSRFSGSGS

GTDFTLTISSLQPEDFATYFCQQYDTYPFTFGCGTKVEIK (MSLNmAb1 HC C-term stapled BHA10 (VH-VL), IgG1s, knob, with pA mutations)

SEQ ID NO: 101

QVQLQQSGPELEKPGASVKISCKASGYSFTGYTMNWVKQSHGKSLEWIGL

ITPYNGASSYNQKFRGKATLTVDKSSSTAYMDLLSLTSEDSAVYFCARGG

YDGRGFDYWGSGTPVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGASSVFLFPPKPK

DTLMISRTPEVTCVVVDVSAEDPEVKFNWYVDGVEVHNAKTKPREEQYNS

TYRVVSVLTVLHQDWLNGKEYKCKVSNKALPSSIEKTISKAKGQPREPQV

YTLPPCREEMTKNQVSLWCLVKGFYPSDIAVEWESNGQPENNYKTTPPVL

DSDGSFFLYSKLTVDKSRWQQGNVFSCSVMHEALHNRFTQKSLSLSPGKG

GGGSGGGGSGGGGSQVQLVQSGAEVKKPGSSVKVSCKASGYTFTTYYLHW

VRQAPGCGLEWMGWIYPGNVHAQYNEKFKGRVTITADKSTSTAYMELSSL

RSEDTAVYYCARSWEGFPYWGQGTTVTVSSGGGSGGGSGCPPCGGGGDIQ

MTQSPSSLSASVGDRVTITCKASQNVGINVAWYQQKPGKAPKSLISSASY

RYSGVPSRFSGSGSGTDFTLTISSLQPEDFATYFCQQYDTYPFTFGCGTK

VEIK (MSLNmAb1 HC, IgG1s, knob, with pA mutations)

SEQ ID NO: 102

QVQLQQSGPELEKPGASVKISCKASGYSFTGYTMNWVKQSHGKSLEWIGL

ITPYNGASSYNQKFRGKATLTVDKSSSTAYMDLLSLTSEDSAVYFCARGG

YDGRGFDYWGSGTPVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGASSVFLFPPKPK

DTLMISRTPEVTCVVVDVSAEDPEVKFNWYVDGVEVHNAKTKPREEQYNS

TYRVVSVLTVLHQDWLNGKEYKCKVSNKALPSSIEKTISKAKGQPREPQV

YTLPPCREEMTKNQVSLWCLVKGFYPSDIAVEWESNGQPENNYKTTPPVL

DSDGSFFLYSKLTVDKSRWQQGNVFSCSVMHEALHNRFTQKSLSLSPGK (HC MSLNmAb1 IgG1s hole)

SEQ ID NO: 103

QVQLQQSGPELEKPGASVKISCKASGYSFTGYTMNWVKQSHGKSLEWIGL

ITPYNGASSYNQKFRGKATLTVDKSSSTAYMDLLSLTSEDSAVYFCARGG

YDGRGFDYWGSGTPVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGASSVFLFPPKPK

DTLMISRTPEVTCVVVDVSAEDPEVKFNWYVDGVEVHNAKTKPREEQYNS

TYRVVSVLTVLHQDWLNGKEYKCKVSNKALPSSIEKTISKAKGQPREPQV

CTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK (LC MLSNmAb1)

SEQ ID NO: 104

DIELTQSPAIMSASPGEKVTMTCSASSSVSYMHWYQQKSGTSPKRWIYDT

SKLASGVPGRFSGSGSGNSYSLTISSVEAEDDATYYCQQWSKHPLTFGSG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

All constructs described above could be expressed and purified with high yield and purity (see Table 11 below), indicating that the bispecific constructs incorporating the spFv provided herein have good biophysical properties.

TABLE 11

Yield and purities of selected EBD/LTBR bispecifics

| Bispecific name | Description | Yield [mg/L] | Purity [% monomer] |
|---|---|---|---|
| COVA1482 | 2:1 heterodimer consisting of EDBmAb1 HC fused to stapled scFv BHA10 (VH-VL) (contains mutation in the Fc that abrogates binding to Protein A to facilitate purification of heterodimer) paired with EDBmAb1 HC and EDBmAb1 LC | 53 | 100 |
| COVA14133 | 2:1 heterodimer consisting of EDBmAb1 HC fused to stapled scFv BHA10 (VH-VL) paired with EDBmAb1 HC and EDBmAb1 LC | 64.3 | 100 |

6.7 Example 7: EDB Dependent In Vitro LTBR Activation—NF-κB Luciferase Reporter Assay To show that the EDB/LTBR bispecifics are able to activate LTBR in an EDB-dependent way, the activity of the compounds was tested in an A549 cell NF-κB luciferase reporter assay in the presence or absence of EDB containing fibronectin (EDB+ fibronectin). NF-κB signaling plays a pivotal role in regulating cell development and immune homeostasis. Activation of NF-κB through tumor necrosis factor receptors (TNFR) or the TNFR superfamily members (e.g., LTBR) occurs upon engagement with their respective ligands. The A549 lung epithelial cell line naturally expresses LTBR and the NF-κB luciferase reporter construct is stably integrated into the genome of the A549 lung epithelial cell line. Following activation by stimulants, endogenous NF-κB transcription factors bind to the DNA response elements to induce transcription of the luciferase gene.

To demonstrate EDB-dependent activation of LTBR, high binding 96-well µClear flat bottom plates (Greiner; Monroe, N.C.) were coated overnight with 150 ng/well human recombinant EDB+fibronectin domains 7-B-8-9 (EDB+; SEQ ID NO: 105) or 150 ng/well human recombinant fibronectin domains 7-8-9 (EDB−; SEQ ID NO: 106), which sequences are listed below.

```
(fibronectin domains 7B89)
                                      SEQ ID NO: 105
PLSPPTNLHLEANPDTGVLTVSWERSTTPDITGYRITTTPTNGQQGNSLE

EVVHADQSSCTFDNLSPGLEYNVSVYTVKDDKESVPISDTIIPEVPQLTD

LSFVDITDSSIGLRWTPLNSSTIIGYRITVVAAGEGIPIFEDFVDSSVGY

YTVTGLEPGIDYDISVITLINGGESAPTTLTQQTAVPPPTDLRFTNIGPD

TMRVTWAPPPSIDLTNFLVRYSPVKNEEDVAELSISPSDNAVVLTNLLPG

TEYVVSVSSVYEQHESTPLRGRQKTGLDSPTGIDFSDITANSFTVHWIAP

RATITGYRIRHHPEHFSGRPREDRVPHSRNSITLTNLTPGTEYVVSIVA

LNGREESPLLIGQQSTHHHHHH (fibronectin domains 789)
                                      SEQ ID NO: 106
PLSPPTNLHLEANPDTGVLTVSWERSTTPDITGYRITTTPTNGQQGNSLE

EVVHADQSSCTFDNLSPGLEYNVSVYTVKDDKESVPISDTIIPAVPPPTD

LRFTNIGPDTMRVTWAPPPSIDLTNFLVRYSPVKNEEDVAELSISPSDNA

VVLTNLLPGTEYVVSVSSVYEQHESTPLRGRQKTGLDSPTGIDFSDITAN
```

```
     -continued
SFTVHWIAPRATITGYRIRHHPEHFSGRPREDRVPHSRNSITLTNLTPGT

EYVVSIVALNGREESPLLIGQQSTHHHHHH
```

After overnight incubation, the coated plates were washed with PBS and blocked for 2 hours at 37° C. with assay medium (DMEM+10% heat inactivated FBS). A 1:5 dilution series of the compounds to be tested was prepared in assay medium as 2-fold concentration stocks (final concentrations tested ranged from 200 nM to 2.6 pM). 50 µl of diluted compounds were added to the pre-blocked plate after the blocking solution was removed by aspiration. 50 µl of a A549 cell suspension (concentration of cell suspension=0.4 Mio cells/ml assay medium) were added to each well (20,000 cells/well). A549 cells were previously detached from cell culture flask by using Accutase/EDTA and were then transferred in assay medium. Cells were incubated with the compounds for 18-20 hours at 37° C./5% $CO_2$.

After incubation for 18 hours, the BIO-GLO Luciferase Assay System (Promega; Madison, Wis.) was used to detect luciferase activity. Luminescence was measured using a TECAN M1000 Pro instrument with an integration time of 500 milliseconds. From the resulting relative light units (RLU), the fold induction of LTBR signaling was calculated as follows: Fold induction=$RLU_{stimulated}$ cells/average $RLU_{unstimulated}$ cells (unstimulated cells were included as control in each plate tested).

Dose response curves, including standard deviations, were plotted using GRAPHPAD Prism, and non-linear fits were applied (log(agonist) vs. response (variable slope—three parameters)), if applicable. In order to fit the data, the x-values (concentrations of compounds) were transformed using the X=Log(x) function of GRAPHPAD Prism.

COVA1482 was compared in the same A549 NF-κB reporter assay to COVA1456. COVA1482 differs from COVA1456 only in the stabilization method used for the scFv. The scFv in COVA1482, which was also derived from LTBRmAb1, was stabilized using the stapled platform described herein (i.e., stabilized via VH/linker and VL linker disulfide bond), wherein COVA1456 is disulfide stabilized between the VH and the VL (i.e., stabilized via VH/VL disulfide bond). FIG. 16A showed that both COVA1482 and COVA1456 potently activated LTBR in an EDB dependent way. The corresponding isotype controls COVA1486 and COVA1462 did not activate LTBR (FIG. 16A). These results demonstrate that incorporation of spFv into a multispecific molecule had no negative impact on the activity of the multispecific molecule. The 2:1 bispecific EDB/LTBR antibodies (COVA1482 or COVA1456) showed increased potency in inducing NF-κB signaling in this reporter assay. The average $EC_{50}$ calculated for COVA1482 over several assays with the same experimental set up was of ca. 30 pM±10 pM, whereas a control 1:1 heterodimer construct showed an $EC_{50}$ of ca. 3 nM in the assay (data not shown here), indicating that the 2:1 bispecifics can be 100 times more potent than 1:1 bispecifics. This could be explained by increased clustering of the LTBR binding site achieved with 2 binding sites to the TAA.

To study the effects of affinity to LTBR on the ability of such bispecifics to TAA-dependently activate LTBR, lower affinity variants (SEQ ID NO: 107, KD≈60 nM and SEQ ID NO: 108, KD≈600 nM) of the scFv fragment derived from LTBRmAb1 were generated and used to construct 2:1 bispecifics COVA14107 and COVA14108 (see Table 9).

[stapled scFv (VL3_Y36F_S49Y_F87Y) BHA10 (VH-VL)]
SEQ ID NO: 107
QVQLVQSGAEVKKPGSSVKVSCKASGYTFTTYYLHWVRQAPGCGLEWMGW

IYPGNVHAQYNEKFKGRVTITADKSTSTAYMELSSLRSEDTAVYYCARSW

EGFPYWGQGTTVTVSSGGGSGGGSGCPPCGGGGDIQMTQSPSSLSASVGD

RVTITCKASQNVGINVAWFQQKPGKAPKSLIYSASYRYSGVPSRFSGSGS

GTDFTLTISSLQPEDFATYYCQQYDTYPFTFGCGTKVEIK

[stapled scFv (VH_CDR1_Y33A) BHA10 (VH-VL)]
SEQ ID NO: 108
QVQLVQSGAEVKKPGSSVKVSCKASGYTFTTYALHWVRQAPGCGLEWMGW

IYPGNVHAQYNEKFKGRVTITADKSTSTAYMELSSLRSEDTAVYYCARSW

EGFPYWGQGTTVTVSSGGGSGGGSGCPPCGGGGDIQMTQSPSSLSASVGD

RVTITCKASQNVGINVAWYQQKPGKAPKSLISSASYRYSGVPSRFSGSGS

GTDFTLTISSLQPEDFATYFCQQYDTYPFTFGCGTKVEIK

The generated bispecifics were tested in the A549 NF-κB reporter assay to see the effects of affinity on activation of LTBR. FIG. 16B showed that lower affinity to LTBR corresponded to lower ability of the bispecific to activate LTBR in a TAA-dependent manner in this assay. The data also demonstrated that incorporation of spFv into a multispecific molecules had no negative impact on the activity of the molecule.

As mentioned in Example 6, mutations (WO2010151792) to abrogate binding to protein A (used for purification of antibodies) were introduced in the Fc of some constructs in order to facilitate the purification of the desired heterodimer. COVA14133 was generated without these mutations, and its activity was compared to COVA1482 to show that the mutations in the Fc region did not influence the activity of the bispecific. COVA14133 and COVA1482 and their respective isotype controls COVA14136 and COVA1486 were compared in the A549 NF-κB reporter assay. FIG. 16C showed that COVA14133 activated LTBR in a TAA-dependent manner with a similar efficiency as COVA1482, demonstrating that the mutations in the Fc did not influence the ability of the bispecific to activate LTBR and had no effect on functioning of the spFv.

In conclusion, COVA14133 was shown to have excellent ability to activate LTBR in a TAA-dependent manner.

6.8 Example 8: EDB Dependent In Vitro LTBR Activation—A375/WI38VA subline2RA Co-Culture Cell Assay The A375/WI38VA subline2RA co-culture assay was performed to verify if activation of LTBR in the presence of EDB+fibronectin (produced and deposited in the extracellular matrix by WI38VA cells (Zardi, L., et al., *EMBO J*, 6, 2337-42 (1987)) leads to the release of cytokines and chemokines and upregulation of the adhesion molecule ICAM-1 on the A375 cells and that incorporation of spFv has no negative impact on activity. WI38VA subline2RA (ATCC® CCL75.1™) cells were seeded in a 96 well plate at a density of 5000 cells/well and incubated for 48 hours in their growth medium (MEM w/o Glutamine+10% heat inactivated FBS+0.1 mM NEAA+2 mM L-Gln+1 mM Sodium pyruvate) at 37° C./5% $CO_2$. A 1:5 dilution series of the compounds to be tested was prepared in assay medium (DMEM+10% heat inactivated FBS) as 2-fold concentration stocks (final concentrations tested ranged from 40 nM to 0.5 pM). Prior to incubation in the co-culture with the WI38VA subline2RA cells, A375 cells (ATCC® CRL-1619™) were labeled with CELLTRACE violet (CTV, Invitrogen; Carlsbad, Calif.). For labeling, a cell suspension, with a concentration of $10 \times 10^6$ cells/ml and 2.5 µM CTV in 5% FBS in PBS, was incubated for 5 minutes at RT while protected from light. Cells were then washed and resuspended in assay medium at a density of $0.4 \times 10^6$ cells/ml. Careful removal of culture medium from the plate containing the 48 hours WI38VA subline2RA culture, was followed by addition of 50 µl A375 cell suspension (20,000 cells/well; CTV+ or CTV−) in each well. 50 µl of the serial diluted compounds (final volume per well 100 µl) were added to the cells and incubated 24 hours at 37° C./5% $CO_2$.

After incubation for 24 hours, the supernatants were cleared by centrifugation and stored for measurement of cytokines and chemokines using MSD assays. The cells were further processed for ICAM-1 measurement by flow cytometry.

6.8.1 Detection of ICAM-1 by Flow Cytometry

Any media left in the 96-well plate was carefully removed, cells were detached with Accutase, transferred to a DeepWell 96-well plate (triplicates were pooled in 1 well), washed, resuspended in 100 µl FACS buffer (PBS+1% FBS+0.1% $NaN_3$) and transferred to a round bottom 96-well plate. Antibody, i.e., anti-human ICAM-1 PE labeled (clone 1H4, Thermo; Waltham, Mass.) or isotype control antibody PE labeled (MPC-11, BioLegend; San Diego, Calif.) and LIVE/DEAD fixable near-IR stain (Invitrogen), single staining or combination staining was diluted as shown in Table 12.

TABLE 12

| | Dilution scheme of single staining or combo staining in FACS buffer | | |
|---|---|---|---|
| | Antibody or stain | Final concentration used (µg/ml) | Dilution factor |
| Single stainings | ICAM-1 | 1.25 | 20 |
| | Isotype control | 1.25 | 160 |
| | LIVE/DEAD | — | 400 |
| Combo staining ICAM-1 + LIVE/DEAD | ICAM-1 | 1.25 | 20 |
| | LIVE/DEAD | — | 400 |

Cells were centrifuged at 400×g at 4° C. for 4 minutes, the supernatant was discarded, and 50 µl antibody solutions were prepared as described in Table 12. Cells and antibodies were incubated in the dark at 4° C. for 30 minutes. After incubation, 120 µl were added in each well, and the cells were then centrifuged at 400×g at 4° C. for 4 minutes. Cells were washed once with FACS buffer, centrifuged and resuspended in 90 µl FACS buffer. Cells were then fixed by adding 90 µl of a 3.7% Formalin solution in PBS and were incubated for 15 minutes on ice in the dark. After fixation, cells were centrifuged at 400×g at 4° C. for 4 minutes and resuspended in 100 µl FACS buffer. Cells were measured using a MACS Quant instrument at a high flowrate in screen mode, 49 µl/well were acquired. Data were analyzed using the FLOWLOGICS Software (Version 700.2A) and plotted with GRAPHPAD Prism.

6.8.2 Cytokine Measurement in the Supernatants of Treated Cells Using MSD Platform Several cytokines that are known to be under the control of NF-κB signaling were measured using the MSD platform and multiplex MSD plates. Listed here are some examples of measured cytokines:
RANTES: using R-Plex Antibody Set human RANTES (MSD);
I-TAC, IP-10, MIP-3b: using 3-PLEX cytokine release assay (MSD);
IL-8, IP-10, MIP-3b: using 3-PLEX cytokine release assay (MSD); and
IL-12p70, IL-6, TNF-α, MIP-3a, SDF-1a: using 5-PLEX cytokine release assay (MSD)

The concentration of cytokines in the supernatant of treated cells was measured using the MSD platform following the manufacturer's instructions. Briefly, the protocol involved following steps:
(1) Preparation of the plate involved coating the provided plate with the linker-coupled capture antibodies. Plates were incubated with shaking overnight at 2-8° C. On the following day, plates were washed with PBST (PBS plus 0.05% Tween-20) using a plate washer (Biotek; Winooski, Vt.);
(2) Preparation of calibrator standard and detection antibody solution;
(3) Supernatants were diluted 1:3 or 1:5 depending on availability of material.

6.8.3 Assay Protocol:
Step 1: The sample or calibrator standard was added to the plate, and the plate was incubated at RT for 1 hour while shaking;
Step 2: The plates were washed, and the detection antibody was added.
The plates were incubated with shaking for 1 hour at RT
Step 3: The plates were washed and 2×read buffer T was added. The plate was analyzed on an MSD instrument
Data were analyzed using MESOSCALE Software (MSD discovery work bench program v 4.0.12.1) and plotted using GRAPHPAD Prism.

6.8.4 Results—Detection of ICAM-1 by Flow Cytometry

It was previously shown that NF-κB signaling can lead to upregulation of ICAM-1 on the surface of cells (da Silva Antunes, et al. Front Immunol, 9:576, (2018)). Therefore, the levels of ICAM-1 expression on the surface of A375 cells after co-culture incubation with EDB/LTBR bispecifics were measured. As an example, FIG. 17 shows the upregulation of ICAM-1 after incubation with the EDB/LTBR bispecific COVA1482, demonstrating functionality of the LTBR binding spFv. The isotype control molecule COVA1486 did not cause upregulation of ICAM-1. These findings indicated that the ability to cluster the LTBR scFv via binding to EDB was a prerequisite for LTBR activation, and as a consequence, ICAM-1 upregulation.

6.8.5 Results—Cytokine Measurement in the Supernatants of Treated Cells

Several cytokines and chemokines, that are expressed as a result of LTBR activation were measured in the supernatant of the co-cultures that were treated with EDB/LTBR bispecifics and control molecules as described above. FIGS. 18A-18D shows 4 representative examples of cytokines (FIG. 18A: RANTES, FIG. 18B: IL-6, FIG. 18C: IL-8 and FIG. 18D: MIP-3b) that were upregulated by activation of LTBR with COVA14133. The untargeted LTBRmAb1 derived scFv in COVA14136 did not activate LTBR, and as a consequence, the concentration of cytokines in the supernatant was not increased above background. The background was represented by the level achieved with the B21M antibody or COVA1440 (a 2(mAb) B21M isotype control mAb) (shown as a single concentration in the plots). The results demonstrate that LTBR binding spFv is functional in vitro.

Taken together, ICAM-1 upregulation and cytokine secretion upon LTBR activation confirmed the expected effects on cells that LTBR activation can have.

In this example, it was demonstrated that the molecules provided herein achieved efficient tumor associated antigen (here EDB-containing fibronectin) dependent activation of LTBR.

6.9 Example 9: Mesothelin-Dependent In Vitro LTBR Activation—Co-Culture Cell Assay with A549 NF-κB Reporter Cells and CHOK1-huMSLN or 11226

In the Examples 7 and 8, it was demonstrated that bispecific antibodies comprising spFv structures provided herein, targeting EDB (a tumor associated antigen in the extracellular matrix) and LTBR, activated LTBR very efficiently in a tumor antigen dependent way. In order to verify if this finding holds true for any tumor antigen despite its location (deposited in the extracellular matrix or on the cell surface of tumor cells), a bispecific 2:1 antibody targeting mesothelin (MSLN), a tumor associated antigen expressed on different types of tumor (Hassan and Ho, Eur. J. Cancer, 44:46-53 (2008)) and LTBR was designed and produced as described in Example 6. COVA14146 is a 2:1 MSLN/LTBR bispecific antibody consisting of an anti-mesothelin antibody (MSLNmAb1) fused to a spFv fragment derived from LTBRmAb1. To show if a LTBR bispecific antibody targeting LTBR and a tumor associated antigen present of the cell surface of tumor cells (e.g., mesothelin) was able to efficiently activate LTBR in a tumor-dependent way, a co-culture cell assay was used. The co-culture assays used were the A549 cell NF-κB luciferase reporter cell assay (described in Example 7) and H226 cells (mesothelioma cell line; ATCC® CRL-5826) known to express mesothelin (Fan et al. Mol. Canc. Ther. 1:595-600 (2002)) and LTBR.

6.9.1 Preparation of H226 Cells 10,000 cells per well (in 75 µl assay medium: DMEM+ 10% FBS-HI) of a H226 cell (express about 200,000 copies of mesothelin and 10,000 copies of LTBR) suspension were seeded in a 96-well tissue culture plate and were incubated for 6 hours at 37° C./5% $CO_2$ in their growth media (MEM+2 mM Glutamine+10% FBS-HI+10 µg/ml Puromycin and RPMI-1640+10% FBS+1 mM Na-Pyruvate respectively) to allow the cells to attach to the plate.

6.9.2 Preparation of Compounds

The compounds were tested in a concentration range from 100 nM down to 1.3 pM. A 4-fold 1 in 5 serial dilution of the compounds was prepared in assay medium (DMEM+ 10% FBS-HI) and stored at 4° C. until use.

6.9.3 Preparation and Addition of A549 Reporter Cells

A549 reporter cells were detached from the cell culture flask with Accutase/EDTA and transferred in to assay medium (DMEM+10% FBS-HI). After adding a total of 20,000 A549 reporter cells per well to the plates containing H226 cells, 50 μL of the pre-diluted compounds were added to each well and incubated for 20 hrs. at 37° C./5% $CO_2$.

6.9.4 Measurement of Luminescence in Treated Co-Cultures

After incubation for 20 hours, the BIO-GLO Luciferase Assay System (Promega; Madison, Wis.) was used according to manufacturer's instructions to detect luciferase activity. Luminescence was measured using a TECAN M1000 Pro instrument with an integration time of 500 milliseconds. From the resulting relative light units (RLU), the fold induction of LTBR signaling was calculated as follows: Fold induction=$RLU_{stimulated}$ cells/average $RLU_{unstimulated}$ cells (unstimulated cells were included as control in each plate tested).

Dose response curves, including standard deviations, were plotted using GRAPHPAD Prism, and non-linear fits were applied (log(agonist) vs. response (variable slope—three parameters)), if applicable. In order to fit the data, the x-values (concentrations of compounds) were transformed using the X=Log(x) function of GRAPHPAD Prism.

6.9.5 Cytokine Measurement in the Supernatants of Treated Cells Using MSD Platform Several cytokines known to be under the control of NF-κB signaling can be measured using the MSD platform and multiplex MSD plates. As an example, the method for the measurement of RANTES using R-Plex Antibody Set human RANTES (MSD) is described herein.

The concentration of RANTES in the supernatant of treated cells was measured using the MSD platform following the manufacturer's instructions. Briefly, the protocol involved following steps:

(1) Preparation of the plate involved coating the provided plate with the linker-coupled capture antibodies. Plates were incubated with shaking overnight at 2-8° C. On the following day, plates were washed with PBST (PBS plus 0.05% Tween-20) using a plate washer (Biotek; Winooski, Vt.);

(2) Preparation of calibrator standard and detection antibody solution;

(3) Supernatants were diluted 1:3 or 1:5 depending on availability of material.

6.9.6 Assay Protocol:

Step 1: The sample or calibrator standard was added to the plate, and the plate was incubated at RT for 1 hour while shaking;

Step 2: The plates were washed, and the detection antibody was added. The plates were incubated with shaking for 1 hour at RT Step 3: The plates were washed and 2×read buffer T was added. The plate was analyzed on an MSD instrument Data were analyzed using MESOSCALE Software (MSD discovery work bench program v 4.0.12.1) and plotted using GRAPHPAD Prism.

6.9.7 Results—Mesothelin-Dependent Activation of LTBR in A549 Reporter Cells/H226 Co-Culture Assay A co-culture assay with A549 reporter cells and H226 cells was performed to verify if COVA14146 was able to activate LTBR in a more physiological system, where, due to its broad expression (Lukashev, et al. *Cancer Res.,* 66(19):9617-24 (2006), LTBR and mesothelin (and other tumor associated antigens on the cell surface of tumor cells, e.g., EGFR) are expected to be co-expressed on the cell surface of tumor cells. In FIG. 19A, it was shown that under these conditions COVA14146 did not activate LTBR efficiently. The concentrations of RANTES secreted in the supernatants of treated cells were measured to confirm the inability of COVA14146 to efficiently activate LTBR. As expected, FIG. 19B shows that RANTES was secreted by cells treated with COVA14146 to same extent as from cells that were treated with the isotype control molecule COVA1486, confirming that LTBR cannot be activated under these conditions.

6.10 Example 10: Bispecific Antibodies Specifically Binding to LTBR and Other TAAs Present in the Extracellular Matrix The examples above demonstrated that bispecific antibodies targeting LTBR and a TAA expressed in the extracellular matrix, in that case EDB of fibronectin, can activate LTBR selectively in tumor-tissue that expresses EDB. This example demonstrated that this is more generally applicable to bispecific antibodies that target LTBR and another TAA present in the extracellular matrix, by providing two more examples of such TAAs, namely domain A2 of tenascin C, and extra domain A of fibronectin.

Generally following the methods described in the examples above, further bispecific antibodies that bind to LTBR and other TAAs present in the extracellular matrix, namely domain A2 of tenascin C (TnCA2) or extra domain A of fibronectin (EDA), were prepared. The sequence of these TAAs have, for instance, been described in:

TnCA2: UniProt Accession number P24821.3;
EDA: UniProt Accession number P02751.

In addition, antibodies against these TAAs have, for instance, been previously described in:

TnCA2: WO2011/020783;
EDA: EP2142567.

Exemplary sequences of the binding domains against these targets used for the present example (by combining with an LTBR scFv to create a multispecific binding molecule of the invention) are provided as:

TnCA2: VH SEQ ID NO: 109 and VL SEQ ID NO: 110;
EDA: VH SEQ ID NO: 111 and VL SEQ ID NO: 112.

These sequences are as follows:

```
(VH of Anti-TnCA2 Ab 2B10)
                                    SEQ ID NO: 109
QVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCARLY

GYAYYGAFDYWGQGTTVTVSS (VL of Anti-TnCA2 Ab 2B10)
                                    SEQ ID NO: 110
DIQMTQSPSSLSASVGDRVTITCRASQGIRNDLGWYQQKPGKAPKRLIYA

ASSLQSGVPSRFSGGGSGTEFTLTISSLQPEDFATYYCLQNGLQPATFGQ

GTKVEIK (VH Anti- EDA Ab F8)
                                    SEQ ID NO: 111
EVQLLESGGGLVQPGGSLRLSCAASGFTFSLFTMSWVRQAPGKGLEWVSA

ISGSGGSTYYADSVKGRFTISRDNSKNTLYLQMNSLRAEDTAVYYCAKST

HLYLFDYWGQGTLVTVSS (VL Anti-EDA Ab F8)
                                    SEQ ID NO: 112
EIVLTQSPGTLSLSPGERATLSCRASQSVSMPFLAWYQQKPGQAPRLLIY

GASSRATGIPDRFSGSGSGTDFTLTISRLEPEDFAVYYCQQMRGRPPTFG

QGTKVEIK
```

Bispecific antibodies that bind to LTBR and these TAAs were prepared and tested for TAA-specific activation of LTBR in a TAA-dependent in vitro LTBR activation—NF-κB Luciferase reporter assay following a similar procedure as described in Example 7.

Asymmetric antibodies, with 2:1 stoichiometry were generated as follows:

COVA14198 was generated by co-expression of an anti-EDA antibody heavy chain carrying a C-terminal stapled scFv BHA10 (VH-VL orientation SEQ ID NO: 77) fusion (SEQ ID NO: 113, comprising SEQ ID NO: 114) with the heavy chain (HC; SEQ ID NO: 115) and light chain (LC; SEQ ID NO: 116) of an anti-EDA antibody. The sequences are listed below.

[stapled scFv BHA10 (VH-VL)]
SEQ ID NO: 77
QVQLVQSGAEVKKPGSSVKVSCKASGYTFTTYYLHWVRQAPGCGLEWMGW
IYPGNVHAQYNEKFKGRVTITADKSTSTAYMELSSLRSEDTAVYYCARSW
EGFPYWGQGTTVTVSSGGGSGGGSGCPPCGGGGDIQMTQSPSSLSASVGD
RVTITCKASQNVGINVAWYQQKPGKAPKSLISSASYRYSGVPSRFSGSGS
GTDFTLTISSLQPEDFATYFCQQYDTYPFTFGCGTKVEIK (F8 HC with BHA10 stapled (VH-VL) scFv C-ter
fused, IgG1 sigma, knob mutations)
SEQ ID NO: 113
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPEAAGASSVFLFPPKPKD
TLMISRTPEVTCVVVDVSAEDPEVKFNWYVDGVEVHNAKTKPREEQYNST
YRVVSVLTVLHQDWLNGKEYKCKVSNKALPSSIEKTISKAKGQPREPQVY
TLPPCREEMTKNQVSLWCLVKGFYPSDIAVEWESNGQPENNYKTTPPVLD
SDGSFFLYSKLTVDKSRWQQGNVFSCSVMHEALHNHYTQKSLSLSPGKGG
GGSGGGGSGGGGSQVQLVQSGAEVKKPGSSVKVSCKASGYTFTTYYLHWV
RQAPGCGLEWMGWIYPGNVHAQYNEKFKGRVTITADKSTSTAYMELSSLR
SEDTAVYYCARSWEGFPYWGQGTTVTVSSGGGSGGGSGCPPCGGGGDIQM
TQSPSSLSASVGDRVTITCKASQNVGINVAWYQQKPGKAPKSLISSASYR
YSGVPSRFSGSGSGTDFTLTISSLQPEDFATYFCQQYDTYPFTFGCGTKV
EIK (F8 HC, IgG1 sigma, knob mutations)
SEQ ID NO: 114
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPEAAGASSVFLFPPKPKD
TLMISRTPEVTCVVVDVSAEDPEVKFNWYVDGVEVHNAKTKPREEQYNST
YRVVSVLTVLHQDWLNGKEYKCKVSNKALPSSIEKTISKAKGQPREPQVY
TLPPCREEMTKNQVSLWCLVKGFYPSDIAVEWESNGQPENNYKTTPPVLD
SDGSFFLYSKLTVDKSRWQQGNVFSCSVMHEALHNHYTQKSLSLSPGK (F8 HC, IgG1 sigma and hole mutations)
SEQ ID NO: 115
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPEAAGASSVFLFPPKPKD
TLMISRTPEVTCVVVDVSAEDPEVKFNWYVDGVEVHNAKTKPREEQYNST
YRVVSVLTVLHQDWLNGKEYKCKVSNKALPSSIEKTISKAKGQPREPQVC
TLPPSREEMTKNQVSLSCAVKGFYPSDIAVEWESNGQPENNYKTTPPVLD
SDGSFFLVSKLTVDKSRWQQGNVFSCSVMHEALHNHYTQKSLSLSPGK (F8 LC)
SEQ ID NO: 116
EIVLTQSPGTLSLSPGERATLSCRASQSVSMPFLAWYQQKPGQAPRLLIY
GASSRATGIPDRFSGSGSGTDFTLTISRLEPEDFAVYYCQQMRGRPPTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC COVA14202 was generated by co-expression of an anti-domain A2 of tenascin C antibody heavy chain carrying a C-terminal stapled scFv BHA10 (VH-VL orientation SEQ ID NO: 77) fusion (SEQ ID NO: 117, comprising SEQ ID NO: 118) with the heavy chain (HC; SEQ ID NO: 119) and light chain (LC; SEQ ID NO: 120) of an anti-domain A2 of tenascin C antibody. The sequences are listed below.

[stapled scFv BHA10 (VH-VL)]
SEQ ID NO: 77
QVQLVQSGAEVKKPGSSVKVSCKASGYTFTTYYLHWVRQAPGCGLEWMGW
IYPGNVHAQYNEKFKGRVTITADKSTSTAYMELSSLRSEDTAVYYCARSW
EGFPYWGQGTTVTVSSGGGSGGGSGCPPCGGGGDIQMTQSPSSLSASVGD
RVTITCKASQNVGINVAWYQQKPGKAPKSLISSASYRYSGVPSRFSGSGS
GTDFTLTISSLQPEDFATYFCQQYDTYPFTFGCGTKVEIK (2B10 HC with BHA10 stapled (VH-VL) scFv C-ter
fused, IgG1 sigma, knob mutations)
SEQ ID NO: 117
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARLY
GYAYYGAFDYWGQGTTVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHTCPPCPAPEAAGASSVFLFPPK
PKDTLMISRTPEVTCVVVDVSAEDPEVKFNWYVDGVEVHNAKTKPREEQY
NSTYRVVSVLTVLHQDWLNGKEYKCKVSNKALPSSIEKTISKAKGQPREP
QVYTLPPCREEMTKNQVSLWCLVKGFYPSDIAVEWESNGQPENNYKTTPP
VLDSDGSFFLYSKLTVDKSRWQQGNVFSCSVMHEALHNHYTQKSLSLSPG
KGGGGSGGGGSGGGGSQVQLVQSGAEVKKPGSSVKVSCKASGYTFTTYYL -continued
HWVRQAPGCGLEWMGWIYPGNVHAQYNEKFKGRVTITADKSTSTAYMELS

SLRSEDTAVYYCARSWEGFPYWGQGTTVTVSSGGGSGGGSGCPPCGGGGD

IQMTQSPSSLSASVGDRVTITCKASQNVGINVAWYQQKPGKAPKSLISSA

SYRYSGVPSRFSGSGSGTDFTLTISSLQPEDFATYFCQQYDTYPFTFGCG

TKVEIK (2B10 HC, IgG1 sigma, knob mutations)
SEQ ID NO: 118
QVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCARLY

GYAYYGAFDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPEAAGASSVFLFPPK

PKDTLMISRTPEVTCVVVDVSAEDPEVKFNWYVDGVEVHNAKTKPREEQY

NSTYRVVSVLTVLHQDWLNGKEYKCKVSNKALPSSIEKTISKAKGQPREP

QVYTLPPCREEMTKNQVSLWCLVKGFYPSDIAVEWESNGQPENNYKTTPP

VLDSDGSFFLYSKLTVDKSRWQQGNVFSCSVMHEALHNHYTQKSLSLSPG

K (2B10 HC, IgG1 sigma and hole mutations)
SEQ ID NO: 119
QVQLVQSGAEVKKPGSSVKVSCKASGGTFSSYAISWVRQAPGQGLEWMGG

IIPIFGTANYAQKFQGRVTITADKSTSTAYMELSSLRSEDTAVYYCARLY

GYAYYGAFDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPEAAGASSVFLFPPK

PKDTLMISRTPEVTCVVVDVSAEDPEVKFNWYVDGVEVHNAKTKPREEQY

NSTYRVVSVLTVLHQDWLNGKEYKCKVSNKALPSSIEKTISKAKGQPREP

QVCTLPPSREEMTKNQVSLSCAVKGFYPSDIAVEWESNGQPENNYKTTPP

VLDSDGSFFLVSKLTVDKSRWQQGNVFSCSVMHEALHNHYTQKSLSLSPG

K (2B10 LC)
SEQ ID NO: 120
DIQMTQSPSSLSASVGDRVTITCRASQGIRNDLGWYQQKPGKAPKRLIYA

ASSLQSGVPSRFSGGGSGTEFTLTISSLQPEDFATYYCLQNGLQPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In order to demonstrate TAA-dependent activation of LTBR, high binding 96-well µClear flat bottom plates (Greiner; Monroe, N.C.) were coated overnight with:

150 ng/well of recombinant domain A2-containing (A2+) tenascin C domains A1-A2-A3 (TnCA2+; SEQ ID NO: 121) or 150 ng/well human recombinant tenascin domains A1-A3 (i.e., lacking domain A2, indicated as A2−) (TnCA2−; SEQ ID NO: 122); or 150 ng/well of recombinant EDA-containing (EDA+) fibronectin domains 11-A-12 (EDA+; SEQ ID NO: 123) or 150 ng/well human recombinant fibronectin domains 11-12 (i.e., not containing EDA, indicated as EDA−) (EDA−; SEQ ID NO: 124).

The above mentioned sequences are as follows:

(Hu tenascin C domains A1-A2-A3, including (His)6- Tag for purification)
SEQ ID NO: 121
EQAPELENLTVTEVGWDGLRLNWTAADQAYEHFIIQVQEANKVEAARNLT

VPGSLRAVDIPGLKAATPYTVSIYGVIQGYRTPVLSAEASTGETPNLGEV

VVAEVGWDALKLNWTAPEGAYEYFFIQVQEADTVEAAQNLTVPGGLRSTD

LPGLKAATHYTITIRGVTQDFSTTPLSVEVLTEEVPDMGNLTVTEVSWDA

LRLNWTTPDGTYDQFTIQVQEADQVEEAHNLTVPGSLRSMEIPGLRAGTP

YTVTLHGEVRGHSTRPLAVEVVTHHHHHH (Hu tenascin C domains A1-A3, including (His)6- Tag for purification)
SEQ ID NO: 122
EQAPELENLTVTEVGWDGLRLNWTAADQAYEHFIIQVQEANKVEAARNLT

VPGSLRAVDIPGLKAATPYTVSIYGVIQGYRTPVLSAEEEVPDMGNLTVT

EVSWDALRLNWTTPDGTYDQFTIQVQEADQVEEAHNLTVPGSLRSMEIPG

LRAGTPYTVTLHGEVRGHSTRPLAVEVVTHHHHHH (Hu fibronectin domains 11-A-12, including (His)6- Tag for purification)
SEQ ID NO: 123
EIDKPSQMQVTDVQDNSISVKWLPSSSPVTGYRVTTTPKNGPGPTKTKTA

GPDQTEMTIEGLQPTVEYVVSVYAQNPSGESQPLVQTAVTNIDRPKGLAF

TDVDVDSIKIAWESPQGQVSRYRVTYSSPEDGIHELFPAPDGEEDTAELQ

GLRPGSEYTVSVVALHDDMESQPLIGTQSTAIPAPTDLKFTQVTPTSLSA

QWTPPNVQLTGYRVRVTPKEKTGPMKEINLAPDSSSVVVSGLMVATKYEV

SVYALKDTLTSRPAQGVVTTLEHHHHHH (Hu fibronectin domains 11-12, including (His)6- Tag for purification)
SEQ ID NO: 124
EIDKPSQMQVTDVQDNSISVKWLPSSSPVTGYRVTTTPKNGPGPTKTKTA

GPDQTEMTIEGLQPTVEYVVSVYAQNPSGESQPLVQTAVTTIPAPTDLKF

TQVTPTSLSAQWTPPNVQLTGYRVRVTPKEKTGPMKEINLAPDSSSVVVS

GLMVATKYEVSVYALKDTLTSRPAQGVVTTLEHHHHHH

The results of these assays were in line with the results shown above for EDB/LTBR bispecifics, i.e., they showed activation of LTBR mainly in the presence of the tumor antigen of the extracellular matrix targeted by the respective bispecific binding molecule (Table 13).

TABLE 13

Maximal fold inductions of NF-κB signaling in presence or absence of EDA or TnCA2 for COVA14198 and COVA14202, respectively.

| Name | Max. fold induction in presence of TAA | Max. fold induction in absence of TAA | Ratio (max fold induction TAA$^+$)/max fold induction TAA$^-$) |
|---|---|---|---|
| COVA14198 (EDA/LTBR) | 4.5 | 1.3 | 3.5 |
| COVA14202 (TnCA2/LTBR) | 4.2 | 1.2 | 3.5 |

In particular, the TnCA2/LTBR bispecific binding molecule could activate LTBR, and therefore trigger NF-κB signaling, strongly in the presence of the TnCA2 antigen, and the EDA/LTBR bispecific binding molecule could activate LTBR, and therefore trigger NF-κB signaling, strongly in the presence of the EDA antigen. In absence of the respective TAA, these bispecifics did not or only minimally activate LTBR.

This example demonstrated that the approach to activate LTBR via a multispecific binding molecule of provided herein, e.g., binding to both LTBR and a tumor associated antigen associated with the extracellular matrix, works for all three different tumor associated antigens of the extracellular matrix that have been tested so far, and thus is generally applicable for tumor associated antigens present in the extracellular matrix. The example also demonstrated that molecules incorporating spFv are functional.

What is claimed:

1. An isolated single chain variable fragment (scFv) comprising a heavy chain variable region (VH), a linker (L) and a light chain variable region (VL),
wherein the scFv comprises:
 a) a first disulfide bond between a structurally conserved surface exposed VH cysteine (Cys) and a first L Cys;
 b) a second disulfide bond between a structurally conserved surface exposed VL Cys and a second L Cys; or
 c) a first disulfide bond between a structurally conserved surface exposed VH Cys and a first L Cys and a second disulfide bond between a structurally conserved surface exposed VL Cys and a second L Cys; and/or
wherein:
 (i) the VH comprises a VH Cys at a structurally conserved surface exposed VH framework residue position and the L comprises a first L Cys;
 (ii) the VL comprises a VL Cys at a structurally conserved surface exposed VL framework residue position and the L comprises a second L Cys; or
 (iii) the VH comprises a VH Cys at a structurally conserved surface exposed VH framework residue position, the VL comprises a VL Cys at a structurally conserved surface exposed VL framework residue position, and the L comprises a first L Cys and a second L Cys, wherein the VH Cys and the first L Cys are capable of forming a disulfide bond and the VL Cys and the second L Cys are capable of forming a disulfide bond.

2. The scFv of claim 1, wherein:
 (i) the distance between the VH Cys and the VL Cys is from about 7 Å to about 9 Å;
 (ii) the VH Cys is at H3, H5, H40, H43, H46 or H105, wherein residue numbering is according to Chothia; and/or
 (iii) the VL Cys is at L3, L5, L39, L42, L45, L100 or L102, wherein residue numbering is according to Chothia.

3. The scFv of claim 2, wherein
 a) the VH Cys is at H105 and the VL Cys is at L42;
 b) the VH Cys is at H43 and the VL Cys is at L100;
 c) the VH Cys is at H3 and the VL Cys is at L3;
 d) the VH Cys is at H3 and the VL Cys is at L5;
 e) the VH Cys is at H3 and the VL Cys is at L39;
 f) the VH Cys is at H3 and the VL Cys is at L42;
 g) the VH Cys is at H3 and the VL Cys is at L45;
 h) the VH Cys is at H3 and the VL Cys is at L100;
 i) the VH Cys is at H3 and the VL Cys is at L102;
 j) the VH Cys is at H5 and the VL Cys is at L3;
 k) the VH Cys is at H5 and the VL Cys is at L5;
 l) The VH Cys is at H5 and the VL Cys is at L39;
 m) the VH Cys is at H5 and the VL Cys is at L42;
 n) the VH Cys is at H5 and the VL Cys is at L45;
 o) the VH Cys is at H5 and the VL Cys is at L100;
 p) the VH Cys is at H5 and the VL Cys is at L102;
 q) the VH Cys is at H40 and the VL Cys is at L3;
 r) the VH Cys is at H40 and the VL Cys is at L5;
 s) the VH Cys is at H40 and the VL Cys is at L39;
 t) the VH Cys is at H40 and the VL Cys is at L42;
 u) the VH Cys is at H40 and the VL Cys is at L45;
 v) the VH Cys is at H40 and the VL Cys is at L100;
 w) the VH Cys is at H40 and the VL Cys is at L102;
 x) the VH Cys is at H43 and the VL Cys is at L3;
 y) the VH Cys is at H43 and the VL Cys is at L5;
 z) the VH Cys is at H43 and the VL Cys is at L39;
 aa) the VH Cys is at H43 and the VL Cys is at L42;
 bb) the VH Cys is at H43 and the VL Cys is at L45;
 cc) the VH Cys is at H43 and the VL Cys is at L102;
 dd) the VH Cys is at H46 and the VL Cys is at L3;
 ee) the VH Cys is at H46 and the VL Cys is at L5;
 ff) the VH Cys is at H46 and the VL Cys is at L39;
 gg) the VH Cys is at H46 and the VL Cys is at L42;
 hh) the VH Cys is at H46 and the VL Cys is at L45;
 ii) the VH Cys is at H46 and the VL Cys is at L100;
 jj) the VH Cys is at H46 and the VL Cys is at L102;
 kk) the VH Cys is at H105 and the VL Cys is at L3;
 ll) The VH Cys is at H105 and the VL Cys is at L5;
 mm) the VH Cys is at H105 and the VL Cys is at L39;
 nn) the VH Cys is at H105 and the VL Cys is at L45;
 oo) the VH Cys is at H105 and the VL Cys is at L100; or
 pp) the VH Cys is at H105 and the VL Cys is at L102,
  wherein residue numbering is according to Chothia.

4. The scFv of claim 1, wherein the L comprises a contiguous amino acid sequence derived from an immunoglobulin (Ig) hinge region, wherein optionally the Ig hinge region is derived from a human or a non-human Ig hinge region, wherein optionally the Ig hinge region is derived from a human Ig hinge region, wherein optionally the human Ig hinge region is an IgG1, IgG2, IgG3 or IgG4 isotype.

5. The scFv of claim 1, wherein
 (i) the L comprises an amino acid sequence C(X)$_y$C (SEQ ID NO: 23), wherein X is glycine (Gly), serine (Ser), proline (Pro), alanine (Ala), arginine (Arg), asparagine (Asn), aspartic acid (Asp), glutamic acid (Glu), glutamine (Gln), histidine (His), isoleucine (Ile), leucine (Leu), lysine (Lys), phenylalanine (Phe), threonine (Thr), tryptophan (Trp) or tyrosine (Tyr), and y is an integer from 1 to 3, wherein optionally the L comprises an amino acid sequence C(X)$_y$C (SEQ ID NO: 24), wherein X is Gly, Ser or Pro, and y is an integer from 1 to 3;
 (ii) the L comprises the amino acid sequence CPC, CGC, CSC, CPPC (SEQ ID NO: 1), CGPC (SEQ ID NO: 28), CPGC (SEQ ID NO: 29), CGGC (SEQ ID NO: 30), CSPG (SEQ ID NO: 31), CPSC (SEQ ID NO: 32), CSSC (SEQ ID NO: 33), CGSC (SEQ ID NO: 34), CSGC (SEQ ID NO: 35), CPPPC (SEQ ID NO: 36), CGPPC (SEQ ID NO: 37), CPGPC (SEQ ID NO: 38), CPPGC (SEQ ID NO: 39), CGGPC (SEQ ID NO: 40), CPGGC (SEQ ID NO: 41), CGGGC (SEQ ID NO: 42), CSPPC (SEQ ID NO: 43), CPSPC (SEQ ID NO: 44), CPPSC (SEQ ID NO: 45), CSSPC (SEQ ID NO: 46), CPSSC (SEQ ID NO: 47), CSSSC (SEQ ID NO: 48), CGSPC (SEQ ID NO: 49), CPGSC (SEQ ID NO: 50), CSGPC (SEQ ID NO: 51) or CPSGC (SEQ ID NO: 52);

(iii) the L comprises from about 14 to about 19 amino acids, wherein optionally the L comprises about 14, about 15, about 16, about 17, about 18 or about 19 amino acids;

(iv) the L comprises the amino acid sequence $(X)_m C(X)_y C(X)_n$ (SEQ ID NO: 25); wherein X is Gly, Ser, Pro, Ala, Arg, Asn, Asp, Glu, Gln, His, Ile, leu, Lys, Phe, Thr, Trp or Tyr, m is an integer from 6 to 9, y is an integer from 1 to 3, and n is an integer from 4 to 6;

(v) the L comprises the amino acid sequence $(X)_m C(X)_y C(X)_n$ (SEQ ID NO: 26); wherein X is Gly, Ser, Pro, Ala, Arg, Asn, Asp, Glu, Gln, His, Ile, Leu, Lys, Thr or Tyr, m is an integer from 6 to 9, y is an integer from 1 to 3, and n is an integer from 4 to 6;

(vi) the L comprises the amino acid sequence $(X)_m C(X)_y C(X)_n$ (SEQ ID NO: 27); wherein X is Gly or Pro, m is an integer from 6 to 9, y is an integer from 1 to 3, and n is an integer from 4 to 6; and/or (vii) the L comprises the amino acid sequence of SEQ ID Nos: 3, 4, 5, 6 or 7.

6. The scFv of claim 1, wherein the scFv is in the VL-L-VH orientation; or wherein the scFv is in the VH-L-VL orientation.

7. The scFv of claim 1, wherein:

(1) a) the VH comprises Cys at H105;
b) the VL comprises Cys at L42;
c) the L comprises an amino acid sequence of SEQ ID Nos: 3, 4, 5, 6 or 7; and
d) the scFv is in the VL-L-VH orientation, (2) a) the VH comprises Cys at H105;
b) the VL comprises Cys at L45;
c) the L comprises an amino acid sequence of SEQ ID Nos: 3, 4, 5, 6 or 7; and
d) the scFv is in the VL-L-VH orientation, (3) a) the VH comprises Cys at H105;
b) the VL comprises Cys at L39;
c) the L comprises an amino acid sequence of SEQ ID Nos: 3, 4, 5, 6 or 7; and
d) the scFv is in the VL-L-VH orientation, (4) a) the VH comprises Cys at H5;
b) the VL comprises Cys at L42;
c) the L comprises an amino acid sequence of SEQ ID Nos: 3, 4, 5, 6 or 7; and
d) the scFv is in the VL-L-VH orientation, (5) a) the VH comprises Cys at H5;
b) the VL comprises Cys at L45;
c) the L comprises an amino acid sequence of SEQ ID Nos: 3, 4, 5, 6 or 7; and
d) the scFv is in the VL-L-VH orientation, (6) a) the VH comprises Cys at H5;
b) the VL comprises Cys at L39;
c) the L comprises an amino acid sequence of SEQ ID Nos: 3, 4, 5, 6 or 7; and
d) the scFv is in the VL-L-VH orientation, (7) a) the VH comprises Cys at H3;
b) the VL comprises Cys at L42;
c) the L comprises an amino acid sequence of SEQ ID Nos: 3, 4, 5, 6 or 7; and
d) the scFv is in the VL-L-VH orientation, (8) a) the VH comprises Cys at H3;
b) the VL comprises Cys at L45;
c) the L comprises an amino acid sequence of SEQ ID Nos: 3, 4, 5, 6 or 7; and
d) the scFv is in the VL-L-VH orientation, (9) a) the VH comprises Cys at H3;
b) the VL comprises Cys at L39;
c) the L comprises an amino acid sequence of SEQ ID Nos: 3, 4, 5, 6 or 7; and
d) the scFv is in the VL-L-VH orientation,

(10) a) the VH comprises Cys at H43;
b) the VL comprises Cys at L100;
c) the L comprises an amino acid sequence of SEQ ID NOs: 3, 4, 5, 6 or 7; and
d) the scFv is in the VH-L-VL orientation,

(11) a) the VH comprises Cys at H43;
b) the VL comprises Cys at L102;
c) the L comprises an amino acid sequence of SEQ ID NOs: 3, 4, 5, 6 or 7; and
d) the scFv is in the VH-L-VL orientation,

(12) a) the VH comprises Cys at H43;
b) the VL comprises Cys at L5;
c) the L comprises an amino acid sequence of SEQ ID NOs: 3, 4, 5, 6 or 7; and
d) the scFv is in the VH-L-VL orientation,

(13) a) the VH comprises Cys at H43;
b) the VL comprises Cys at L3;
c) the L comprises an amino acid sequence of SEQ ID NOs: 3, 4, 5, 6 or 7; and
d) the scFv is in the VH-L-VL orientation,

(14) a) the VH comprises Cys at H40;
b) the VL comprises Cys at L100;
c) the L comprises an amino acid sequence of SEQ ID NOs: 3, 4, 5, 6 or 7; and
d) the scFv is in the VH-L-VL orientation,

(15) a) the VH comprises Cys at H40;
b) the VL comprises Cys at L102;
c) the L comprises an amino acid sequence of SEQ ID NOs: 3, 4, 5, 6 or 7; and
d) the scFv is in the VH-L-VL orientation,

(16) a) the VH comprises Cys at H40;
b) the VL comprises Cys at L5;
c) the L comprises an amino acid sequence of SEQ ID NOs: 3, 4, 5, 6 or 7; and
d) the scFv is in the VH-L-VL orientation,

(17) a) the VH comprises Cys at H40;
b) the VL comprises Cys at L3;
c) the L comprises an amino acid sequence of SEQ ID NOs: 3, 4, 5, 6 or 7; and
d) the scFv is in the VH-L-VL orientation,

(18) a) the VH comprises Cys at H46;
b) the VL comprises Cys at L100;
c) the L comprises an amino acid sequence of SEQ ID NOs: 3, 4, 5, 6 or 7; and
d) the scFv is in the VH-L-VL orientation,

(19) a) the VH comprises Cys at H46;
b) the VL comprises Cys at L102;
c) the L comprises an amino acid sequence of SEQ ID NOs: 3, 4, 5, 6 or 7; and
d) the scFv is in the VH-L-VL orientation,

(20) a) the VH comprises Cys at H46;
b) the VL comprises Cys at L5;
c) the L comprises an amino acid sequence of SEQ ID NOs: 3, 4, 5, 6 or 7; and
d) the scFv is in the VH-L-VL orientation, or

(21) a) the VH comprises Cys at H46;
b) the VL comprises Cys at L3;
c) the L comprises an amino acid sequence of SEQ ID NOs: 3, 4, 5, 6 or 7; and
d) the scFv is in the VH-L-VL orientation.

8. The scFv of claim 7, wherein:
(i) the L comprises the amino acid sequence of SEQ ID NO: 3;
(ii) the L comprises the amino acid sequence of SEQ ID NO: 6; or
(iii) the L comprises the amino acid sequence of SEQ ID NO: 7.

9. The scFv of claim 1, wherein the scFv is conjugated to a second molecule, wherein optionally,
(i) the second molecule is a half-life extending moiety, wherein optionally the half-life extending moiety is an immunoglobulin (Ig), a fragment of the Ig, an Ig constant region, a fragment of the Ig constant region, a Fc region, transferrin, albumin, an albumin binding domain or polyethylene glycol;
(ii) the second molecule is a cytotoxic agent or a detectable label;
(iii) the second molecule is an antibody or a fragment thereof, wherein optionally the scFv or the antibody or the fragment thereof bind distinct antigens;
(iv) the second molecule is a chimeric antigen receptor (CAR).

10. A pharmaceutical composition comprising the scFv of claim 1 and a pharmaceutically acceptable carrier.

11. A kit comprising the scFv of claim 1.

12. A multispecific molecule comprising the scFv of claim 1, wherein optionally the multispecific molecule comprises an antibody or an antibody fragment.

13. The multispecific molecule of claim 12, wherein the multispecific protein comprises an Ig constant region or a fragment of the Ig constant region, wherein:
(i) the fragment of the Ig constant region comprises a Fc region;
(ii) the fragment of the Ig constant region comprises a CH2 domain;
(iii) the fragment of the Ig constant region comprises a CH3 domain;
(iv) the fragment of the Ig constant region comprises a CH2 domain and a CH3 domain;
(v) the fragment of the Ig constant region comprises at least a portion of a hinge, a CH2 domain, and the CH3 domain; or
(vi) the fragment of the Ig constant region comprises a hinge, a CH2 domain, and a CH3 domain,
wherein optionally the Ig constant region or the fragment of the Ig constant region is an IgG1, an IgG2, an IgG3 or an IgG4 isotype.

14. The multispecific molecule of claim 13, wherein:
(i) the scFv is conjugated to the N-terminus of the Ig constant region or to the N-terminus of the fragment of the Ig constant region, or
(ii) the scFv is conjugated to the C-terminus of the Ig constant region or to the C-terminus of the fragment of the Ig constant region,
wherein optionally the Ig constant region or the fragment of the Ig constant region is an IgG1, an IgG2, an IgG3 or an IgG4 isotype.

15. The multispecific molecule of claim 13, wherein:
(i) the Ig constant region or the fragment of the Ig constant region comprises at least one mutation that results in reduced binding of the multispecific molecule to FcγR, wherein optionally the at least one mutation that results in reduced binding of the multispecific molecule to FcγR is selected from the group consisting of F234A/L235A, L234A/L235A, L234A/L235A/D265S, V234A/G237A/P238S/H268A/V309L/A330S/P331S, F234A/L235A, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S and S228P/F234A/L235A/G236-deleted/G237A/P238S, wherein residue numbering is according to the EU index; or
(ii) the Ig constant region or the fragment of the Ig constant region comprises at least one mutation that results in enhanced binding of the multispecific molecule to FcγR, wherein optionally the at least one mutation that results in enhanced binding of the multispecific molecule to FcγR is selected from the group consisting of S239D/I332E, S298A/E333A/K334A, F243L/R292P/Y300L, F243L/R292P/Y300L/P396L, F243L/R292P/Y300L/V305I/P396L and G236A/S239D/I332E, wherein residue numbering is according to the EU index;
(iii) the Ig constant region or fragment of the Ig constant region comprises at least one mutation that modulates a half-life of the multispecific molecule, wherein optionally the at least one mutation that modulates the half-life of the multispecific molecule is selected from the group consisting of H435A, P257I/N434H, D376V/N434H, M252Y/S254T/T256E/H433K/N434F, T308P/N434A and H435R, wherein residue numbering is according to the EU index;
(iv) the Ig constant region or fragment of the Ig constant region comprises at least one mutation in the CH3 domain, wherein optionally the at least one mutation in the CH3 domain is selected from the group consisting of T350V, L351Y, F405A, Y407V, T366Y, T366W, F405W, T394W, T394S, Y407T, Y407A, T366S/L368A/Y407V, L351Y/F405A/Y407V, T366I/K392M/T394W, F405A/Y407V, T366L/K392M/T394W, L351Y/Y407A, T366A/K409F, L351Y/Y407A, T366V/K409F, T366A/K409F, T350V/L351Y/F405A/Y407V and T350V/T366L/K392L/T394W, wherein residue numbering is according to the EU index,
wherein optionally FcγR is FcγRI, FcγRIIA, FcγRIIB or FcγRIII, or any combination thereof.

16. The multispecific molecule of claim 12, wherein:
(i) the multispecific molecule is bispecific;
(ii) the multispecific molecule is trispecific; or
(iii) the multispecific molecule is tetraspecific.

17. A pharmaceutical composition comprising the multispecific molecule of claim 12 and a pharmaceutically acceptable carrier.

18. A heterologous molecule comprising the scFv of claim 1.

19. The heterologous molecule of claim 18, wherein the scFv is conjugated to a second protein, a polynucleotide, a therapeutic agent, a cytotoxic agent or a detectable label, wherein optionally,
(i) the second protein is an antibody or a fragment thereof;
(ii) the second protein is an alternative scaffold; or
(iii) the second protein is a chimeric antigen receptor (CAR) or a fragment thereof.

20. The heterologous molecule of claim 18, wherein:
(i) the heterologous molecule is monospecific; or
(ii) the heterologous molecule is multispecific, wherein optionally the heterologous molecule is bispecific, trispecific, or tetraspecific.

21. A pharmaceutical composition comprising the heterologous molecule of claim 18 and a pharmaceutically acceptable carrier.

22. An isolated single chain variable fragment (scFv) comprising a heavy chain variable region (VH), a means for linking (L) and a light chain variable region (VL), wherein the scFv comprises:
(i) a) a first disulfide bond between a structurally conserved surface exposed VH cysteine (Cys) and a first L Cys;
b) a second disulfide bond between a structurally conserved surface exposed VL Cys and a second L Cys; or
c) a first disulfide bond between a structurally conserved surface exposed VH Cys and a first L Cys and a second disulfide bond between a structurally conserved surface exposed VL Cys and a second L Cys;
(ii) a) a first disulfide bond between a structurally conserved surface exposed antigen binding means cysteine (Cys) and a first L Cys;
b) a second disulfide bond between a structurally conserved surface exposed VL Cys and a second L Cys; or
c) a first disulfide bond between a structurally conserved surface exposed antigen binding means Cys and a first L Cys and a second disulfide bond between a structurally conserved surface exposed VL Cys and a second L Cys; or
(iii) a) a first disulfide bond between a structurally conserved surface exposed VH cysteine (Cys) and a first L Cys;
b) a second disulfide bond between a structurally conserved surface exposed antigen binding means Cys and a second L Cys; or
c) a first disulfide bond between a structurally conserved surface exposed VH Cys and a first L Cys and a second disulfide bond between a structurally conserved surface exposed antigen binding means Cys and a second L Cys.

23. A multispecific molecule comprising a single chain variable fragment (scFv) of claim 22.

24. A heterologous molecule comprising the single chain variable fragment (scFv) of claim 22.

25. The scFv of claim 1, wherein the scFv comprises a first disulfide bond between a structurally conserved surface exposed VH Cys and a first L Cys and a second disulfide bond between a structurally conserved surface exposed VL Cys and a second L Cys.

26. The scFv of claim 1, wherein the VH comprises a VH Cys at a structurally conserved surface exposed VH framework residue position, the VL comprises a VL Cys at a structurally conserved surface exposed VL framework residue position, and the L comprises a first L Cys and a second L Cys, wherein the VH Cys and the first L Cys are capable of forming a disulfide bond and the VL Cys and the second L Cys are capable of forming a disulfide bond.

* * * * *